US012714755B2

(12) United States Patent
Kelley et al.

(10) Patent No.: US 12,714,755 B2
(45) Date of Patent: Aug. 25, 2026

(54) EFFECTIVE DOSAGES OF AN ADENOVIRAL-BASED BIOLOGICAL DELIVERY AND EXPRESSION SYSTEM FOR USE IN THE TREATMENT OF OSTEOARTHRITIS IN HUMANS, AND COMPOSITIONS COMPRISING THE SAME

(71) Applicant: Pacira Therapeutics, Inc., Burlington, MA (US)

(72) Inventors: Scott Kelley, Burlington, MA (US); Rebecca Senter, Boston, MA (US); Monika Chabicovsky, Vienna (AT); Emily Walsh Martin, Boston, MA (US); Neil Bodick, Boston, MA (US); Won Hong, Burlington, MA (US); Kris Wang, Burlington, MA (US); Mark Douglas, Burlington, MA (US); John Derek Jackson, Burlington, MA (US)

(73) Assignee: Pacira Therapeutics, Inc., Brisbane, CA (US)

( * ) Notice: Subject to any disclaimer, the term of this patent is extended or adjusted under 35 U.S.C. 154(b) by 1018 days.

(21) Appl. No.: 17/760,715

(22) PCT Filed: Sep. 18, 2020

(86) PCT No.: PCT/US2020/051642
§ 371 (c)(1),
(2) Date: Mar. 15, 2022

(87) PCT Pub. No.: WO2021/055860
PCT Pub. Date: Mar. 25, 2021

(65) Prior Publication Data

US 2022/0403415 A1 Dec. 22, 2022

Related U.S. Application Data

(60) Provisional application No. 62/966,632, filed on Jan. 28, 2020, provisional application No. 62/902,041, filed on Sep. 18, 2019.

(51) Int. Cl.

| | |
|---|---|
| ***A61K 48/00*** | (2006.01) |
| ***A61K 9/00*** | (2006.01) |
| ***A61K 38/00*** | (2006.01) |
| ***A61P 19/02*** | (2006.01) |
| ***C07K 14/545*** | (2006.01) |
| ***C07K 14/715*** | (2006.01) |
| ***C12N 15/86*** | (2006.01) |

(52) U.S. Cl.
CPC ............ *A61K 48/00* (2013.01); *A61K 9/0019* (2013.01); *A61K 48/005* (2013.01); *A61P 19/02* (2018.01); *C07K 14/7155* (2013.01); *C12N 15/86* (2013.01); *A61K 38/00* (2013.01); *C07K 14/545* (2013.01); *C12N 2710/10343* (2013.01); *C12N 2750/14122* (2013.01); *C12N 2750/14142* (2013.01); *C12N 2750/14171* (2013.01)

(58) Field of Classification Search
CPC .......... C12N 15/86; C12N 2750/14122; C12N 2750/14142; C12N 2750/14171; C12N 2710/10343; A61K 9/0019; A61K 38/00; A61K 48/00; A61K 48/005; A61P 19/02; C07K 14/7155; C07K 14/545
USPC ............... 435/456, 320.1; 536/23.5; 530/351
See application file for complete search history.

(56) References Cited

U.S. PATENT DOCUMENTS

| | | |
|---|---|---|
| 5,747,072 A | 5/1998 | Davidson et al. |
| 5,919,676 A | 7/1999 | Graham et al. |
| 6,083,750 A | 7/2000 | Chamberlain et al. |
| 6,743,774 B1 | 6/2004 | Jay |
| 6,890,528 B1 | 5/2005 | Colloca |
| 7,419,808 B2 | 9/2008 | Zhang et al. |

(Continued)

FOREIGN PATENT DOCUMENTS

| | | |
|---|---|---|
| EP | 0 832 267 B1 | 2/2002 |
| EP | 0 821 739 B1 | 6/2003 |

(Continued)

OTHER PUBLICATIONS

U.S. Department of Health and Human Services Food and Drug Administration 2016, Recommendations for Microbial Vectors used for Gene Therapy: Guidance for Industry, 1-27. (Year: 2016).*

(Continued)

*Primary Examiner* — Anne Marie S Wehbe
*Assistant Examiner* — Katie L Pennington
(74) *Attorney, Agent, or Firm* — Knobbe, Martens, Olson & Bear, LLP

(57) ABSTRACT

The disclosure relates to pharmaceutical compositions and methods of using pharmaceutical compositions comprising effective dosages of an adenoviral-based biological delivery and expression system for use in the treatment or prevention of osteoarthritis in human or mammalian joints by long-term inducible gene expression of human or mammalian interleukin-1 receptor antagonist (IL-1Ra) in synovial cells, comprising a helper-dependent adenoviral vector containing a nucleic acid sequence encoding for human or mammalian interleukin-1 receptor antagonist (IL-1Ra), left and right inverted terminal repeats (L ITR and R ITR), the adenoviral packaging signal and non-viral, non-coding stuffer nucleic acid sequences, wherein the expression of the human or mammalian interleukin-1 receptor antagonist (IL-1Ra) gene within synovial cells is regulated by an inflammation-sensitive promoter.

15 Claims, 27 Drawing Sheets

Specification includes a Sequence Listing.

(56) References Cited

U.S. PATENT DOCUMENTS

| | | | | |
|---|---|---|---|---|
| 8,877,445 | B2 | 11/2014 | Shackney | |
| 10,301,647 | B2 | 5/2019 | Lee et al. | |
| 11,746,359 | B2 | 9/2023 | Ruan et al. | |
| 2001/0006948 | A1 | 7/2001 | Kang et al. | |
| 2002/0081719 | A1 | 6/2002 | Massaad | |
| 2002/0099024 | A1 | 7/2002 | Wickham et al. | |
| 2002/0146392 | A1 | 10/2002 | Graham et al. | |
| 2003/0091536 | A1 | 5/2003 | Frisbee et al. | |
| 2003/0104626 | A1 | 6/2003 | Fallaux et al. | |
| 2004/0072741 | A1 | 4/2004 | Jay | |
| 2005/0260596 | A1 | 11/2005 | Fallaux et al. | |
| 2008/0019975 | A1 | 1/2008 | Gorman | |
| 2008/0038233 | A1 | 2/2008 | Freemont et al. | |
| 2009/0023196 | A1 | 1/2009 | Fallaux et al. | |
| 2009/0104148 | A1 | 4/2009 | Jay et al. | |
| 2009/0274688 | A1 | 11/2009 | Boyle et al. | |
| 2010/0215731 | A1 | 8/2010 | Emans et al. | |
| 2010/0254937 | A1 | 10/2010 | Han | |
| 2010/0255572 | A1 | 10/2010 | Schmidt et al. | |
| 2012/0045764 | A1 | 2/2012 | Grompe | |
| 2013/0102028 | A1 | 4/2013 | Chun et al. | |
| 2015/0031083 | A1* | 1/2015 | Lee | C12N 15/86 435/69.52 |
| 2015/0118187 | A1 | 4/2015 | Shapir et al. | |
| 2015/0232836 | A1 | 8/2015 | Krieg | |
| 2015/0361452 | A1 | 12/2015 | Ruan et al. | |
| 2016/0304572 | A1 | 10/2016 | Schmidt et al. | |
| 2019/0350968 | A1 | 11/2019 | Erwin | |
| 2019/0376080 | A1 | 12/2019 | Lee et al. | |
| 2020/0071371 | A1* | 3/2020 | Ghivizzani | C12N 15/86 |
| 2022/0017923 | A1 | 1/2022 | Ruan et al. | |
| 2022/0073948 | A1 | 3/2022 | Lee et al. | |
| 2022/0282280 | A1 | 9/2022 | Ruan et al. | |
| 2022/0348963 | A1 | 11/2022 | Lee et al. | |
| 2023/0158170 | A1 | 5/2023 | Senter | |
| 2024/0102049 | A1 | 3/2024 | Ruan et al. | |

FOREIGN PATENT DOCUMENTS

| | | |
|---|---|---|
| EP | 2 298 925 | 3/2011 |
| WO | WO 02/082908 | 10/2002 |
| WO | WO 05/016130 | 2/2005 |
| WO | WO 05/085421 | 9/2005 |
| WO | WO 07/002261 | 1/2007 |
| WO | WO 08/143816 | 11/2008 |
| WO | WO 10/052505 | 5/2010 |
| WO | WO 10/135736 | 11/2010 |
| WO | WO 10/138939 | 12/2010 |
| WO | WO 13/114199 | 8/2013 |
| WO | WO 14/115022 | 7/2014 |
| WO | WO 17/191274 | 11/2017 |
| WO | WO 20/132226 | 6/2020 |
| WO | WO 00/46360 | 8/2020 |
| WO | WO 22/241228 | 11/2022 |

OTHER PUBLICATIONS

Gallaher & Berk 2013, J. Virol. Methods, 192(0), 28-38. (Year: 2013).*

Roamer & Sharov 2019, BioProcess International, retrieved on Apr. 25, 2025 from the Internet: <https://www.bioprocessintl.com/sponsored-content/qualitative-and-quantitative-host-cell-protein-analysis-using-mass-spectrometry>. (Year: 2109).*

Puntel et al. 2006, Human Gene Therapy, 17, 531-544. (Year: 2006).*

Roessler et al. 1995, Human Gene Therapy, 6, 307-316. (Year: 1995).*

Takahashi et al. 2006, Analytical Biochemistry, 349, 208-217. (Year: 2006).*

Vellekamp et al. 2001, Human Gene Therapy, 12, 1923-1936. (Year: 2001).*

Johnson 2018, Comments submitted by PDA for Docket ID: FDA-2008-D-0205, PDA, 1-10. (Year: 2018).*

NCBI 2010, *Homo sapiens* interleukin 1 receptor antagonist (IL1RN), transcript variant 1, mRNA, National Library of Medicine, deposited Mar. 21, 2010, retrieved on Nov. 11, 2025 from the Internet :< https://www.ncbi.nlm.nih.gov/nuccore/NM_173842.1> . (Year: 2010).*

Benneker et al., 2005, 2004 Young investigator award winner: vertebral endplate marrow contact channel occlusions and intervertebral disc degeneration, Spine, 30(2):167-173.

Bibby et al., 2004, Effect of nutrient deprivation on the viability of intervertebral disc cells, Eur Spine J. 13:695-701.

Brooks, 2002, Impact of osteoarthritis on individuals and society: how much disability? Social consequences and health economic implications. Curr Opin Rheumatol, 14:573-577.

Dolan et al., 2001, An EMG technique for measuring spinal loading during asymmetric lifting, Clin. Biomech. 16(Supplement 1):S17-S24.

Dolan et al., 2001, Recent advanced in lumbar spinal mechanics and their significance for modelling, Clin.Biomech. 16(Supplement 1):S8-S16.

Eskola et al., 2012, Gender difference in genetic association between IL1A variant and early lumbar disc degeneration: a three-year follow-up, Int J Mol Epidemiol Genet. 3(3):195-204.

Gruber et al., 1998, Analysis of aging and degeneration of the human intervertebral disc, Spine, 23(7):751-757.

Heathfield et al., 2008, Caveolin-1 expression and stress-induced premature senescence in human intervertebral disc degeneration, Arthritis Res.Ther., 10(4):1-9.

Hoyland et al., 2008, Investigation of the role of IK-1 and TNF in matrix degradation in the intervertebral disc, Rheumatology, 47:809-814.

Hunter et al., Sep. 2011, Emerging drugs for osteoarthritis, Expert Opin. Emerging Drugs, 16(3):479-491.

Inkinen et al., Relative increase of biglycan and decorin and altered chondroitin sulfate epitopes in the degenerating human intervertebral disc, The Journal of Rheumatology, 25(3):506-514.

Le Maetre et al., 2021, Development of a standardized histopathology scoring system for human intervertebral disc degeneration: an Orphopaedic Research Society Spine Section initiative, JOR Spine, 4:e1167.

Le Maitre et al., 2005, The role of interleukin-1 in the pathogenesis of human intervertebral disc degeneration, Arthritis Res Ther. 7:R732-R745.

Le Maitre et al., 2004, Localization of degradative enzymes and their inhibitors in the degenerate human intervertebral disc, J Pathol. 204:47-54.

Le Maitre et al., 2006, A preliminary in vitro study into the use of IL-1Ra gene therapy for the inhibition of intervertebral disc degeneration, Int J Exp Pathol. 87:17-28.

Le Maitre et al., 2007, Matrix synthesis and degradation in human intervertebral disc degeneration, Arthritis Res Ther., 35(4):652-655.

Luoma et al., 2000, Low back pain in relation to lumbar disc degeneration, Spine, 25(4):487-492.

Mwale et al., 2004, Distinction between the extracellular matrix of the nucleus pulposus and hyaline cartilage: a requisite for tissue engineering of intervertebral disc, European Cells and Materials, 8:58-64.

Palmer et al., 2003, Improved system for helper-dependent adenoviral vector production. Mol Ther 8:846-852.

Paz Aparicio et al., 2011, The IL-1? (+3953 T/C) gene polymorphism associates to symptomatic lumbar disc herniation, Eur Spine J., 29(Suppl 3):S383-S389.

Phillips et al., 2013, Interleukin-1 receptor antagonist deficient mice provide insights into pathogenesis of human intervertebral disc degeneration, Ann Rheum Dis, 72:1860-1867.

Phillips et al., 2013, The cytokine and chemokine expression profile of nucleus pulposus cells: implications for degeneration and regeneration of the intervertebral disc, Arthritis Res Ther. 15:R213.

Phillips et al., 2015, Potential roles of cytokines and chemokines in human intervertebral disc degeneration: interleukin-1 is a master regulator of catabolic processes, Osteoarthritis Cartilage, 23:1165-1177.

Pockert et al., Feb. 2009, Modified expression of the ADAMTX enzymes and tissue inhibitor of metalloproteinases 3 during human intervertebral disc degeneration, Arthritis Rheum. 69(2):482-491.

(56) References Cited

OTHER PUBLICATIONS

Pohl et al., Aug. 2016, Catabolic effects of endothelial cell-derived microparticles on disc cells: implications in intervertebral disc neovascularization and degeneration, pp. 1466-1474.
Roberts et al., 2006, Senescence in human intervertebral discs, Eur Spine J. 15(Suppl. 3):S312-S316.
Roberts et al., 2006, Topographical guidance of intervertebral disc cell growth in vitro: towards the development of tissue repair strategies for the anulus fibrosus, Eur Spine J. 15(Suppl. 3)S389-S396.
Shamji et al., Jul. 2010, Proinflammatory cytokine expression profile in degenerated and herniated human intervertebral disc tissues, Arthritis Rheum. 62(7):1974-1982.
Shankar et al., 2009, Anatomy and pathophysiology of intervertebral disc disease, Techniques in Regional Anesthesia and Pain Management, 13:67-75.
Sheskey et al., Oct. 2020, Handbook of Pharmaceutical Excipients Ninth edition, TOC, 3 pp.
Solovieva et al., 2004, Possible association of interleukin 1 gene locus polymorphisms with low back pain, Pain, 109:8-19.
Solovieva et al., 2005, Intervertebral disc degeneration in relation to the COL9A3 and the IL-1? gene polymorphism, Eur Spine J. 15:613-618.
Solovieva et al., Sep. 2004, Interleukin 1 polymorphisms and intervertebral disc degeneration, Epidemiology. 15(5):626-633.
Suzuki et al., Jan. 2010, large-scale production of high-quality helper-dependent adenoviral vectors using adherent cells in cell factories, Human Gene Therapy, 21(1):120-126.
The United States pharmacopeia, USP 30, The National formulary: NF 25, May 1, 2007 (TOC).
Toietta et al., 2002, Generation of helper-dependent adenoviral vectors by homologous recombination. Mol Ther 5:204-210.
Vo et al., Aug. 2016, Molecular mechanisms of biological aging in intervertebral discs, Orthop Res., pp. 1289-1306.
International Search Report and Written Opinion dated Jan. 13, 2021 in application No. PCT/US20/51642.
Abe et al., 2002, Enhancement of bone repair with a helper-dependent adenoviral transfer of bone morphogenetic protein-2, Biochemical and Biophysical Research Communications, 297(3):523-527.
Accession No. NM_001082525.2 Equus caballus interleukin 1 receptor antagonist (IL1RN), mRNA, 2015, 3 pages.
Accession No. NM_001082770 Oryctolagus cuniculus interleukin 1 receptor antagonist (ILIRN, mRNA 2011, 2 pages.
Accession No. NM_174357.3, Bos taurus interleukin 1 receptor antagonist (IL1RN), mRNA, 2009, 2 pages.
Adriaansen et al., 2006, Gene therapy as a therapeutic approach for the treatment of rheumatoid arthritis: innovative vectors and therapeutic genes, Rheumatology, 45:656-668.
Backstrom et al., 2003, Recombinant MUC1 mucin with a breast cancer-like 0-glycosylation produced in large amounts in Chinese-hamsterovary cells, Biochem. J., 376:677-686.
Bakker et al., Jun. 2002, C3-Tat/HIV-Regulated Intraarticular Human Interleukin-1 Receptor Antagonist Gene Therapy Results in Efficient Inhibition of Collagen-Induced Arthritis Superior to Cytomegalovirus-Regulated Expression of the Same Transgene, Arthritis & Rheumatism 46(6):1661-1670.
Bakker et al., 2001, A tropism-modified adenoviral vector increased the effectiveness of gene therapy for arthritis, Gene Therapy, 8(23):1785-1793.
Bergelson et al., 1997, Isolation of a Common Receptor for Coxsackie B Viruses and Adenoviruses 2 and 5, Science, 275:1320-1323.
Borzi et al., Aug. 2010, Matrix metalloproteinase 13 loss associated with impaired extracellular matrix remodeling disrupts Chondrocyte differentiation by concerted effects on multiple regulatory factors, Arthritis & Rheumatism, 62(8):2370-2381.
Brunetti-Pierri et al., May 2011, Multi-Year Transgene expression in nonhuman primates following Hepatic transduction with helper-dependent adenoviral vectors, American Society of Gene & Cell Therapy, Annual Meeting 2011 Molecular Therapy, 19(Supp. 1).
Brunetti-Pierri et al., 2004, Acute Toxicity After High-Dose Systemic Injection of Helper-Dependent Adenoviral Vectors into Nonhuman Primates, Human Gene Therapy, 15:35-46.
Brunetti-Pierri et al., Aug. 2013, Transgene expression up to 7 years in nonhuman primates following hepatic transduction with helper-dependent adenoviral vectors, Human Gene Therapy, 24:1-5.
Cao et al., 2011, The promotion of cartilage defect repair using adenovirus mediated Sox9 gene transfer of rabbit bone marrow mesenchymal stem cells, Biomaterials, 32:3910-3920.
Caron et al., 2003, Principals and practices of joint disease treatment, In: Diagnosis and management of lameness in the horse, 1st Edition, Philadelphia: Saunders, pp. 746-764.
Caron et al., Sep. 1996, Chondroprotective effect of intraarticular injections of interlukin-1 receptor antagonist in experimental osteoarthritis. Suppression of collagenase-1 expression., Arthritis Rheumatism, 39:9:1535-1544.
Castello et al., Feb. 2016, Helper-dependent adenoviral vectors for liver-directed gene therapy of primary hyperoxaluria type 1 Gene Therapy, 23(2):129-134.
Chen et al., Jan. 19, 2018, Sirt6 overexpression suppresses senescence and apoptosis of nucleus pulposus cells by inducing autophagy in a model of intervertebral disc degeneration, Cell Death & Disease, 9(2), 13 pp.
Chen et al., Mar. 1997, Persistence in muscle of an adenoviral vector that lacks all viral genes, Proc. Natl. Acad. Sci. USA, 94:1645-1650.
Chen et al., Oct. 16, 2021, SIRT6 inhibits endothelial-to-mesenchymal transition through attenuating the vascular endothelial inflammatory response, International Immunopharmacology 101(108240), 9 pp.
Chen et al., Oct. 2010, Effects of adenovirus-mediated bFGF, IL-1Ra and IGF-1 gene transfer on human osteoarthritic chondrocytes and osteoarthritis in rabbits, Experimental and Molecular Medicine, 42(10):684-695.
Coles et al., Jun. 2010, Loss of cartilage structure, stiffness, and frictional properties in mice lacking PRG4, Arthritis & Rheumatism, 62(6):1666-1674.
Daheshia et al., 2008, The interleukin 1-beta pathway in the pathogenesis of osteoarthritis, The Journal of Rheumatology, 35(12):2306-2312.
Daya et al., 2008, Gene Therapy Using Adeno-Associated Virus Vectors, Clin. Microbiol. Rev, 21(4):583-593.
Dehne et al., 2009, Chondrogenic differentiation potential of osteoarthritic chondrocytes and their possible use in matrix-associated autologous chondrocyte transplantation, Arthritic Research and Therapy, 11(5):R133.
Dinarello, 2003, Chapter 27-Interlukin-1 family, in The Cytokine Handbook, 4th Edition, 2:643-668.
Dinser et al., 2001, Comparison of long-term transgene expression after non-viral and adenoviral gene transfer into primary articular chondrocytes, Histochemistry and Cell Biology 116:69-77.
Dong et al., May 2023, Modulation of SIRT6 activity acts as an emerging therapeutic implication for pathological disorders in the skeletal system, Genes & Diseases, 10(3):864-876.
Dormond et al., 2010, An efficient process for the purification of helper-dependent adenoviral vector and removal of helper virus by iodixanol ultracentrifugation, Journal of Virological Methods, 165:83-89.
Dormond et al., Feb. 15, 2009, An Efficient and Scalable Process for Helper-Dependent Adenoviral Vector Production Using Polyethylenimine-Adenofection, Biotechnology and Bioengineering, 102(3):800-810.
Echtermeyer et al., 2009, Syndecan-4 regulates ADAMTS-5 activation and cartilage breakdown in osteoarthritis, Nature Medicine, 15(9):1072-1077.
Ehrke-Schulz et al., Jan. 28, 2016, Cloning and Large-Scale Production of High-Capacity Adenoviral Vectors Based on the Human Adenovirus Type 5, Journal of Visualized Experiments, 107:e52894, 15 pp.
Evans et al., 1994,, Gene therapy for arthritis, Gene Therapeutics: Methods and Applications of direct Gene Transferm, Birkhauser: Boston, MA, pp. 320-343.
Evans et al., 2004, Osteoarthritis gene therapy, Gene Therapy, Nature Publishing Group, 11:379-389.

(56) References Cited

OTHER PUBLICATIONS

Evans et al., Jan. 1999, Gene Therapy for Rheumatic Diseases, Arthritis & Rheumatism, 42(1):1-16.
Evans et al., Jan. 2018, Gene delivery to joints by intra-articular injection. Human Gene Therapy. 29(1):2-14.
Flannery et al., Mar. 2009, Prevention of cartilage degeneration in a rat model of osteoarthritis by intraarticular treatment with recombinant lubricin, Arthritis & Rheumatism, 60(3):840-847.
Flexion Press Release, Apr. 29, 2018, Flexion Therapeutics Announces Presentation of Positive FX201 Data at the Osteoarthritis Research Society International World Congress, 2 pp.
Frisbie et al., 2002, Treatment of experimental equine osteoarthritis by in vivo delivery of the equine interleukin-1 receptor antagonist gene, Gene Therapy, 9:12-20.
Fumoto et al., 2013, Targeted Gene Delivery: Importance of Administration Routes, Chapter 1 in Novel Gene Therapy Approaches, Intech, pp. 3-31.
Ghivizzani et al., Apr. 1998, Direct adenovirus-mediated gene transfer of interleukin 1 and tumor necrosis factor a soluble receptors to rabbit knees with experimental arthritis has local and distal anti- arthritic effects, Proc. Natl. Acad. Sci. USA, 95:4613-4618.
Giannoukakis et al., Sep. 1999, Adenoviral gene transfer of the interleukin-1 receptor antagonist protein to human islets prevents IL-1β-induced β-cell impairment and activation of islet cell apoptosis in vitro, Diabetes, 48:1730-1736.
Glasson et al., 2020, The OARSI histopathology initiative—recommendations for histological assessments of osteoarthritis in the mouse, Osteoarthritic and Cartilage, 18:S17-S23.
Goodrich et al., 2006, Direct adenovirus-mediated IGF-I gene transduction of synovium induces persisting synovial fluid IGF-I ligand elevations, Gene Therapy, 13:1253-1262.
Goodrich et al., 2009, Ex Vivo Serotype-Specific Transduction of Equine Joint Tissue by Self-Complementary Adeno-Associated Viral Vectors, Human Gene Therapy, 20:1697-1702.
Goodrich et al., 2015, scAAVIL-Ira dosing trial in a large animal model and validation of long-term expression with repeat administration for osteoarthritis therapy, Gene Therapy, 22(7):536-545.
Goodrich et al.. , 2013, Optimization of scAAVIL-Ira In Vitro and In Vivo to Deliver High Levels of Therapeutic Protein for Treatment of Osteoarthritis, Molecular Therapy Nucleic Acids, 5(2):e70, 10 pp.
Goossens et al., 2001, Infection Efficiency of Type 5 Adenoviral Vectors in Synovial Tissue Can Be Enhanced With a Type 16 Fiber, Arthritis & Rheumatism, 44(3):570-577.
Goossens et al., 2001, The Influence of Synovial Fluid on Adenovirus-Mediated Gene Transfer to the Synovial Tissue, Arthritis & Rheumatism,. 44(1):48-52.
Goupille et al., 2007, Is interleukin-1 a good target for therapeutic intervention in intervertebral disc degeneration: lessons from the osteoarthritic experience, Arthritis Res Ther, 9(6):110.
Grol et al., Apr. 26-29, 2018, Interleukin-1 Receptor Antagonist Gene Therapy Prevents and Delays Surgically-Induced Osteoarthritis in Small and Large Animal Models, 2018 World Congress of Osteoarthritis, 26 pp.
Harui et al., Jul. 1999, Frequency and Stability of Chromosomal Integration of Adenovirus Vectors, Journal of Virology, 73(7):6141-6146.
Horwood et al., 2002, High-efficiency gene transfer into nontransformed cells: utility for studying gene regulation and analysis of potential therapeutic targets, Arthritis Research, 4(Suppl. 3):S215-S225.
Ishihara et al., 2012, Inflammation and Immune Response of Intra-Articular Serotype 2 Adeno-Associated Virus or Adenovirus Vectors in a Large Animal Model, Arthritis, vol. 2012, Article ID: 735472, 8 pages.
Jay et al., 2007, The role of lubricin in the mechanical behavior of synovial fluid, PNAS, 104(15):6194-6199.
Jerebtsova et al., A Simple Technique to Establish a Long-Term Adenovirus Mediated Gene Transfer to the Heart of Newborn Mice, Cardiovasc Hematol Disord Drug Targets. Jun. 2009; 9(2): 136-140.
Johnson et al., Mar. 11, 2012, A stem cell-based approach to cartilage repair, Science, 336:717-721.
Kaditis et al., Mar. 14, 2007, Anti-inflammatory pharmacotherapy for wheezing in preschool children, Pediatric Pulmonology, 42(5):407-420.
Kang et al., Mar. 2017, Sirtuin 6 prevents matrix degradation through inhibition of the NF-[kappa]B pathway in intervertebral disc degeneration, Experimental Cell Research, 352(2):322-332.
Kay et al., Jul. 2009, Intra-articular gene delivery and expression of interleukin-1 Ra mediated by self-complementary adenoassociated virus, The Journal of Gene Medicine, 11:605-614.
Khoury, Jul. 2007, Inflammation-inducible anti-TNF gene expression mediated by intra-articular injection of serotype 5 adeno-associated virus reduces arthritis, The Journal of Gene Medicine, 9(7):596-604.
Kochanek, Oct. 10, 1999, High-capacity adenoviral vectors for gene transfer and somatic gene therapy, Human Gene Therapy, 10:2451-2459.
Le Maitre et al., 2007, Interleukin-1 receptor antagonist delivered directly and by gene therapy inhibits matrix degradation in the intact degenerate human intervertebral disc: an in situ zymographic and gene therapy study, Arthritis Res Ther, 9(4):R83.
Lee et al., 2017, Adenovirus-mediated gene delivery: potential applications for gene and cell-based therapies in the new era of personalized medicine, Genes & Diseases, 4:43-63.
Lee et al., Oct. 2019, No more helper adenovirus: production of gutless adenovirus (GLAd) free of adenovirus and replication-competent adenovirus (RCA) contaminants, Experimental & Molecular Medicine, S1:127 and supplementary information.
Lin et al., Jun. 16, 2003, Enhancing adenovirus-mediated gene transfer in vitro and in vivo by addition of protamine and hydrocortisone, The Journal of Gene Medicine, 5(10):868-875.
Lopez Castel et al., Mar. 2010, Repeat instability as the basis for human diseases and as a potential target for therapy, Mol. Cell Biol., 11:165-170.
Makino et al., 2001, Inhibitory PAS domain protein is a negative regulator of hypoxia-inducible gene expression, Nature, 389(6863):550-554.
Manno et al., Apr. 15, 2003, AAV-mediated factor IX gene transfer to skeletal muscle in patients with severe hemophilia B, Blood, 101(8):2963-2972.
Marcelino et al., CACP, encoding a secreted proteoglycan, is mutated in camptodactyly-arthropathy-coxa vara pericarditis syndrome, Nature Genetics, 23:319-322.
Mingozzi et al., 2007, CD8+ T-cell responses to adeno associated virus capsid in humans, Nature Medicine, 13(4):419-422.
Mitani et al., Apr. 1995, Rescue, propagation, and partial purification of a helper virus-dependent adenovirus vector, Proc. Natl. Acad. Sci. USA, 92:3854-3858.
Morral et al., 2002, Lethal Toxicity, Severe Endothelial Injury, and a Threshold Effect with High Doses of an Adenoviral Vector in Baboons, Human Gene Therapy, 13:143-154.
Muruve et al., 2004, Helper-Dependent Adenovirus Vectors Elicit Intact Innate but Attenuated Adaptive Host Immune Responses In Vivo, Journal of Virology, 78(11):5966-5972.
Nakao et al., 1997, Identification of SMAD7, a TGFbeta-inducible antagonist of TGF-beta signalling, Nature, 389(6651):631-635.
Nathwani et al., Dec. 22, 2011, Adenovirus-associated virus vector-mediated gene transfer in Hemophilia B, N. Engl. J. Med., 365(25):2357-2365.
NCT00126724 Study of Intra-articular Delivery of tgAAC94 in Inflammatory Arthritis Subjects, 11 pages, 2005.
NCT00617032 Phase 1 Dose Escalation Study of Intra-Articular Administration of tgAAC94, 8 pages, 2008.
NCT02790723 Safety of Intra-Articular Sc-rAAV2.51L-1Ra in Subjects With Moderate Knee Oa (AAVIL-1Ra), 2016.
Nixon et al., Nov. 2018, Disease-modifying osteoarthritis treatment with interleukin-1 receptor antagonist gene therapy in small and large animal models, Arthritis Rheumatol, 70(11):1757-1768.
Ogawa et al., 2013, Mechanical motion promotes expression of Prg4 in articular cartilage via multiple GREB-dependent, fluid flow shear stress-induced signaling pathways, Genes & Development, 28:127-139.

(56) References Cited

OTHER PUBLICATIONS

Oren et al., Short tandem repeats, segmental duplications, gene deletion, and genomic instability in a rapidly diversified immune gene family, BMC Genomics, 17:900-919 (2016).
Pacira Biosciences, Better is Possible. EXP22000162, PowerPoint presentation, 5 pp.
Palmer et al., 2005, Helper-Dependent Adenoviral Vectors for Gene Therapy, Human Gene Therapy, 16:1-16.
Pano et al., 2023, A scalable, suspension-based platform to produce virus-like particles (VLPs) for in vivo gene therapy, Ensoma conference poster, 1 p.
Parks et al., Nov. 1996, A helper-dependent adenovirus vector system: Removal of helper virus by Cre-mediated excision of the viral packaging signal, Proc. Natl. Acad. Sci. USA, 92:13565-13570.
Parks, 2000, Improvements in adenoviral vector technology: overcoming barriers for gene therapy, Clinical Genetics, 58:1-11.
Paul et al., Apr. 15, 2003, Potential use of Sox9 gene therapy for intervertebral degenerative disc disease, Spine, 28(8):755-763.
Paz-Gonzalez et al., 2023 An Atlas of the Knee Joint Proteins and Their Role in Osteoarthritis Defined by Literature Mining, Mol Cell Proteomics, 22(8):100606.
Pearson et al., Repeat instability: mechanisms of dynamic mutations, Genetics, 6:729-742 (Oct. 2005).
Pritzker et al., 2006, Osteoarthritis cartilage histopathology: grading and staging, Osteoarthritis and Cartilige, 14(1):13-29.
Rhee et al., 2005, The secreted glycoprotein lubricin protects cartilage surfaces and inhibits synovial cell overgrowth, The Journal of Clinical Investigation, 115(3):622-631.
Roessler et al., Mar. 1995, Inhibition of Interleukin-1-Induced Effects in Synoviocytes Trans duce d with the Human IL-1 Receptor Antagonist cDNA Using an Adenoviral Vector, Human Gene Therapy, 6:307-316.
Ross et al., Sep. 2009, Host Cell Detection of Noncoding Stuffer DNA Contained in Helper- Dependent Adenovirus Vectors Leads to Epigenetic Repression of Transgene Expression. Journal of Virology, 83(17):8409-8417.
Ruan et al., 2013, Proteoglycan 4 Expression Protects Against the Development of Osteoarthritis, Science Translational Medicine, 5(176):176ra34, 26 pp.
Ruan et al., 2016, Treatment of osteoarthritis using a helper-dependent adenoviral vector retargeted to chondrocytes, Molecular Therapy Methods & Clinical Development, 3:16008.
Ruan et al., Feb. 2013, Quantitative imaging of murine osteoarthritic cartilage by phase contrast micro-computed tomography, Arthritis Rheumatism, 65:2:388-396.
Ruan, Jan. 2013, Prevention of osteoarthritis by combination of prteoglycan 4 and interleukin 1 receptor antagonist expression, ASBMR 2013 Annual meeting, S200, https://www/asbmr.org/meetings/2013-abstracts.
Saito et al., Jun. 2010, Transcriptional regulation of endochondral ossification by HIF-2alpha during skeletal growth and osteoarthritis development, Nature Medicine, 16(6):678-687.
Sampara et al., 2018, Understanding the molecular biology of intervertebral disc degeneration and potential gene therapy strategies for regeneration: a review, Gene Therapy, 25:67-82.
Sandig et al., Feb. 1, 2000, Optimization of the helper-dependent adenovirus system for production and potency in vivo, PNAS, 97(3):1002-1007.
Santangelo et al., 2010, Detectable Reporter Gene Expression following Transduction of Adenovirus and Adeno-Associated Virus Serotype 2 Vectors within Full-Thickness Osteoarthritic and Unaffected Canine Cartilage In Vitro and Unaffected Guinea Pig Cartilage In Vivo, Journal of Orthopedic Research, 28(2):149-155.
Schmidt et al., 2009, Disulfide-bonded multimers of proteoglycan 4 (PRG4) are present in normal synovial fluids, Biochimica et Biophysica Acta, 1790:375-384.
Smith et al., Sep. 11, 1998 Secretory Interleukin-1 Receptor Antagonist Gene Expression Requires both a PU.1 and a Novel Composite NF-kB/PU.1/GA-binding Protein Binding Site, JBC, 273(37):24272-24279.
Stone et al., 2019, Combinatorial Prg4 and 11-1 ra Gene Therapy Protects Against Hyperalgesia and Cartilage Degeneration in Post-Traumatic Osteoarthritis, Human gene therapy, 30(2):225-235.
Suzuki et al., 2010, MyD88-Dependent Silencing of Transgene Expression During the Innate and Adaptive Immune Response to Helper-Dependent Adenovirus, Human Gene Therapy, 21:325-336.
Takahata et al., 2022, Regulatory Mechanisms of Prg4 and Gdf5 Expression in Articular Cartilage and Functions in Osteoarthritis, Int. J. Mol. Sci., 23:4672.
Tellez et al., 2005, Adenoviral overexpression of interleukin-1 receptor antagonist protein increases β-cell replication in rat pancreatic islets, Gene Therapy, 12:120-128.
Toh et al., 2005, Enhancement of Adenovirus-Mediated Gene Delivery to Rheumatoid Arthritis Synoviocytes and Synovium by Fiber Modifications: Role of Arginine-Glycine-Aspartic Acid (RGD)- and Non-RGD-Binding Integrins, Journal of Immunology, 175(11):7687-7698.
Ulrich-Vintner et al., 2004, In vivo gene delivery to articular chondrocytes mediated by an adeno- associated virus vector, Journal of Orthopedic Research, 22:726-734.
Vetrini et al., 2010,, Gene Therapy with Helper-Dependent Adenoviral Vectors: Current Advances and Future Perspectives. Viruses 2:1886-1917.
Wang et al., 2006, Adenovirus expressing niterleukin-1 receptor antagonist alleviates allergic airway inflammation in a murine model of asthma, Gene Therapy, 13:1414-1421.
White et al., 2007, Gene therapy for hemophilia A, Textbook of Hemophilia, Chapter 39, 4 pp.
Willet et al., 2013, Immunology of AAV-mediated gene transfer in the eye, Frontiers in Immunology, 4(Article 261), 8 pp.
Xie et al., Sep. 29, 2020, Sirtuin 6: A potential therapeutic target for cardiovascular diseases, Pharmacological Research, 163(105214), 10 pp.
Yang et al., 1997, Overexpression of interleukin-1 receptor antagonist in the mouse brain reduces ischemic brain injury, Brain Research, 751:181-188.
Yeh et a., 1997, Advances in adenoviral vectors: from genetic engineering to their biology, FASEB Journal, 11(8):615-623.

* cited by examiner

LITR — nfkb — eqIl-1Ra — RITR

HDAd-mIl-1Ra

LITR — nfkb — mIl-1Ra — RITR

HDAd-huIL-1Ra

LITR — nfkb — huIl-1Ra — RITR

Group 1 HDAd-GFP

Group 4 AAV6-GFP

Ad-luc x10$^6$ 5 4 3 2 1

HDAd-luc
Ad-luc
Total flux (luciferase bioluminescence imaging)
1.00E+08
1.00E+07
1.00E+06
1.00E+05
1.00E+04
1.00E+03
1.00E+02
1.00E+01
1.00E+00
0
50
100
150
200
250
300
350
400
Days

10^9
S
C
C

10^8
S
S
C
C osteoarthritis score
6
5
4
3
2
1
*
*
HDAd-Il-1Ra
HDAd-GFP
mock

OARSI score
12
10
8
6
4
2
0
*
Group 3 Vehicle
Group 2 HDAd-GFP
Group 1 HDAd-mIL-1Ra Synovitis score
3
2
1
0
Group 3 Vehicle
Group 2 HDAd-GFP
Group 1 HDAd-mIL-1Ra % osteophytes
60
40
20
0
Group 3 Vehicle
Group 2 HDAd-GFP
Group 1 HDAd-mIL-1Ra CARTILAGE VOLUME
mm3
0.35
0.3
0.25
0.2
0.15
0.1
0.05
0
*
*
HDAd-mIl-1Ra
HDAd-GFP
mock
untransected CARTILAGE SURFACE AREA
mm3
25
20
15
10
5
0
*
*
HDAd-mIl-1Ra
HDAd-GFP
mock
untransected Structural Change
Total Score
25
20
15
10
5
0
Sham Untreated
ACLT Vehicle
ACLT 3 x 10^7
ACLT 2.4 x 10^8
VP/dose SOFG Staining Loss
Total Score
16
14
12
10
8
6
4
2
0
Sham
Untreated
ACLT
Vehicle
ACLT
3 x 10^7
ACLT
2.4 x 10^8
VP/dose Equine IL-1Ra [ng/mL]
200
180
160
140
120
100
80
60
40
20
0
1
2
3
4
Days
1A. GQ-201 100 VP/cell
1B. GQ-201 100 VP/cell + LPS
2A. GQ-201 1,000 VP/cell
2B. GQ-201 1,000 VP/cell + LPS
3A. HDAd-GFP 100 VP/cell
3B. HDAd-GFP 100 VP/cell + LPS
4A. HDAd-GFP 1,--- VP/cell
1B. HDAd-GFP 1,000 VP/cell + LPS
5A. Vehicle
5B. Vehicle + LPS

FIG. 16

GQ-201 low dose
GQ-201 high dose
placebo

Score
3
2.5
2
1.5
1
0.5
0

*
*
*
*
*
*

Lameness
Range of motion limitations
Flexion
Effusion

GQ-201 low dose
GQ-201 high dose
placebo
sham
Score
0
0.5
1
1.5
2
2.5
3
3.5
4
CI
CR
C3IF
C3RF
Score
0
1
2
3
4
5
6
7
Total fibrillation score

FIG. 18

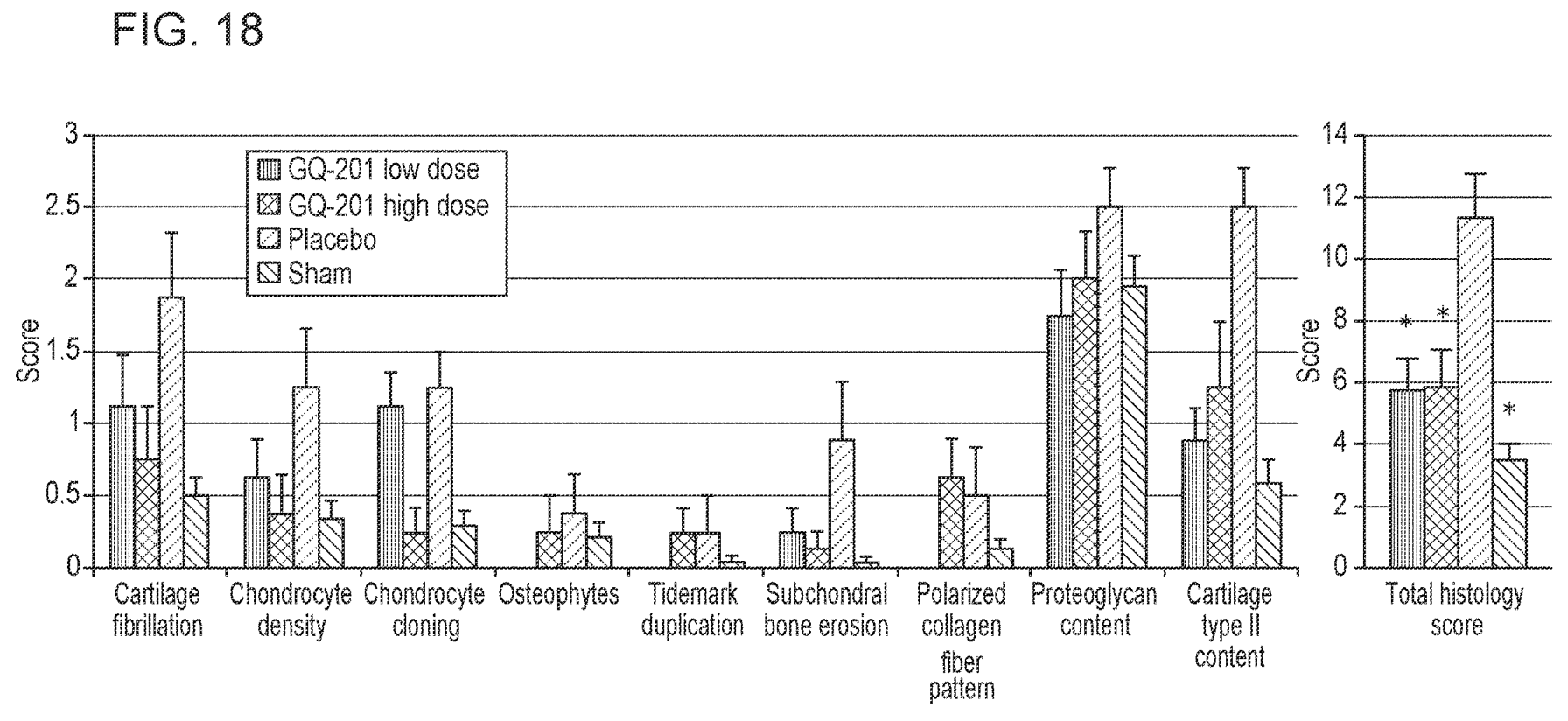

GQ-201 low dose
GQ-201 high dose
Placebo
Sham

Score
0
0.5
1
1.5
2
2.5
3

Cartilage fibrillation
Chondrocyte density
Chondrocyte cloning
Osteophytes
Tidemark duplication
Subchondral bone erosion
Polarized collagen fiber pattern
Proteoglycan content
Cartilage type II content Score
0
2
4
6
8
10
12
14

Total histology score

*
*
*

Viability (%)
100
80
60
40
20
0
P1 P2 P3 P4 P5 Infection
Tox (Human) Tox (Rat) ENG GMP Tox (Human)
Tox (Rat)
ENG
GMP
180
160
140
120
100
80
60
40
20
0
Pre-Purification Batch Productivity
Post-Purification Batch Yield
Post-Purification % Yield

FIG. 21

Tox (Human) Tox (Rat) ENG GMP 750
700
200
150
100
50

Infectivity ($TCID_{50}$)

Genome Copies to Infectious Ratio

IL-1Ra Expression

SEQUENCE LISTING

```
<160> NUMBER OF SEQ ID NOS: 7

<210> SEQ ID NO 1
<211> LENGTH: 535
<212> TYPE: DNA
<213> ORGANISM: Artificial Sequence
<220> FEATURE:
<223> OTHER INFORMATION: murine Il-1Ra

<400> SEQUENCE: 1
```

atggaaatct gctggggacc ctacagtcac ctaatctctc tccttctcat ccttctgttt 60
cattcagagg cagcctgccg cccttctggg aaaagaccct gcaagatgca agccttcaga 120
atctgggata ctaaccagaa gaccttttac ctgagaaaca accagctcat tgctgggtac 180
ttacaaggac caaatatcaa actagaagaa aagatagaca tggtgcctat tgaccttcat 240
agtgtgttct tgggcatcca cgggggcaag ctgtgcctgt cttgtgccaa gtctggagat 300
gatatcaagc tccagctgga ggaagttaac atcactgatc tgagcaagaa caaagaagaa 360
gacaagcgct ttaccttcat ccgctctgag aaaggcccca ccaccagctt tgagtcagct 420
gcctgtccag gatggttcct ctgcacaaca ctagaggctg accgtcctgt gagcctcacc 480
aacacaccgg aagagcccct tatagtcacg aagttctact tccaggaaga ccaat 535

<210> SEQ ID NO 2
<211> LENGTH: 29612
<212> TYPE: DNA
<213> ORGANISM: Artificial Sequence
<220> FEATURE:
<223> OTHER INFORMATION: helper-dependent adenoviral vector-murine Il-1Ra gene

<400> SEQUENCE: 2
aaacatcatc aataatatac cttattttgg attgaagcca atatgataat gaggggtgg 60 agtttgtgac gtggcgcggg gcgtgggaac ggggcgggtg acgtagtagt gtggcggaag 120
tgtgatgttg caagtgtggc ggaacacatg taagcgacgg atgtggcaaa agtgacgttt 180
ttggtgtgcg ccggtgtaca caggaagtga caattttcgc gcggttttag gcggatgttg 240
tagtaaattt gggcgtaacc gagtaagatt tggccatttt cgcgggaaaa ctgaataaga 300
ggaagtgaaa tctgaataat tttgtgttac tcatagcgcg taatatttgt ctagggccgc 360
ggggactttg accgtttacg tggagactcg cccaggtgtt tttctcaggt gttttccgcg 420
ttccgggtca aagttggcgt tttgatatca agcttatcga taccgtaaac aagtctttaa 480
ttcaagcaag actttaacaa gttaaaagga gcttatgggt aggaagtagt gttatgatgt 540
atgggcataa agggttttaa tgggatagtg aaaatgtcta taataatact taaatggctg 600
cccaatcacc tacaggattg atgtaaacat ggaaaaggtc aaaaacttgg gtcactaaaa 660
tagatgatta atggagagga tgaggttgat agttaaatgt agataagtgg tcttattctc 720
aataaaaatg tgaacataag gcgagtttct acaaagatgg acaggactca ttcatgaaac 780
agcaaaaact ggacatttgt tctaatcttt gaagagtatg aaaaattcct attttaaagg 840
taaaacagta actcacagga aataccaacc caacataaaa tcagaaacaa tagtctaaag 900
taataaaaat caaacgtttg cacgatcaaa ttatgaatga aattcactac taaaattcac 960
actgattttg tttcatccac agtgtcaatg ttgtgatgca tttcaattgt gtgacacagg 1020
cagactgtgg atcaaaagtg gtttctggtg cgacttactc tcttgagtat acctgcagtc 1080
ccctttctta agtgtgttaa aaaaaaaggg ggatttcttc aattcgccaa tactctagct 1140
ctccatgtgc tttctaggaa acaagtgtta acccacctta tttgtcaaac ctagctccaa 1200
aggacttttg actccccaca aaccgatgta gctcaagaga gggtatctgt caccagtatg 1260
tatagtgaaa aaagtatccc aagtcccaac agcaattcct aaaaggagtt tatttaaaaa 1320
accacacaca cctgtaaaat aagtatatat cctccaaggt gactagtttt aaaaaaacag 1380
tattggcttt gatgtaaagt actagtgaat atgttagaaa aatctcactg taaccaagtg 1440
aaatgaaagc aagtatggtt tgcagagatt caaagaaaat ataagaaaac ctactgttgc 1500

```
cactaaaaag aatcatatat taaatatact cacacaatag ctcttcagtc tgataaaatc   1560
tacagtcata ggaatggatc tatcactatt tctattcagt gctttgatgt aatccagcag   1620
gtcagcaaag aatttatagc ccccttgag cacacagagg gctacaatgt gatggcctcc   1680
catctccttc atcacatctc gagcaagacg ttcagtccta cagaaataaa atcaggaatt   1740
taatagaaag tttcatacat taaactttat aacaaacacc tcttagtcat taaacttcca   1800
caccaacctg ggcaatatag tgagacccca tgcctgcaaa aaaaaaaaaa ttagccaggc   1860
atggtagcat gtacctgtag tcccagctac ttgagaggtg aggtgggaaa atcactttag   1920
tgcaggatgt tgaggctgga gtgaactgtg attgtgccac tgcactccag cctggacaat   1980
agagcaagac cttgtctcaa aaaaatgcat taaaaatttt ttttaaatct tccacgtatc   2040
acatcctttg ccctcatgtt tcataaggta aaaaatttga taccttcaaa aaaaccaagc   2100
ataccactat cataattttt tttaaatgca aataaaaaca agataccatt ttcacctatc   2160
agactggcag gttctgatta aatgaaattt tctggataat atacaatatt aagagagact   2220
gtagaaactg ggccagtggc tcatgcctgt aatcccagca ctttgggagg ctgggtaaca   2280
tggcgaaccc tgtttctaca aaataaaaat attagctggg agtggtggcg cacacctata   2340
gtcccagcta ctcaggaggc tgaggtggaa ggatcgcttg aacccaggag gttgagactg   2400
cagtgaactg tgatcattct gctgcactgc accccagcct gggcaacaga gaccttgtct   2460
caaaaaaaaa aaaaaaagag acaaattgtg aagagaaagg tactctcata taacatcagg   2520
agtataaaat gattcaactt cttagaggaa aatttggcaa taccaaaata ttcaataaac   2580
tctttcccct tgacccagaa attccacttg aataaagctg aacaagtacc aaacatgtaa   2640
aagaatgttt cttctagtac agtcggtaag aacaaaatag tgtctatcaa tagtggactg   2700
gttaaatcag ttatggtatc tccataagac agaatgctat gcaaccttta aaatatatta   2760
gatagctcta gacacactaa tattaaaagt gtccaataac atttaaaact atactcatac   2820
gttaaaatat aaatgtatat atgtactttt gcatatagta tacatgcata ggccagtgct   2880
tgagaagaaa tgtgtacaga aggctgaaag gagagaactt tagtcttctt gtttatggcc   2940
tccatagtta gaatatttta taacacaaat attttgatat tataatttta aaataaaaac   3000
acagaatagc cagacataca atgcaagcat tcaataccag gtaaggtttt tcactgtaat   3060
tgacttaaca gaaaattttc aagctagatg tgcataataa taaaaatctg accttgcctt   3120
catgtgattc agccccagtc cattaccctg tttaggactg agaaatgcaa gactctggct   3180
agagttcctt cttccatctc ccttcaatgt ttactttgtt ctggtcccta cagagtccca   3240
ctataccaca actgatacta agtaattagt aaggccctcc tcttttattt ttaataaaga   3300
agattttaga aagcatcagt tatttaataa gttggcctag tttatgttca aatagcaagt   3360
actcagaaca gctgctgatg tttgaaatta acacaagaaa aagtaaaaaa cctcatttta   3420
agatcttact tacctgtcca taattagtcc atgaggaata aacacccttt ccaaatcctc   3480
agcataatga ttaggtatgc aaaataaatc aaggtcataa cctggttcat catcactaat   3540
ctgaaaaaga aatatagctg tttcaatgag agcattacag gatacaaaca tttgattgga   3600
ttaagatgtt aaaaaataac cttagtctat cagagaaatt taggtgtaag atgatattag   3660
taactgttaa ctttgtaggt atgataatga attatgtaag aaaacaacag gccgggcggg   3720
ttggttcaca cgtgtaatcc cagcactttg ggaggctgag gcaggcagac tgcctgagct   3780
caggagttcg agaccagcct gggcaacacg gtgaaatccc gtctctacta aaaatacaaa   3840
```

```
aaaattagcc gggtgtggtg acacatgcct gtagtcccag ctacttggga ggctgaggca   3900
ggagaatcac ttgaacctgg gaggtgaagg ttgcagtgag ccaagatggc accacttcac   3960
tccagcctgg gaaacagagc aagactctgt ctctgagctg agatggcacc acttcactcc   4020
agcctgggaa acagagcaag actctgtctc aaaaaaaaca aaacacacaa acaaaaaaac   4080
aggctgggcg cggtggctca cgcctgtaat cccagcactt tgggaggccg aggcgggtgg   4140
atcacctgag gtcaggagtt ccagaccagc cttgtcaaca tggtgaaacc tccccccgcc   4200
gtctctacta aaaatacaaa aattagccag gcgtggtggc aggagcctgt aatcccagct   4260
acttgggagg ctgaggcagg agaatcgctt gtacccagaa ggcagaggtt gcactgagct   4320
gagatggcac cattgcactc cagcctgggg gacaagagcg agatttcgtc tttaaaaaac   4380
aaaaacaaaa caaaaaacca tgtaactata tgtcttagtc atcttagtca agaatgtaga   4440
agtaaagtga taagatatgg aatttccttt aggtcacaaa gagaaaaaga aaaattttaa   4500
agagctaaga caaacgcagc aaaatcttta tatttaataa tattctaaac atgggtgatg   4560
aacatacggg tattcattat actattctct ccacttttga gtatgtttga aaatttagta   4620
aaacaagttt taacacactg tagtctaaca agataaaata tcacactgaa caggaaaaac   4680
tggcatggtg tggtggctca cacttgtaat cccagtgctt tgggaggctg agacaggaga   4740
gttgcttgag gccaggagtt caagaccgac atggggaatg tagcaagacc ccgtccctac   4800
aaaaaacttt gtaaaaattt gccaggtatg gtggtgcata cctgtagtcc cagctactcg   4860
ggaggcggag gcagaaggaa tcacttgagc ccaggagttt gaggctgcag tgagctacga   4920
tcataccaca gcactccagc gtggacaaca gagtaagacc ctatctcaaa aacaaaacaa   4980
aacaaaacaa acaaaaaaaa ccacaagaaa aactgctggc tgatgcagcg gctcatgcct   5040
gtaatcccag tattttggga ggcccaggtg ggcgtatcac ctgaggtcag gagttagaga   5100
ccagcctggc caacatggtg aaaccccatc tctactaaaa atacaaaatt agccaggcat   5160
gtggcacgcg cctgtagtcc cagttactgg gaggctgaag caggaggatc acctgagccc   5220
gggaggtgga ggttgcagtg agccgagatc acaccactgc actccagcct gggtgacaca   5280
gcaataccct acctcaaaat aaaaaagaaa aagaaaagaa aagttgctgt ccccgctacc   5340
ccaatcccaa atccaaacag cctctctcat ctcacagtaa gggggaaaaa tcacccaaaa   5400
aagctaagtg atcttttgaa aacccaaact cttagaagtc taagattatt atagtcaact   5460
catgaagtgt catcataaaa gatactctaa tattatttaa gtagaaccac atattggttg   5520
tcttggtatg tctagcccct ggcatacaaa atatttaata acactgatat ggtacctgtg   5580
atgtgaaaat gtactatgag tacagcttta taaatactat atatgtacct atatacagaa   5640
aaaaatacaa caaaatcata aaagcactta tctttgaaag aggagttaca gcaattttat   5700
ttagttcttt attgctttgc tatatattct aaattttttt caatgaatat atatcacttt   5760
taaaaaaatt caatggtctt tcttataaat tatctttggc agcatgcgtt tttatatata   5820
catataaaat gtatgggaaa tttttaaagg atacattaaa ttaaagcaaa atatacaaac   5880
aaaaaatcag aatacaaaaa gataaaaaga ttgggaaggg agggagggag taaggaggaa   5940
gggtgggtgg gtatagagaa atataccaaa taatggtaag aagtggggtc ttgacacttt   6000
ctacactttt tttaaataaa aaaaattttt ttctctctct tttttttttt tagagacgaa   6060
gtctcgctat gttgcccagg ctggtcttga actcctggga tcaagagatc ctcctgcctc   6120
agcctcccaa ggtgcttgga ttacaggtgt gagccaccac gcctggtcac tttctacact   6180
ttaatatata tattttttca ttttcaatgt catttttatt agttaattta taatacccat   6240
```

```
tcaccattat attcaaagtc tatttgaaga aataaaccag aaagaatgaa atactctagc   6300
tcacatgcta ttcaatacta aattaccttt caaatcacat tcaagaagct gatgatttaa   6360
gctttggcgg tttccaataa atattggtca aaccataatt aaatctcaat atatcagtta   6420
gtacctattg agcatctcct tttacaacct aagcattgta ttaggtgctt aaatacaagc   6480
agcttgactt ttaatacatt taaaaataca tatttaagac ttaaaatctt atttatggaa   6540
ttcagttata ttttgaggtt tccagtgctg agaaatttga ggtttgtgct gtctttcagt   6600
ccccaaagct cagttctgag ttctcagact ttggtggaac ttcatgtatt gtcaggttgg   6660
cccgtaatac ctgtgggaca acttcagccc ctgtgcacat ggccaggagg ctggttgcaa   6720
acattttcag gtaggtggac caggacatgc ccctggtcat ggccaggtgg aggcatagtg   6780
ctatacagca ggcagaagtc aatattgatt tgtttttaaa gaaacatgta ctactttcat   6840
aagcagaaaa aatttctatt cttgggggaa aagattatgc cagatcctct aggattaaat   6900
gctgatgcat ctgctaaacc ttcacatatc agaacatatt tactatagaa agaatgaaaa   6960
tgggacattt gtgtgtcacc tatgtgaaca ttccaaaaat attttacaac aactaagtat   7020
tttataaatt ttatgaactg aaatttagtt caagttctag gaaaatacaa accttgctag   7080
atattataaa aatgatacaa tatatattca tttcaggctc atcagaatat atctgttatc   7140
acttgacaag aatgaaaatg caccattttg tagtgcttta aaatcaggaa gatccagagt   7200
actaaaaatg acttcttcct tgaagcttac tcaccaactt cctcccagtt actcactgct   7260
tctgccacaa gcataaacta ggacccagcc agaactccct tgaaatatac acttgcaacg   7320
attactgcat ctatcaaaat ggttcagtgc ctggctacag gttctgcaga tcgactaaga   7380
atttgaaaag tcttgtttat ttcaaaggaa gcccatgtga attctgccca gagttcatcc   7440
cagatatgca gtctaagaat acagacagat cagcagagat gtattctaaa acaggaattc   7500
tggcaatata acaaattgat ttccaatcaa aacagattta cataccatac ttatgtcaag   7560
aagttgtttt gttttattgc atcctagatt ttattttttt gatttatggt ttactttaag   7620
cataaaaaat ttgtcaatac aactcttccc aaaaggcata aacaaaaatt cataaaactt   7680
gcatcacttg agatacttca ggtatgaatt cacaactttg ttacaactta ctatatatat   7740
gcacacatat atatatattt gggtatattg ggggggttct aatttaagaa atgcataatt   7800
ggctatagac agacagttgt cagaacttgg caatgggtac gtgcaggttc attataccaa   7860
gtctacttgt agttgttcaa aatgtatcat aatacaaggc cgggcgaggt cgtcacgcct   7920
gtaatcccag cattttggga ggctaaggca ggaggattgc ttgaggtcag gagtttgtga   7980
ccagcctggg caacagagca agaccctgtc tccaaaaaga aaaaaaataa tttttttacaa   8040
aataaaaaca aaatgtatca tcagacgaaa ttaaataaga ggcaattcat ttaaatgaca   8100
acttttccca gcttgacatt taacaaaaag tctaagtcct cttaattcat atttaatgat   8160
caaatatcaa atactaattt tttttttttt ttttttttg agacggagtc tcgctctgtc   8220
gcccaggctg gagtgcagtg gcgcgatcct ggctcactgc aagctccgcc tcccgggttc   8280
acgccattct cctgcctcag cctcccgagt agctgggatt acagacatgc gccaccacgc   8340
ccggctaatt ttgtattttt agtagagatg gggtttctcc atgttggtca ggctggtctt   8400
gaatttccca cctcaggtga tctgcctgcc tcagcctcac aaagcagtag ctgggactac   8460
aggcacccac caccacactt ggttaattct tttgtatttt ttttgtaaag acgggatttc   8520
accatgttag ccaggatggt ctcgatctcc tgatctcatg atccgcccgc ctcagcctcc   8580
```

-continued

```
caaagtgctg ggattacagg cgtgagccac cccgcccggc catcaaatac taattcttaa   8640
atggtaagga cccactattc agaacctgta tccttatcac taatatgcaa atatttattg   8700
aatacttact atgtcatgca tactagagag agttagataa atttgataca gctaccctca   8760
cagaacttac agtgtaatag atggcatgac atgtacatga gtaactgtga acagtgttaa   8820
attgctattt aaaaaaaaag acggctgggc gctgtggctc atgcctgtaa tcccagcact   8880
ttgggaggcc aaggcaagtt gatcgctcga ggtcaagagt tcgagaccag cctggccaac   8940
gtggtaaaac cccgtctcta ctaaaaatac aaaaaaaaaa ttagccaggc atggtggcac   9000
aggcctgtaa tcccagctac tagggaggct gagacatgga gaactgcttg aatccaggag   9060
gcagaggtta cagtgagccg agatcatacc actacactcc agcctgagtg acagagcgag   9120
actcctgtct aaaaaaaaaa aaaaaaaaaa agatacaggt taagtgttat ggtagttgaa   9180
gagagaactc aaactctgtc tcagaagcct cacttgcatg tggaccactg atatgaaata   9240
atataaatag gtataattca ataaatagga acttcagttt taatcatccc aaacaccaaa   9300
acttcctatc aaacaggtcc aataaactca atctctataa gagctagaca gaaatctact   9360
tggtggccta taatcttatt agcccttact tgtcccatct gatattaatt aaccccatct   9420
aatatggatt agttaacaat ccagtggctg ctttgacagg aacagttgga gagagttggg   9480
gattgcaaca tattcaatta tacaaaaatg cattcagcat ctaccttgat taaggcagtg   9540
tgcaacagaa tttgcaggag agtaaaagaa tgattataaa tttacaaccc ttaaagagct   9600
atagctgggc gtggtggctc atgcctgtaa atcccagcac tttgggaggc tgaggcgggt   9660
ggatcacctg aggccagaag ttcaagacca gcctagccaa catggcgaaa ccctgtctct   9720
acaaaaaata caaaaattag ccgggtgtgg tggcacgtgc ctgtagtccc agttacttgg   9780
gaggccgagg caggagaatc gcttgaacct aggaggtgga ggctgcagtg agccgagatt   9840
gtgccactgc actccacttc agcctgggcg acaagagcaa gactccgtca caaaaaaaaa   9900
aaaaaaaaaa aagcttaaaa tctagtggga aaggcatata tacatacaac taactgtata   9960
gcataataaa gctcataatc tgtaacaaaa tctaattcga caagcccaga aacttgtgat  10020
ttaccaaaaa cagttatata tacacaaaaa gtaaacctag aacccaaagt tacccagcac  10080
caatgattct ctccctaagc agtatcaagt ttaaagcagt gattacattc tactgcctag  10140
attgtaaact gagtaaagga gaccagcacc tttctgctac tgaactagca cagccgtgta  10200
aaccaacaag gcaatggcag tgcccaactt tctgtatgaa tataagttac atctgtttta  10260
ttatttgtga cttggtgttg catgtggtta ttatcaacac cttctgaaag aacaactacc  10320
tgctcaggct gccataacaa aataccacag actgagtgac ttaacagaaa cttatttctc  10380
acagttttgg aggctgggaa gtccaaaatt aaggtacctg caaggtaggt ttcaatctca  10440
ggcctcttct ttggcttgaa ggtcttctaa ctgtgtgctc acatgacctc ttctaacaag  10500
ctctctggtg tctctttttt tttttttttc ttttttgaga cagagtctca ctctgtcacc  10560
caggctggag tacagtggca caatctgggc tcactgcaac ctccaactcc cgggttcaag  10620
tgattctcat gcctcaccct cccgagtagc ttggatgaca ggagcccgct accacaccca  10680
gctaattttt gtatttttag tagagatggt gtttcactac attggccagg ctggtctcaa  10740
actcctgacc tcgtgatcca cccaccttgg cctcccaaag tgctgggatt acaggtgtga  10800
gccactgcgc ccgtcctggt gtcttttcat ataagggcac taatccaatc agacctgggc  10860
ccaaccctcc cgacttcttc taactgtaat taccttccaa aggccctgtc tccaaatacc  10920
atcacactgg gggttaggac ttcaaaaaag gtatgggggg ggtgtgggag gacataaatg  10980
```

```
ctcagtccat aacaagcacc caacataaaa atggctagaa cagatcacaa aaaaaaggtc  11040
ctgtatggct ttggggaagg gctcaacccc aaaatatctg agagctctgg aggggcctag  11100
aagtggtaaa tgaatgaaaa cgtggttact ctccagatct gcctttccca aatatggcca  11160
ttcttggctg aatcagaaat caaaggacag gttattaatt actagctcta agttacttac  11220
catttgctga gacagttcag aaatctgact gcatctcctc agagatctag aacacagttc  11280
tcaaattcta acttacttgt gatatacttg tgaatgataa aaatcgctac aggtactttt  11340
attaatctga aagagtattg agaaattacc tttcattctg acttttgtct ggaatgaaaa  11400
tcaatacttt tgctataatc gattactgaa ataattttac tttccagtaa aactggcatt  11460
ataatttttt ttaattttta aaacttcata attttttgcc agactgaccc atgtaaacat  11520
acaaattact aataattatg cacgtcacat ctgtaataat ggccttcatg taaacatttt  11580
tgtggtttac acataaaatc tctaattaca aagctatatt atctaaaatt acagtaagca  11640
agaaaattaa tccaagctaa gacaatactt gcaacatcaa ttcatcatct gtgacaagga  11700
ctgcttaagt ctctttgtgg ttaaaaagga aaaaaaaaaa aaagacatgt tggccagatg  11760
cggtggctca cacctgtaat cccagcactt tgggaggctg aggtgggcgg atcacccctg  11820
gcctgcccaa catggtgaaa ccccgtctct actaaaaaca caaaaattag ctgggcgtgg  11880
tggcgggcgc ctgtaattcc agctactcgg gaggctgagg caggagaatt gctagaaccc  11940
aggaggcaga gattgcagtg agctgagatt gcaccattgc actacagtct gggcaacaaa  12000
agtgaaactc catcttaaaa aaaaaaagac aatgttcgtg ggtccaaaca agacttaatg  12060
gaagtgagtc taaaaatgag ctatgtgggc caggcgtagt ggctcccacc tgtaatccca  12120
gcactttggg aggccgaagc aggcagatca tgaggtcagg agatggagac catcctggcc  12180
aacacggtga aatcctgtct ctacaaaaat tagctgggcg tggtggtgcc tgcctgtaat  12240
cccagctact cagaaggctc aggcaggaga atcgcttgaa ccagggagtc ggtggctaga  12300
gtgagccgag atttgcatca ctgcactcct gcctggtgac agagcaagac tccatctcaa  12360
aaaaaacaaa caaaaataaa agataaaaat gagctatgtg aattaaaaga ggtataacaa  12420
tagataaacc atattttatt taattcctag taatgagtaa tatttccaaa cttctggaat  12480
gggcagaaat tgctagttgg catattttta cctttttatat tcagatacat taaaattctc  12540
aaaaaaaaac acctcaaagc agatgatccg ccatctcctt ggataatttg tgttaactca  12600
ggataacaga aaaccaaaat tatgagttac tgatgcaata ttcctaaatg taaaaataat  12660
taaagctaat agtagattca tcttccaatt tcatatcagt cttacaaata aactacatat  12720
ataacttgct tgccttccct tctgagggat aaagctgtta gaagaattaa aatcagcatt  12780
cttgactatt caaccaaggg agggataaat tattactcat tctagggaca tgggctcata  12840
actactacat gtgtaaggac atgaatttac ccaatattac aatttttcct tttattagtg  12900
tgtacagtgg aagaatagac atgttcactc tggacaaaaa aaaaattata cttatcagtt  12960
atcagaagca caatgctgaa gacagtagtt ccataacaat ttgaagtatg tgatcgaact  13020
agtagattat cttagtagta gtgaattatt gtaaatgtta gtaatttggc agccactggg  13080
cagaaaaata agaattgagg ctcaatattg atattaatgg tggtgattga cacataaatt  13140
ttatcaagtc tacacaatat aaaattacag aaaggtagaa gagtatacca gtacaacttc  13200
aacatatctt cactacaagg gagtaaaatg acatggccta gttactatct aatgaactgc  13260
agaaaactaa aagaaaactc caaggcaact cttctctgct gatctggttg gtccttttcc  13320
```

-continued

```
taccttttgc aatacccaga tacaaacaat ggatagaaaa caaagtagac ttgtagtatg  13380
caggtcacag tgctaaattc acagaaagaa acccctgaac tgaactgctc tatttcctgg  13440
tggtcacaaa gagtaattct ggtttacacc tacagattga tgtcaatcta caccctgttg  13500
ataacagtgt ggccaaggac aaaaaaaagg tgctccgttt taccaattct gtaaaaaatt  13560
attggcaggg taagctcggc tagggcagga ttacatttct aggactacca tccccgaaat  13620
ttagaagata ttatatccac ataaagcata tctttcacat taatttgcaa aaatctaaaa  13680
gctttttctt agctcaagtg tgtccaagtt taccctggca gtttaaaacg atagttacaa  13740
gcagcatggg ttgtatcaga cacatttgag ggccaatttc atgtaagtga tattgggcaa  13800
gttacttcaa ctatctgtgc ctccaaggtc atactagtgt ttatttacct aaagggtacc  13860
tgttatgtaa ctttagggtg tttacattag ataatgcctg caaaatattt acttcaacgc  13920
ctaaaacata gttaagtatt caataaatac ctactattgt cactactaac ttaaaagttt  13980
agagattaag agcagaatct ggggtgagac aaacttaggt tcaaatccta gtattgttgg  14040
gtaatcttgg gcaagttact taacctctct gatttgtgta atttaaaaaa ttagttaata  14100
tacataacag ggcttagaag agtatctagc acatagcacc atttaagcat ttgttattgc  14160
taacatgcaa acaatttaag ggaaagaaat tttttaaaaa ggaagaggga tttgcaaact  14220
aaaaacaatg agtatcttat gttcaaagaa aactaacaaa cagccagctc tagcaataat  14280
taaattcact atatactggg gcaggcatca caccccaaag ctaaaagcgt ctacctaggc  14340
caggcacggt ggctcatgcc tgtaatccca gcactttggg aagcagaggc gggcagatcg  14400
cttgagctca ggagttcaag accagcctgg acaacatggc aaaacaccat ctctacaaaa  14460
aatacaaata ttaggccggg cgcagtggct cacgcctgta atcccagcac tttgggaggc  14520
caaggcgggt ggatcacctg agatcaggag ttcgagagta gcctggccaa catggtgaaa  14580
cctcgtctct attaaaaata caaaaaatta gccaggcatg gtggcaggcg cctgtaatcc  14640
cagctactca gggggatgag gtaggagaat cgcttgaacc cgggaggcag aggttgcact  14700
gagccgagat catgccactg tactccagcc cgggcaacaa gagcgaaact ccatctcaaa  14760
aaataaataa ataaataaat aaaataaagt acaaatatta gccagggatg gtggtgcgca  14820
cctgtagtcc cagctacttg ggaggctgaa gtgggagaat cccctgagcc tggggagaat  14880
cacccgagcc cgggaagtcg aggctgcagt gagcagtgat tgtgccactg cactccatcc  14940
taggtgacag agtgagaccc tgtctcaaaa aaaagaaatt ggcagaatta agtaagttga  15000
tgtttagaga tgaaaaatca acattttttc ctcagcaact gaataaaaac aacagccact  15060
accatttttt tgagtaccta tttgtagcct attttttaac tggtattact cgagagagag  15120
agagctaggt tcgagacaga gctccttctc ttaataactg tatgacctag ggtatgtctg  15180
ttagcctctc tgaggcttca aaggttcctc atctgtaaaa tggtaataat cataccattg  15240
ctacagggct gttttgaaga ctaattagga ctatgtaagt aaacatgatg atggctatta  15300
ttactgttcc ccgccagggg ccatgcaagg gttgctgatt cacatagact gtcttataat  15360
cctctcaata actccaagag gtagccagca cctcagatat acataaaatg acttaagccc  15420
agagaggtga agtaagttgc ccacagccac acaactagta aatagcccaa acaagctgga  15480
ttcccagtta gactccgtta atagcactgc tctttacctt aagtcattac aatgcctaat  15540
atgaaataga atcgcttctt tcttagggtt caagtggtta attatttaat gtattcattc  15600
aacaaaccat catcgaggac ctcttacaag ccaagtactg tgctaagtgc tagagttacg  15660
gcggtgattc ctgcccttaa aaagttttag tgggagaaac aacaggtaac caggtcattg  15720
```

```
ccaaaacaac aaaaataatc ataataaagc aggctaaagc atatttaact ggccggggtt  15780
ttgactattt tagcaagcat gatcagaacg gttgaggagg gaggccagca gcttggccgg  15840
ttcaacaaac aagaaaaaac cagtgagggt ggagctaaga taccagaggc tgattacggt  15900
taagaatgtt cttgaaggta aggaccagat tctcattttc tatatcctgg ggcatcggtc  15960
agcatggaat ctggattcta gcacatgtga atttcggctt gaaatgacct aatgcctttt  16020
ccctagttcc ttcgtgtgtc aaatacgcat ggttaccgct accagagctg tagtggggct  16080
tcaatgaggc catgagcatc tccataaaga tgaactacag tgtgtgcaaa actaaaggca  16140
aaacctggtc cccacacgcc ctcccaggtg gtcgctttcc gtgccgaggc ccctccagag  16200
gtgccccgag aacctcacca tcgcacccca aacttccagg gaagggcctc tcccgagaaa  16260
gcccccacgc ccccaccccg cgccatcatt cccgaatctg ccctcggccc ctccccgcag  16320
cacgctcgca ggcggcacat gtcaaccaaa acgccatttc caccttctct tcccacacgc  16380
agtcctcttt tcccagggct cccccgagga gggacccacc ccaaaccccg ccattccgtc  16440
ctccctgccg ccctcgcgtg acgtaaagcc gaacccggga aactggccgc ccccgcctgc  16500
ggggttccct gggcccggcc gctctagaac tagtggatcc caattgaagg cctggtctaa  16560
atgactccaa aatcaccact taattcaaga gactgatttc cctgagtcag gccccttaaa  16620
gcagctattt caatgggaca gggaaacaac cctaggatct ggattagaat cacttggggg  16680
ctgccacacc cccagggctc tgatcctgcc cttctcccac acgcacattc acatactgct  16740
gcagtgacct tccatttcta atgggttcct gggccatctg tcaggtatag ggaatggaaa  16800
aggggttggg gaggctctgc ttcagaaagt ttgtgtcagg ggctcccaga gcctccacag  16860
atagatagca ggggtcccca ccctaccatg gcagctataa atgtgatcaa catttattgg  16920
cctaggatac agcagttagc aaaatgcctg atgtagttcc cactccgtgg aggttgcagg  16980
ctagccaaga agtcatgagt tcagcaaccc ttacgcacca gtgggatgag attggaccag  17040
gccgagggta gtcttgggaa cactcagcat ttgtctgagg gccagaagag gctgcttgcc  17100
ctcagacagg aggtcagcat ctttattgta gcccatgaca cctctacacc attgctcttc  17160
tggtcttatg gaagacatct ttgggcctga taacagcgga gtctgtgtcc cacttgtcca  17220
ggctggagtg ccacatcagg cacactccag ttgcagggac agcacagaca agtttcagga  17280
aggctggtgg cctccaggag gttaacctta taaggccaga ttgtaaccta gttgaaaaac  17340
atacacatgc catgataata aaagaaccta ggcaccatta caagagaaaa aatcattttt  17400
gtagatacga gcatggattc ttgggtgggt cagacacact gggcttgtgc tctgactgca  17460
ctgtctcccc tacctgacct tgggtaaacc ataagactgc tgcatgactc agtgtccacc  17520
ccaaaaaagt accggtagat attggccaca gtagatatca gctagagtgg actctcatga  17580
caatgagggg agatgtattc cccatcttag gcacctggga ctctaccttc catcttctgc  17640
tccgtgtctc tccatcccca ggctcttcag aactcaggga gtccagaatg tcagctccca  17700
gatttcagcc ttcagaaagg aaacccatta ccgttcagtt gaacaaatgt tgtctgagcc  17760
ccagatctgg gctcagaggc catctaggct atgagacaag aggggaacaa agcaccgtct  17820
gcactcactc accacactca cttgctgtcc caggtcacat ccatcgggta gagaatctaa  17880
gaggctgagc tagctcccgc caccagccca gcccacccca cctggcccct tccttccttc  17940
tacaaaatat gcaccacctg tcaaagggtg ggcagtgcca ggcctgcata cagagcactg  18000
agtgtaaaag cagacatgga ccctgacctc caggagcttc caattttctt gaagagacaa  18060
```

```
atcagctggc atttcagtcc agtgtgatct gctcttggtg agcacagacc tagggagttg  18120
gggcagcttc ccagaagaac tgcagtccag gctgagggca gagaaatgag gggaatggcg  18180
aggaattggg gagcaggggg gagctcagta gagagccaag ggcgggaggt gagaagtccg  18240
tgttgggcca ggagctaccc tccggtggcc acagccgaag tcgaggatgc ctttggaact  18300
catccccact tctctctttc tgtatgtagc cgtccaagaa caagtcacct ccaagtgtag  18360
ccggatcaag gcaagccccc catctagcaa gcacttgatg ccacccagaa ctgggcttct  18420
tcagaacaat ctgagtccag gaatgatccc actcaccagg caccagagct gcgagggcat  18480
gggagtgatc tcaccaactc tggggaagcg gcaaggaatt ttcacctcca gcccccagtg  18540
tcccatcctc tcacactcag gccagactcc cctgggcaga cttgactctg tctgccagca  18600
tatgcagagc cccaaggcca ccccaccaga agtgcccctg cctgggttct gtcccagctc  18660
cctgggcacc cagtccttga gtccccacca gctcagacgg cctagtgtgc caagaatgcc  18720
cactgcgttc aacaatgctg catgggtcac agcggcagca gctgtgacca cagcagtttc  18780
ggggaaaaca cccctcagcc aagtggataa tagcgttcag cagcactcac cttctggcca  18840
ggcctgcctt cagaggccat ctgattggga ggcacaagtg cccgctgcga tgggaacaca  18900
agtgcccctg gccaacaacc ccagcttcag cctgctgggc agccagagcc tcaggcagag  18960
cccggtacag ggcccggtgc ctgtagcaaa caccaccaag ttcctccagc agggtatggc  19020
cagctttagt cccctgagcc ccatacaggg catcgagcca ccaagctatg tggctgctgc  19080
tgccaccgct gctgctgctt ctgccgttgc tgccagccag ttcccaggtc cgttcgacag  19140
aacggatatt ccccctgagc tgccacctgc cgactttttg cgccagcccc aacccccact  19200
aaatgatctg atttcgtcac ctgactgcaa tgaggtagat ttcattgaag ctctcttgaa  19260
aggctcctgt gtgagcccag atgaagactg ggtgtgcaac ttgaggctga tcgacgacat  19320
tttggaacag catgctgctg ctcaaaatgc cacagcccag aattctgggc aagtcaccca  19380
ggatgctggg gcactttaaa tctgagcagg atgcccatag aaacccccat ggtgacatca  19440
ctctaggaag tggtgtcgat ccatacccgc agttgtctcc cgttacaatt tgagtggtgt  19500
tgtcagccca tgcttatccc tctctctacc tgtgacaaaa tggaaagctg gtgatttttc  19560
aagctacgtg tacatatttg aaaattttgt aaatggtttt cctaaacatt aatgacagaa  19620
gtatttatac ttcattttgt gactttgtaa ataaagcgac ggcttttgtt tcagtagagt  19680
tgtgtttact atgcattgtt ttgtgtttat tatacaatgt tacaaatatg cagaccgtgt  19740
tgtttgctcc agtgatacct tgttaagcta ggtggctgag tcgcttatgg ttttaatgca  19800
atgagcaatg tggatatgac caagagttgt tgtgcaagtt gacaaatgcc aaatagaaaa  19860
ccacttggcc atttatttct atgttcacta aaaatcctat tgccttgtgt gattcttaat  19920
ctcttttgcg aacctttcag tctccgctag ctctttccta atgagcttta cagcagaagc  19980
tgttttatcg ttaagtgccc cacagagaca ctttaccagg aggctgggag agttctccag  20040
atttgggaga ggcgcagaga cagtgtgtga gccgagccct gtctcagcaa tccacctgga  20100
ggagctagag tatcctcctc cctttaccat tcagaccgag agaaaaagcc cagcttgtgt  20160
gcaccctcgt ggggttaagg cgagctgttc ctggtttaaa gcctttcagt atttgttttg  20220
atgtaaggct ctgtggtttg ggggggaaca tctgtaaaca ttattagttg atttggggtt  20280
tgtctttgat ggtttctatc tgcaattatc gtcatgtata tttaagtgtc tgttatagaa  20340
aacccacacc cactgtcctg taaacttttc tcagtgtcca gactttctgt aatcacattt  20400
taattgccac ctcgtatttc acctctacat ttgaaatctg gcgtctgttt caagccagtg  20460
```

```
tgttttttct tcgttctgta ataaacagcc aggagaaaag tgcctctatg tttttatttt  20520
tcaagggagt attcagtacc tacaaaccca agtcaggaag cctgctagtg gctttggttc  20580
tttcagaggc tgctcgatgc cttgtgtgtc agaaagaaag attcagcagt tttgcatcat  20640
ggcaaagaag cctgttattt tggggctcag cccctcattt tatagaggat gaaacagagg  20700
gggatgggag gtcacaaaga caactgcccc gggagcaggt gtgggggaga cttgccctga  20760
gggtctagac gctctgcacc accgtcctgt ctcccttgct gaagaccaca catgcccttc  20820
tttgaccaga ccctgccacc tgataggcca ggacctggta ggcgggtacc caggtttcat  20880
ggatggaacc acatctcccc aaaagtgggg aggtagctac tgggatgcac gcctcccgcc  20940
atgtgctata ggagagcagc tgaagcaaca gttgggatca gatgtagtca caattgaatg  21000
catcatcaca tttatccctc taagtggctg ggagagttga tatcctcatc cctaaggtac  21060
aaaatgttcc aatttgatca gtggctttca ggagctgaga aaggcatgtg ctctgaggca  21120
gagctgttat gtcccgcaga gcctaaaaat gctctaagaa catgctccct gccaaaattc  21180
tcaatggctg tgacaaggga caacgatcga ccaatggggg tggaagcaga cctccgcagt  21240
ccaggggcca gagctaggac agaggggtcg gagaaagagt cattttccca acactccagc  21300
tcttggccag tcctcacaca gtcccctcct gcttcctgct gagagagata tcctcatagg  21360
tctgggtaaa gtccttcagt cagctttcat tccctgtcac caactttgtc tctgttctcc  21420
ctgcccgtct caggcagcac tcctcaggaa acctctccaa gagccagcct cactgcagcg  21480
cccactattg tccctctgcc tcaagtgtcc catccatgcc aggccccagg caggctgcag  21540
ctttccctca gggccacacc aaagcacttg ggctcagctg tgctgtcccc ctccatcact  21600
gagctcaggg gcagcagggg tggggtgcca ggaggcccat tcacccttct ctggctctgt  21660
gttggaccca cctgcccagc cactgctgct tagaacctac ccgctgggaa aatgaagccc  21720
tcccggaggg gccacctcaa cctgagagcc tcacggatca cagttgtccc cactcagctc  21780
tgccagccct cagagaccca tagataaaag ctgagcttgg ctcgcagagc tggttccatc  21840
ttccattccc agagggttca acttcctacc ccaaccacac agggaacctc aaggctgagc  21900
cagtgtgggc tgcagtgcag accagcttcc tggacacgtc ctgccacctg accccaggct  21960
ggcctcactg cccctggcac tcctgaccct atcctcattc ctcctggcag tgcgtgttct  22020
gccattccgc tttcccttag ctgtcctctc actgtactgt cagcttctcc ttttccaggt  22080
gccccccagg ggctttccac atgaccctgt caccccacag cccatccagc accaattcca  22140
gctctctgcc acccttcaaa ggagtgacag tgccctgctt cacctcccac tcacccctca  22200
acccagagca atctggctcc agtcttgcct ccttccccct aagtactcta gtcacagttc  22260
caaattcctc ctggtcataa agccaaatga agcttcctgg tcctcagcgg acttgccact  22320
tcagcagtac tggactctct cctcccagaa acctgtttcc ccttggctcc tggagcccac  22380
actctgctgg aatccttctg cctctctggc ctgtagcctg gccctctctc ccaacctgag  22440
gtccattctc tcctgctcct ccacaagatg ttgctccttc cattacttcc tccctctcaa  22500
ccaaagctcc ttcattagct ctttatcttc tggtttcttc ccctgggcag acgaatggat  22560
tcaagagcct gtggcccagc agcccagcac tccaggatct cagcacttca gcatcccagt  22620
accctagcat ctcaataccc cagcacccca gcaccatagt attccagcac cccattgtcc  22680
aagcatctca gcactccagc atcccagcac cccaacactc cagcagccca gaatctcagc  22740
accctagcac tgcagcatct caggacccca gcacttcagc atcccagcac actagtactc  22800
```

```
cagcatctcg gcaccccagc acctaggcat cccaacaccc agcaccccag cacttaagca  22860
tcccaccact acagtatctc aacactccag caccccagca ccatagtgtt ccagcacccc  22920
agcatcccaa caccccagca cttaagcatc ccaacacctc ggcatcccaa caccccagca  22980
ctgcagcatc tcagcacctt agcatcccag tgccctagca tctcaatgct ccagcacacc  23040
agtactacag tattccagca ccccagcact ccagcatctc agcactgcag cactgcagca  23100
ctccagcatc ccaaaatccc agcatcccaa caccccagca gaccagcaga ccagcatctc  23160
agcaccgcag catccaagga ctatcccagc atcccagcaa cccagcacct cagcatccca  23220
acaccccagc atttcagcat ggcaacaccc cagtacccca gcacttcagc accccagtat  23280
cccagcatct cagcgaccca gtatcacaaa acctcagcat cctagcaccc cagcacccca  23340
gcaccttagc accttagcat cccagcatct cagcgcctca gcatcttgat attctggctg  23400
aggtcagcgt ggtgtatcta gtcagggtcc taactttcac ttcgcaggga aatgctgctg  23460
gactgggtct catgttgggc tgaagctctc tagacccctt gaagacagca taaaagagct  23520
tggagacgct gggtgtcccc catggaagag ttcactctca tcctgctttg acaacagcct  23580
tctctggggt ccctcacggg cccctctttc ttactgcaag tttgtctctg agaagactgt  23640
gatgcagaag tcactcagct gcctgtggct cctgaagagc tgaaggtgga ggcctgtagg  23700
cctccctatg agaggcgcag aaaaaaccat gattgctagt ggggaggtgc tccctctaca  23760
acccactcca taatctgccc ccgcccagct ctgaggccag ccccagggga aaatgccaga  23820
tccccaggga ggtgtgtgag acctcagggg ctccctcctc ccttacagca ggctcaggcc  23880
cctgggggcc tcagggccaa ggtctgtggg taagctacta tctctcactt gtcctctagc  23940
cacaaaagcc agggagatct ggcaatggac atgaggttct gaagaagcac atatgactgg  24000
cttcctaatg cgtggttgtt cagtgattca ataaacacgc atgggccagg catggggaaa  24060
tagacaaaca tgatccccaa cctctcccag agtgaactgg gagggaggag tgttcatccc  24120
tcaggattac accagagaaa caaaccagca ggagatatat atggttttgg ggggtcaaga  24180
aagaggaaaa acctggcaag gcaagtccaa aatcatagga caggctgtca ggaagggcag  24240
cctggaacct ctcaagcagg agctgatgct gcagtccaca ggcagaattt cttcttcctc  24300
ggggaaatct cagctttgtt cttaaggcct ttcaactgat tggctgaggt ctgccccttc  24360
ccccacattc tccaggataa tcttccttac ttaaagtcaa ctattaatca cagctacaaa  24420
atcccttcac agctacacat agatcagtgt ttgattgacg aacagcccct acagcctagc  24480
caagttgaca cataaaacta accatcacag gggacaaat gatgtaaaca catcaacaaa  24540
taaaacagta acaagttaag gtctatggaa aaaacacaga aggggcagag agaaagaaag  24600
caagaaggag agtcccagtt tgctagggct tgtgggaagt ggggagcagt tctctttagc  24660
taggatattt gggaaaggca tatctgaagg agtgatattt gagcttagat taaaagatgg  24720
gaaggagcaa gccatgcaaa gagctaggat gttccaagca gagacggaac agcaagtgca  24780
aatgtcagga ggaatagaag gaggctggtg ggtggggtcc agtgagcaag aggagggcag  24840
gcaggagagg ggatggggag gtgggcaggc ccagaccacc cagggccctg gagactatcc  24900
tgatccaaca agggaagcct tgagtcactt cagtgtccat gtggagaatg gacctcagac  24960
tgaatgaggg aggcagtaag gagggcctct acctccaggg cttcgccctg tggactgcgc  25020
atagacatct ccaactcaga aagtctgaac caaactttcc atagttcccc caagtctggg  25080
catcctccta ctcagtgaaa ggcagccatc acacctccct gccctgctcc cggatgcccc  25140
aaatcctctt ggtctccaag tccagaacct gagacttgtc cttgatgttt gtctttccct  25200
```

```
caccctttct gtattctggg aagatgggtt tttttccccc agatgaatct gtaaaacttc  25260
tgtgatcaca ataaaaattc tggcagtatt attttctgga acatgacaaa gtgattcaaa  25320
attatttatc tggaagacta caaaacaaga atagccagga aatttctaaa aagaaagaag  25380
aaggaggagg agaaagaagg aggaggaaaa ggaggagaag aagaaaagaa aaagaaccaa  25440
gaaagggttc tagctctacc aaatattaaa acatatcatg aagctattta aaacaatatg  25500
gttgtggata ctgaaaaaga tgtgaataaa gtggaaggaa aataaataga aatgcacatg  25560
gggattgaga ctgtgaaaaa ggcagcatct cacatcagtg agggatgttc aacacctggt  25620
gttgggaaaa ctggctagtc atttaaacca aacaactggg tcctctacct cactcctgac  25680
attaagatac atttagatga ttcaaagagt aagacagaaa aaataacacg tgaaaacact  25740
atcagaaaac aacgtgggcc aggtgtggtg ggtcacgcct gtaatcccag cactttggga  25800
ggccgaggca gacagatcac ctgaggtggg gagttcaaga ccagcctgac caacatggtg  25860
aaatcctgtc tctactaaaa atacaaaatt agctgagcgt ggtggcgcat gcctgtaatc  25920
ccagctactc aggaggccga ggcaggagaa tcacttgaac ctgggaggca gaggttgtgg  25980
tgagccgaga tcacgccatt gcactccagc ctgggcaaca agagtgaaaa tccatctaaa  26040
aaaaaaaaaa aaagccaagg tggatatttt tatagtatca gggtagatca agcttctcca  26100
atcatgacat gaaacccaga aaccataaaa gaaaagaatg ataaaattgc ccacgtaaag  26160
taaaaagctt gcacacagaa aaacaccata caggttacaa gatgagcagc aaaatcagag  26220
aaaaaacatt gcaattcagg acacacagag gctattgttc ctaatattta aaaataaaag  26280
tagtggattg tctacaaaaa gatgaagaca agaatttcag aaaaccaaat actgcatgtt  26340
ttcacttaca agtggaagct aaacactgag tacacgtgta cacaaagaat ggaaccatag  26400
gccaggcacc gtggctcacg cctgtaatcc cagtactttg cgaggccgaa gcgggcggat  26460
cacctgaggt gaggagttcg agaccatcct ggccaacatg gtgaaaccca gtctctacta  26520
aaaatacaaa aattagccgg gcgtggtggt gggtgcctgt aatcccagct actcgggagg  26580
ctgcggcagt agaatcgctt gaaccctgga ggtggacctt gcagtgagcc gagatcgcac  26640
cactgcactc cagcctgggc aacagagtga gactccatct caaaaaaaaa aaaaaggaat  26700
agaacaatag acactggggc ctacttgagg gaggagggtg aggatcaaaa acctgcctat  26760
caggtactat gcttattacc tgggtggtga aataatctgt acaccaaacc ccagtgacat  26820
gcaatttacc gatgtaacaa acctgcccat gtacccgctg aacctaaaat aaaagttgga  26880
aaaaaatata gaaatttttct ttgtaatagc caaaaactgc aaacagccca ggtgtctatt  26940
agtagaatgc ataaacaaac tcgggcatgt tcatacaatg taaaactact catcaataaa  27000
aagtgatact tctcagcaat gaaaagaaac tagctactga taccagctac aacatggatg  27060
gatttcaagt gctttatgat gagagcaaga agccagacac aaaagtgtct atatatatat  27120
acagtatata tacgtatata tacacatata tacagtatat atatacatat acatgtatat  27180
atatactgta tatatactgt atatatatac acagtatata tatacatata tacagtgtat  27240
atatactgtg tatatataca tgtatatata ctgtgtatat atacatgtat atatactgtg  27300
tatatataca tgtatatata ctgtgtatat atacatgtat atatatgtat actgtatata  27360
tactgtatat atatatacac atatatacag tatatatata cagtatatac tgtatatata  27420
cagtatatac gtgtatatat acatatatac agtatatatg taaatataca tatatacagt  27480
atatatgtaa atatacatat atacatgtat atatatacac tatatatata catatatagt  27540
```

```
gtatatatac atatatacat gtatatattt actatatgat tccatttata taaagtgcca  27600
aaacagtcaa aaataatcta tgtggaaaaa atcaacaaag ggatcccccg ggctgcagga  27660
attcgatggc gcgccgacgt cgcatgctcc tctagactcg aggaattcgg taccccgggt  27720
tcgaaatcga taagcttgga tcggccgcaa taaaatatct ttattttcat tacatctgtg  27780
tgttggtttt ttgtgtgaat cgtaactaac atacgctctc catcaaaaca aaacgaaaca  27840
aaacaaacta gcaaaatagg ctgtccccag tgcaagtgca ggtgccagaa catttctcta  27900
tcgaggatct gcgatcgctg aattctgggg actttccact ggggactttc cactggggac  27960
tttccactgg ggactttcca ctggggactt tccactcctg cagcagtgga tattcccaga  28020
aaactttttg gatgcagttg ggatttcct ctttactgga tgtggacaat atcctcctat  28080
tattcacagg aagcaatccc tcctataaaa gggcctcaga ggaagtagtg ttcagctgtt  28140
cttggctgac ttcacatcaa agctcctata ctgacctgag acagagccat gaattccgtt  28200
ttttttttt tttttggaaa tatgagggtt tttccgcttc tgacagtgga acggaatgac  28260
agcagcacag gctggtgaat gactactttc tttataagca accaccttga gcctgaaatg  28320
gcagtcgcta gtctctattg ccttgctgtg gcctcgggat ggaaatctgc tggggaccct  28380
acagtcacct aatctctctc cttctcatcc ttctgtttca ttcagaggca gcctgccgcc  28440
cttctgggaa aagaccctgc aagatgcaag ccttcagaat ctgggatact aaccagaaga  28500
ccttttacct gagaaacaac cagctcattg ctgggtactt acaaggacca aatatcaaac  28560
tagaagaaaa gatagacatg gtgcctattg accttcatag tgtgttcttg ggcatccacg  28620
gggcaagct gtgcctgtct tgtgccaagt ctggagatga tatcaagctc cagctggagg  28680
aagttaacat cactgatctg agcaagaaca aagaagaaga caagcgcttt accttcatcc  28740
gctctgagaa aggccccacc accagctttg agtcagctgc ctgtccagga tggttcctct  28800
gcacaacact agaggctgac cgtcctgtga gcctcaccaa cacaccggaa gagcccctta  28860
tagtcacgaa gttctacttc caggaagacc aatagtctag ctcgacatga taagatacat  28920
tgatgagttt ggacaaacca caactagaat gcagtgaaaa aaatgcttta tttgtgaaat  28980
ttgtgatgct attgctttat ttgtgaaatt tgtgatgcta ttgctttatt tgtaaccatt  29040
ataagctgca ataaacaagt taacaacaac aattgcattc attttatgtt tcaggttcag  29100
ggggaggtgt gggaggtttt ttaaagcaag taaaacctct acaaatgtgg tagatccatt  29160
taaatgttag atccggagag ctcccaacgc gttgggtcga cggcgcgcct accagtaaaa  29220
aagaaaacct attaaaaaaa caccactcga cacggcacca gctcaatcag tcacagtgta  29280
aaaaagggcc aagtgcagag cgagtatata taggactaaa aaatgacgta acggttaaag  29340
tccacaaaaa acacccagaa aaccgcacgc gaacctacgc ccagaaacga aagccaaaaa  29400
acccacaact tcctcaaatc gtcacttccg ttttcccacg ttacgtcact tcccatttta  29460
agaaaactac aattcccaac acatacaagt tactccgccc taaaacctac gtcacccgcc  29520
ccgttcccac gccccgcgcc acgtcacaaa ctccaccccc tcattatcat attggcttca  29580
atccaaaata aggtatatta ttgatgatgt tt                                29612
```

<210> SEQ ID NO 3
<211> LENGTH: 29273
<212> TYPE: DNA
<213> ORGANISM: Artificial Sequence
<220> FEATURE:
<223> OTHER INFORMATION: helper-dependent adenoviral vector-equine Il-1Ra gene

<400> SEQUENCE: 3

```
aaacatcatc aataatatac cttattttgg attgaagcca atatgataat gagggggtgg     60
agtttgtgac gtggcgcggg gcgtgggaac ggggcgggtg acgtagtagt gtggcggaag    120
tgtgatgttg caagtgtggc ggaacacatg taagcgacgg atgtggcaaa agtgacgttt    180
ttggtgtgcg ccggtgtaca caggaagtga caattttcgc gcggttttag gcggatgttg    240
tagtaaattt gggcgtaacc gagtaagatt tggccatttt cgcgggaaaa ctgaataaga    300
ggaagtgaaa tctgaataat tttgtgttac tcatagcgcg taatatttgt ctagggccgc    360
ggggactttg accgtttacg tggagactcg cccaggtgtt tttctcaggt gttttccgcg    420
ttccgggtca aagttggcgt tttgatatca agcttatcga taccgtaaac aagtctttaa    480
ttcaagcaag actttaacaa gttaaaagga gcttatgggt aggaagtagt gttatgatgt    540
atgggcataa agggttttaa tgggatagtg aaaatgtcta taataatact taaatggctg    600
cccaatcacc tacaggattg atgtaaacat ggaaaaggtc aaaaacttgg gtcactaaaa    660
tagatgatta atggagagga tgaggttgat agttaaatgt agataagtgg tcttattctc    720
aataaaaatg tgaacataag gcgagtttct acaaagatgg acaggactca ttcatgaaac    780
agcaaaaact ggacatttgt tctaatcttt gaagagtatg aaaaattcct attttaaagg    840
taaaacagta actcacagga aataccaacc caacataaaa tcagaaacaa tagtctaaag    900
taataaaaat caaacgtttg cacgatcaaa ttatgaatga aattcactac taaaattcac    960
actgattttg tttcatccac agtgtcaatg ttgtgatgca tttcaattgt gtgacacagg   1020
cagactgtgg atcaaaagtg gtttctggtg cgacttactc tcttgagtat acctgcagtc   1080
ccctttctta agtgtgttaa aaaaaaaggg ggatttcttc aattcgccaa tactctagct   1140
ctccatgtgc tttctaggaa acaagtgtta acccacctta tttgtcaaac ctagctccaa   1200
aggacttttg actccccaca aaccgatgta gctcaagaga gggtatctgt caccagtatg   1260
tatagtgaaa aaagtatccc aagtcccaac agcaattcct aaaaggagtt tatttaaaaa   1320
accacacaca cctgtaaaat aagtatatat cctccaaggt gactagtttt aaaaaaacag   1380
tattggcttt gatgtaaagt actagtgaat atgttagaaa aatctcactg taaccaagtg   1440
aaatgaaagc aagtatggtt tgcagagatt caaagaaaat ataagaaaac ctactgttgc   1500
cactaaaaag aatcatatat taaatatact cacacaatag ctcttcagtc tgataaaatc   1560
tacagtcata ggaatggatc tatcactatt tctattcagt gctttgatgt aatccagcag   1620
gtcagcaaag aatttatagc ccccccttgag cacacagagg gctacaatgt gatggcctcc   1680
catctccttc atcacatctc gagcaagacg ttcagtccta cagaaataaa atcaggaatt   1740
taatagaaag tttcatacat taaactttat aacaaacacc tcttagtcat taaacttcca   1800
caccaacctg ggcaatatag tgagacccca tgcctgcaaa aaaaaaaaaa ttagccaggc   1860
atggtagcat gtacctgtag tcccagctac ttgagaggtg aggtgggaaa atcactttag   1920
tgcaggatgt tgaggctgga gtgaactgtg attgtgccac tgcactccag cctggacaat   1980
agagcaagac cttgtctcaa aaaaatgcat taaaaatttt ttttaaatct tccacgtatc   2040
acatcctttg ccctcatgtt tcataaggta aaaaatttga taccttcaaa aaaaccaagc   2100
ataccactat cataattttt tttaaatgca aataaaaaca agataccatt ttcacctatc   2160
agactggcag gttctgatta aatgaaattt tctggataat atacaatatt aagagagact   2220
gtagaaactg ggccagtggc tcatgcctgt aatcccagca ctttgggagg ctgggtaaca   2280
tggcgaaccc tgtttctaca aaataaaaat attagctggg agtggtggcg cacacctata   2340
```

```
gtcccagcta ctcaggaggc tgaggtggaa ggatcgcttg aacccaggag gttgagactg   2400
cagtgaactg tgatcattct gctgcactgc accccagcct gggcaacaga gaccttgtct   2460
caaaaaaaaa aaaaaaagag acaaattgtg aagagaaagg tactctcata taacatcagg   2520
agtataaaat gattcaactt cttagaggaa aatttggcaa taccaaaata ttcaataaac   2580
tctttcccct tgacccagaa attccacttg aataaagctg aacaagtacc aaacatgtaa   2640
aagaatgttt cttctagtac agtcggtaag aacaaaatag tgtctatcaa tagtggactg   2700
gttaaatcag ttatggtatc tccataagac agaatgctat gcaaccttta aaatatatta   2760
gatagctcta gacacactaa tattaaaagt gtccaataac atttaaaact atactcatac   2820
gttaaaatat aaatgtatat atgtactttt gcatatagta tacatgcata ggccagtgct   2880
tgagaagaaa tgtgtacaga aggctgaaag gagagaactt tagtcttctt gtttatggcc   2940
tccatagtta gaatatttta taacacaaat attttgatat tataatttta aaataaaaac   3000
acagaatagc cagacataca atgcaagcat tcaataccag gtaaggtttt tcactgtaat   3060
tgacttaaca gaaaatttc aagctagatg tgcataataa taaaaatctg accttgcctt    3120
catgtgattc agccccagtc cattaccctg tttaggactg agaaatgcaa gactctggct   3180
agagttcctt cttccatctc ccttcaatgt ttactttgtt ctggtcccta cagagtccca   3240
ctataccaca actgatacta agtaattagt aaggccctcc tcttttattt ttaataaaga   3300
agattttaga aagcatcagt tatttaataa gttggcctag tttatgttca aatagcaagt   3360
actcagaaca gctgctgatg tttgaaatta acacaagaaa aagtaaaaaa cctcatttta   3420
agatcttact tacctgtcca taattagtcc atgaggaata aacacccttt ccaaatcctc   3480
agcataatga ttaggtatgc aaaataaatc aaggtcataa cctggttcat catcactaat   3540
ctgaaaaaga aatatagctg tttcaatgag agcattacag gatacaaaca tttgattgga   3600
ttaagatgtt aaaaaataac cttagtctat cagagaaatt taggtgtaag atgatattag   3660
taactgttaa ctttgtaggt atgataatga attatgtaag aaaacaacag gccgggcggg   3720
ttggttcaca cgtgtaatcc cagcactttg ggaggctgag gcaggcagac tgcctgagct   3780
caggagttcg agaccagcct gggcaacacg gtgaaatccc gtctctacta aaaatacaaa   3840
aaaattagcc gggtgtggtg acacatgcct gtagtcccag ctacttggga ggctgaggca   3900
ggagaatcac ttgaacctgg gaggtgaagg ttgcagtgag ccaagatggc accacttcac   3960
tccagcctgg gaaacagagc aagactctgt ctctgagctg agatggcacc acttcactcc   4020
agcctgggaa acagagcaag actctgtctc aaaaaaaaca aaacacacaa acaaaaaaac   4080
aggctgggcg cggtggctca cgcctgtaat cccagcactt tgggaggccg aggcgggtgg   4140
atcacctgag gtcaggagtt ccagaccagc cttgtcaaca tggtgaaacc tccccccgcc   4200
gtctctacta aaaatacaaa aattagccag gcgtggtggc aggagcctgt aatcccagct   4260
acttgggagg ctgaggcagg agaatcgctt gtacccagaa ggcagaggtt gcactgagct   4320
gagatggcac cattgcactc cagcctgggg gacaagagcg agatttcgtc tttaaaaaac   4380
aaaaacaaaa caaaaaacca tgtaactata tgtcttagtc atcttagtca agaatgtaga   4440
agtaaagtga taagatatgg aatttccttt aggtcacaaa gagaaaaaga aaaattttaa   4500
agagctaaga caaacgcagc aaaatcttta tatttaataa tattctaaac atgggtgatg   4560
aacatacggg tattcattat actattctct ccacttttga gtatgtttga aaatttagta   4620
aaacaagttt taacacactg tagtctaaca agataaaata tcacactgaa caggaaaaac   4680
```

```
tggcatggtg tggtggctca cacttgtaat cccagtgctt tgggaggctg agacaggaga   4740
gttgcttgag gccaggagtt caagaccgac atggggaatg tagcaagacc ccgtccctac   4800
aaaaaacttt gtaaaaattt gccaggtatg gtggtgcata cctgtagtcc cagctactcg   4860
ggaggcggag gcagaaggaa tcacttgagc ccaggagttt gaggctgcag tgagctacga   4920
tcataccaca gcactccagc gtggacaaca gagtaagacc ctatctcaaa aacaaaacaa   4980
aacaaaacaa acaaaaaaaa ccacaagaaa aactgctggc tgatgcagcg gctcatgcct   5040
gtaatcccag tattttggga ggcccaggtg ggcgtatcac ctgaggtcag gagttagaga   5100
ccagcctggc caacatggtg aaaccccatc tctactaaaa atacaaaatt agccaggcat   5160
gtggcacgcg cctgtagtcc cagttactgg gaggctgaag caggaggatc acctgagccc   5220
gggaggtgga ggttgcagtg agccgagatc acaccactgc actccagcct gggtgacaca   5280
gcaataccct acctcaaaat aaaaaagaaa aagaaaagaa aagttgctgt ccccgctacc   5340
ccaatcccaa atccaaacag cctctctcat ctcacagtaa gggggaaaaa tcacccaaaa   5400
aagctaagtg atcttttgaa aacccaaact cttagaagtc taagattatt atagtcaact   5460
catgaagtgt catcataaaa gatactctaa tattatttaa gtagaaccac atattggttg   5520
tcttggtatg tctagcccct ggcatacaaa atatttaata acactgatat ggtacctgtg   5580
atgtgaaaat gtactatgag tacagcttta taaatactat atatgtacct atatacagaa   5640
aaaaatacaa caaaatcata aaagcactta tctttgaaag aggagttaca gcaattttat   5700
ttagttcttt attgctttgc tatatattct aaattttttt caatgaatat atatcacttt   5760
taaaaaaatt caatggtctt tcttataaat tatctttggc agcatgcgtt tttatatata   5820
catataaaat gtatgggaaa tttttaaagg atacattaaa ttaaagcaaa atatacaaac   5880
aaaaaatcag aatacaaaaa gataaaaaga ttgggaaggg agggagggag taaggaggaa   5940
gggtgggtgg gtatagagaa atataccaaa taatggtaag aagtggggtc ttgacacttt   6000
ctacactttt tttaaataaa aaaaattttt ttctctctct tttttttttt tagagacgaa   6060
gtctcgctat gttgcccagg ctggtcttga actcctggga tcaagagatc ctcctgcctc   6120
agcctcccaa ggtgcttgga ttacaggtgt gagccaccac gcctggtcac tttctacact   6180
ttaatatata tatttttca ttttcaatgt catttttatt agttaattta taatacccat   6240
tcaccattat attcaaagtc tatttgaaga aataaaccag aaagaatgaa atactctagc   6300
tcacatgcta ttcaatacta aattaccttt caaatcacat tcaagaagct gatgatttaa   6360
gctttggcgg tttccaataa atattggtca aaccataatt aaatctcaat atatcagtta   6420
gtacctattg agcatctcct tttacaacct aagcattgta ttaggtgctt aaatacaagc   6480
agcttgactt ttaatacatt taaaaataca tatttaagac ttaaaatctt atttatggaa   6540
ttcagttata ttttgaggtt tccagtgctg agaaatttga ggtttgtgct gtctttcagt   6600
ccccaaagct cagttctgag ttctcagact ttggtggaac ttcatgtatt gtcaggttgg   6660
cccgtaatac ctgtgggaca acttcagccc ctgtgcacat ggccaggagg ctggttgcaa   6720
acattttcag gtaggtggac caggacatgc ccctggtcat ggccaggtgg aggcatagtg   6780
ctatacagca ggcagaagtc aatattgatt tgtttttaaa gaaacatgta ctactttcat   6840
aagcagaaaa aatttctatt cttgggggaa aagattatgc cagatcctct aggattaaat   6900
gctgatgcat ctgctaaacc ttcacatatc agaacatatt tactatagaa agaatgaaaa   6960
tgggacattt gtgtgtcacc tatgtgaaca ttccaaaaat attttacaac aactaagtat   7020
tttataaatt ttatgaactg aaatttagtt caagttctag gaaaatacaa accttgctag   7080
```

```
atattataaa aatgatacaa tatatattca tttcaggctc atcagaatat atctgttatc   7140
acttgacaag aatgaaaatg caccattttg tagtgcttta aaatcaggaa gatccagagt   7200
actaaaaatg acttcttcct tgaagcttac tcaccaactt cctcccagtt actcactgct   7260
tctgccacaa gcataaacta ggacccagcc agaactccct tgaaatatac acttgcaacg   7320
attactgcat ctatcaaaat ggttcagtgc ctggctacag gttctgcaga tcgactaaga   7380
atttgaaaag tcttgtttat ttcaaaggaa gcccatgtga attctgccca gagttcatcc   7440
cagatatgca gtctaagaat acagacagat cagcagagat gtattctaaa acaggaattc   7500
tggcaatata acaaattgat ttccaatcaa aacagattta cataccatac ttatgtcaag   7560
aagttgtttt gttttattgc atcctagatt ttattttttt gatttatggt ttactttaag   7620
cataaaaaat ttgtcaatac aactcttccc aaaaggcata aacaaaaatt cataaaactt   7680
gcatcacttg agatacttca ggtatgaatt cacaactttg ttacaactta ctatatatat   7740
gcacacatat atatatattt gggtatattg gggggggttct aatttaagaa atgcataatt   7800
ggctatagac agacagttgt cagaacttgg caatgggtac gtgcaggttc attataccaa   7860
gtctacttgt agttgttcaa aatgtatcat aatacaaggc cgggcgaggt cgtcacgcct   7920
gtaatcccag cattttggga ggctaaggca ggaggattgc ttgaggtcag gagtttgtga   7980
ccagcctggg caacagagca agaccctgtc tccaaaaaga aaaaaaataa tttttttacaa   8040
aataaaaaca aaatgtatca tcagacgaaa ttaaataaga ggcaattcat ttaaatgaca   8100
acttttccca gcttgacatt taacaaaaag tctaagtcct cttaattcat atttaatgat   8160
caaatatcaa atactaattt tttttttttt tttttttttg agacggagtc tcgctctgtc   8220
gcccaggctg gagtgcagtg gcgcgatcct ggctcactgc aagctccgcc tcccgggttc   8280
acgccattct cctgcctcag cctcccgagt agctgggatt acagacatgc gccaccacgc   8340
ccggctaatt ttgtattttt agtagagatg gggtttctcc atgttggtca ggctggtctt   8400
gaatttccca cctcaggtga tctgcctgcc tcagcctcac aaagcagtag ctgggactac   8460
aggcacccac caccacactt ggttaattct tttgtatttt ttttgtaaag acgggatttc   8520
accatgttag ccaggatggt ctcgatctcc tgatctcatg atccgcccgc ctcagcctcc   8580
caaagtgctg ggattacagg cgtgagccac cccgcccggc catcaaatac taattcttaa   8640
atggtaagga cccactattc agaacctgta tccttatcac taatatgcaa atatttattg   8700
aatacttact atgtcatgca tactagagag agttagataa atttgataca gctaccctca   8760
cagaacttac agtgtaatag atggcatgac atgtacatga gtaactgtga acagtgttaa   8820
attgctattt aaaaaaaaag acggctgggc gctgtggctc atgcctgtaa tcccagcact   8880
ttgggaggcc aaggcaagtt gatcgctcga ggtcaagagt tcgagaccag cctggccaac   8940
gtggtaaaac cccgtctcta ctaaaaatac aaaaaaaaaa ttagccaggc atggtggcac   9000
aggcctgtaa tcccagctac tagggaggct gagacatgga gaactgcttg aatccaggag   9060
gcagaggtta cagtgagccg agatcatacc actacactcc agcctgagtg acagagcgag   9120
actcctgtct aaaaaaaaaa aaaaaaaaaa agatacaggt taagtgttat ggtagttgaa   9180
gagagaactc aaactctgtc tcagaagcct cacttgcatg tggaccactg atatgaaata   9240
atataaatag gtataattca ataaatagga acttcagttt taatcatccc aaacaccaaa   9300
acttcctatc aaacaggtcc aataaactca atctctataa gagctagaca gaaatctact   9360
tggtggccta taatcttatt agcccttact tgtcccatct gatattaatt aaccccatct   9420
```

```
aatatggatt agttaacaat ccagtggctg ctttgacagg aacagttgga gagagttggg   9480
gattgcaaca tattcaatta tacaaaaatg cattcagcat ctaccttgat taaggcagtg   9540
tgcaacagaa tttgcaggag agtaaaagaa tgattataaa tttacaaccc ttaaagagct   9600
atagctgggc gtggtggctc atgcctgtaa atcccagcac tttgggaggc tgaggcgggt   9660
ggatcacctg aggccagaag ttcaagacca gcctagccaa catggcgaaa ccctgtctct   9720
acaaaaaata caaaaattag ccgggtgtgg tggcacgtgc ctgtagtccc agttacttgg   9780
gaggccgagg caggagaatc gcttgaacct aggaggtgga ggctgcagtg agccgagatt   9840
gtgccactgc actccacttc agcctgggcg acaagagcaa gactccgtca caaaaaaaaa   9900
aaaaaaaaaa aagcttaaaa tctagtggga aaggcatata tacatacaac taactgtata   9960
gcataataaa gctcataatc tgtaacaaaa tctaattcga caagcccaga aacttgtgat  10020
ttaccaaaaa cagttatata tacacaaaaa gtaaacctag aacccaaagt tacccagcac  10080
caatgattct ctccctaagc agtatcaagt ttaaagcagt gattacattc tactgcctag  10140
attgtaaact gagtaaagga gaccagcacc tttctgctac tgaactagca cagccgtgta  10200
aaccaacaag gcaatggcag tgcccaactt tctgtatgaa tataagttac atctgtttta  10260
ttatttgtga cttggtgttg catgtggtta ttatcaacac cttctgaaag aacaactacc  10320
tgctcaggct gccataacaa aataccacag actgagtgac ttaacagaaa cttatttctc  10380
acagttttgg aggctgggaa gtccaaaatt aaggtacctg caaggtaggt ttcaatctca  10440
ggcctcttct ttggcttgaa ggtcttctaa ctgtgtgctc acatgacctc ttctaacaag  10500
ctctctggtg tctctttttt tttttttttc ttttttgaga cagagtctca ctctgtcacc  10560
caggctggag tacagtggca caatctgggc tcactgcaac ctccaactcc cgggttcaag  10620
tgattctcat gcctcaccct cccgagtagc ttggatgaca ggagcccgct accacaccca  10680
gctaattttt gtatttttag tagagatggt gtttcactac attggccagg ctggtctcaa  10740
actcctgacc tcgtgatcca cccaccttgg cctcccaaag tgctgggatt acaggtgtga  10800
gccactgcgc ccgtcctggt gtcttttcat ataagggcac taatccaatc agacctgggc  10860
ccaaccctcc cgacttcttc taactgtaat taccttccaa aggccctgtc tccaaatacc  10920
atcacactgg gggttaggac ttcaaaaaag gtatgggggg ggtgtgggag gacataaatg  10980
ctcagtccat aacaagcacc caacataaaa atggctagaa cagatcacaa aaaaaaggtc  11040
ctgtatggct ttggggaagg gctcaacccc aaaatatctg agagctctgg aggggcctag  11100
aagtggtaaa tgaatgaaaa cgtggttact ctccagatct gcctttccca aatatggcca  11160
ttcttggctg aatcagaaat caaaggacag gttattaatt actagctcta agttacttac  11220
catttgctga gacagttcag aaatctgact gcatctcctc agagatctag aacacagttc  11280
tcaaattcta acttacttgt gatatacttg tgaatgataa aaatcgctac aggtactttt  11340
attaatctga aagagtattg agaaattacc tttcattctg acttttgtct ggaatgaaaa  11400
tcaatacttt tgctataatc gattactgaa ataattttac tttccagtaa aactggcatt  11460
ataatttttt ttaattttta aaacttcata attttttgcc agactgaccc atgtaaacat  11520
acaaattact aataattatg cacgtcacat ctgtaataat ggccttcatg taaacatttt  11580
tgtggtttac acataaaatc tctaattaca aagctatatt atctaaaatt acagtaagca  11640
agaaaattaa tccaagctaa gacaatactt gcaacatcaa ttcatcatct gtgacaagga  11700
ctgcttaagt ctctttgtgg ttaaaaagga aaaaaaaaaa aaagacatgt tggccagatg  11760
cggtggctca cacctgtaat cccagcactt tgggaggctg aggtgggcgg atcacccctg  11820
```

```
gcctgcccaa catggtgaaa ccccgtctct actaaaaaca caaaaattag ctgggcgtgg  11880
tggcgggcgc ctgtaattcc agctactcgg gaggctgagg caggagaatt gctagaaccc  11940
aggaggcaga gattgcagtg agctgagatt gcaccattgc actacagtct gggcaacaaa  12000
agtgaaactc catcttaaaa aaaaaaagac aatgttcgtg ggtccaaaca agacttaatg  12060
gaagtgagtc taaaaatgag ctatgtgggc caggcgtagt ggctcccacc tgtaatccca  12120
gcactttggg aggccgaagc aggcagatca tgaggtcagg agatggagac catcctggcc  12180
aacacggtga aatcctgtct ctacaaaaat tagctgggcg tggtggtgcc tgcctgtaat  12240
cccagctact cagaaggctc aggcaggaga atcgcttgaa ccagggagtc ggtggctaga  12300
gtgagccgag atttgcatca ctgcactcct gcctggtgac agagcaagac tccatctcaa  12360
aaaaaacaaa caaaaataaa agataaaaat gagctatgtg aattaaaaga ggtataacaa  12420
tagataaacc atattttatt taattcctag taatgagtaa tatttccaaa cttctggaat  12480
gggcagaaat tgctagttgg catattttta ccttttatat tcagatacat taaaattctc  12540
aaaaaaaaac acctcaaagc agatgatccg ccatctcctt ggataatttg tgttaactca  12600
ggataacaga aaaccaaaat tatgagttac tgatgcaata ttcctaaatg taaaaataat  12660
taaagctaat agtagattca tcttccaatt tcatatcagt cttacaaata aactacatat  12720
ataacttgct tgccttccct tctgagggat aaagctgtta gaagaattaa aatcagcatt  12780
cttgactatt caaccaaggg agggataaat tattactcat tctagggaca tgggctcata  12840
actactacat gtgtaaggac atgaatttac ccaatattac aatttttcct tttattagtg  12900
tgtacagtgg aagaatagac atgttcactc tggacaaaaa aaaaattata cttatcagtt  12960
atcagaagca caatgctgaa gacagtagtt ccataacaat ttgaagtatg tgatcgaact  13020
agtagattat cttagtagta gtgaattatt gtaaatgtta gtaatttggc agccactggg  13080
cagaaaaata agaattgagg ctcaatattg atattaatgg tggtgattga cacataaatt  13140
ttatcaagtc tacacaatat aaaattacag aaaggtagaa gagtatacca gtacaacttc  13200
aacatatctt cactacaagg gagtaaaatg acatggccta gttactatct aatgaactgc  13260
agaaaactaa aagaaaactc caaggcaact cttctctgct gatctggttg gtccttttcc  13320
taccttttgc aatacccaga tacaaacaat ggatagaaaa caaagtagac ttgtagtatg  13380
caggtcacag tgctaaattc acagaaagaa acccctgaac tgaactgctc tatttcctgg  13440
tggtcacaaa gagtaattct ggtttacacc tacagattga tgtcaatcta caccctgttg  13500
ataacagtgt ggccaaggac aaaaaaaagg tgctccgttt taccaattct gtaaaaaatt  13560
attggcaggg taagctcggc tagggcagga ttacatttct aggactacca tccccgaaat  13620
ttagaagata ttatatccac ataaagcata tctttcacat taatttgcaa aaatctaaaa  13680
gctttttctt agctcaagtg tgtccaagtt taccctggca gtttaaaacg atagttacaa  13740
gcagcatggg ttgtatcaga cacatttgag ggccaatttc atgtaagtga tattgggcaa  13800
gttacttcaa ctatctgtgc ctccaaggtc atactagtgt ttatttacct aaagggtacc  13860
tgttatgtaa ctttagggtg tttacattag ataatgcctg caaaatattt acttcaacgc  13920
ctaaaacata gttaagtatt caataaatac ctactattgt cactactaac ttaaaagttt  13980
agagattaag agcagaatct ggggtgagac aaacttaggt tcaaatccta gtattgttgg  14040
gtaatcttgg gcaagttact taacctctct gatttgtgta atttaaaaaa ttagttaata  14100
tacataacag ggcttagaag agtatctagc acatagcacc atttaagcat ttgttattgc  14160
```

```
taacatgcaa acaatttaag ggaaagaaat tttttaaaaa ggaagaggga tttgcaaact  14220
aaaaacaatg agtatcttat gttcaaagaa aactaacaaa cagccagctc tagcaataat  14280
taaattcact atatactggg gcaggcatca caccccaaag ctaaaagcgt ctacctaggc  14340
caggcacggt ggctcatgcc tgtaatccca gcactttggg aagcagaggc gggcagatcg  14400
cttgagctca ggagttcaag accagcctgg acaacatggc aaaacaccat ctctacaaaa  14460
aatacaaata ttaggccggg cgcagtggct cacgcctgta atcccagcac tttgggaggc  14520
caaggcgggt ggatcacctg agatcaggag ttcgagagta gcctggccaa catggtgaaa  14580
cctcgtctct attaaaaata caaaaaatta gccaggcatg gtggcaggcg cctgtaatcc  14640
cagctactca gggggatgag gtaggagaat cgcttgaacc cgggaggcag aggttgcact  14700
gagccgagat catgccactg tactccagcc cgggcaacaa gagcgaaact ccatctcaaa  14760
aaataaataa ataaataaat aaaataaagt acaaatatta gccagggatg gtggtgcgca  14820
cctgtagtcc cagctacttg ggaggctgaa gtgggagaat cccctgagcc tggggagaat  14880
cacccgagcc cgggaagtcg aggctgcagt gagcagtgat tgtgccactg cactccatcc  14940
taggtgacag agtgagaccc tgtctcaaaa aaaagaaatt ggcagaatta agtaagttga  15000
tgtttagaga tgaaaaatca acattttttc ctcagcaact gaataaaaac aacagccact  15060
accatttttt tgagtaccta tttgtagcct attttttaac tggtattact cgagagagag  15120
agagctaggt tcgagacaga gctccttctc ttaataactg tatgacctag ggtatgtctg  15180
ttagcctctc tgaggcttca aaggttcctc atctgtaaaa tggtaataat cataccattg  15240
ctacagggct gttttgaaga ctaattagga ctatgtaagt aaacatgatg atggctatta  15300
ttactgttcc ccgccagggg ccatgcaagg gttgctgatt cacatagact gtcttataat  15360
cctctcaata actccaagag gtagccagca cctcagatat acataaaatg acttaagccc  15420
agagaggtga agtaagttgc ccacagccac acaactagta aatagcccaa acaagctgga  15480
ttcccagtta gactccgtta atagcactgc tctttacctt aagtcattac aatgcctaat  15540
atgaaataga atcgcttctt tcttagggtt caagtggtta attatttaat gtattcattc  15600
aacaaaccat catcgaggac ctcttacaag ccaagtactg tgctaagtgc tagagttacg  15660
gcggtgattc ctgcccttaa aaagttttag tgggagaaac aacaggtaac caggtcattg  15720
ccaaaacaac aaaaataatc ataataaagc aggctaaagc atatttaact ggccggggtt  15780
ttgactattt tagcaagcat gatcagaacg gttgaggagg gaggccagca gcttggccgg  15840
ttcaacaaac aagaaaaaac cagtgagggt ggagctaaga taccagaggc tgattacggt  15900
taagaatgtt cttgaaggta aggaccagat tctcattttc tatatcctgg ggcatcggtc  15960
agcatggaat ctggattcta gcacatgtga atttcggctt gaaatgacct aatgcctttt  16020
ccctagttcc ttcgtgtgtc aaatacgcat ggttaccgct accagagctg tagtggggct  16080
tcaatgaggc catgagcatc tccataaaga tgaactacag tgtgtgcaaa actaaaggca  16140
aaacctggtc cccacacgcc ctcccaggtg gtcgctttcc gtgccgaggc ccctccagag  16200
gtgccccgag aacctcacca tcgcacccca aacttccagg gaagggcctc tcccgagaaa  16260
gcccccacgc ccccaccccg cgccatcatt cccgaatctg ccctcggccc ctccccgcag  16320
cacgctcgca ggcggcacat gtcaaccaaa acgccatttc caccttctct tcccacacgc  16380
agtcctcttt tcccagggct cccccgagga gggacccacc ccaaaccccg ccattccgtc  16440
ctccctgccg ccctcgcgtg acgtaaagcc gaacccggga aactggccgc ccccgcctgc  16500
ggggttccct gggcccggcc gctctagaac tagtggatcc caattgaagg cctggtctaa  16560
```

```
atgactccaa aatcaccact taattcaaga gactgatttc cctgagtcag gccccttaaa  16620
gcagctattt caatgggaca gggaaacaac cctaggatct ggattagaat cacttggggg  16680
ctgccacacc cccagggctc tgatcctgcc cttctcccac acgcacattc acatactgct  16740
gcagtgacct tccatttcta atgggttcct gggccatctg tcaggtatag ggaatggaaa  16800
aggggttggg gaggctctgc ttcagaaagt ttgtgtcagg ggctcccaga gcctccacag  16860
atagatagca ggggtcccca ccctaccatg gcagctataa atgtgatcaa catttattgg  16920
cctaggatac agcagttagc aaaatgcctg atgtagttcc cactccgtgg aggttgcagg  16980
ctagccaaga agtcatgagt tcagcaaccc ttacgcacca gtgggatgag attggaccag  17040
gccgagggta gtcttgggaa cactcagcat ttgtctgagg gccagaagag gctgcttgcc  17100
ctcagacagg aggtcagcat ctttattgta gcccatgaca cctctacacc attgctcttc  17160
tggtcttatg gaagacatct ttgggcctga taacagcgga gtctgtgtcc cacttgtcca  17220
ggctggagtg ccacatcagg cacactccag ttgcagggac agcacagaca agtttcagga  17280
aggctggtgg cctccaggag gttaacctta taaggccaga ttgtaaccta gttgaaaaac  17340
atacacatgc catgataata aaagaaccta ggcaccatta caagagaaaa aatcattttt  17400
gtagatacga gcatggattc ttgggtgggt cagacacact gggcttgtgc tctgactgca  17460
ctgtctcccc tacctgacct tgggtaaacc ataagactgc tgcatgactc agtgtccacc  17520
ccaaaaaagt accggtagat attggccaca gtagatatca gctagagtgg actctcatga  17580
caatgagggg agatgtattc cccatcttag gcacctggga ctctaccttc catcttctgc  17640
tccgtgtctc tccatcccca ggctcttcag aactcaggga gtccagaatg tcagctccca  17700
gatttcagcc ttcagaaagg aaacccatta ccgttcagtt gaacaaatgt tgtctgagcc  17760
ccagatctgg gctcagaggc catctaggct atgagacaag aggggaacaa agcaccgtct  17820
gcactcactc accacactca cttgctgtcc caggtcacat ccatcgggta gagaatctaa  17880
gaggctgagc tagctcccgc caccagccca gcccacccca cctggcccct tccttccttc  17940
tacaaaatat gcaccacctg tcaaagggtg ggcagtgcca ggcctgcata cagagcactg  18000
agtgtaaaag cagacatgga ccctgacctc caggagcttc caattttctt gaagagacaa  18060
atcagctggc atttcagtcc agtgtgatct gctcttggtg agcacagacc tagggagttg  18120
gggcagcttc ccagaagaac tgcagtccag gctgagggca gagaaatgag gggaatggcg  18180
aggaattggg gagcaggggg gagctcagta gagagccaag ggcgggaggt gagaagtccg  18240
tgttgggcca ggagctaccc tccggtggcc acagccgaag tcgaggatgc ctttggaact  18300
catccccact tctctctttc tgtatgtagc cgtccaagaa caagtcacct ccaagtgtag  18360
ccggatcaag gcaagccccc catctagcaa gcacttgatg ccacccagaa ctgggcttct  18420
tcagaacaat ctgagtccag gaatgatccc actcaccagg caccagagct gcgagggcat  18480
gggagtgatc tcaccaactc tggggaagcg gcaaggaatt ttcacctcca gcccccagtg  18540
tcccatcctc tcacactcag gccagactcc cctgggcaga cttgactctg tctgccagca  18600
tatgcagagc cccaaggcca ccccaccaga agtgcccctg cctgggttct gtcccagctc  18660
cctgggcacc cagtccttga gtccccacca gctcagacgg cctagtgtgc caagaatgcc  18720
cactgcgttc aacaatgctg catgggtcac agcggcagca gctgtgacca cagcagtttc  18780
ggggaaaaca cccctcagcc aagtggataa tagcgttcag cagcactcac cttctggcca  18840
ggcctgcctt cagaggccat ctgattggga ggcacaagtg cccgctgcga tgggaacaca  18900
```

```
agtgcccctg gccaacaacc ccagcttcag cctgctgggc agccagagcc tcaggcagag  18960
cccggtacag ggcccggtgc ctgtagcaaa caccaccaag ttcctccagc agggtatggc  19020
cagctttagt cccctgagcc ccatacaggg catcgagcca ccaagctatg tggctgctgc  19080
tgccaccgct gctgctgctt ctgccgttgc tgccagccag ttcccaggtc cgttcgacag  19140
aacggatatt ccccctgagc tgccacctgc cgactttttg cgccagcccc aacccccact  19200
aaatgatctg atttcgtcac ctgactgcaa tgaggtagat ttcattgaag ctctcttgaa  19260
aggctcctgt gtgagcccag atgaagactg ggtgtgcaac ttgaggctga tcgacgacat  19320
tttggaacag catgctgctg ctcaaaatgc cacagcccag aattctgggc aagtcaccca  19380
ggatgctggg gcactttaaa tctgagcagg atgcccatag aaacccccat ggtgacatca  19440
ctctaggaag tggtgtcgat ccatacccgc agttgtctcc cgttacaatt tgagtggtgt  19500
tgtcagccca tgcttatccc tctctctacc tgtgacaaaa tggaaagctg gtgatttttc  19560
aagctacgtg tacatatttg aaaattttgt aaatggtttt cctaaacatt aatgacagaa  19620
gtatttatac ttcattttgt gactttgtaa ataaagcgac ggcttttgtt tcagtagagt  19680
tgtgtttact atgcattgtt ttgtgtttat tatacaatgt tacaaatatg cagaccgtgt  19740
tgtttgctcc agtgatacct tgttaagcta ggtggctgag tcgcttatgg ttttaatgca  19800
atgagcaatg tggatatgac caagagttgt tgtgcaagtt gacaaatgcc aaatagaaaa  19860
ccacttggcc atttatttct atgttcacta aaaatcctat tgccttgtgt gattcttaat  19920
ctcttttgcg aacctttcag tctccgctag ctctttccta atgagcttta cagcagaagc  19980
tgttttatcg ttaagtgccc cacagagaca ctttaccagg aggctgggag agttctccag  20040
atttgggaga ggcgcagaga cagtgtgtga gccgagccct gtctcagcaa tccacctgga  20100
ggagctagag tatcctcctc cctttaccat tcagaccgag agaaaaagcc cagcttgtgt  20160
gcaccctcgt ggggttaagg cgagctgttc ctggtttaaa gcctttcagt atttgttttg  20220
atgtaaggct ctgtggtttg ggggggaaca tctgtaaaca ttattagttg atttggggtt  20280
tgtctttgat ggtttctatc tgcaattatc gtcatgtata tttaagtgtc tgttatagaa  20340
aacccacacc cactgtcctg taaacttttc tcagtgtcca gactttctgt aatcacattt  20400
taattgccac ctcgtatttc acctctacat ttgaaatctg gcgtctgttt caagccagtg  20460
tgttttttct tcgttctgta ataaacagcc aggagaaaag tgcctctatg tttttatttt  20520
tcaagggagt attcagtacc tacaaaccca agtcaggaag cctgctagtg gctttggttc  20580
tttcagaggc tgctcgatgc cttgtgtgtc agaaagaaag attcagcagt tttgcatcat  20640
ggcaaagaag cctgttattt tggggctcag cccctcattt tatagaggat gaaacagagg  20700
gggatgggag gtcacaaaga caactgcccc gggagcaggt gtgggggaga cttgccctga  20760
gggtctagac gctctgcacc accgtcctgt ctcccttgct gaagaccaca catgcccttc  20820
tttgaccaga ccctgccacc tgataggcca ggacctggta ggcgggtacc caggtttcat  20880
ggatggaacc acatctcccc aaaagtgggg aggtagctac tgggatgcac gcctcccgcc  20940
atgtgctata ggagagcagc tgaagcaaca gttgggatca gatgtagtca caattgaatg  21000
catcatcaca tttatccctc taagtggctg ggagagttga tatcctcatc cctaaggtac  21060
aaaatgttcc aatttgatca gtggctttca ggagctgaga aaggcatgtg ctctgaggca  21120
gagctgttat gtcccgcaga gcctaaaaat gctctaagaa catgctccct gccaaaattc  21180
tcaatggctg tgacaaggga caacgatcga ccaatggggg tggaagcaga cctccgcagt  21240
ccaggggcca gagctaggac agaggggtcg gagaaagagt cattttccca acactccagc  21300
```

```
tcttggccag tcctcacaca gtcccctcct gcttcctgct gagagagata tcctcatagg  21360
tctgggtaaa gtccttcagt cagctttcat tccctgtcac caactttgtc tctgttctcc  21420
ctgcccgtct caggcagcac tcctcaggaa acctctccaa gagccagcct cactgcagcg  21480
cccactattg tccctctgcc tcaagtgtcc catccatgcc aggccccagg caggctgcag  21540
ctttccctca gggccacacc aaagcacttg ggctcagctg tgctgtcccc ctccatcact  21600
gagctcaggg gcagcagggg tggggtgcca ggaggcccat tcacccttct ctggctctgt  21660
gttggaccca cctgcccagc cactgctgct tagaacctac ccgctgggaa aatgaagccc  21720
tcccggaggg gccacctcaa cctgagagcc tcacggatca cagttgtccc cactcagctc  21780
tgccagccct cagagaccca tagataaaag ctgagcttgg ctcgcagagc tggttccatc  21840
ttccattccc agagggttca acttcctacc ccaaccacac agggaacctc aaggctgagc  21900
cagtgtgggc tgcagtgcag accagcttcc tggacacgtc ctgccacctg accccaggct  21960
ggcctcactg cccctggcac tcctgaccct atcctcattc ctcctggcag tgcgtgttct  22020
gccattccgc tttcccttag ctgtcctctc actgtactgt cagcttctcc ttttccaggt  22080
gccccccagg ggctttccac atgaccctgt caccccacag cccatccagc accaattcca  22140
gctctctgcc acccttcaaa ggagtgacag tgccctgctt cacctcccac tcacccctca  22200
acccagagca atctggctcc agtcttgcct ccttcccccct aagtactcta gtcacagttc  22260
caaattcctc ctggtcataa agccaaatga agcttcctgg tcctcagcgg acttgccact  22320
tcagcagtac tggactctct cctcccagaa acctgtttcc ccttggctcc tggagcccac  22380
actctgctgg aatccttctg cctctctggc ctgtagcctg gccctctctc ccaacctgag  22440
gtccattctc tcctgctcct ccacaagatg ttgctccttc cattacttcc tccctctcaa  22500
ccaaagctcc ttcattagct ctttatcttc tggtttcttc ccctgggcag acgaatggat  22560
tcaagagcct gtggcccagc agcccagcac tccaggatct cagcacttca gcatcccagt  22620
accctagcat ctcaataccc cagcacccca gcaccatagt attccagcac cccattgtcc  22680
aagcatctca gcactccagc atcccagcac cccaacactc cagcagccca gaatctcagc  22740
accctagcac tgcagcatct caggacccca gcacttcagc atcccagcac actagtactc  22800
cagcatctcg gcaccccagc acctaggcat cccaacaccc agcaccccag cacttaagca  22860
tcccaccact acagtatctc aacactccag caccccagca ccatagtgtt ccagcacccc  22920
agcatcccaa caccccagca cttaagcatc ccaacacctc ggcatcccaa caccccagca  22980
ctgcagcatc tcagcacctt agcatcccag tgccctagca tctcaatgct ccagcacacc  23040
agtactacag tattccagca ccccagcact ccagcatctc agcactgcag cactgcagca  23100
ctccagcatc ccaaaatccc agcatcccaa caccccagca gaccagcaga ccagcatctc  23160
agcaccgcag catccaagga ctatcccagc atcccagcaa cccagcacct cagcatccca  23220
acaccccagc atttcagcat ggcaacaccc cagtacccca gcacttcagc accccagtat  23280
cccagcatct cagcgaccca gtatcacaaa acctcagcat cctagcaccc cagcacccca  23340
gcaccttagc accttagcat cccagcatct cagcgcctca gcatcttgat attctggctg  23400
aggtcagcgt ggtgtatcta gtcagggtcc taactttcac ttcgcaggga aatgctgctg  23460
gactgggtct catgttgggc tgaagctctc tagacccctt gaagacagca taaaagagct  23520
tggagacgct gggtgtcccc catggaagag ttcactctca tcctgctttg acaacagcct  23580
tctctggggt ccctcacggg cccctctttc ttactgcaag tttgtctctg agaagactgt  23640
```

```
gatgcagaag tcactcagct gcctgtggct cctgaagagc tgaaggtgga ggcctgtagg  23700
cctccctatg agaggcgcag aaaaaaccat gattgctagt ggggaggtgc tccctctaca  23760
acccactcca taatctgccc ccgcccagct ctgaggccag ccccagggga aaatgccaga  23820
tccccaggga ggtgtgtgag acctcagggg ctccctcctc ccttacagca ggctcaggcc  23880
cctgggggcc tcagggccaa ggtctgtggg taagctacta tctctcactt gtcctctagc  23940
cacaaaagcc agggagatct ggcaatggac atgaggttct gaagaagcac atatgactgg  24000
cttcctaatg cgtggttgtt cagtgattca ataaacacgc atgggccagg catggggaaa  24060
tagacaaaca tgatccccaa cctctcccag agtgaactgg gagggaggag tgttcatccc  24120
tcaggattac accagagaaa caaaccagca ggagatatat atggttttgg ggggtcaaga  24180
aagaggaaaa acctggcaag gcaagtccaa aatcatagga caggctgtca ggaagggcag  24240
cctggaacct ctcaagcagg agctgatgct gcagtccaca ggcagaattt cttcttcctc  24300
ggggaaatct cagctttgtt cttaaggcct ttcaactgat tggctgaggt ctgccccttc  24360
ccccacattc tccaggataa tcttccttac ttaaagtcaa ctattaatca cagctacaaa  24420
atcccttcac agctacacat agatcagtgt ttgattgacg aacagcccct acagcctagc  24480
caagttgaca cataaaacta accatcacag gggacaaat gatgtaaaca catcaacaaa  24540
taaaacagta acaagttaag gtctatggaa aaaacacaga aggggcagag agaaagaaag  24600
caagaaggag agtcccagtt tgctagggct tgtgggaagt ggggagcagt tctctttagc  24660
taggatattt gggaaaggca tatctgaagg agtgatattt gagcttagat taaaagatgg  24720
gaaggagcaa gccatgcaaa gagctaggat gttccaagca gagacggaac agcaagtgca  24780
aatgtcagga ggaatagaag gaggctggtg ggtggggtcc agtgagcaag aggagggcag  24840
gcaggagagg ggatggggag gtgggcaggc ccagaccacc cagggccctg gagactatcc  24900
tgatccaaca agggaagcct tgagtcactt cagtgtccat gtggagaatg gacctcagac  24960
tgaatgaggg aggcagtaag gagggcctct acctccaggg cttcgccctg tggactgcgc  25020
atagacatct ccaactcaga aagtctgaac caaactttcc atagttcccc caagtctggg  25080
catcctccta ctcagtgaaa ggcagccatc acacctccct gccctgctcc cggatgcccc  25140
aaatcctctt ggtctccaag tccagaacct gagacttgtc cttgatgttt gtctttccct  25200
cacccttttct gtattctggg aagatgggtt tttttccccc agatgaatct gtaaaacttc  25260
tgtgatcaca ataaaaattc tggcagtatt attttctgga acatgacaaa gtgattcaaa  25320
attatttatc tggaagacta caaaacaaga atagccagga aatttctaaa aagaaagaag  25380
aaggaggagg agaaagaagg aggaggaaaa ggaggagaag aagaaaagaa aaagaaccaa  25440
gaaagggttc tagctctacc aaatattaaa acatatcatg aagctattta aaacaatatg  25500
gttgtggata ctgaaaaaga tgtgaataaa gtggaaggaa aataaataga aatgcacatg  25560
gggattgaga ctgtgaaaaa ggcagcatct cacatcagtg agggatgttc aacacctggt  25620
gttgggaaaa ctggctagtc atttaaacca aacaactggg tcctctacct cactcctgac  25680
attaagatac atttagatga ttcaaagagt aagacagaaa aaataacacg tgaaaacact  25740
atcagaaaac aacgtgggcc aggtgtggtg ggtcacgcct gtaatcccag cactttggga  25800
ggccgaggca gacagatcac ctgaggtggg gagttcaaga ccagcctgac caacatggtg  25860
aaatcctgtc tctactaaaa atacaaaatt agctgagcgt ggtggcgcat gcctgtaatc  25920
ccagctactc aggaggccga ggcaggagaa tcacttgaac ctgggaggca gaggttgtgg  25980
tgagccgaga tcacgccatt gcactccagc ctgggcaaca agagtgaaaa tccatctaaa  26040
```

```
aaaaaaaaaa aaagccaagg tggatatttt tatagtatca gggtagatca agcttctcca  26100
atcatgacat gaaacccaga aaccataaaa gaaaagaatg ataaaattgc ccacgtaaag  26160
taaaaagctt gcacacagaa aaacaccata caggttacaa gatgagcagc aaaatcagag  26220
aaaaaacatt gcaattcagg acacacagag gctattgttc ctaatattta aaaataaaag  26280
tagtggattg tctacaaaaa gatgaagaca agaatttcag aaaaccaaat actgcatgtt  26340
ttcacttaca agtggaagct aaacactgag tacacgtgta cacaaagaat ggaaccatag  26400
gccaggcacc gtggctcacg cctgtaatcc cagtactttg cgaggccgaa gcgggcggat  26460
cacctgaggt gaggagttcg agaccatcct ggccaacatg gtgaaaccca gtctctacta  26520
aaaatacaaa aattagccgg gcgtggtggt gggtgcctgt aatcccagct actcgggagg  26580
ctgcggcagt agaatcgctt gaaccctgga ggtggacctt gcagtgagcc gagatcgcac  26640
cactgcactc cagcctgggc aacagagtga gactccatct caaaaaaaaa aaaaaggaat  26700
agaacaatag acactggggc ctacttgagg gaggagggtg aggatcaaaa acctgcctat  26760
caggtactat gcttattacc tgggtggtga aataatctgt acaccaaacc ccagtgacat  26820
gcaatttacc gatgtaacaa acctgcccat gtacccgctg aacctaaaat aaaagttgga  26880
aaaaaatata gaaattttct ttgtaatagc caaaaactgc aaacagccca ggtgtctatt  26940
agtagaatgc ataaacaaac tcgggcatgt tcatacaatg taaaactact catcaataaa  27000
aagtgatact tctcagcaat gaaaagaaac tagctactga taccagctac aacatggatg  27060
gatttcaagt gctttatgat gagagcaaga agccagacac aaaagtgtct atatatatat  27120
acagtatata tacgtatata tacacatata tacagtatat atatacatat acatgtatat  27180
atatactgta tatatactgt atatatatac acagtatata tatacatata tacagtgtat  27240
atatactgtg tatatataca tgtatatata ctgtgtatat atacatgtat atatactgtg  27300
tatatataca tgtatatata ctgtgtatat atacatgtat atatatgtat actgtatata  27360
tactgtatat atatatacac atatatacag tatatatata cagtatatac tgtatatata  27420
cagtatatac gtgtatatat acatatatac agtatatatg taaatataca tatatacagt  27480
atatatgtaa atatacatat atacatgtat atatatacac tatatatata catatatagt  27540
gtatatatac atatatacat gtatatattt actatatgat tccatttata taaagtgcca  27600
aaacagtcaa aaataatcta tgtggaaaaa atcaacaaag ggatcccccg ggctgcagga  27660
attcgatggc gcgccgacgt cgcatgctcc tctagactcg aggaattcgg taccccgggt  27720
tcgaaatcga taagcttgga tccggagagc tcgataacat ttaaatggat ctaccacatt  27780
tgtagaggtt ttacttgctt taaaaaacct cccacacctc cccctgaacc tgaaacataa  27840
aatgaatgca attgttgttg ttaacttgtt tattgcagct tataatggtt acaaataaag  27900
caatagcatc acaaatttca caaataaagc aatagcatca caaatttcac aaataaagca  27960
tttttttcac tgcattctag ttgtggtttg tccaaactca tcaatgtatc ttatcatgtc  28020
gagctaggat cccgcggccg cctactggtc ctcctggagg tagaacttgg tgaccatgaa  28080
ggactctttg ggcttgttgg tgaggctgac gggccggtct gcctcctgcg ccgtgcagag  28140
gaaccagcca gggcaggcgg cagactcgaa gctggtggtg gggccactgt ttgagcggat  28200
gaaggtgaag cgcttgttct cctccttgtt cttgctcagg tcagtgatgt taactgcctc  28260
caattggaac ctaatctcat caccagactt gacacaggcc aggcacagct tcctcccatg  28320
gagtcccagg aatagagcat caggctcaat gggcaccaca tctatcttct cttgtaattt  28380
```

```
agtatttgat tcttgcaagt atccagcaac tagttggtta ttcctcatgt agaaggtctt  28440

ctggttaaca tcccagattc tgaaggcttg catcttgcag ggtctcttcc ccaaagggtg  28500

gcaggctgtc tctgagtaga gcaagaaaag gaggagagag attaggtgtc tgacagaacg  28560

cctgcggatt tccataccgg tggatccatg gctctgtctc aggtcagtat aggagctttg  28620

atgtgaagtc agccaagaac agctgaacac tacttcctct gaggcccttt tataggaggg  28680

attgcttcct gtgaataata ggaggatatt gtccacatcc agtaaagagg aaatccccaa  28740

ctgcatccaa aaagttttct gggaatatcc actgctgcag gagtggaaag tccccagtgg  28800

aaagtcccca gtggaaagtc cccagtggaa agtccccagt ggaaagtccc cagaatttcg  28860

acggcgcgcc taccagtaaa aaagaaaacc tattaaaaaa acaccactcg acacggcacc  28920

agctcaatca gtcacagtgt aaaaaagggc caagtgcaga gcgagtatat ataggactaa  28980

aaaatgacgt aacggttaaa gtccacaaaa aacacccaga aaaccgcacg cgaacctacg  29040

cccagaaacg aaagccaaaa aacccacaac ttcctcaaat cgtcacttcc gttttcccac  29100

gttacgtcac ttcccatttt aagaaaacta caattcccaa cacatacaag ttactccgcc  29160

ctaaaaccta cgtcacccgc cccgttccca cgccccgcgc cacgtcacaa actccacccc  29220

ctcattatca tattggcttc aatccaaaat aaggtatatt attgatgatg ttt         29273
```

<210> SEQ ID NO 4
<211> LENGTH: 534
<212> TYPE: DNA
<213> ORGANISM: Artificial Sequence
<220> FEATURE:
<223> OTHER INFORMATION: codon optimized human IL-1Ra

<400> SEQUENCE: 4

```
atggaaatct gcagaggcct gcggagccac ctgattaccc tgctgctgtt cctgttccac     60

agcgagacaa tctgccggcc cagcggcaga aagtccagca agatgcaggc cttccggatc    120

tgggacgtga accagaaaac cttctacctg cggaacaatc agctggtggc cggctacctg    180

cagggcccca atgtgaacct ggaagagaag atcgacgtgg tgcccatcga gccccacgcc    240

ctgtttctgg gaatccacgg cggcaagatg tgcctgagct gcgtgaagtc cggcgacgag    300

acacggctgc agctggaagc cgtgaacatc accgacctga gcgagaaccg gaagcaggac    360

aagagattcg ccttcatcag aagcgacagc ggccccacca ccagctttga gtctgccgct    420

tgccctggct ggttcctgtg cactgccatg gaagccgacc agcccgtgtc cctgaccaac    480

atgcctgacg agggcgtgat ggtcaccaag ttctattttc aagaggacga gtga          534
```

<210> SEQ ID NO 5
<211> LENGTH: 534
<212> TYPE: DNA
<213> ORGANISM: Artificial Sequence
<220> FEATURE:
<223> OTHER INFORMATION: original human IL-1Ra

<400> SEQUENCE: 5

```
atggaaatct gcagaggcct ccgcagtcac ctaatcactc tcctcctctt cctgttccat     60

tcagagacga tctgccgacc ctctgggaga aaatccagca agatgcaagc cttcagaatc    120

tgggatgtta accagaagac cttctatctg aggaacaacc aactagttgc tggatacttg    180

caaggaccaa atgtcaattt agaagaaaag atagatgtgg tacccattga gcctcatgct    240

ctgttcttgg gaatccatgg agggaagatg tgcctgtcct gtgtcaagtc tggtgatgag    300

accagactcc agctggaggc agttaacatc actgacctga gcgagaacag aaagcaggac    360
```

```
aagcgcttcg ccttcatccg ctcagacagt ggccccacca ccagttttga gtctgccgcc    420

tgccccggtt ggttcctctg cacagcgatg gaagctgacc agcccgtcag cctcaccaat    480

atgcctgacg aaggcgtcat ggtcaccaaa ttctacttcc aggaggacga gtag         534


<210> SEQ ID NO 6
<211> LENGTH: 177
<212> TYPE: PRT
<213> ORGANISM: ArtificialSequence
<220> FEATURE:
<223> OTHER INFORMATION: human IL-1Ra protein

<400> SEQUENCE: 6

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu


<210> SEQ ID NO 7
<211> LENGTH: 29260
<212> TYPE: DNA
<213> ORGANISM: Artificial Sequence
<220> FEATURE:
<223> OTHER INFORMATION: helper-dependent adenoviral vector-human Il-1Ra
      gene

<400> SEQUENCE: 7

catcatcaat aatatacctt attttggatt gaagccaata tgataatgag ggggtggagt     60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgtacacag gaagtgacaa ttttcgcgcg gttttaggcg gatgttgtag    240

taaatttggg cgtaaccgag taagatttgg ccattttcgc gggaaaactg aataagagga    300

agtgaaatct gaataatttt gtgttactca tagcgcgtaa tatttgtcta gggccgcggg    360

gactttgacc gtttacgtgg agactcgccc aggtgttttt ctcaggtgtt ttccgcgttc    420

cgggtcaaag ttggcgtttt gatatcaagc ttatcgatac cgtaaacaag tctttaattc    480
```

```
aagcaagact ttaacaagtt aaaaggagct tatgggtagg aagtagtgtt atgatgtatg    540
ggcataaagg gttttaatgg gatagtgaaa atgtctataa taatacttaa atggctgccc    600
aatcacctac aggattgatg taaacatgga aaaggtcaaa aacttgggtc actaaaatag    660
atgattaatg gagaggatga ggttgatagt taaatgtaga taagtggtct tattctcaat    720
aaaaatgtga acataaggcg agtttctaca aagatggaca ggactcattc atgaaacagc    780
aaaaactgga catttgttct aatctttgaa gagtatgaaa aattcctatt ttaaagtaaa    840
acagtaactc acaggaaata ccaacccaac ataaaatcag aaacaatagt ctaaagtaat    900
aaaaatcaaa cgtttgcacg atcaaattat gaatgaaatt cactactaaa attcacactg    960
attttgtttc atccacagtg tcaatgttgt gatgcatttc aattgtgtga cacaggcaga   1020
ctgtggatca aaagtggttt ctggtgcgac ttactctctt gagtatacct gcagtcccct   1080
ttcttaagtg tgttaaaaaa aaagggggat ttcttcaatt cgccaatact ctagctctcc   1140
atgtgctttc taggaaacaa gtgttaaccc accttatttg tcaaacctag ctccaaagga   1200
cttttgactc cccacaaacc gatgtagctc aagagagggt atctgtcacc agtatgtata   1260
gtgaaaaaag tatcccaagt cccaacagca attcctaaaa ggagtttatt taaaaaacca   1320
cacacacctg taaaataagt atatatcctc caaggtgact agttttaaaa aaacagtatt   1380
ggctttgatg taaagtacta gtgaatatgt tagaaaaatc tcactgtaac caagtgaaat   1440
gaaagcaagt atggtttgca gagattcaaa gaaaatataa gaaaacctac tgttgccact   1500
aaaaagaatc atatattaaa tatactcaca caatagctct tcagtctgat aaaatctaca   1560
gtcataggaa tggatctatc actatttcta ttcagtgctt tgatgtaatc cagcaggtca   1620
gcaaagaatt tatagccccc cttgagcaca cagagggcta caatgtgatg gcctcccatc   1680
tccttcatca catctcgagc aagacgttca gtcctacaga aataaaatca ggaatttaat   1740
agaaagtttc atacattaaa ctttataaca aacacctctt agtcattaaa cttccacacc   1800
aacctgggca atatagtgag accccatgcc tgcaaaaaaa aaaaaattag ccaggcatgg   1860
tagcatgtac ctgtagtccc agctacttga gaggtgaggt gggaaaatca ctttagtgca   1920
ggatgttgag gctggagtga actgtgattg tgccactgca ctccagcctg gacaatagag   1980
caagaccttg tctcaaaaaa atgcattaaa aatttttttt aaatcttcca cgtaacacat   2040
cctttgccct catgtttcat aaggtaaaaa atttgatacc ttcaaaaaaa ccaagcatac   2100
cactatcata atttttttta aatgcaaata aaaacaagat accattttca cctatcagac   2160
tggcaggttc tgattaaatg aaatttcttg gataatatac aatattaaga gagactgtag   2220
aaactgggcc agtggctcat gcctgtaatc ccagcacttt gggaggctgg gtaacatggc   2280
gaaccctgtt tctacaaaat aaaaatatta gctgggagtg gtggcgcaca cctatagtcc   2340
cagctactca ggaggctgag gtggaaggat cgcttgaacc caggaggttg agactgcagt   2400
gaactgtgat cattctgctg cactgcaccc cagcctgggc aacagagacc ttgtctcaaa   2460
aaaaaaaaaa aaagagacaa attgtgaaga gaaaggtact ctcatataac atcaggagta   2520
taaaatgatt caacttctta gaggaaaatt tggcaatacc aaaatattca ataaactctt   2580
tccccttgac ccagaaattc cacttgaata aagctgaaca agtaccaaac atgtaaaaga   2640
atgtttcttc tagtacagtc ggtaagaaca aaatagtgtc tatcaatagt ggactggtta   2700
aatcagttat ggtatctcca taagacagaa tgctatgcaa cctttaaaat atattagata   2760
gctctagaca cactaatatt aaaagtgtcc aataacattt aaaactatac tcatacgtta   2820
aaatataaat gtatatatgt acttttgcat atagtataca tgcatagcca gtgcttgaga   2880
```

```
agaaatgtgt acagaaggct gaaaggagag aactttagtc ttcttgttta tggcctccat   2940
agttagaata ttttataaca caaatatttt gatattataa ttttaaaata aaaacacaga   3000
atagccagac atacaatgca agcattcaat accaggtaag gtttttcact gtaattgact   3060
taacagaaaa ttttcaagct agatgtgcat aataataaaa atctgacctt gccttcatgt   3120
gattcagccc cagtccatta ccctgtttag gactgagaaa tgcaagactc tggctagagt   3180
tccttcttcc atctcccttc aatgtttact ttgttctggt ccctacagag tcccactata   3240
ccacaactga tactaagtaa ttagtaaggc cctcctcttt tatttttaat aaagaagatt   3300
ttagaaagca tcagttattt aataagttgg cctagtttat gttcaaatag caagtactca   3360
gaacagctgc tgatgtttga aattaacaca agaaaaagta aaaaacctca ttttaagatc   3420
ttacttacct gtccataatt agtccatgag gaataaacac cctttccaaa tcctcagcat   3480
aatgattagg tatgcaaaat aaatcaaggt cataacctgg ttcatcatca ctaatctgaa   3540
aaagaaatat agctgtttca atgagagcat tacaggatac aaacatttga ttggattaag   3600
atgttaaaaa ataaccttag tctatcagag aaatttaggt gtaagatgat attagtaact   3660
gttaactttg taggtatgat aatgaattat gtaagaaaac aacaggccgg gcgggttggt   3720
tcacacgtgt aatcccagca ctttgggagg ctgaggcagg cagactgcct gagctcagga   3780
gttcgagacc agcctgggca acacggtgaa atcccgtctc tactaaaaat acaaaaaaat   3840
tagccgggtg tggtgacaca tgcctgtagt cccagctact tgggaggctg aggcaggaga   3900
atcacttgaa cctgggaggt gaaggttgca gtgagccaag aatgcgccac ttcactccag   3960
cctgggaaac agagcaagac tctgtctctg agctgagats gcrccacttc actccagcct   4020
gggaaacaga gcaagactct gtctcaaaaa aaacaaaaca aacaaacaaa aaaacaggct   4080
gggcgcggtg gctcacgcct gtaatcccag cactttggga ggccgaggcg ggtggatcac   4140
ctgaggtcag gagttccaga ccagccttgt caacatggtg aaacctcccc ccgccgtctc   4200
tactaaaaat acaaaaatta gccaggcgtg gtggcaggag cctgtaatcc cagctacttg   4260
ggaggctgag gcaggagaat cgcttgtacc cagaaggcag aggttgcact gagctgagat   4320
ggcaccattg cactccagcc tgggggacaa gagcgagatt tcgtctttaa aaaacaaaaa   4380
acaaaacaaa aaaccatgta actatatgtc ttagtcatct tagtcaagaa tgtagaagta   4440
aagtgataag atatggaatt tcctttaggt cacaaagaga aaaagaaaaa ttttaaagag   4500
ctaagacaaa cgcagcaaaa tctttatatt taataatatt ctaaacatgg gtgatgaaca   4560
tacgggtatt cattatacta ttctctccac ttttgagtat gtttgaaaat ttagtaaaac   4620
aagttttaac acactgtagt ctaacaagat aaaatatcac actgaacagg aaaaactggc   4680
atggtgtggt ggctcacact tgtaatccca gtgctttggg aggctgagac aggagagttg   4740
cttgaggcca ggagttcaag accgacatgg ggaatgtagc aagaccccgt ccctacaaaa   4800
aactttgtaa aaatttgcca ggtatggtgg tgcatacctg tagtcccagc tactcgggag   4860
gcggaggcag aaggaatcac ttgagcccag gagtttgagg ctgcagtgag ctacgatcat   4920
accacagcac tccagcgtgg acaacagagt aagaccctat ctcaaaaaca aaacaaaaca   4980
aaacaaacaa aaaaaaccac aagaaaaact gctggctgat gcagcggctc atgcctgtaa   5040
tcccagtatt ttgggaggcc caggtgggcg tatcacctga ggtcaggagt tagagaccag   5100
cctggccaac atggtgaaac cccatctcta ctaaaaatac aaaattagcc aggcatgtgg   5160
cacgcgcctg tagtcccagt tactggggag gctgaagcag gaggatcacc tgagcccggg   5220
```

```
aggtggaggt tgcagtgagc cgagatcaca ccactgcact ccagcctggg tgacacagca   5280
ataccctacc tcaaaataaa aaagaaaaag aaaagaaaag ttgctgtccc cgctacccca   5340
atcccaaatc caaacagcct ctctcatctc acagtaaggg ggaaaaatca cccaaaaaag   5400
ctaagtgatc ttttgaaaac ccaaactctt agaagtctaa gattattata gtcaactcat   5460
gaagtgtcat cataaaagat actctaatat tatttaagta gaaccacata ttggttgtct   5520
tggtatgtct agcccctggc atacaaaata tttaataaca ctgatatggt acctgtgatg   5580
tgaaaatgta ctatgagtac agctttataa atactatata tgtacctata tacagaaaaa   5640
aatacaacaa aatcataaaa gcacttatct ttgaaagagg agttacagca attttattta   5700
gttctttatt gctttgctat atattctaaa tttttttcaa tgaatatata tcacttttaa   5760
aaaaattcaa tggtctttct tataaattat ctttggcagc atgcgttttt atatatacat   5820
ataaaatgta tgggaaattt ttaaaggata cattaaatta aagcaaaata tacaaacaaa   5880
aaatcagaat acaaaaagat aaaaagattg ggaagggagg gagggagtaa ggaggaaggg   5940
tgggtgggta tagagaaata taccaaataa tggtaagaag tggggtcttg acactttcta   6000
cacttttttt aaataaaaaa aatttttttc tctctctttt tttttttag agacgaagtc    6060
tcgctatgtt gcccaggctg gtcttgaact cctgggatca agagatcctc ctgcctcagc   6120
ctcccaaggt gcttggatta caggtgtgag ccaccacgcc tggtcacttt ctacacttta   6180
atatatatat tttttcattt tcaatgtcat ttttattagt taatttataa tacccattca   6240
ccattatatt caaagtctat ttgaagaaat aaaccagaaa gaatgaaata ctctagctca   6300
catgctattc aatactaaat tacctttcaa atcacattca agaagctgat gatttaagct   6360
ttggcggttt ccaataaata ttggtcaaac cataattaaa tctcaatata tcagttagta   6420
cctattgagc atctcctttt acaacctaag cattgtatta ggtgcttaaa tacaagcagc   6480
ttgactttta atacatttaa aaatacatat ttaagactta aaatcttatt tatggaattc   6540
agttatattt tgaggtttcc agtgctgaga aatttgaggt ttgtgctgtc tttcagtccc   6600
caaagctcag ttctgagttc tcagactttg gtggaacttc atgtattgtc aggttggccc   6660
gtaatacctg tgggacaact tcagcccctg tgcacatggc caggaggctg gttgcaaaca   6720
ttttcaggta ggtggaccag gacatgcccc tggtcatggc caggtggagg catagtgcta   6780
tacagcaggc agaagtcaat attgatttgt ttttaaagaa acatgtacta ctttcataag   6840
cagaaaaaat ttctattctt gggggaaaag attatgccag atcctctagg attaaatgct   6900
gatgcatctg ctaaaccttc acatatcaga acatatttac tatagaaaga atgaaaatgg   6960
gacatttgtg tgtcacctat gtgaacattc caaaaatatt ttacaacaac taagtatttt   7020
ataaatttta tgaactgaaa tttagttcaa gttctaggaa aatacaaacc ttgctagata   7080
ttataaaaat gatacaatat atattcattt caggctcatc agaatatatc tgttatcact   7140
tgacaagaat gaaaatgcac cattttgtag tgctttaaaa tcaggaagat ccagagtact   7200
aaaaatgact tcttccttga agcttactca ccaacttcct cccagttact cactgcttct   7260
gccacaagca taaactagga cccagccaga actccttgaa atatacactt gcaacgatta   7320
ctgcatctat caaaatggtt cagtgcctgg ctacaggttc tgcagatcga ctaagaattt   7380
gaaaagtctt gtttatttca aaggaagccc atgtgaattc tgcccagagt tcatcccaga   7440
tatgcagtct aagaatacag acagatcagc agagatgtat tctaaaacag gaattctggc   7500
aatataacaa attgatttcc aatcaaaaca gatttacata ccatacttat gtcaagaagt   7560
tgttttgttt tattgcatcc tagattttat ttttttgatt tatggtttac tttaagcata   7620
```

```
aaaaatttgt caatacaact cttcccaaaa ggcataaaca aaaattcata aaacttgcat   7680
cacttgagat acttcaggta tgaattcaca actttgttac aacttactat atatatgcac   7740
acatatatat atatttgggt atattggggg ggttctaatt taagaaatgc ataattggct   7800
atagacagac agttgtcaga acttggcaat gggtacgtgc aggttcatta taccaagtct   7860
acttgtagtt gttcaaaatg tatcataata caaggccggg cgaggtsgct cacgcctgta   7920
atcccagcat tttgggaggc taaggcagga ggattgcttg aggtcaggag tttgtgacca   7980
gcctgggcaa cagagcaaga ccctgtctcc aaaaagaaaa aaaataattt tttacaaaat   8040
aaaaacaaaa tgtatcatca gacgaaatta aataagaggc aattcattta aatgacaact   8100
tttcccagct tgacatttaa caaaaagtct aagtcctctt aattcatatt taatgatcaa   8160
atatcaaata ctaatttttt tttttttttt ttttttgaga cggagtctcg ctctgtcgcc   8220
caggctggag tgcagtggcg cgatcytggc tcactgcaag ctccgcctcc cgggttcacg   8280
ccattctcct gcctcagcct cccgagtagc tgggattaca gacatgcgcc accacgcccg   8340
gctaattttg tatttttagt agagatgggg tttctccatg ttggtcaggc tggtcttgaa   8400
tttcccacct caggtgatct gcctgcctca gcctcacaaa gcagtagctg ggactacagg   8460
cacccaccac cacacttggt taattctttt gtattttttt tgtaaagacg ggatttcacc   8520
atgttagcca ggatggtctc gatctcctga tctcatgatc cgcccgcctc agcctcccaa   8580
agtgctggga ttacaggcgt gagccacccc gcccggccat caaatactaa ttcttaaatg   8640
gtaaggaccc actattcaga acctgtatcc ttatcactaa tatgcaaata tttattgaat   8700
acttactatg tcatgcatac tagagagagt tagataaatt tgatacagct accctcacag   8760
aacttacagt gtaatagatg gcatgacatg tacatgagta actgtgaaca gtgttaaatt   8820
gctatttaaa aaaaaagacg gctgggcgct gtggctcatg cctgtaatcc cagcactttg   8880
ggaggccaag gcaagttgat cgctcgaggt caagagttcg agaccagcct ggccaacgtg   8940
gtaaaacccc gtctctacta aaaatacaaa aaaaaaatta gccaggcatg gtggcacagg   9000
cctgtaatcc cagctactag ggaggctgag acatggagaa ctgcttgaat ccaggaggca   9060
gaggttacag tgagccgaga tcataccact acactccagc ctgagtgaca gagcgagact   9120
ccgtctaaaa aaaaaaaaaa aaaaaaagat acaggttaag tgttatggta gttgaagaga   9180
gaactcaaac tctgtctcag aagcctcact tgcatgtgga ccactgatat gaaataatat   9240
aaataggtat aattcaataa ataggaactt cagttttaat catcccaaac accaaaactt   9300
cctatcaaac aggtccaata aactcaatct ctataagagc tagacagaaa tctacttggt   9360
ggcctataat cttattagcc cttacttgtc ccatctgata ttaattaacc ccatctaata   9420
tggattagtt aacaatccag tggctgcttt gacaggaaca gttggagaga gttggggatt   9480
gcaacatatt caattataca aaaatgcatt cagcatctac cttgattaag gcagtgtgca   9540
acagaatttg caggagagta aaagaatgat tataaattta caacccttaa agagcttata   9600
gctgggcgtg gtggctcatg cctgtaaatc ccagcacttt gggaggctga ggcgggtgga   9660
tcacctgagg ccagaagttc aagaccagcc tagccaacat ggcgaaaccc tgtctctaca   9720
aaaaatacaa aaattagccg ggtgtggtgg cacgtgcctg tagtcccagt tacttgggag   9780
gccgaggcag gagaatcgct tgaacctagg aggtggaggc tgcagtgagc cgagattgtg   9840
ccactgcact ccacttcagc ctgggcgaca agagcaagac tccgtcacaa aaaaaaaaaa   9900
aaaaaaaaag cttaaaatct agtgggaaag gcatatatac atacaactaa ctgtatagca   9960
```

-continued

```
taataaagct cataatctgt aacaaaatct aattcgacaa gcccagaaac ttgtgattta  10020
ccaaaaacag ttatatatac acaaaaagta aacctagaac ccaaagttac ccagcaccaa  10080
tgattctctc cctaagcagt atcaagttta aagcagtgat tacattctac tgcctagatt  10140
gtaaactgag taaaggagac cagcaccttt ctgctactga actagcacag ccgtgtaaac  10200
caacaaggca atggcagtgc ccaactttct gtatgaatat aagttacatc tgttttatta  10260
tttgtgactt ggtgttgcat gtggttatta tcaacacctt ctgaaagaac aactacctgc  10320
tcaggctgcc ataacaaaat accacagact gagtgactta acagaaactt atttctcaca  10380
gttttggagg ctgggaagtc caaaattaag gtacctgcaa ggtaggtttc aatctcaggc  10440
ctcttctttg gcttgaaggt cttctaactg tgtgctcaca tgacctcttc taacaagctc  10500
tctggtgtct cttttttttt ttttttcttt tttgagacag agtctcactc tgtcacccag  10560
gctggagtac agtggcacaa tctgggctca ctgcaacctc caactcccgg gttcaagtga  10620
ttctcatgcc tcaccctccc gagtagcttg gatgacagga gcccgctacc acacccagct  10680
aatttttgta tttttagtag agatggtgtt tcactacatt ggccaggctg gtctcaaact  10740
cctgacctcg tgatccaccc accttggcct cccaaagtgc tgggattaca ggtgtgagcc  10800
actgcgcccg tcctggtgtc ttttcatata agggcactaa tccaatcaga cctgggccca  10860
accctcccga cttcttctaa ctgtaattac cttccaaagg ccctgtctcc aaataccatc  10920
acactggggg ttaggacttc aaaaaaggta tgggggggt gtgggaggac ataaatgctc  10980
agtccataac aagcacccaa cataaaaatg gctagaacag atcacaaaaa aaaggtcctg  11040
tatggctttg gggaagggct caaccccaaa atatctgaga gctctggagg ggcctagaag  11100
tggtaaatga atgaaaacgt ggttactctc cagatctgcc tttcccaaat atggccattc  11160
ttggctgaat cagaaatcaa aggacaggtt attaattact agctctaagt tacttaccat  11220
ttgctgagac agttcagaaa tctgactgca tctcctcaga gatctagaac acagttctca  11280
aattctaact tacttgtgat atacttgtga atgataaaaa tcgctacagg tacttttatt  11340
aatctgaaag agtattgaga aattaccttt cattctgact tttgtctgga atgaaaatca  11400
atacttttgc tataatcgat tactgaaata attttacttt ccagtaaaac tggcattata  11460
atttttttta atttttaaaa cttcataatt ttttgccaga ctgacccatg taaacataca  11520
aattactaat aattatgcac gtcacatctg taataatggc cttcatgtaa acatttttgt  11580
ggtttacaca taaaatctct aattacaaag ctatattatc taaaattaca gtaagcaaga  11640
aaattaatcc aagctaagac aatacttgca acatcaattc atcatctgtg acaaggactg  11700
cttaagtctc tttgtggtta aaaaggaaaa aaaaaaaaaa gacatgttgg ccagatgcgg  11760
tggctcacac ctgtaatccc agcactttgg gaggctgagg tgggcggatc acccctggcc  11820
tgcccaacat ggtgaaaccc cgtctctact aaaaacacaa aaattagctg ggcgtggtgg  11880
cgggcgcctg taattccagc tactcgggag gctgaggcag gagaattgct agaacccagg  11940
aggcagagat tgcagtgagc tgagattgca ccattgcact acagtctggg caacaaaagt  12000
gaaactccat cttaaaaaaa aaaagacaat gttcgtgggt ccaaacaaga cttaatggaa  12060
gtgagtctaa aaatgagcta tgtgggccag gcgtagtggc tcccacctgt aatcccagca  12120
ctttgggagg ccgaagcagg cagatcatga ggtcaggaga tggagaccat cctggccaac  12180
acggtgaaat cctgtctcta caaaaattag ctgggcgtgg tggtgcctgc ctgtaatccc  12240
agctactcag aaggctcagg caggagaatc gcttgaacca gggagtcggt ggctagagtg  12300
agccgagatt gcatcactgc actcctgcct ggtgacagag caagactcca tctcaaaaaa  12360
```

```
aacaaacaaa aataaaagat aaaaatgagc tatgtgaatt aaaagaggta taacaataga 12420
taaaccatat tttatttaat tcctagtaat gagtaatatt tccaaacttc tggaatgggc 12480
agaaattgct agttggcata tttttacctt ttatattcag atacattaaa attctcaaaa 12540
aaaaacacct caaagcagat gatccgccat ctccttggat aatttgtgtt aactcaggat 12600
aacagaaaac caaaattatg agttactgat gcaatattcc taaatgtaaa aataattaaa 12660
gctaatagta gattcatctt ccaatttcat atcagtctta caaataaact acatatataa 12720
cttgcttgcc ttcccttctg agggataaag ctgttagaag aattaaaatc agcattcttg 12780
actattcaac caagggaggg ataaattatt actcattcta gggacatggg ctcataacta 12840
ctacatgtgt aaggacatga atttacccaa tattacaatt tttcctttta ttagtgtgta 12900
cagtggaaga atagacatgt tcactctgga caaaaaaaaa attatactta tcagttatca 12960
gaagcacaat gctgaagaca gtagttccat aacaatttga agtatgtgat cgaactagta 13020
gattatctta gtagtagtga attattgtaa atgttagtaa tttggcagcc actgggcaga 13080
aaaataagaa ttgaggctca atattgatat taatggtggt gattgacaca taaattttat 13140
caagtctaca caatataaaa ttacagaaag gtagaagagt ataccagtac aacttcaaca 13200
tatcttcact acaagggagt aaaatgacat ggcctagtta ctatctaatg aactgcagaa 13260
aactaaaaga aaactccaag gcaactcttc tctgctgatc tggttggtcc ttttcctacc 13320
ttttgcaata cccagataca aacaatggat agaaaacaaa gtagacttgt agtatgcagg 13380
tcacagtgct aaattcacag aaagaaaccc ctgaactgaa ctgctctatt tcctggtggt 13440
cacaaagagt aattctggtt tacacctaca gattgatgtc aatctacacc ctgttgataa 13500
cagtgtggcc aaggacaaaa aaaaggtgct ccgttttacc aattctgtaa aaaattattg 13560
gcagggtaag ctcggctagg gcaggattac atttctagga ctaccatccc cgaaatttag 13620
aagatattat atccacataa agcatatctt tcacattaat ttgcaaaaat ctaaaagctt 13680
tttcttagct caagtgtgtc caagtttacc ctggcagttt aaaacgatag ttacaagcag 13740
catgggttgt atcagacaca tttgagggcc aatttcatgt aagtgatatt gggcaagtta 13800
cttcaactat ctgtgcctcc aaggtcatac tagtgtttat ttacctaaag ggtacctgtt 13860
atgtaacttt agggtgttta cattagataa tgcctgcaaa atatttactt caacgcctaa 13920
aacatagtta agtattcaat aaatacctac tattgtcact actaacttaa aagtttagag 13980
attaagagca gaatctgggg tgagacaaac ttaggttcaa atcctagtat tgttgggtaa 14040
tcttgggcaa gttacttaac ctctctgatt tgtgtaattt aaaaaattag ttaatataca 14100
taacagggct tagaagagta tctagcacat agcaccattt aagcatttgt tattgctaac 14160
atgcaaacaa tttaagggaa agaaattttt taaaaaggaa gagggatttg caaactaaaa 14220
acaatgagta tcttatgttc aaagaaaact aacaaacagc cagctctagc aataattaaa 14280
ttcactatat actggggcag gcatcacacc ccaaagctaa aagcgtctac ctaggccagg 14340
cacggtggct catgcctgta atcccagcac tttgggaagc agaggcgggc agatcgcttg 14400
agctcaggag ttcaagacca gcctggacaa catggcaaaa caccatctct acaaaaaata 14460
caaatattag gccgggcgca gtggctcacg cctgtaatcc cagcactttg ggaggccaag 14520
gcgggtggat cacctgagat caggagttcg agagtagcct ggccaacatg gtgaaacctc 14580
gtctctatta aaaatacaaa aaattagcca ggcatggtgg caggcgcctg taatcccagc 14640
tactcagggg gatgaggtag gagaatcgct tgaacccggg aggcagaggt tgcactgagc 14700
```

```
cgagatcatg ccactgtact ccagcccggg caacaagagc gaaactccat ctcaaaaaat  14760
aaataaataa ataaataaaa taaagtacaa atattagcca gggatggtgg tgcgcacctg  14820
tagtcccagc tacttgggag gctgaagtgg gagaatcccc tgagcctggg gagaatcacc  14880
cgagcccggg aagtcgaggc tgcagtgagc agtgattgtg ccactgcact ccatcctagg  14940
tgacagagtg agaccctgtc tcaaaaaaaa gaaattggca gaattaagta agttgatgtt  15000
tagagatgaa aaatcaacat tttttcctca gcaactgaat aaaaacaaca gccactacca  15060
ttttttgag tacctatttg tagcctattt tttaactggt attactcgag agagagagag  15120
ctaggttcga gacagagctc cttctcttaa taactgtatg acctagggta tgtctgttag  15180
cctctctgag gcttcaaagg ttcctcatct gtaaaatggt aataatcata ccattgctac  15240
agggctgttt tgaagactaa ttaggactat gtaagtaaac atgatgatgg ctattattac  15300
tgttccccgc caggggccat gcaagggttg ctgattcaca tagactgtct tataatcctc  15360
tcaataactc caagaggtag ccagcacctc agatatacat aaaatgactt aagcccagag  15420
aggtgaagta agttgcccac agccacacaa ctagtaaata gcccaaacaa gctggattcc  15480
cagttagact ccgttaatag cactgctctt taccttaagt cattacaatg cctaatatga  15540
aatagaatcg cttctttctt agggttcaag tggttaatta tttaatgtat tcattcaaca  15600
aaccatcatc gaggacctct tacaagccaa gtactgtgct aagtgctaga gttacggcgg  15660
tgattcctgc ccttaaaaag ttttagtggg agaaacaaca ggtaaccagg tcattgccaa  15720
aacaacaaaa ataatcataa taaagcaggc taaagcatat ttaactggcc ggggttttga  15780
ctattttagc aagcatgatc agaacggttg aggagggagg ccagcagctt ggccggttca  15840
acaaacaaga aaaaaccagt gagggtggag ctaagatacc agaggctgat tacggttaag  15900
aatgttcttg aaggtaagga ccagattctc attttctata tcctggggca tcggtcagca  15960
tggaatctgg attctagcac atgtgaattt cggcttgaaa tgacctaatg ccttttccct  16020
agttccttcg tgtgtcaaat acgcatggtt accgctacca gagctgtagt ggggcttcaa  16080
tgaggccatg agcatctcca taaagatgaa ctacagtgtg tgcaaaacta aaggcaaaac  16140
ctggtcccca cacgccctcc caggtggtcg ctttccgtgc cgaggcccct ccagaggtgc  16200
cccgagaacc tcaccatcgc accccaaact tccagggaag ggcctctccc gagaaagccc  16260
ccacgccccc accccgcgcc atcattcccg aatctgccct cggcccctcc ccgcagcacg  16320
ctcgcaggcg gcacatgtca accaaaacgc catttccacc ttctcttccc acacgcagtc  16380
ctcttttccc agggctcccc cgaggaggga cccaccccaa accccgccat tccgtcctcc  16440
ctgccgccct cgcgtgacgt aaagccgaac ccgggaaact ggccgccccc gcctgcgggg  16500
ttccctgggc ccggccgctc tagaactagt ggatcccaat tgaaggcctg gtctaaatga  16560
ctccaaaatc accacttaat tcaagagact gatttccctg agtcaggccc cttaaagcag  16620
ctatttcaat gggacaggga aacaacccta ggatctggat tagaatcact tgggggctgc  16680
cacaccccca gggctctgat cctgcccttc tcccacacgc acattcacat actgctgcag  16740
tgaccttcca tttctaatgg gttcctgggc catctgtcag gtatagggaa tggaaaaggg  16800
gttggggagg ctctgcttca gaaagtttgt gtcaggggct cccagagcct ccacagatag  16860
atagcagggg tccccaccct accatggcag ctataaatgt gatcaacatt tattggccta  16920
ggatacagca gttagcaaaa tgcctgatgt agttcccact ccgtggaggt tgcaggctag  16980
ccaagaagtc atgagttcag caacccttac gcaccagtgg gatgagattg gaccaggccg  17040
agggtagtct tgggaacact cagcatttgt ctgagggcca gaagaggctg cttgccctca  17100
```

```
gacaggaggt cagcatcttt attgtagccc atgacacctc tacaccattg ctcttctggt  17160
cttatggaag acatctttgg gcctgataac agcggagtct gtgtcccact tgtccaggct  17220
ggagtgccac atcaggcaca ctccagttgc agggacagca cagacaagtt tcaggaaggc  17280
tggtggcctc caggaggtta accttataag gccagattgt aacctagttg aaaaacatac  17340
acatgccatg ataataaaag aacctaggca ccattacaag agaaaaaatc atttttgtag  17400
atacgagcat ggattcttgg gtgggtcaga cacactgggc ttgtgctctg actgcactgt  17460
ctcccctacc tgaccttggg taaaccataa gactgctgca tgactcagtg tccaccccaa  17520
aaaagtaccg gtagatattg gccacagtag atatcagcta gagtggactc tcatgacaat  17580
gaggggagat gtattcccca tcttaggcac ctgggactct accttccatc ttctgctccg  17640
tgtctctcca tccccaggct cttcagaact cagggagtcc agaatgtcag ctcccagatt  17700
tcagccttca gaaaggaaac ccattaccgt tcagttgaac aaatgttgtc tgagccccag  17760
atctgggctc agaggccatc taggctatga gacaagaggg gaacaaagca ccgtctgcac  17820
tcactcacca cactcacttg ctgtcccagg tcacatccat cgggtagaga atctaagagg  17880
ctgagctagc tcccgccacc agcccagccc accccacctg gccccttcct tccttctaca  17940
aaatatgcac cacctgtcaa agggtgggca gtgccaggcc tgcatacaga gcactgagtg  18000
taaaagcaga catggaccct gacctccagg agcttccaat tttcttgaag agacaaatca  18060
gctggcattt cagtccagtg tgatctgctc ttggtgagca cagacctagg gagttggggc  18120
agcttcccag aagaactgca gtccaggctg agggcagaga aatgagggga atggcgagga  18180
attggggagc aggggggagc tcagtagaga gccaagggcg ggaggtgaga agtccgtgtt  18240
gggccaggag ctaccctccg gtggccacag ccgaagtcga ggatgccttt ggaactcatc  18300
cccacttctc tctttctgta tgtagccgtc caagaacaag tcacctccaa gtgtagccgg  18360
atcaaggcaa gccccccatc tagcaagcac ttgatgccac ccagaactgg gcttcttcag  18420
aacaatctga gtccaggaat gatcccactc accaggcacc agagctgcga gggcatggga  18480
gtgatctcac caactctggg gaagcggcaa ggaattttca cctccagccc ccagtgtccc  18540
atcctctcac actcaggcca gactcccctg ggcagacttg actctgtctg ccagcatatg  18600
cagagcccca aggccacccc accagaagtg cccctgcctg ggttctgtcc cagctccctg  18660
ggcacccagt ccttgagtcc ccaccagctc agacggccta gtgtgccaag aatgcccact  18720
gcgttcaaca atgctgcatg ggtcacagcg gcagcagctg tgaccacagc agtttcgggg  18780
aaaacacccc tcagccaagt ggataatagc gttcagcagc actcaccttc tggccaggcc  18840
tgccttcaga ggccatctga ttgggaggca caagtgcccg ctgcgatggg aacacaagtg  18900
cccctggcca acaaccccag cttcagcctg ctgggcagcc agagcctcag gcagagcccg  18960
gtacagggcc cggtgcctgt agcaaacacc accaagttcc tccagcaggg tatggccagc  19020
tttagtcccc tgagccccat acagggcatc gagccaccaa gctatgtggc tgctgctgcc  19080
accgctgctg ctgcttctgc cgttgctgcc agccagttcc caggtccgtt cgacagaacg  19140
gatattcccc ctgagctgcc acctgccgac tttttgcgcc agccccaacc cccactaaat  19200
gatctgattt cgtcacctga ctgcaatgag gtagatttca ttgaagctct cttgaaaggc  19260
tcctgtgtga gcccagatga agactgggtg tgcaacttga ggctgatcga cgacattttg  19320
gaacagcatg ctgctgctca aaatgccaca gcccagaatt ctgggcaagt cacccaggat  19380
gctggggcac tttaaatctg agcaggatgc ccatagaaac cccatggtg acatcactct  19440
```

```
aggaagtggt gtcgatccat acccgcagtt gtctcccgtt acaatttgag tggtgttgtc  19500
agcccatgct tatccctctc tctacctgtg acaaaatgga aagctggtga tttttcaagc  19560
tacgtgtaca tatttgaaaa ttttgtaaat ggttttccta aacattaatg acagaagtat  19620
ttatacttca ttttgtgact ttgtaaataa agcgacggct tttgtttcag tagagttgtg  19680
tttactatgc attgttttgt gtttattata caatgttaca aatatgcaga ccgtgttgtt  19740
tgctccagtg ataccttgtt aagctaggtg gctgagtcgc ttatggtttt aatgcaatga  19800
gcaatgtgga tatgaccaag agttgttgtg caagttgaca aatgccaaat agaaaaccac  19860
ttggccattt atttctatgt tcactaaaaa tcctattgcc ttgtgtgatt cttaatctct  19920
tttgcgaacc tttcagtctc cgctagctct ttcctaatga gctttacagc agaagctgtt  19980
ttatcgttaa gtgccccaca gagacacttt accaggaggc tgggagagtt ctccagattt  20040
gggagaggcg cagagacagt gtgtgagccg agccctgtct cagcaatcca cctggaggag  20100
ctagagtatc ctcctccctt taccattcag accgagagaa aaagcccagc ttgtgtgcac  20160
cctcgtgggg ttaaggcgag ctgttcctgg tttaaagcct ttcagtattt gttttgatgt  20220
aaggctctgt ggtttggggg ggaacatctg taaacattat tagttgattt ggggtttgtc  20280
tttgatggtt tctatctgca attatcgtca tgtatattta agtgtctgtt atagaaaacc  20340
cacacccact gtcctgtaaa cttttctcag tgtccagact ttctgtaatc acattttaat  20400
tgccacctcg tatttcacct ctacatttga aatctggcgt ctgtttcaag ccagtgtgtt  20460
ttttcttcgt tctgtaataa acagccagga gaaaagtgcc tctatgtttt tatttttcaa  20520
gggagtattc agtacctaca aacccaagtc aggaagcctg ctagtggctt tggttctttc  20580
agaggctgct cgatgccttg tgtgtcagaa agaaagattc agcagttttg catcatggca  20640
aagaagcctg ttattttggg gctcagcccc tcattttata gaggatgaaa cagaggggga  20700
tgggaggtca caaagacaac tgccccggga gcaggtgtgg gggagacttg ccctgagggt  20760
ctagacgctc tgcaccaccg tcctgtctcc cttgctgaag accacacatg cccttctttg  20820
accagaccct gccacctgat aggccaggac ctggtaggcg ggtacccagg tttcatggat  20880
ggaaccacat ctccccaaaa gtggggaggt agctactggg atgcacgcct cccgccatgt  20940
gctataggag agcagctgaa gcaacagttg ggatcagatg tagtcacaat tgaatgcatc  21000
atcacattta tccctctaag tggctgggag agttgatatc ctcatcccta aggtacaaaa  21060
tgttccaatt tgatcagtgg ctttcaggag ctgagaaagg catgtgctct gaggcagagc  21120
tgttatgtcc cgcagagcct aaaaatgctc taagaacatg ctccctgcca aaattctcaa  21180
tggctgtgac aagggacaac gatcgaccaa tgggggtgga agcagacctc cgcagtccag  21240
gggccagagc taggacagag gggtcggaga aagagtcatt ttcccaacac tccagctctt  21300
ggccagtcct cacacagtcc cctcctgctt cctgctgaga gagatatcct cataggtctg  21360
ggtaaagtcc ttcagtcagc tttcattccc tgtcaccaac tttgtctctg ttctccctgc  21420
ccgtctcagg cagcactcct caggaaacct ctccaagagc cagcctcact gcagcgccca  21480
ctattgtccc tctgcctcaa gtgtcccatc catgccaggc cccaggcagg ctgcagcttt  21540
ccctcagggc cacaccaaag cacttgggct cagctgtgct gtccccctcc atcactgagc  21600
tcaggggcag caggggtggg gtgccaggag gcccattcac ccttctctgg ctctgtgttg  21660
gacccacctg cccagccact gctgcttaga acctacccgc tgggaaaatg aagccctccc  21720
ggaggggcca cctcaacctg agagcctcac ggatcacagt tgtccccact cagctctgcc  21780
agccctcaga gacccataga taaaagctga gcttggctcg cagagctggt tccatcttcc  21840
```

```
attcccagag ggttcaactt cctaccccaa ccacacaggg aacctcaagg ctgagccagt  21900
gtgggctgca gtgcagacca gcttcctgga cacgtcctgc cacctgaccc caggctggcc  21960
tcactgcccc tggcactcct gaccctatcc tcattcctcc tggcagtgcg tgttctgcca  22020
ttccgctttc ccttagctgt cctctcactg tactgtcagc ttctcctttt ccaggtgccc  22080
cccaggggct ttccacatga ccctgtcacc ccacagccca tccagcacca attccagctc  22140
tctgccaccc ttcaaaggag tgacagtgcc ctgcttcacc tcccactcac ccctcaaccc  22200
agagcaatct ggctccagtc ttgcctcctt ccccctaagt actctagtca cagttccaaa  22260
ttcctcctgg tcataaagcc aaatgaagct tcctggtcct cagcggactt gccacttcag  22320
cagtactgga ctctctcctc ccagaaacct gtttcccctt ggctcctgga gcccacactc  22380
tgctggaatc cttctgcctc tctggcctgt agcctggccc tctctcccaa cctgaggtcc  22440
attctctcct gctcctccac aagatgttgc tccttccatt acttcctccc tctcaaccaa  22500
agctccttca ttagctcttt atcttctggt ttcttcccct gggcagacga atggattcaa  22560
gagcctgtgg cccagcagcc cagcactcca ggatctcagc acttcagcat cccagtaccc  22620
tagcatctca ataccccagc accccagcac catagtattc cagcacccca ttgtccaagc  22680
atctcagcac tccagcatcc cagcacccca acactccagc agcccagaat ctcagcaccc  22740
tagcactgca gcatctcagg accccagcac ttcagcatcc cagcacacta gtactccagc  22800
atctcggcac cccagcacct aggcatccca acacccagca ccccagcact taagcatccc  22860
accactacag tatctcaaca ctccagcacc ccagcaccat agtgttccag caccccagca  22920
tcccaacacc ccagcactta agcatcccaa cacctcggca tcccaacacc ccagcactgc  22980
agcatctcag caccttagca tcccagtgcc ctagcatctc aatgctccag cacaccagta  23040
ctacagtatt ccagcacccc agcactccag catctcagca ctgcagcact gcagcactcc  23100
agcatcccaa aatcccagca tcccaacacc ccagcagacc agcagaccag catctcagca  23160
ccgcagcatc caaggactat cccagcatcc cagcaaccca gcacctcagc atcccaacac  23220
cccagcattt cagcatggca acaccccagt accccagcac ttcagcaccc cagtatccca  23280
gcatctcagc gacccagtat cacaaaacct cagcatccta gcaccccagc accccagcac  23340
cttagcacct tagcatccca gcatctcagc gcctcagcat cttgatattc tggctgaggt  23400
cagcgtggtg tatctagtca gggtcctaac tttcacttcg cagggaaatg ctgctggact  23460
gggtctcatg ttgggctgaa gctctctaga ccccttgaag acagcataaa agagcttgga  23520
gacgctgggt gtcccccatg gaagagttca ctctcatcct gctttgacaa cagccttctc  23580
tggggtccct cacgggcccc tctttcttac tgcaagtttg tctctgagaa gactgtgatg  23640
cagaagtcac tcagctgcct gtggctcctg aagagctgaa ggtggaggcc tgtaggcctc  23700
cctatgagag gcgcagaaaa aaccatgatt gctagtgggg aggtgctccc tctacaaccc  23760
actccataat ctgcccccgc ccagctctga ggccagcccc aggggaaaat gccagatccc  23820
cagggaggtg tgtgagacct caggggctcc ctcctccctt acagcaggct caggcccctg  23880
ggggcctcag ggccaaggtc tgtgggtaag ctactatctc tcacttgtcc tctagccaca  23940
aaagccaggg agatctggca atggacatga ggttctgaag aagcacatat gactggcttc  24000
ctaatgcgtg gttgttcagt gattcaataa acacgcatgg gccaggcatg gggaaataga  24060
caaacatgat ccccaacctc tcccagagtg aactgggagg gaggagtgtt catccctcag  24120
gattacacca gagaaacaaa ccagcaggag atatatatgg ttttgggggg tcaagaaaga  24180
```

```
ggaaaaacct ggcaaggcaa gtccaaaatc ataggacagg ctgtcaggaa gggcagcctg  24240
gaacctctca agcaggagct gatgctgcag tccacaggca gaatttcttc ttcctcgggg  24300
aaatctcagc tttgttctta aggcctttca actgattggc tgaggtctgc cccttccccc  24360
acattctcca ggataatctt ccttacttaa agtcaactat taatcacagc tacaaaatcc  24420
cttcacagct acacatagat cagtgtttga ttgacgaaca gcccctacag cctagccaag  24480
ttgacacata aaactaacca tcacaggggg acaaatgatg taaacacatc aacaaataaa  24540
acagtaacaa gttaaggtct atggaaaaaa cacagaaggg gcagagagaa agaaagcaag  24600
aaggagagtc ccagtttgct agggcttgtg ggaagtgggg agcagttctc tttagctagg  24660
atatttggga aaggcatatc tgaaggagtg atatttgagc ttagattaaa agatgggaag  24720
gagcaagcca tgcaaagagc taggatgttc caagcagaga cggaacagca agtgcaaatg  24780
tcaggaggaa tagaaggagg ctggtgggtg gggtccagtg agcaagagga gggcaggcag  24840
gagaggggat ggggaggtgg gcaggcccag accacccagg gccctggaga ctatcctgat  24900
ccaacaaggg aagccttgag tcacttcagt gtccatgtgg agaatggacc tcagactgaa  24960
tgagggaggc agtaaggagg gcctctacct ccagggcttc gccctgtgga ctgcgcatag  25020
acatctccaa ctcagaaagt ctgaaccaaa ctttccatag ttcccccaag tctgggcatc  25080
ctcctactca gtgaaaggca gccatcacac ctccctgccc tgctcccgga tgccccaaat  25140
cctcttggtc tccaagtcca gaacctgaga cttgtccttg atgtttgtct ttccctcacc  25200
ctttctgtat tctgggaaga tgggtttttt tcccccagat gaatctgtaa aacttctgtg  25260
atcacaataa aaattctggc agtattattt tctggaacat gacaaagtga ttcaaaatta  25320
tttatctgga agactacaaa acaagaatag ccaggaaatt tctaaaaaga aagaagaagg  25380
aggaggagaa agaaggagga ggaaaaggag gagaagaaga aaagaaaaag aaccaagaaa  25440
gggttctagc tctaccaaat attaaaacat atcatgaagc tatttaaaac aatatggttg  25500
tggatactga aaaagatgtg aataaagtgg aaggaaaata aatagaaatg cacatgggga  25560
ttgagactgt gaaaaaggca gcatctcaca tcagtgaggg atgttcaaca cctggtgttg  25620
ggaaaactgg ctagtcattt aaaccaaaca actgggtcct ctacctcact cctgacatta  25680
agatacattt agatgattca aagagtaaga cagaaaaaat aacacgtgaa aacactatca  25740
gaaaacaacg tgggccaggt gtggtgggtc acgcctgtaa tcccagcact ttgggaggcc  25800
gaggcagaca gatcacctga ggtggggagt tcaagaccag cctgaccaac atggtgaaat  25860
cctgtctcta ctaaaaatac aaaattagct gagcgtggtg gcgcatgcct gtaatcccag  25920
ctactcagga ggccgaggca ggagaatcac ttgaacctgg gaggcagagg ttgtggtgag  25980
ccgagatcac gccattgcac tccagcctgg gcaacaagag tgaaaatcca tctaaaaaaa  26040
aaaaaaaaag ccaaggtgga tatttttata gtatcagggt agatcaagct tctccaatca  26100
tgacatgaaa cccagaaacc ataaaagaaa agaatgataa aattgcccac gtaaagtaaa  26160
aagcttgcac acagaaaaac accatacagg ttacaagatg agcagcaaaa tcagagaaaa  26220
aacattgcaa ttcaggacac acagaggcta ttgttcctaa tatttaaaaa taaaagtagt  26280
ggattgtcta caaaaagatg aagacaagaa tttcagaaaa ccaaatactg catgttttca  26340
cttacaagtg gaagctaaac actgagtaca cgtgtacaca aagaatggaa ccataggcca  26400
ggcaccgtgg ctcacgcctg taatcccagt actttgcgag gccgaagcgg gcggatcacc  26460
tgaggtgagg agttcgagac catcctggcc aacatggtga aacccagtct ctactaaaaa  26520
tacaaaaatt agccgggcgt ggtggtgggt gcctgtaatc ccagctactc gggaggctgc  26580
```

```
ggcagtagaa tcgcttgaac cctggaggtg gaccttgcag tgagccgaga tcgcaccact  26640
gcactccagc ctgggcaaca gagtgagact ccatctcaaa aaaaaaaaaa aggaatagaa  26700
caatagacac tggggcctac ttgagggagg agggtgagga tcaaaaacct gcctatcagg  26760
tactatgctt attacctggg tggtgaaata atctgtacac caaaccccag tgacatgcaa  26820
tttaccgatg taacaaacct gcccatgtac ccgctgaacc taaaataaaa gttggaaaaa  26880
aatatagaaa ttttctttgt aatagccaaa aactgcaaac agcccaggtg tctattagta  26940
gaatgcataa acaaactcgg gcatgttcat acaatgtaaa actactcatc aataaaaagt  27000
gatacttctc agcaatgaaa agaaactagc tactgatacc agctacaaca tggatggatt  27060
tcaagtgctt tatgatgaga gcaagaagcc agacacaaaa gtgtctatat atatatacag  27120
tatatatacg tatatataca catatataca gtatatatat acatatacat gtatatatat  27180
actgtatata tactgtatat atatacacag tatatatata catatataca gtgtatatat  27240
actgtgtata tatacatgta tatatactga gtatatatac atgtatatat actgtgtata  27300
tatacatgta tatatactga gtatatatac atgtatatat atgtatactg tatatatact  27360
gtatatatat atacacatat atacagtata tatatacagt atatactgta tatatacagt  27420
atatacgtgt atatatacat atatacagta tatatgtaaa tatacatata tacagtatat  27480
atgtaaatat acatatatac atgtatatat atacactata tatatacata tatagtgtat  27540
atatacatat atacatgtat atatttacta tatgattcca tttatataaa gtgccaaaac  27600
agtcaaaaat aatctatgtg gaaaaaatca acaaagggat cccccgggct gcaggaattc  27660
gatggcgcgc cgacgcgcat gctcctctag actcgaggaa ttcggtaccc cgggttcgaa  27720
atcgataagc ttggatccgg agagctcgtt aacatttaaa tggatctacc acatttgtag  27780
aggttttact tgctttaaaa aacctcccac acctccccct gaacctgaaa cataaaatga  27840
atgcaattgt tgttgttaac ttgtttattg cagcttataa tggttacaaa taaagcaata  27900
gcatcacaaa tttcacaaat aaagcaatag catcacaaat ttcacaaata aagcattttt  27960
ttcactgcat tctagttgtg gtttgtccaa actcatcaat gtatcttatc atgtcgagat  28020
ccgcgcggcc gctcactcgt cctcttgaaa atagaacttg gtgaccatca cgccctcgtc  28080
aggcatgttg gtcagggaca cggctggtc ggcttccatg gcagtgcaca ggaaccagcc  28140
agggcaagcg gcagactcaa agctggtggt ggggccgctg tcgcttctga tgaaggcgaa  28200
tctcttgtcc tgcttccggt tctcgctcag gtcggtgatg ttcacggctt ccagctgcag  28260
ccgtgtctcg tcgccggact tcacgcagct caggcacatc ttgccgccgt ggattcccag  28320
aaacagggcg tggggctcga tgggcaccac gtcgatcttc tcttccaggt tcacattggg  28380
gccctgcagg tagccggcca ccagctgatt gttccgcagg tagaaggttt tctggttcac  28440
gtcccagatc cggaaggcct gcatcttgct ggactttctg ccgctgggcc ggcagattgt  28500
ctcgctgtgg aacaggaaca gcagcagggt aatcaggtgg ctccgcaggc ctctgcagat  28560
ttccataccg gtggatcatg gctctgtctc aggtcagtat aggagctttg atgtgaagtc  28620
agccaagaac agctgaacac tacttctgct gaggcccttt tataggaggg attgcttcct  28680
gtgaataata ggaggatatt gtccacatcc agtaaagagg aaatccccaa ctgcatccaa  28740
aaagttttct gggaatatcc actgctgcag gagtggaaag tccccagtgg aaagtcccca  28800
gtggaaagtc cccagtggaa agtccccagt ggaaagtccc cagaatttcg acggcgcgcc  28860
taccagtaaa aaagaaaacc tattaaaaaa acaccactcg acacggcacc agctcaatca  28920
```

-continued

```
gtcacagtgt aaaaaagggc caagtgcaga gcgagtatat ataggactaa aaaatgacgt  28980

aacggttaaa gtccacaaaa aacacccaga aaaccgcacg cgaacctacg cccagaaacg  29040

aaagccaaaa aacccacaac ttcctcaaat cgtcacttcc gttttcccac gttacgtcac  29100

ttcccatttt aagaaaacta caattcccaa cacatacaag ttactccgcc ctaaaaccta  29160

cgtcacccgc cccgttccca cgccccgcgc cacgtcacaa actccacccc ctcattatca  29220

tattggcttc aatccaaaat aaggtatatt attgatgatg                        29260
```

EFFECTIVE DOSAGES OF AN ADENOVIRAL-BASED BIOLOGICAL DELIVERY AND EXPRESSION SYSTEM FOR USE IN THE TREATMENT OF OSTEOARTHRITIS IN HUMANS, AND COMPOSITIONS COMPRISING THE SAME

CROSS-REFERENCE TO RELATED APPLICATIONS

This application is a U.S. National Phase Application, filed under 35 U.S.C. § 371(c), of International Application No. PCT/US2020/051642, filed Sep. 18, 2020, which claims the benefit of U.S. Provisional Application No. 62/966,632, filed on Jan. 28, 2020, and U.S. Provisional Application No. 62/902,041 filed on Sep. 18, 2019, the contents of each of which are hereby incorporated by reference in their entirety.

INCORPORATION-BY-REFERENCE OF SEQUENCE LISTING

The instant application contains a Sequence Listing which has been submitted in ASCII format via EFS-Web and is hereby incorporated by reference in its entirety. Said ASCII copy, created on Mar. 15, 2022, is named "FLEX-011_N01US_Sequence Listing. txt" and is 117 kilobytes in size.

BACKGROUND OF THE INVENTION

Osteoarthritis (OA) is a degenerative joint disease that occurs in human or mammalian joints and constitutes a severe economical and medical problem (Matthews, G. L., and Hunter, D. J. (2011). Emerging drugs for osteoarthritis. Expert Opin. Emerging Drugs 1-13.; Brooks P M. Impact of osteoarthritis on individuals and society: how much disability? Social consequences and health economic implications. Curr Opin Rheumatol 2002; 14: 573-577). Cartilage is the tough connective tissue that covers the ends of bones in joints. It provides for a relatively frictionless, highly lubricated surface between rigid bones and allows for smooth movement. The development of OA development begins with inflammation followed by partial or complete loss of cartilage due to abnormal or excessive wearing, which leads to exposed bone ends that rub against each other resulting in pain, swelling or loss of mobility. By now, the detailed reasons for the initial cartilage loss that leads to OA are not known, but there is a strong correlation between the incidence and age, obesity and joint overuse such as excessive athletic activity.

While there are estimated to be more than 100 types of arthritis, osteoarthritis (OA) is the most common form of arthritis, affecting 32.5 million US adults. The high prevalence of arthritis manifests in enormous societal and personal costs.

No curative treatment is currently available for OA—neither for humans, nor for any other mammalian species. Medical treatment is mostly aimed at alleviating the symptoms using analgesic drugs rather than reestablishing worn-away cartilage. An analgesic treatment usually involves the administration of steroids and non-steroidal anti-inflammatory drugs (NSAIDS), which have shown efficacy in the treatment of OA for decades.

Additional existing treatments for OA include the administration of hyaluronic acid, which restores viscoelasticity and lubrication of the joints. Polysulphated glycosaminoglycans injected into the joint or intramuscularly, as well as orally administered glucosamine and chondroitin sulphate, have also shown some efficacy in the treatment of OA. However, the mechanisms of action of these various treatments are not fully understood. Thus, these currently used therapies have shown only limited efficacy in the treatment of OA, and treatment success often depends on the severity of the case. Moreover, these drugs must be administered frequently, sometimes even in combination with each other. Such frequent drug injections into the joint are laborious, bear the risk for infections, cause stress for the subject and are costly. In addition, surgery for the treatment of OA has generally shown low efficacy and is typically only performed in severe advanced-stage subjects. Accordingly, there is a clear and unmet medical need for more efficacious, sustained and cost-effective treatments for OA. The present disclosure addresses this need.

SUMMARY OF THE INVENTION

The present disclosure provides a pharmaceutical composition comprising an adenoviral-based biological delivery and expression system for the treatment of osteoarthritis or an osteoarthritic condition in a human joint or for the prevention of such conditions in a human identified to be at risk of developing osteoarthritis or an osteoarthritic condition, wherein the adenoviral-based biological delivery and expression system comprises genome copies (GC) of a helper-dependent adenoviral vector comprising a nucleic acid sequence encoding a human interleukin-1 receptor antagonist (IL-1Ra) protein, left and right inverted terminal repeats, an adenoviral packaging signal and non-viral, non-coding stuffer nucleic acid sequences, wherein the expression of the human IL-1Ra gene is regulated by a NF-κB inducible promoter, which is located upstream of the reading frame of the nucleic acid sequence encoding the human IL-1Ra protein, wherein the nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can be at least 95% homologous to the nucleic acid sequence of SEQ ID NO: 2, SEQ ID NO: 3 or SEQ ID NO: 7, and wherein adenoviral-based biological delivery and expression system comprises $1.4\times10^8$ to $1.4\times10^{12}$ GC of the helper-dependent adenoviral vector per milliliter (GC per ml).

The nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can be at least 99% homologous to the nucleic acid sequence of SEQ ID NO: 2, SEQ ID NO: 3 or SEQ ID NO: 7.

The nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can comprise the nucleic acid sequence of SEQ ID NO: 2, SEQ ID NO: 3 or SEQ ID NO: 7.

In some embodiments, the nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can be at least 95% homologous to the nucleic acid sequence of SEQ ID NO: 7. In some embodiments, the nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can be at least 99% homologous to the nucleic acid sequence of SEQ ID NO: 7. In some embodiments, the nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can comprise the nucleic acid sequence of SEQ ID NO: 7.

The nucleic acid sequence encoding the IL-1Ra in the nucleic acid sequence of the adenoviral-based biological delivery and expression system can comprise the nucleic acid of can comprise the nucleic acid of SEQ ID NO 4.

The nucleic acid according to SEQ ID NO: 4 expresses a human IL-1Ra protein of amino acid sequence that is at least 95% homologous to SEQ ID NO: 6.

The adenoviral-based biological delivery and expression system can comprise: a) $1.4\times10^{9}$ to $1.4\times10^{12}$; b) $1.4\times10^{9}$ to $1.4\times10^{11}$; or c) $1.4\times10^{9}$ to $1.4\times10^{10}$, GC per ml.

The adenoviral-based biological delivery and expression system can comprise $1.4\times10^{9}$ to $5.6\times10^{9}$ GC per ml. The adenoviral-based biological delivery and expression system can comprise $1.4\times10^{10}$ to $5.6\times10^{10}$ GC per ml. The adenoviral-based biological delivery and expression system can comprise $1.4\times10^{11}$ to $5.6\times10^{11}$ GC per ml.

The adenoviral-based biological delivery and expression system can comprise $2.8\times10^{9}$ GC per ml. The adenoviral-based biological delivery and expression system can comprise $2.8\times10^{10}$ GC per ml. The adenoviral-based biological delivery and expression system can comprise $2.8\times10^{11}$ GC per ml.

The adenoviral-based biological delivery and expression system can comprise a dose volume of up to 5 ml.

The adenoviral-based biological delivery and expression system can comprise a total dose of $7\times10^{9}$ to $2.8\times10^{10}$ GC. The adenoviral-based biological delivery and expression system can comprise a total dose of $7\times10^{10}$ to $2.8\times10^{11}$ GC. The adenoviral-based biological delivery and expression system can comprise a total dose of $7\times10^{11}$ to $2.8\times10^{12}$ GC.

The adenoviral-based biological delivery and expression system can comprise a total dose of $1.4\times10^{10}$ GC. The adenoviral-based biological delivery and expression system can comprise a total dose of $1.4\times10^{11}$ GC. The adenoviral-based biological delivery and expression system can comprise a total dose of $1.4\times10^{12}$ GC.

The pharmaceutical composition can be formulated for intra-articular, intra-tendinous, intra-muscular, or sub-acromial injection to the human joint. In a preferred embodiment, the pharmaceutical composition can be formulated for intra-articular injection to the human joint.

The present disclosure provides a method of infecting joint cells of one or more osteoarthritis-affected joints of a human suffering from osteoarthritis or an osteoarthritic condition with an adenoviral-based biological delivery and expression system, wherein the method comprises the steps of; a) infecting the joint cells of the osteoarthritis-affected joint of the human in need thereof with the pharmaceutical composition comprising an adenoviral-based biological delivery and expression system as disclosed herein; and b) expressing IL-1Ra in the target area within the osteoarthritis-affected joint.

The joint cells can be infected once with the adenoviral-based biological delivery and expression system. The joint cells can be infected two or more times with the adenoviral-based biological delivery and expression system.

In one embodiment, when the joint cells are infected two or more times with the adenoviral-based biological delivery and expression system, each infection comprises the same number of genome copies of the helper-dependent adenoviral vector. In another embodiment, when the joint cells are infected two or more times with the adenoviral-based biological delivery and expression system, each infection comprises different number of genome copies of the helper-dependent adenoviral vector.

When the joint cells are infected two or more times with an adenoviral-based biological delivery and expression system, each infection is done in the same osteoarthritis-affected joint of the human. When the joint cells are infected two or more times with an adenoviral-based biological delivery and expression system, every second and subsequent infection is done in an osteoarthritis-affected joint of the human that is different than the osteoarthritis-affected joint in which the previous infection was done.

In some embodiments, the infecting of the joint cells can comprise intra-articular, intra-tendinous, intra-muscular, or sub-acromial injection. In a preferred embodiment, the infecting of the joint cells can comprise intra-articular injection.

The method can further comprise the step of; c) monitoring the treatment or progress of osteoarthritis or an osteoarthritic condition in the osteoarthritis-affected joint by following the expression of the IL-1Ra in the target area within the osteoarthritis-affected joint.

The method can further comprise the steps of; (d) continuing to administer the amount of the adenoviral-based biological delivery and expression system to the osteoarthritis-affected joint of the human in need thereof, if the step of monitoring of the treatment or progress of osteoarthritis or an osteoarthritic condition in the osteoarthritis-affected joint shows that the osteoarthritis or an osteoarthritic condition in the human joint is not managed or treated; or (e) further adjusting the number of genome copies of the helper-dependent adenoviral vector in the amount of the adenoviral-based biological delivery and expression system and administering to the osteoarthritis-affected joint of the human in need thereof, if the step of monitoring of the treatment or progress of osteoarthritis or an osteoarthritic condition in the osteoarthritis-affected joint shows that the osteoarthritis or an osteoarthritic condition in the human joint has progressed.

The present disclosure provides a process for manufacturing the pharmaceutical composition of claim 1, wherein the process comprises: a) culturing and serially expanding host cells; b) infecting the serially expanded host cells of (a) with the Helper-dependent Adenovirus (HDAd) of the present invention and a Helper Virus; c) culturing the infected cells of b); d) harvesting and lysing the infected cells of c) to produce a cell lysate; e) digesting host cell DNA in the cell lysate of d); f) clarifying the cell lysate of e); g) conducting ultracentrifugation of the clarified cell lysate of f); h) collecting the virus from the ultracentrifugated cell lysate of (g); i) conducting gradient ultracentrifugation the virus sample of (h); j) collecting virus from the gradient ultracentrifugated virus sample of (i); k) conducting isopycnic ultracentrifugation of the virus sample of (j); l) collecting the virus from the isopycnic ultracentrifugated virus sample of (k); m) conducting isopycnic ultracentrifugation of the virus sample of (l); n) collecting the virus from the isopycnic ultracentrifugated virus sample of (m); o) dialyzing the collected virus of (n); p) collecting and diluting the dialyzed virus of (o); q) formulating the diluted virus of (p); and r) filtering the formulated virus of (o).

The present disclosure provides an adenoviral-based biological delivery and expression system for treatment of osteoarthritis or an osteoarthritic condition in a human joint or for the prevention of such conditions in a human identified to beat risk of developing osteoarthritis or an osteoarthritic condition, wherein the adenoviral-based biological delivery and expression system comprises genome copies (GC) of a helper-dependent adenoviral vector comprising a nucleic acid sequence encoding a human interleukin-1 receptor antagonist (IL-1Ra), left and right inverted terminal repeats, an adenoviral packaging signal and non-viral, non-coding stuffer nucleic acid sequences, wherein the expression of the human IL-1Ra gene is regulated by a NF-κB inducible promoter, which is located upstream of the reading frame of the nucleic acid sequence encoding the human IL-1Ra protein, wherein the nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can be at least 95% homologous to the nucleic acid sequence of SEQ ID NO: 2, SEQ ID NO: 3 or SEQ ID NO: 7, wherein the adenoviral-based biological delivery and expression system is isolated from a host cell that is infected with the helper-dependent adenoviral vector and a helper virus, wherein the adenoviral-based biological delivery and expression system comprises: a) $1.4\times10^{8}$ to $1.4\times10^{12}$ GC of the helper-dependent adenoviral vector per milliliter (GC per ml) of synovial fluid in a human joint; b) less than 15% helper virus particles; c) less than 10% empty capsids; d) not more than 100 μg/ml of host cell protein; e) not more than 20 ng/ml of host cell nucleic acid; f) not more than 35 EU/ml of endotoxin; and g) a Viral Particle to Infectious Unit Ratio of ≤than 300 GC/$TCID_{50}$.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed disclosure. In the case of conflict, the present Specification, including definitions, will control. In addition, the materials, methods, and examples are illustrative only and are not intended to be limiting. Other features and advantages of the disclosure will be apparent from the following detailed description and claims.

BRIEF DESCRIPTION OF THE DRAWINGS

FIG. 2 depicts the basic gene map of the helper-dependent adenoviral vector of the disclosure. The vector backbone consists of the left and right inverted terminal repeats (ITR), adenoviral packaging signal (Ψ) and non-coding, non-viral stuffer sequences (remaining unmarked sequence between ITRs). The cDNA of equine IL-1Ra (GQ-201), murine IL-1Ra or human IL-1Ra, is cloned between the viral left and right ITRs of the used adenoviral vector. The gene of IL-1-Ra is controlled by inflammation-sensitive NF-KB5-ELAM promoter.

FIG. 3A depicts comparison of representative joints injected with HDAd-GFP and AAV6-GFP, which appeared to be the AAV serotype with the strongest GFP expression (upper pictures: fluorescent photos; lower pictures: respective brightfield photos).

FIG. 3B depicts comparison of HDAd-GFP with all AAV serotypes. Images of individual joints from two mice per group are shown.

FIG. 4A depicts bioluminescence imaging of mice infected with Helper-dependent and first-generation adenoviral vectors showing that both vectors mediate the same level of marker gene expression. Representative pictures of two mice of each group are shown.

FIG. 4B depicts Luciferase expression of the mice described in FIG. 4A followed by repeated bioluminescence imaging and quantification.

FIG. 5A and FIG. 5B depict pictures of LacZ expression on sectioned joints of mice infected with 10'VP and $10^{9}$ VP of a LacZ expressing HDAd respectively, with a higher magnification (lower panel) photograph (40×) of the framed area in the lower magnification photograph (upper panel) and FIG. 5B (left picture) (5×). S represents synovium, C represents chondrocytes and thick dark line indicated with arrowhead depicts LacZ staining.

FIG. 8A depicts OARSI score, FIG. 8B depicts synovitis score and FIG. 8C depicts % of joints with osteophytes, in mice administered with HDAd-mIL-1Ra, HDAd-GFP, or Vehicle. Mean t SD and individual knee data are shown. *P<0.05; one-way ANOVA with Tukey multiple comparison test.

FIG. 9A. depicts OA scores of HDAd-IL-1Ra treated joints compared to controls. OA scores for mice injected intra-articularly with $10^8$ VP of HDAd-IL-1 Ra, HDAd-GFP or mock are depicted on y-axis. A blinded pathologist evaluated the level of OA according to OARSI (Osteoarthritis Research Society International) standard (assignment of scores on a scale of 1-6, 1: no signs of OA at all, 6: maximum OA). * indicates significant difference: p<0.05 by one-way ANOVA; n=8 joints per group.

FIG. 9B depicts cartilage volume of HDAd-IL-1Ra treated joints compared to controls. * indicates significant difference: p<0.05, one-way ANOVA, n=6 joints/group.

FIG. 9C. depicts cartilage surface area of HDAd-IL-1 Ra treated joints compared to controls. * indicates significant difference: p<0.05, one-way ANOVA, n=6 joints/group.

FIG. 10A depicts changes in cartilage volume, and FIG. 10B depicts changes in bone area covered by cartilage as assessed by micro-CT imaging in mice with pre-established OA dosed IA with HDAd-mIL-1Ra, HDAd-GFP or Vehicle two weeks post-surgery, as well in age-matched mice that did not undergo CLT surgery. Mean±SD and individual joint values are shown. *P<0.05; one-way ANOVA with Tukey multiple comparison test.

FIG. 16 depicts Clinical Scoring of OA in Horse Osteochondral Chip Model. FIG. 16 depicts on y-axis the mean±SEM clinical scores of injected joints at final evaluation time point on Day 72, corresponding to parameters as indicated on x-axis. Parameter "Flexion" represents lameness after joint flexion for 20 seconds. *P<0.05; Kruskal-Wallis test with pairwise comparisons to the vehicle group.

FIG. 18 depicts histological Analysis of Treated Joints in Horse Osteochondral Chip Model. Left panel: Mean±SEM scores for evaluated parameters in the joints injected with HDAd-eqIL-1Ra (GQ-201), PBS (placebo) or sham-operated joints. Right panel: Mean±SEM total histological score; sum of individual histological scores. *P<0.05; Kruskal-Wallis test with pairwise comparisons to the vehicle group.

FIG. 19A depicts the viable cell density shown as cells/cm$^2$ on the y-axis at seeding and end (harvesting) corresponding to 5 passages (P1-P5) and of infection, on the x axis, for three batches of FX201 and one batch of rat ortholog, as indicated. FIG. 19B depicts the end of stage viability (percentage viability) on the y-axis measured at the end of each of the 5 passages (P1-P5) and of infection, as indicated on the x-axis. Data is shown for all five passages and infection of Tox (Human), Tox (Rat), ENG and GMP lots in both graphs. Cell expansions were split into two streams after passage 5 for one additional co-infection. The first stream of cell expansion data is shown. Cell counts were not taken prior to infection. Viable cell density (VCD) were calculated at passage seeding, and were quantified at the end of each passage.

FIG. 21 depicts the infectivity and gene expression for the different lots. Infectivity measured as $TCID_{50}$ and genome copies to infectious ratio, and IL-1Ra expression is depicted for the Tox (Human), Tox (Rat), ENG and GMP lots, as indicated.

DETAILED DESCRIPTION OF THE INVENTION

The present disclosure provides compositions for an improved delivery and expression system that allows for a long-term expression of biologically active recombinant interleukin-1 receptor antagonist (IL-1Ra) in cells at human joints for the treatment and prevention of osteoarthritis. Disclosed herein is a novel IL-1Ra gene therapy (FX201, humantakinogene hadenovec), for intra-articular (IA) administration that is being developed for the treatment of patients' osteoarthritis or osteoarthritic conditions. FX201 (humantakinogene hadenovec), is a helper-dependent adenovirus (HDAd) delivering the nucleic acid sequence encoding the human IL-1Ra under the control of a nuclear factor-κB (NF-κB)-inducible promoter for IA administration to patients with osteoarthritis or osteoarthritic condition. Following IA injection, FX201 infects cells in the joint to produce IL-1Ra locally in response to inflammation. FX201 is a non-replicating, non-integrating HDAd vector with no viral coding sequences that has been engineered to carry the genetic coding sequence for IL-1Ra. Only the adenoviral packaging signal and inverted terminal repeats (ITRs) remain in the FX201 genome as they are required for manufacturing. Transcription is controlled by the inflammation-sensitive NF-κB-inducible promoter, which drives expression of IL-1Ra in response to an inflammatory environment.

FX201 can be administered as a single dose by IA injection. The expected clinical benefits are sustained symptomatic relief, including both reduction in pain and improvement or restoration of function, and a beneficial modification of the underlying disease process in patients with osteoarthritis or an osteoarthritic condition in a human joint. Advantageously, the adenoviral delivery and expression systems of the present disclosure specifically locates in the joints when administered intra-articularly. Most importantly, no measurable concentration of vector sequences could be detected in the liver of mice treated with the adenoviral system of the disclosure. Therefore, IL-1Ra concentrations are expected to be highest in the joints injected with the vector of the disclosure while no significant side effects are expected in any other organ. Described below are the properties of FX201.

Figure 1:
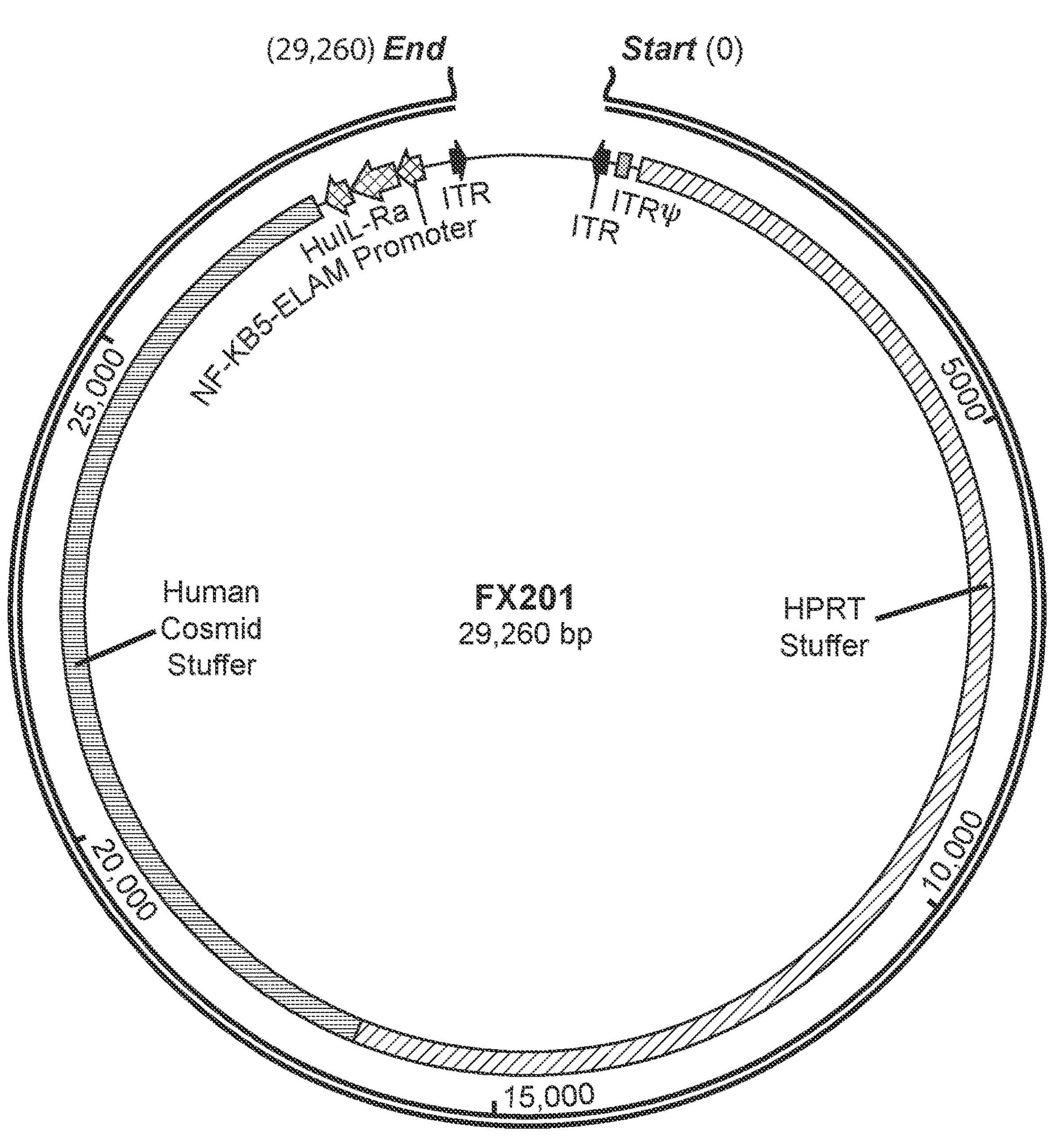
FIG. 1 depicts the genome map of Humantakinogene Hadenovec (FX201). ITR=inverted terminal repeats (1-103 bp on 5'; 29,158-29,260 bp on 3'), Ψ=packaging signals (240-375 bp), HPRT Stuffer=human hypoxanthine phosphoribosyltransferase (463-16,518 bp), Human Cosmid Insert=human cosmid (16,532-27,637 bp), SV40 Poly A=Simian virus 40 Poly A (27,750-28,020 bp), huIL-1Ra=human interleukin-1 receptor antagonist, the genome of interest (28,033-28,566 bp), NF-kB5-ELAM Promoter=NΦ-κB ινδυχιβλε promoter (28,581-28,842 bp).

Vector Backbone: FX201 is a non-replicating, non-integrating HDAd vector. The genomic component is composed of double-stranded linear DNA approximately 29.3 kilobases (kb) in size. The annotated sequence obtained by next-generation sequencing confirms the key elements in the FX201 genome. The FX201 genome contains minimal adenoviral elements required for amplification and packaging to allow for its manufacturing: left and right inverted terminal repeats (hereafter referred to as "L ITR" and "R ITR", respectively) and the packaging signal (Ψ). Approximately 1.1 kb of the FX201 genome is composed of the nucleic acid sequence encoding human IL-1Ra, which is inserted on the right end of the genome in reverse (right-to-left) orientation, and the promoter, placed just before the R ITR. The promoter is 5 species-conserved NF-κB binding motif repeats fused to a proximal promoter region of the human ELAM gene, responding to pro-inflammatory cytokines (Schindler 1994). Approximately 27 kb of the FX201 genome consists of non-coding stuffer sequence composed of human hypoxanthine phosphoribosyltransferase (HPRT) and human cosmid insert, which is inserted to enlarge the FX201 genome to a size which allows efficient packaging of the vector genome into each viral particle. A genome map for FX201 is presented in FIG. 1.

Gene of Interest: The FX201 genome contains a 534 base pair (bp) sequence of human IL-1Ra, which is regulated by a 262 bp sequence of NF-κB-inducible promoter.

Figure 2:
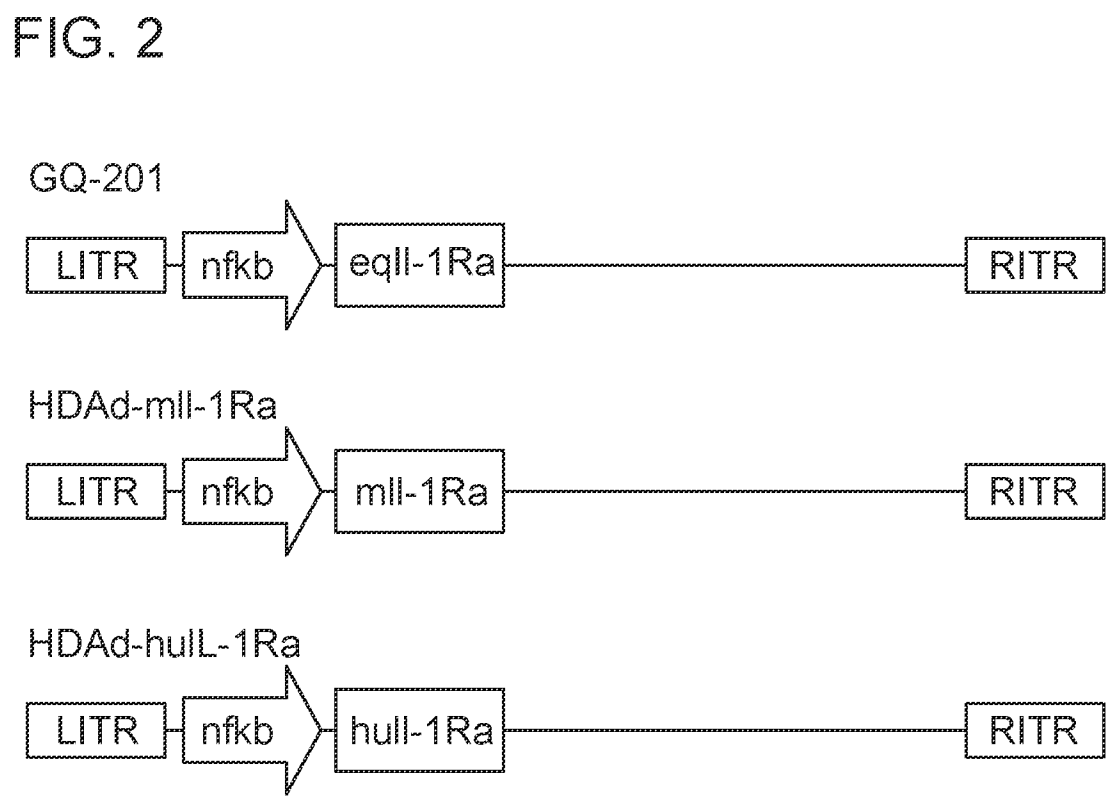

Disclosed herein are gene maps of the FX201, HDAd vectors of the invention (FIG. 2). All three vectors contain the inflammation-sensitive NF-κB5-ELAM promoter upstream of the IL-1Ra cDNA according to any one of SEQ ID NOs: 1 or 4, as well as ITR and an adenoviral packaging signal. The full vector sequence of GQ-201, HDAd-mIL-Ra and HDAd-human IL-1Ra, is shown in SEQ ID NOs: 2, 3 and 7 respectively. The only difference between the three vectors is that GQ-201 carries the equine variant of IL-1Ra, HDAd-mIL-Ra has the murine IL-1Ra variant and HDAd-huIL-1Ra carries the human IL-1Ra. As an example, the HDAd-mIL-Ra of nucleic acid sequence according to SEQ ID NO: 3 can comprise a nucleic acid encoding a murine IL-1Ra according to SEQ ID NO: 1. As an example, the HDAd-mIL-Ra of nucleic acid sequence according to SEQ ID NO: 7 can comprise a nucleic acid encoding a murine IL-1Ra according to SEQ ID NO: 4.

The vectors were cloned by standard digestion/ligation reactions according to the following strategy. The luciferase cDNA in pNifty-luc, a plasmid that contains the luciferase cDNA driven by a NF-KB5-ELAM promoter, was excised with Ncol and Nhel and cDNAs for equine or murine IL-1Ra were ligated into this position. The NF-κB5-ELAM promoter—murine IL-1Ra or NF-KB5-ELAM promoter—equine IL-1Ra cassettes were excised with Notl and Pad or EcoRI and Pad, blunted and inserted into pLPBL shuttle plasmid, which had been linearized with Sail and blunted. The NF-KB5-ELAM promoter—murine IL-1Ra or NF-KB5-ELAM promoter—equine IL-1Ra cassettes were then excised with Ascl, which flanks both sides of the multiple cloning site, and ligated into Asci linearized ρΔ28 plasmid (Toietta, G., Pastore, L, Cerullo, V., Finegold, M., Beaudet, A. L., and Lee, B. (2002). Generation of helper-dependent adenoviral vectors by homologous recombination. Mol Ther 5, 204-210.), which yielded the genomic plasmids pA28-m11-1Ra and pA28-eq11-1Ra. These plasmids were digested with Pmel in order to linearize the vector, liberate the inverted terminal repeats and excise bacterial resistance genes. Vectors were rescued and amplified as described before using the helper-virus AdNG163R-2 and 116 cell factories (Palmer, D., and Ng, P. (2003). Improved system for helper-dependent adenoviral vector production. Mol Ther 8, 846-852; Suzuki, M., Cela, R., Clarke, C, Bertin, T. K., Mourino, S., and Lee, B. (2010).

Large-scale production of high-quality helper-dependent adenoviral vectors using adherent cells in cell factories. Hum Gene Ther 21, 120-126.)

Compositions of the Present Disclosure

Compositions of the present disclosure can comprise adenoviral-based biological delivery and expression systems based on a helper-dependent adenoviral vectors, wherein the helper-dependent adenoviral vectors comprise a nucleic acid sequence encoding for human or mammalian interleukin-1 receptor antagonist (IL-1Ra), L ITR, R ITR, adenoviral packaging signal and non-viral, non-coding stuffer nucleic acid sequences.

The helper-dependent adenoviral vectors of the present disclosure minimizes immune responses in the host and confers long-term gene expression of human or mammalian IL-1Ra in joints that are affected by osteoarthritis.

In some aspects, the sequence encoding for the human or mammalian interleukin-1 receptor antagonist (IL-1Ra) in the compositions of the present disclosure can be controlled by an inflammation-sensitive promoter. Without wishing to be bound by theory, the use of an inflammation-sensitive promoter in the compositions of the present disclosure provides for specific control of IL-1Ra gene expression in osteoarthritic condition tissue cells, as only cells that are affected by the disease will express and secrete the IL-1Ra gene product, whereas cells that are not affected will not express and secret the IL-1Ra. In some aspects, the promoter sequences can be located upstream of the reading frame of the sequence encoding for the human or mammalian IL-1Ra.

Without wishing to be bound by theory, the inflammation-sensitive promoters used in the compositions of the present disclosure can be specifically activated by increased levels of factors including immune stimulatory substances and/or cytokines. During osteoarthritis, a variety of immune stimulatory substances and cytokines are released, resulting in high levels of promoter-activating substances. In a non-limiting example, an immune stimulatory substance can be lipopolysaccharide (LPS), which is a major component of the outer cell membrane of gram-negative bacteria. The released immune stimulatory substances and/or cytokines can activate transcription factors such as NF-κB, which regulates the NF-κB promoter. Therefore, the release of such osteoarthritic condition-specific immune stimulatory substances and/or cytokines can allow for the control of gene expression in joints of humans or mammals for treating or preventing an osteoarthritic condition.

Any inflammation-sensitive promoter that results in a specific expression of the IL-1Ra gene product in osteoarthritic condition tissue can be used in context of the present disclosure. Preferred inflammation-sensitive promoters for use in the present disclosure include, but are not limited to promoters inducible by NF-κB, interleukin 6 (II-6), interleukin-1 (IL-1), tumor necrosis factor (TNF), cyclooxygenase 2 (COX-2), complement factor 3 (C3), serum amyloid A3 (SAA3), macrophage inflammatory protein-1a (MIP-1a), or hybrid constructs of the above.

In preferred aspects, the inflammation-sensitive promoter is an NF-κB5-ELAM promoter. The NF-κB-inducible promoter, composed of five species-conserved NF-κB binding motif repeats fused to a proximal promoter region of the human endothelial leukocyte adhesion molecule (ELAM) gene, was chosen to drive the expression of IL-1Ra for several reasons. First, NF-κB, as a transcription factor, is ubiquitously expressed in all cells of the body, and any transduced cell, when stimulated with inflammatory cues, can in principle express the IL-1Ra transgene. Therefore, there is no cell specificity requirement for FX201 to induce IL-1Ra expression. Additionally, NF-κB is the terminal signaling molecule for receptors of pro-inflammatory cytokines, such as interleukin-1 (IL-1) and tumor necrosis factor-α and other immune cell receptors such as toll-like receptors, where it acts to initiate a cellular response to many pro-inflammatory inputs. As such, the activation of IL-1Ra production is designed to be stimulated in the joint by a variety of inflammatory signals.

Without wishing to be bound by theory, following intra-articular injection, the gene of IL-1Ra is delivered to joint cells, including, but not limited to synoviocytes. Synovial cells that are affected by inflammation start to produce recombinant IL-1Ra protein under the control of the inflammation-sensitive promoter (e.g. the NF-κB promoter). High amounts of IL-1Ra are then secreted into the joint space, where IL-1Ra inhibits inflammation and stops cartilage degradation by blocking the interleukin-1 receptor on the surface of synoviocytes and the cells embedded in the cartilage. Most importantly, high local concentrations of recombinant IL-1Ra do not show any side effects.

As described herein, pain, inflammation and cartilage degradation are inhibited effectively using the adenoviral-based biological delivery and expression system of the present disclosure. High local and low systemic concentrations of the therapeutic protein IL-1Ra are achieved through administration of the compositions of the present disclosure, resulting in maximum efficacy in the treatment of OA at no or minimal side effects. It is further exemplified that cells containing the helper-dependent adenoviral vector of the present disclosure are capable to produce recombinant IL-1Ra for an extended period of any one of at least 3 months, at least 6 months or at least one year. Consequently, medical and economic burden associated with frequent joint injections that were required in the known short-term treatments will be significantly reduced. Thus, potential complications associated with OA treatment are minimized and joint health will be preserved resulting in sustained health improvement of the treated animal or human.

In addition, the inflammation-sensitive IL-1Ra production of the helper-dependent adenoviral vectors of the disclosure allows for the prevention of the development of an osteoarthritic condition as joint cells that are infected with the adenoviral vector of the disclosure remain silent in the absence of immune stimulatory substances that could activate the NF-κB5-ELAM promoter or any other inflammation-sensitive promoter. Only if the osteoarthritic condition initiates, the promoter is activated as a result of inflammation and subsequently IL-1Ra is produced and secreted. Thus, by using the adenoviral delivery and expression system of the disclosure, this mechanism allows for the prevention of the development of osteoarthritis in an early stage.

An inflammation-sensitive IL-1Ra production of the helper-dependent adenoviral vectors of the disclosure are also safer for administration to a subject as IL-1Ra will no longer be produced when the osteoarthritic condition is resolved or has disappeared.

The helper-dependent adenoviral vectors of the present disclosure does not carry any viral sequences, except for the L ITR, R ITR and the adenoviral packaging signal. Preferred helper-dependent adenoviral vectors to be used in the present disclosure are those based on the helper virus and helper-dependent backbone system developed by Palmer and Ng (Palmer, D., and Ng, P. (2003). Improved system for helper-dependent adenoviral vector production. Mol Ther 8, 846-852.) and Toietta et al (Toietta, G., Pastore, L., Cerullo, V., Finegold, M., Beaudet, A. L., and Lee, B. (2002).

Generation of helper-dependent adenoviral vectors by homologous recombination. Mol Ther 5, 204-210.). A preferred adenoviral delivery and expression system according to the present disclosure can comprise a nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences as set forth in SEQ ID NO: 2, SEQ ID NO: 3 or SEQ ID NO: 7, or a biologically effective part thereof. The nucleic acid sequence of SEQ ID NO 2 describes a murine helper-dependent adenoviral vector, the sequence set forth in SEQ ID NO 3 describes an equine helper-dependent adenoviral vector, the sequence set forth in SEQ ID NO 7 describes a human helper-dependent adenoviral vector, all three vectors bearing any one of a murine, an equine IL-1Ra gene or human IL-1Ra gene respectively. Preferably, the system of the disclosure has any one of at least 96%, 97%, 98%, or 99% sequence homology with the vector set forth in SEQ ID NO: 2, SEQ ID NO: 3 or SEQ ID NO: 7.

"Long term expression" in the context of the present disclosure means that the gene product of the adenoviral delivery and expression system (i.e. IL-1Ra), is expressed in the joint(s) infected with the helper-dependent adenoviral vector of the disclosure, for at least 3 months, 6 months or 12 months. In a preferred aspect, the IL-1Ra is expressed in the joint(s) infected with the helper-dependent adenoviral vector of the disclosure for at least 3 months.

"Biologically effective" in the context of the present disclosure means that the gene product of the adenoviral delivery and expression system comprises the full or partial polypeptide sequence of IL-1Ra having the in-joint activity to neutralize the effect of IL-1 on joint inflammation.

The helper-dependent adenoviral vector of the disclosure preferably comprises a nucleic acid sequence of IL-1Ra under control of an inflammation-sensitive promoter. Although IL-1Ra contains species-specific nucleic acid sequences, the adenoviral vector is able to express interleukin-1 receptor antagonist (IL-1Ra) from any mammalian species or human. Preferably, the cDNA of the mammalian interleukin-1 receptor antagonist (IL-1Ra) used for cloning is a cDNA selected from the group consisting of human IL-1Ra, murine IL-1Ra, equine IL-1Ra, canine IL-1Ra, cat IL-1Ra, rabbit IL-1Ra, hamster IL-1Ra, bovine IL-1Ra, camel IL-1Ra or their homologs in other mammalian species.

In order to monitor the presence of genomic vector sequences in synovial cells, the helper-dependent adenoviral vector according to the disclosure can further comprise a sequence encoding a marker gene that is visually or instrumentally detectable. Preferred marker genes include, but are not limited to, green fluorescence protein (GFP), LacZ, or luciferase enzyme.

As an example, the nucleic acid sequence of murine IL-1Ra as used in the present disclosure is shown in the sequence listing set forth in SEQ ID NO: 1. As noted above, any nucleic acid sequence resulting in a biologically active IL-1Ra protein of any mammalian or human species can be used in the context of the present disclosure. Furthermore, conserved nucleic acid sequences encoding for the same amino acids, polypeptide or protein fall under scope of the present disclosure. Preferably, the helper-dependent adenoviral vector according to the disclosure contains a nucleic acid sequence (e.g. cDNA) of IL-1Ra having at least 95%, 96%, 97%, 98% or 99% sequence homology with the nucleic acid sequence shown in SEQ ID NO: 1. The disclosure also comprises biologically active nucleic acid sequences of IL-1Ra or fragments thereof. Thus, the help-dependent adenoviral vectors of the present disclosure can comprise a biologically active fragment of the nucleic acid sequence put forth in SEQ ID NO: 1.

As an example, the nucleic acid sequence of human IL-1Ra as used in the present disclosure is shown in the sequence listing set forth in SEQ ID NO: 4. As noted above, any nucleic acid sequence resulting in a biologically active IL-1Ra protein of a human can be used in the context of the present disclosure. Furthermore, conserved nucleic acid sequences encoding for the same amino acids, polypeptide or protein fall under scope of the present disclosure. Preferably, the helper-dependent adenoviral vector according to the disclosure contains a nucleic acid sequence (e.g. cDNA) of IL-1Ra having at least 95%, 96%, 97%, 98% or 99% sequence homology with the nucleic acid sequence shown in SEQ ID NO: 4. The disclosure also comprises biologically active nucleic acid sequences of IL-1Ra or fragments thereof. Thus, the help-dependent adenoviral vectors of the present disclosure can comprise a biologically active fragment of the nucleic acid sequence put forth in SEQ ID NO: 4.

As an example, the nucleic acid sequence of human IL-1Ra as used in the present disclosure as set forth in SEQ ID NO: 4 can express a human IL-1Ra protein of amino acid sequence that is at least 95% homologous to SEQ ID NO: 6. The nucleic acid sequence of human IL-1Ra as used in the present disclosure as set forth in SEQ ID NO: 4 can express a human IL-1Ra protein of amino acid sequence that is at least 96%, 97%, 98% or 99% homologous to SEQ ID NO: 6. The nucleic acid sequence of human IL-1Ra as used in the present disclosure as set forth in SEQ ID NO: 4 can express a human IL-1Ra protein of amino acid sequence that is at least 99% homologous to SEQ ID NO: 6. Preferably, the nucleic acid sequence of human IL-1Ra as used in the present disclosure as set forth in SEQ ID NO: 4 can express a human IL-1Ra protein of amino acid sequence according to SEQ ID NO: 6.

In some embodiments, the human-IL-1Ra can have an amino acid sequence that is at least 95% to 99% homologous to the amino acid sequence of a wild type human IL-1Ra protein. In some embodiments, the human-IL-1Ra can have an amino acid sequence that is 95% to 99% homologous to a human IL-1Ra protein of amino acid sequence according to SEQ ID NO: 6.

The present invention provides an adenoviral-based biological delivery and expression system for treatment of osteoarthritis or an osteoarthritic condition in a human joint or for the prevention of such conditions in a human identified to be at risk of developing osteoarthritis or an osteoarthritic condition, wherein the adenoviral-based biological delivery and expression system comprises genome copies (GC) of a helper-dependent adenoviral vector comprising a nucleic acid sequence encoding a human interleukin-1 receptor antagonist (IL-1Ra), left and right inverted terminal repeats, an adenoviral packaging signal and non-viral, and non-coding stuffer nucleic acid sequences, wherein the expression of the human IL-1Ra gene is regulated by a NF-κB inducible promoter, which is located upstream of the reading frame of the nucleic acid sequence encoding the human IL-1Ra, wherein the nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can be at least 95% homologous to the nucleic acid sequence of SEQ ID NO: 2, SEQ ID NO: 3 or SEQ ID NO: 7, wherein the adenoviral-based biological delivery and expression system is isolated from a host cell that is infected with the helper-dependent adenoviral vector and a helper virus, wherein the adenoviral-based biological delivery and expression system comprises: a) $1.4\times10^8$ to $1.4\times10^{12}$ GC of the helper-dependent adenoviral vector per milliliter (GC per ml); b) less than 15% helper virus particles; c) less than 10% empty capsids; d) not more than 100 μg/ml of host cell protein; e) not more than 20 ng/ml of host cell nucleic acid; f) not more than 35 EU/ml of endotoxin; and g) a Viral Particle to Infectious Unit Ratio of ≤than 300 GC/$TCID_{50}$.

The level of helper virus in the adenoviral-based biological delivery and expression system disclosed herein, can be any one of less than 15%, less than 14%, less than 13%, less than 12%, less than 11%, less than 10%, less than 9%, less than 8%, less than 7%, less than 6%, less than 5%, less than 4%, less than 3%, less than 2% or less than 1% helper virus particles. The level of helper virus in the adenoviral-based biological delivery and expression system disclosed herein, can be between 1% to 2% helper virus particles. The level of helper virus in the adenoviral-based biological delivery and expression system disclosed herein, can be between 2% to 3% helper virus particles. The level of helper virus in the adenoviral-based biological delivery and expression system disclosed herein, can be between 3% to 4% helper virus particles. The level of helper virus in the adenoviral-based biological delivery and expression system disclosed herein, can be between 4% to 5% helper virus particles. The level of helper virus in the adenoviral-based biological delivery and expression system disclosed herein, can be between 5% to 6% helper virus particles. The level of helper virus in the adenoviral-based biological delivery and expression system disclosed herein, can be between 6% to 7% helper virus particles. The level of helper virus in the adenoviral-based biological delivery and expression system disclosed herein, can be between 7% to 8% helper virus particles. The level of helper virus in the adenoviral-based biological delivery and expression system disclosed herein, can be between 8% to 9% helper virus particles. The level of helper virus in the adenoviral-based biological delivery and expression system disclosed herein, can be between 9% to 10% helper virus particles.

The level of helper virus in the adenoviral-based biological delivery and expression system disclosed herein, can be between 10% to 11% helper virus particles. The level of helper virus in the adenoviral-based biological delivery and expression system disclosed herein, can be between 11% to 12% helper virus particles. The level of helper virus in the adenoviral-based biological delivery and expression system disclosed herein, can be between 12% to 13% helper virus particles. The level of helper virus in the adenoviral-based biological delivery and expression system disclosed herein, can be between 13% to 14% helper virus particles. The level of helper virus in the adenoviral-based biological delivery and expression system disclosed herein, can be between 14% to <15% helper virus particles.

The level of empty capsids in the adenoviral-based biological delivery and expression system disclosed herein, can be any one of less than 10%, less than 9%, less than 8%, less than 7%, less than 6%, less than 5%, less than 4%, less than 3%, less than 2% or less than 1% empty capsids. The level of empty capsids in the adenoviral-based biological delivery and expression system disclosed herein, can be between 1% to 2% empty capsids. The level of empty capsids in the adenoviral-based biological delivery and expression system disclosed herein, can be between 2% to 3% empty capsids. The level of empty capsids in the adenoviral-based biological delivery and expression system disclosed herein, can be between 3% to 4% empty capsids. The level of empty capsids in the adenoviral-based biological delivery and expression system disclosed herein, can be between 4% to 5% empty capsids. The level of empty capsids in the adenoviral-based biological delivery and expression system disclosed herein, can be between 5% to 6% empty capsids. The level of empty capsids in the adenoviral-based biological delivery and expression system disclosed herein, can be between 6% to 7% empty capsids. The level of empty capsids in the adenoviral-based biological delivery and expression system disclosed herein, can be between 7% to 8% empty capsids. The level of empty capsids in the adenoviral-based biological delivery and expression system disclosed herein, can be between 8% to 9% empty capsids. The level of empty capsids in the adenoviral-based biological delivery and expression system disclosed herein, can be between 9% to <10% empty capsids. The level of empty capsids and helper virus, in the adenoviral-based biological delivery and expression system disclosed herein, can be same.

In some embodiments, the terms "empty capsid," and "empty particle," refer to an adenoviral vector virion that includes a helper-dependent adenoviral protein shell but that lacks in whole or part the polynucleotide construct comprising a nucleic acid sequence encoding a human interleukin-1 receptor antagonist (IL-1Ra), a left and right inverted terminal repeats, an adenoviral packaging signal and non-viral, non-coding stuffer nucleic acid sequences, wherein the expression of the human IL-1Ra gene is regulated by a NF-κB-inducible promoter, which is located upstream of the reading frame of the nucleic acid sequence encoding the human IL-1Ra and which is specifically activated by factors including but not limited to immune stimulatory substances, wherein the nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can be at least 95% homologous to the nucleic acid sequence of SEQ ID NO: 2, SEQ ID NO: 3 or SEQ ID NO: 7.

The term "host cell" denotes, for example, microorganisms, yeast cells, insect cells, and mammalian cells, that can be, or have been, used as recipients of an a helper-dependent adenoviral vector construct of the present and a helper virus. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

The adenoviral-based biological delivery and expression system of the present invention, can comprise a pH of 7.0±1.0. The adenoviral-based biological delivery and expression system of the present invention, can comprise a pH of 6.0 to 6.5. The adenoviral-based biological delivery and expression system of the present invention, can comprise a pH of 6.5 to 7.0. The adenoviral-based biological delivery and expression system of the present invention, can comprise a pH of 7.0 to 7.5. The adenoviral-based biological delivery and expression system of the present invention, can comprise a pH of 7.0 to 8.0.

The adenoviral-based biological delivery and expression system of the present invention, can comprise an osmolality of ≤600 mOsm/kg. The adenoviral-based biological delivery and expression system of the present invention, can comprise an osmolality of any one of 100 mOsm/kg to 200 mOsm/kg. The adenoviral-based biological delivery and expression system of the present invention, can comprise an osmolality of any one of 200 mOsm/kg to 300 mOsm/kg. The adenoviral-based biological delivery and expression system of the present invention, can comprise an osmolality of any one of 300 mOsm/kg to 400 mOsm/kg. The adenoviral-based biological delivery and expression system of the present invention, can comprise an osmolality of any one of 400 mOsm/kg to 500 mOsm/kg. The adenoviral-based biological delivery and expression system of the present invention, can comprise an osmolality of any one of 500 mOsm/kg to 600 mOsm/kg.

The adenoviral-based biological delivery and expression system of the present invention, can comprise the helper-dependent adenoviral vector (HDAd) at: a) $1.4\times10^9$ to $1.4\times10^2$; b) $1.4\times10^9$ to $1.4\times10^{11}$; or c) $1.4\times10^9$ to $1.4\times10^{10}$, GC per ml.

The adenoviral-based biological delivery and expression system of the present invention, can comprise the helper-dependent adenoviral vector (HDAd) at $\geq1.4\times10^9$ GC per ml to $<5.6\times10^9$ GC per mL. The adenoviral-based biological delivery and expression system of the present invention, can comprise the helper-dependent adenoviral vector (HDAd) at $2.8\times10^9$ GC per mL. The adenoviral-based biological delivery and expression system of the present invention, can comprise the helper-dependent adenoviral vector (HDAd) at $\geq1.4\times10^{10}$ GC per ml to $<5.6\times10^{10}$ GC per mL. The adenoviral-based biological delivery and expression system of the present invention, can comprise the helper-dependent adenoviral vector (HDAd) at $2.8\times10^{10}$ GC per mL. The adenoviral-based biological delivery and expression system of the present invention, can comprise the helper-dependent adenoviral vector (HDAd) at $>1.4\times10^{11}$ GC per ml to $<5.6\times10^{11}$ GC per mL. The adenoviral-based biological delivery and expression system of the present invention, can comprise the helper-dependent adenoviral vector (HDAd) at $2.8\times10^{11}$ GC per mL.

The adenoviral-based biological delivery and expression system of the present invention, can comprise the helper-dependent adenoviral vector (HDAd) at $1.4\times10^9$ to $5.6\times10^9$ GC per ml. The adenoviral-based biological delivery and expression system of the present invention, can comprise the helper-dependent adenoviral vector (HDAd) at $1.4\times10^{10}$ to $5.6\times10^{10}$ GC per ml. The adenoviral-based biological delivery and expression system of the present invention, can comprise the helper-dependent adenoviral vector (HDAd) at $1.4\times10^{11}$ to $5.6\times10^{11}$ GC per ml. The adenoviral-based biological delivery and expression system of the present invention, can comprise the helper-dependent adenoviral vector (HDAd) at $2\times10^9$ to $5.6\times10^9$ GC per ml. The adenoviral-based biological delivery and expression system of the present invention, can comprise the helper-dependent adenoviral vector (HDAd) at $2\times10^{10}$ to $5.6\times10^{10}$ GC per ml. The adenoviral-based biological delivery and expression system can comprise $2\times10^{11}$ to $5.6\times10^{11}$ GC per ml.

The adenoviral-based biological delivery and expression system of the present invention, can comprise the helper-dependent adenoviral vector (HDAd) at $2.8\times10^9$ to $5.6\times10^9$ GC per ml. The adenoviral-based biological delivery and expression system of the present invention, can comprise the helper-dependent adenoviral vector (HDAd) at $2.8\times10^{10}$ to $5.6\times10^{10}$ GC per ml. The adenoviral-based biological delivery and expression system of the present invention, can comprise the helper-dependent adenoviral vector (HDAd) at $2.8\times10^{11}$ to $5.6\times10^{11}$ GC per ml.

The adenoviral-based biological delivery and expression system of the present invention, can comprise the helper-dependent adenoviral vector (HDAd) at $2\times10^9$ to $2.8\times10^9$ GC per ml. The adenoviral-based biological delivery and expression system of the present invention, can comprise the helper-dependent adenoviral vector (HDAd) at $2\times10^{10}$ to $2.8\times10^{10}$ GC per ml. The adenoviral-based biological delivery and expression system of the present invention, can comprise the helper-dependent adenoviral vector (HDAd) at $2\times10^{11}$ to $2.8\times10^{11}$ GC per ml.

The adenoviral-based biological delivery and expression system of the present invention, can comprise the helper-dependent adenoviral vector (HDAd) at $1.4\times10^9$ to $2.8\times10^{10}$ GC per ml. The adenoviral-based biological delivery and expression system of the present invention, can comprise the helper-dependent adenoviral vector (HDAd) at $1.4\times10^{10}$ to $2.8\times10^{11}$ GC per ml. The adenoviral-based biological delivery and expression system of the present invention, can comprise the helper-dependent adenoviral vector (HDAd) at $1.4\times10^{11}$ to $2.8\times10^{11}$ GC per ml.

The adenoviral-based biological delivery and expression system of the present invention, can comprise the helper-dependent adenoviral vector (HDAd) at $2.8\times10^9$ to $1.4\times10^{12}$ GC per ml. The adenoviral-based biological delivery and expression system of the present invention, can comprise the helper-dependent adenoviral vector (HDAd) at $2.8\times10^{10}$ to $1.4\times10^{12}$ GC per ml. The adenoviral-based biological delivery and expression system of the present invention, can comprise the helper-dependent adenoviral vector (HDAd) at $2.8\times10^{11}$ to $1.4\times10^{12}$ GC per ml.

The adenoviral-based biological delivery and expression system of the present invention, can comprise the helper-dependent adenoviral vector (HDAd) at $2.8\times10^9$ to $2.8\times10^{11}$ GC per ml. The adenoviral-based biological delivery and expression system of the present invention, can comprise the helper-dependent adenoviral vector (HDAd) at $2.8\times10^9$ to $1.4\times10^{10}$ GC per ml. The adenoviral-based biological delivery and expression system of the present invention, can comprise the helper-dependent adenoviral vector (HDAd) at $2.8\times10^{10}$ to $2.8\times10^{11}$ GC per ml.

The adenoviral-based biological delivery and expression system can comprise $1.4\times10^9$ GC per ml. The adenoviral-based biological delivery and expression system of the present invention, can comprise the helper-dependent adenoviral vector (HDAd) at $1.4\times10^{10}$ GC per ml. The adenoviral-based biological delivery and expression system of the present invention, can comprise the helper-dependent adenoviral vector (HDAd) at $1.4\times10^{11}$ GC per ml. The adenoviral-based biological delivery and expression system can comprise $1.4\times10^{12}$ GC per ml.

The adenoviral-based biological delivery and expression system of the present invention, can comprise the helper-dependent adenoviral vector (HDAd) at $2\times10^9$ GC per ml. The adenoviral-based biological delivery and expression system of the present invention, can comprise the helper-dependent adenoviral vector (HDAd) at $2\times10^{10}$ GC per ml. The adenoviral-based biological delivery and expression system of the present invention, can comprise the helper-dependent adenoviral vector (HDAd) at $2\times10^{11}$ GC per ml.

The adenoviral-based biological delivery and expression system of the present invention, can comprise the helper-dependent adenoviral vector (HDAd) at $2.8\times10^9$ GC per ml. The adenoviral-based biological delivery and expression system of the present invention, can comprise the helper-dependent adenoviral vector (HDAd) at $2.8\times10^{10}$ GC per ml. The adenoviral-based biological delivery and expression system of the present invention, can comprise the helper-dependent adenoviral vector (HDAd) at $2.8\times10^{11}$ GC per ml.

The adenoviral-based biological delivery and expression system of the present invention, can comprise the helper-dependent adenoviral vector (HDAd) at $5.6\times10^{9}$ GC per ml. The adenoviral-based biological delivery and expression system of the present invention, can comprise the helper-dependent adenoviral vector (HDAd) at $5.6\times10^{10}$ GC per. The adenoviral-based biological delivery and expression system of the present invention, can comprise the helper-dependent adenoviral vector (HDAd) at $5.6\times10^{11}$ GC per ml.

The adenoviral-based biological delivery and expression system can comprise a dose volume of 1 ml to 5 ml. The adenoviral-based biological delivery and expression system can comprise a dose volume of 2 ml to 5 ml. The adenoviral-based biological delivery and expression system can comprise a dose volume of 3 ml to 5 ml. The adenoviral-based biological delivery and expression system can comprise a dose volume of 4 ml to 5 ml. The adenoviral-based biological delivery and expression system can comprise a dose volume of 5 ml.

The adenoviral-based biological delivery and expression system of the present invention, can comprise the helper-dependent adenoviral vector (HDAd) at a total dose of $7\times10^{9}$ to $7\times10^{12}$ GC. The adenoviral-based biological delivery and expression system of the present invention, can comprise the helper-dependent adenoviral vector (HDAd) at a total dose of $7\times10^{9}$ to $7\times10^{11}$ GC. The adenoviral-based biological delivery and expression system of the present invention, can comprise the helper-dependent adenoviral vector (HDAd) at a total dose of $7\times10^{9}$ to $7\times10^{10}$ GC.

The adenoviral-based biological delivery and expression system of the present invention, can comprise the helper-dependent adenoviral vector (HDAd) at a total dose of $7\times10^{9}$ to $2.8\times10^{10}$ GC. The adenoviral-based biological delivery and expression system of the present invention, can comprise the helper-dependent adenoviral vector (HDAd) at a total dose of $7\times10^{10}$ to $2.8\times10^{11}$ GC. The adenoviral-based biological delivery and expression system of the present invention, can comprise the helper-dependent adenoviral vector (HDAd) at a total dose of $7\times10^{11}$ to $2.8\times10^{12}$ GC.

The adenoviral-based biological delivery and expression system of the present invention, can comprise the helper-dependent adenoviral vector (HDAd) at a total dose of $7\times10^{10}$ to $7\times10^{11}$ GC. The adenoviral-based biological delivery and expression system of the present invention, can comprise the helper-dependent adenoviral vector (HDAd) at a total dose of $7\times10^{10}$ to $7\times10^{11}$ GC. The adenoviral-based biological delivery and expression system of the present invention, can comprise the helper-dependent adenoviral vector (HDAd) at a total dose of $7\times10^{11}$ to $7\times10^{12}$ GC.

The adenoviral-based biological delivery and expression system of the present invention, can comprise the helper-dependent adenoviral vector (HDAd) at a total dose of $7\times10^{9}$ to $2.8\times10^{10}$ GC. The adenoviral-based biological delivery and expression system of the present invention, can comprise the helper-dependent adenoviral vector (HDAd) at a total dose of $7\times10^{10}$ to $2.8\times10^{11}$ GC. The adenoviral-based biological delivery and expression system of the present invention, can comprise the helper-dependent adenoviral vector (HDAd) at a total dose of $7\times10^{11}$ to $2.8\times10^{12}$ GC.

The adenoviral-based biological delivery and expression system of the present invention, can comprise the helper-dependent adenoviral vector (HDAd) at a total dose of $10^{10}$ to $2.8\times10^{10}$ GC. The adenoviral-based biological delivery and expression system of the present invention, can comprise the helper-dependent adenoviral vector (HDAd) at a total dose of $10^{11}$ to $2.8\times10^{11}$ GC. The adenoviral-based biological delivery and expression system of the present invention, can comprise the helper-dependent adenoviral vector (HDAd) at a total dose of $10^{12}$ to $2.8\times10^{12}$ GC.

The adenoviral-based biological delivery and expression system of the present invention, can comprise the helper-dependent adenoviral vector (HDAd) at a total dose of $2.8\times10^{9}$ to $5.6\times10^{9}$ GC. The adenoviral-based biological delivery and expression system of the present invention, can comprise the helper-dependent adenoviral vector (HDAd) at a total dose of $2.8\times10^{10}$ to $5.6\times10^{10}$ GC. The adenoviral-based biological delivery and expression system of the present invention, can comprise the helper-dependent adenoviral vector (HDAd) at a total dose of $2.8\times10^{11}$ to $5.6\times10^{11}$ GC.

The adenoviral-based biological delivery and expression system of the present invention, can comprise the helper-dependent adenoviral vector (HDAd) at a total dose of $10^{10}$ to $1.4\times10^{10}$ GC. The adenoviral-based biological delivery and expression system of the present invention, can comprise the helper-dependent adenoviral vector (HDAd) at a total dose of $10^{11}$ to $1.4\times10^{11}$ GC. The adenoviral-based biological delivery and expression system of the present invention, can comprise the helper-dependent adenoviral vector (HDAd) at a total dose of $10^{12}$ to $1.4\times10^{12}$ GC.

The adenoviral-based biological delivery and expression system of the present invention, can comprise the helper-dependent adenoviral vector (HDAd) at a total dose of $7\times10^{9}$ to $5.6\times10^{11}$ GC. The adenoviral-based biological delivery and expression system of the present invention, can comprise the helper-dependent adenoviral vector (HDAd) at a total dose of $7\times10^{10}$ to $5.6\times10^{12}$ GC. The adenoviral-based biological delivery and expression system of the present invention, can comprise the helper-dependent adenoviral vector (HDAd) at a total dose of $7\times10^{11}$ to $5.6\times10^{12}$ GC.

The adenoviral-based biological delivery and expression system of the present invention, can comprise the helper-dependent adenoviral vector (HDAd) at a total dose of $1.4\times10^{10}$ to $7\times10^{12}$ GC. The adenoviral-based biological delivery and expression system of the present invention, can comprise the helper-dependent adenoviral vector (HDAd) at a total dose of $1.4\times10^{11}$ to $7\times10^{12}$ GC. The adenoviral-based biological delivery and expression system of the present invention, can comprise the helper-dependent adenoviral vector (HDAd) at a total dose of $1.4\times10^{12}$ to $7\times10^{12}$ GC.

The adenoviral-based biological delivery and expression system of the present invention, can comprise the helper-dependent adenoviral vector (HDAd) at a total dose of $1.4\times10^{10}$ to $1.4\times10^{12}$ GC. The adenoviral-based biological delivery and expression system of the present invention, can comprise the helper-dependent adenoviral vector (HDAd) at a total dose of $1.4\times10^{10}$ to $1.4\times10^{11}$ GC. The adenoviral-based biological delivery and expression system of the present invention, can comprise the helper-dependent adenoviral vector (HDAd) at a total dose of $1.4\times10^{11}$ to $1.4\times10^{12}$ GC.

The adenoviral-based biological delivery and expression system of the present invention, can comprise the helper-dependent adenoviral vector (HDAd) at a total dose of $7\times10^{9}$ GC. The adenoviral-based biological delivery and expression system of the present invention, can comprise the helper-dependent adenoviral vector (HDAd) at a total dose of $7\times10^{10}$ GC The adenoviral-based biological delivery and expression system of the present invention, can comprise the helper-dependent adenoviral vector (HDAd) at a total dose of $7\times10^{11}$ GC. The adenoviral-based biological delivery and expression system of the present invention, can comprise the helper-dependent adenoviral vector (HDAd) at a total dose of $7\times10^{12}$ GC.

The adenoviral-based biological delivery and expression system of the present invention, can comprise the helper-dependent adenoviral vector (HDAd) at a total dose of $1.4\times10^{10}$ GC The adenoviral-based biological delivery and expression system of the present invention, can comprise the helper-dependent adenoviral vector (HDAd) at a total dose of $1.4\times10^{11}$ GC. The adenoviral-based biological delivery and expression system of the present invention, can comprise the helper-dependent adenoviral vector (HDAd) at a total dose of $1.4\times10^{12}$ GC.

The adenoviral-based biological delivery and expression system of the present invention, can comprise the helper-dependent adenoviral vector (HDAd) at a total dose of $2.8\times10^{10}$ GC. The adenoviral-based biological delivery and expression system of the present invention, can comprise the helper-dependent adenoviral vector (HDAd) at a total dose of $2.8\times10^{11}$ GC. The adenoviral-based biological delivery and expression system of the present invention, can comprise the helper-dependent adenoviral vector (HDAd) at a total dose of $2.8\times10^{12}$ GC.

Pharmaceutical Compositions

The adenoviral-based biological delivery and expression system of the present invention can be incorporated into pharmaceutical compositions suitable for administration. The compositions of the present disclosure include pharmaceutical compositions comprising an adenoviral helper-dependent adenoviral vector comprising a nucleic acid sequence encoding for human or mammalian interleukin-1 receptor antagonist (IL-1Ra), L ITR, R ITR, packaging signal and non-viral, non-coding stuffer nucleic acid sequences, wherein the expression of the human or mammalian interleukin-1 receptor antagonist (IL-1Ra) gene is regulated by an inflammation-sensitive promoter located upstream of the reading frame of the nucleic acid sequence encoding for the human or mammalian IL-1Ra. In some aspects, the pharmaceutical composition can be used for the treatment or prevention of osteoarthritis.

Preferred inflammation-sensitive promoters as used in the context of the present disclosure are promoters inducible by NF-κB, interleukin 6 (Il-6), interleukin-1 (IL-1), tumor necrosis factor (TNF), cyclooxygenase 2 (COX-2), complement factor 3 (C3), serum amyloid A3 (SAA3), macrophage inflammatory protein-1a (MIP-1a), or hybrid constructs of the above. In preferred aspects, the inflammation-sensitive promoter is an NF-κB5-ELAM promoter.

Such compositions typically comprise the helper-dependent adenoviral vector viral particles as disclosed herein, a helper adenovirus and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intraarticular, intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Chemical Properties of the Adenoviral Expression and Delivery System of the Disclosure The capsid of the adenoviral-based biological delivery and expression system of the disclosure (FX201) can be unenveloped and can comprise of 29.3 kb double-stranded DNA. The theoretical molecular weight of the capsid can be 103.9 megadaltons (MDa) and the genome can be 18.1 MDa. The capsid of FX201 can have a diameter of approximately 100 nm.

Formulations: FX201 can be formulated in a buffer composed of about 1-20 mM, TRIS, about 50-100 mM NaCl, 0.01-1% weight/volume (w/v) Polysorbate 80, 1-10% (w/v) sucrose, 0.1-10 mM $MgCl_2$, 50-500 μM EDTA, 1-5% volume/volume (v/v) ethanol, and 5-50 mM L-histidine. In a preferred aspect, FX201 can be formulated in a buffer composed of 10 mM TRIS, 75 mM NaCl, 0.02% (weight/volume (w/v) Polysorbate 80, 5% (w/v) sucrose, 1.0 mM $MgCl_2$, 100 μM EDTA, 0.5% (volume/volume (v/v) of ethanol), and 10 mM L-histidine. The product can be a clear to slightly opalescent, colorless suspension with no visible particulates.

Storage Conditions and Stability: FX201 can be stored as a frozen liquid at ≤−65° C. FX201 can be stable for at least 3 months, at least 6 months or at least 12 months when stored at ≤−65° C. Once thawed, the product must be stored at 2-8° C. and used within 7 days. FX201 may be kept at room temperature (RT) for some period of time. Once a vial is ready for use it can be held at RT in vial for no more than 7 hours (vials held at RT cannot be returned to refrigeration for later use). Once the FX201 dosage is prepared in the syringe, it must be held at RT and used within 4 hours.

The pharmaceutical compositions of the present disclosure comprising an adenoviral-based biological delivery and expression system can be used for the treatment of osteoarthritis or an osteoarthritic condition in a human joint or for the prevention of such conditions in a human identified to be at risk of developing osteoarthritis or an osteoarthritic condition, wherein the adenoviral-based biological delivery and expression system comprises genome copies (GC) of a helper-dependent adenoviral vector comprising a nucleic acid sequence encoding a human interleukin-1 receptor antagonist (IL-1Ra), left and right inverted terminal repeats, an adenoviral packaging signal and non-viral, and non-coding stuffer nucleic acid sequences, wherein the expression of the human IL-1Ra gene is regulated by an inflammation-sensitive promoter, which is located upstream of the reading frame of the nucleic acid sequence encoding the human IL-1Ra, wherein the nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can be at least 95% homologous to the nucleic acid sequence of SEQ ID NO: 2, SEQ ID NO: 3 or SEQ ID NO: 7, and wherein adenoviral-based biological delivery and expression system comprises $1.4\times10^{8}$ to $1.4\times10^{12}$ GC of the helper-dependent adenoviral vector per milliliter (ml). The inflammation-sensitive promoter can be promoters inducible by any one of NF-κB, interleukin 6 (11-6), interleukin-1 (IL-1), tumor necrosis factor (TNF), cyclooxygenase 2 (COX-2), complement factor 3 (C3), serum amyloid A3 (SAA3), macrophage inflammatory protein-1a (MIP-1a), or hybrid constructs of the above. In a preferred aspect, the inflammation-sensitive promoter is a NF-κB inducible promoter. In preferred aspects, the NF-κB inducible promoter is an NF-KB5-ELAM promoter.

The nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can be at least 96%, 97%, 98% or 99% homologous to the nucleic acid sequence of SEQ ID NO: 2, SEQ ID NO: 3 or SEQ ID NO: 7. The nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can be at least 99% homologous to the nucleic acid sequence of SEQ ID NO: 2, SEQ ID NO: 3 or SEQ ID NO: 7. The nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can be of SEQ ID NO: 2, SEQ ID NO: 3 or SEQ ID NO: 7.

In some embodiments, the nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can be at least 95% homologous to the nucleic acid sequence of SEQ ID NO: 7. In some embodiments, the nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can be at least at least 96%, 97%, 98% or 99% homologous to the nucleic acid sequence of SEQ ID NO: 7.

The nucleic acid sequence encoding the IL-1Ra can comprise the nucleic acid of SEQ ID NO 1. The nucleic acid sequence encoding the IL-1Ra can comprise the nucleic acid of comprise the nucleic acid of SEQ ID NO 4. SEQ ID NO: 4 is a codon optimized version of the original coding sequence of human IL-1Ra (SEQ ID NO: 5), wherein the codon optimized sequence according to SEQ ID NO: 4 has:

a) a codon adaptive index (CAI) of 0.96 compared a CAI of 0.78 in the wild type human IL-1Ra protein, b) 85% of the codons within the highest usage frequency, as compared to a highest usage frequency of 56% in the wild type human IL-1Ra protein, c) an average GC content of 60.4 as compared to an average GC content of 51.98 in the wild type human IL-1Ra protein, and d) no negative cis acting elements including: splice site (GGTAAG), splice site (GGTGAT), polyA (AATAAA), polyA (ATTAAA), destabilizing (ATTTA), polyT (TTTTTT) and polyA (AAAAAAA) as compared to the wild type human IL-1Ra protein.

The amino acid sequence of the human IL-1Ra is according to SEQ ID NO: 6.

The nucleic acid sequence of the adenoviral-based biological delivery and expression system comprising the promoter, the nucleic acid sequence encoding the IL-1Ra, the left and the right inverted terminal repeats, the adenoviral packaging signal and the non-viral, non-coding stuffer nucleic acid sequences can comprise, can consist essentially or, or can consist the nucleic acid sequence of SEQ ID NO: 2, SEQ ID NO: 3 or SEQ ID NO: 7.

The helper-dependent adenoviral vector additionally can comprise a marker gene encoding a protein product that is visually or instrumentally detectable to monitor the presence of the vector sequences in infected cells. The marker gene can be a gene encoding any one of a fluorescent protein, an enzyme or a detectable cell surface protein. The marker gene can be a gene encoding any one of green fluorescent protein LacZ, or luciferase enzyme.

The pharmaceutical compositions of the present disclosure comprising the adenoviral-based biological delivery and expression system can comprise: a) $1.4\times10^9$ to $1.4\times10^{12}$; b) $1.4\times10^9$ to $1.4\times10^{11}$; or c) $1.4\times10^9$ to $1.4\times10^{10}$ genome copies (GC) of the helper-dependent adenoviral vector (HDAd) per ml of the pharmaceutical composition.

The pharmaceutical compositions of the present disclosure comprising the adenoviral-based biological delivery and expression system can comprise $1.4\times10^{10}$ to $1.4\times10^{12}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $1.4\times10^{10}$ to $1.4\times10^{11}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $1.4\times10^{11}$ to $1.4\times10^{12}$ genome copies (GC) of the helper-dependent adenoviral vector (HDAd) per ml of the pharmaceutical composition.

The pharmaceutical compositions of the present disclosure comprising the adenoviral-based biological delivery and expression system can comprise $1.4\times10^9$ to $5.6\times10^9$ genome copies (GC) of the helper-dependent adenoviral vector (HDAd) per ml of the pharmaceutical composition. The pharmaceutical compositions of the present disclosure comprising the adenoviral-based biological delivery and expression system can comprise $1.4\times10^{10}$ to $5.6\times10^{10}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $1.4\times10^{11}$ to $5.6\times10^{11}$ genome copies (GC) of the helper-dependent adenoviral vector (HDAd) per ml of the pharmaceutical composition.

The pharmaceutical compositions of the present disclosure comprising the adenoviral-based biological delivery and expression system can comprise $2\times10^9$ to $5.6\times10^9$ genome copies (GC) of the helper-dependent adenoviral vector (HDAd) per ml of the pharmaceutical composition. The pharmaceutical compositions of the present disclosure comprising the adenoviral-based biological delivery and expression system can comprise $2\times10^{10}$ to $5.6\times10^{10}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $2\times10^{11}$ to $5.6\times10^{11}$ genome copies (GC) of the helper-dependent adenoviral vector (HDAd) per ml of the pharmaceutical composition.

The pharmaceutical compositions of the present disclosure comprising the adenoviral-based biological delivery and expression system can comprise $2.8\times10^9$ to $5.6\times10^9$ genome copies (GC) of the helper-dependent adenoviral vector (HDAd) per ml of the pharmaceutical composition. The pharmaceutical compositions of the present disclosure comprising the adenoviral-based biological delivery and expression system can comprise $2.8\times10^{10}$ to $5.6\times10^{10}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $2.8\times10^{11}$ to $5.6\times10^{11}$ genome copies (GC) of the helper-dependent adenoviral vector (HDAd) per ml of the pharmaceutical composition.

The pharmaceutical compositions of the present disclosure comprising the adenoviral-based biological delivery and expression system can comprise $2\times10^9$ to $2.8\times10^9$ genome copies (GC) of the helper-dependent adenoviral vector (HDAd) per ml of the pharmaceutical composition. The pharmaceutical compositions of the present disclosure comprising the adenoviral-based biological delivery and expression system can comprise $2\times10^{10}$ to $2.8\times10^{10}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $2\times10^{11}$ to $2.8\times10^{11}$ genome copies (GC) of the helper-dependent adenoviral vector (HDAd) per ml of the pharmaceutical composition.

The pharmaceutical compositions of the present disclosure comprising the adenoviral-based biological delivery and expression system can comprise $1.4\times10^9$ to $2.8\times10^{10}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $1.4\times10^{10}$ to $2.8\times10^{11}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $1.4\times10^{11}$ to $2.8\times10^{11}$ genome copies (GC) of the helper-dependent adenoviral vector (HDAd) per ml of the pharmaceutical composition.

The pharmaceutical compositions of the present disclosure comprising the adenoviral-based biological delivery and expression system can comprise $2.8\times10^9$ to $1.4\times10^{12}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $2.8\times10^{10}$ to $1.4\times10^{12}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $2.8\times10^{11}$ to $1.4\times10^{12}$ genome copies (GC) of the helper-dependent adenoviral vector (HDAd) per ml of the pharmaceutical composition.

The pharmaceutical compositions of the present disclosure comprising the adenoviral-based biological delivery and expression system can comprise $2.8\times10^9$ to $2.8\times10^{11}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $2.8\times10^9$ to $1.4\times10^{10}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $2.8\times10^{10}$ to $2.8\times10^{11}$ genome copies (GC) of the helper-dependent adenoviral vector (HDAd) per ml of the pharmaceutical composition.

The pharmaceutical compositions of the present disclosure comprising the adenoviral-based biological delivery and expression system can comprise $1.4\times10^9$ genome copies (GC) of the helper-dependent adenoviral vector (HDAd) per ml of the pharmaceutical composition. The pharmaceutical compositions of the present disclosure comprising the adenoviral-based biological delivery and expression system can comprise $1.4\times10^{10}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $1.4\times10^{11}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $1.4\times10^{11}$ genome copies (GC) of the helper-dependent adenoviral vector (HDAd) per ml of the pharmaceutical composition.

The pharmaceutical compositions of the present disclosure comprising the adenoviral-based biological delivery and expression system can comprise $2\times10^9$ genome copies (GC) of the helper-dependent adenoviral vector (HDAd) per ml of the pharmaceutical composition. The pharmaceutical compositions of the present disclosure comprising the adenoviral-based biological delivery and expression system can comprise $2\times10^{10}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $2\times10^{11}$ genome copies (GC) of the helper-dependent adenoviral vector (HDAd) per ml of the pharmaceutical composition.

The pharmaceutical compositions of the present disclosure comprising the adenoviral-based biological delivery and expression system can comprise $2.8\times10^9$ genome copies (GC) of the helper-dependent adenoviral vector (HDAd) per ml of the pharmaceutical composition. The pharmaceutical compositions of the present disclosure comprising the adenoviral-based biological delivery and expression system can comprise $2.8\times10^{10}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $2.8\times10^{11}$ genome copies (GC) of the helper-dependent adenoviral vector (HDAd) per ml of the pharmaceutical composition.

The pharmaceutical compositions of the present disclosure comprising the adenoviral-based biological delivery and expression system can comprise $5.6\times10^9$ genome copies (GC) of the helper-dependent adenoviral vector (HDAd) per ml of the pharmaceutical composition. The pharmaceutical compositions of the present disclosure comprising the adenoviral-based biological delivery and expression system can comprise $5.6\times10^{10}$ genome copies (GC) of the helper-dependent adenoviral vector (HDAd) per ml of the pharmaceutical composition. The pharmaceutical compositions of the present disclosure comprising the adenoviral-based biological delivery and expression system can comprise $5.6\times10^{11}$ genome copies (GC) of the helper-dependent adenoviral vector (HDAd) per ml of the pharmaceutical composition.

The pharmaceutical compositions of the present disclosure comprising the adenoviral-based biological delivery and expression system can comprise a dose volume of 1 ml to 5 ml. The pharmaceutical compositions of the present disclosure comprising the adenoviral-based biological delivery and expression system can comprise a dose volume of 2 ml to 5 ml. The pharmaceutical compositions of the present disclosure comprising the adenoviral-based biological delivery and expression system can comprise a dose volume of 4 ml to 5 ml. The pharmaceutical compositions of the present disclosure comprising the adenoviral-based biological delivery and expression system can comprise a dose volume of 3 ml to 5 ml. The pharmaceutical compositions of the present disclosure comprising the adenoviral-based biological delivery and expression system can comprise a dose volume of up to 5 ml.

The pharmaceutical compositions of the present disclosure comprising the adenoviral-based biological delivery and expression system can comprise a total dose of $7\times10^9$ to $7\times10^{12}$ GC of the helper-dependent adenoviral vector (HDAd). The pharmaceutical compositions of the present disclosure comprising the adenoviral-based biological delivery and expression system can comprise a total dose of $7\times10^9$ to $7\times10^{11}$ GC of the helper-dependent adenoviral vector (HDAd). The pharmaceutical compositions of the present disclosure comprising the adenoviral-based biological delivery and expression system can comprise a total dose of $7\times10^9$ to $7\times10^{10}$ GC of the helper-dependent adenoviral vector (HDAd).

The pharmaceutical compositions of the present disclosure comprising the adenoviral-based biological delivery and expression system can comprise a total dose of $7\times10^{10}$ to $7\times10^{12}$ GC of the helper-dependent adenoviral vector (HDAd). The pharmaceutical compositions of the present disclosure comprising the adenoviral-based biological delivery and expression system can comprise a total dose of $7\times10^{10}$ to $7\times10^{11}$ GC of the helper-dependent adenoviral vector (HDAd). The pharmaceutical compositions of the present disclosure comprising the adenoviral-based biological delivery and expression system can comprise a total dose of $7\times10^{11}$ to $7\times10^{12}$ GC of the helper-dependent adenoviral vector (HDAd).

The pharmaceutical compositions of the present disclosure comprising the adenoviral-based biological delivery and expression system can comprise a total dose of $7\times10^9$ to $2.8\times10^{10}$ GC of the helper-dependent adenoviral vector (HDAd). The pharmaceutical compositions of the present disclosure comprising the adenoviral-based biological delivery and expression system can comprise a total dose of $7\times10^{10}$ to $2.8\times10^{11}$ GC of the helper-dependent adenoviral vector (HDAd). The pharmaceutical compositions of the present disclosure comprising the adenoviral-based biological delivery and expression system can comprise a total dose of $7\times10^{11}$ to $2.8\times10^{12}$ GC of the helper-dependent adenoviral vector (HDAd).

The pharmaceutical compositions of the present disclosure comprising the adenoviral-based biological delivery and expression system can comprise a total dose of $7\times10^9$ to $2.8\times10^{11}$ GC of the helper-dependent adenoviral vector (HDAd). The pharmaceutical compositions of the present disclosure comprising the adenoviral-based biological delivery and expression system can comprise a total dose of $7\times10^9$ to $2.8\times10^{12}$ GC of the helper-dependent adenoviral vector (HDAd). The pharmaceutical compositions of the present disclosure comprising the adenoviral-based biological delivery and expression system can comprise a total dose of $7\times10^{10}$ to $2.8\times10^{11}$ GC of the helper-dependent adenoviral vector (HDAd).

The pharmaceutical compositions of the present disclosure comprising the adenoviral-based biological delivery and expression system can comprise a total dose of $1\times10^{10}$ to $2.8\times10^{11}$ GC of the helper-dependent adenoviral vector (HDAd). The pharmaceutical compositions of the present disclosure comprising the adenoviral-based biological delivery and expression system can comprise a total dose of $1\times10^{11}$ to $2.8\times10^{11}$ GC of the helper-dependent adenoviral vector (HDAd). The adenoviral-based biological delivery and expression system can comprise a total dose of $1\times10^{12}$ to $2.8\times10^{12}$ GC of the helper-dependent adenoviral vector (HDAd).

The pharmaceutical compositions of the present disclosure comprising the adenoviral-based biological delivery and expression system can comprise a total dose of $2.8\times10^{9}$ to $5.6\times10^{9}$ GC of the helper-dependent adenoviral vector (HDAd). The pharmaceutical compositions of the present disclosure comprising the adenoviral-based biological delivery and expression system can comprise a total dose of $2.8\times10^{10}$ to $5.6\times10^{10}$ GC of the helper-dependent adenoviral vector (HDAd). The pharmaceutical compositions of the present disclosure comprising the adenoviral-based biological delivery and expression system can comprise a total dose of $2.8\times10^{11}$ to $5.6\times10^{11}$ GC of the helper-dependent adenoviral vector (HDAd).

The pharmaceutical compositions of the present disclosure comprising the adenoviral-based biological delivery and expression system can comprise a total dose of $1\times10^{10}$ to $1.4\times10^{10}$ GC of the helper-dependent adenoviral vector (HDAd). The pharmaceutical compositions of the present disclosure comprising the adenoviral-based biological delivery and expression system can comprise a total dose of $1\times10^{11}$ to $1.4\times10^{11}$ GC of the helper-dependent adenoviral vector (HDAd). The pharmaceutical compositions of the present disclosure comprising the adenoviral-based biological delivery and expression system can comprise a total dose of $1\times10^{12}$ to $1.4\times10^{12}$ GC of the helper-dependent adenoviral vector (HDAd).

The adenoviral-based biological delivery and expression system can comprise a total dose of $7\times10^{9}$ to $5.6\times10^{11}$ GC of the helper-dependent adenoviral vector (HDAd). The adenoviral-based biological delivery and expression system can comprise a total dose of $7\times10^{10}$ to $5.6\times10^{12}$ GC of the helper-dependent adenoviral vector (HDAd). The adenoviral-based biological delivery and expression system can comprise a total dose of $7\times10^{11}$ to $5.6\times10^{12}$ GC of the helper-dependent adenoviral vector (HDAd).

The pharmaceutical compositions of the present disclosure comprising the adenoviral-based biological delivery and expression system can comprise a total dose of $1.4\times10^{10}$ to $7\times10^{12}$ GC of the helper-dependent adenoviral vector (HDAd). The pharmaceutical compositions of the present disclosure comprising the adenoviral-based biological delivery and expression system can comprise a total dose of $1.4\times10^{11}$ to $7\times10^{12}$ GC of the helper-dependent adenoviral vector (HDAd). The pharmaceutical compositions of the present disclosure comprising the adenoviral-based biological delivery and expression system can comprise a total dose of $1.4\times10^{12}$ to $7\times10^{12}$ GC of the helper-dependent adenoviral vector (HDAd).

The pharmaceutical compositions of the present disclosure comprising the adenoviral-based biological delivery and expression system can comprise a total dose of $1.4\times10^{10}$ to $1.4\times10^{12}$ GC of the helper-dependent adenoviral vector (HDAd). The pharmaceutical compositions of the present disclosure comprising the adenoviral-based biological delivery and expression system can comprise a total dose of $1.4\times10^{10}$ to $1.4\times10^{11}$ GC of the helper-dependent adenoviral vector (HDAd). The pharmaceutical compositions of the present disclosure comprising the adenoviral-based biological delivery and expression system can comprise a total dose of $1.4\times10^{11}$ to $1.4\times10^{12}$ GC of the helper-dependent adenoviral vector (HDAd).

The pharmaceutical compositions of the present disclosure comprising the adenoviral-based biological delivery and expression system can comprise a total dose of $7\times10^{9}$ GC of the helper-dependent adenoviral vector (HDAd). The pharmaceutical compositions of the present disclosure comprising the adenoviral-based biological delivery and expression system can comprise a total dose of $7\times10^{10}$ GC of the helper-dependent adenoviral vector (HDAd). The pharmaceutical compositions of the present disclosure comprising the adenoviral-based biological delivery and expression system can comprise a total dose of $7\times10^{11}$ GC of the helper-dependent adenoviral vector (HDAd). The pharmaceutical compositions of the present disclosure comprising the adenoviral-based biological delivery and expression system can comprise a total dose of $7\times10^{12}$ GC of the helper-dependent adenoviral vector (HDAd).

The pharmaceutical compositions of the present disclosure comprising the adenoviral-based biological delivery and expression system can comprise a total dose of $1.4\times10^{10}$ GC of the helper-dependent adenoviral vector (HDAd). The pharmaceutical compositions of the present disclosure comprising the adenoviral-based biological delivery and expression system can comprise a total dose of $1.4\times10^{11}$ GC of the helper-dependent adenoviral vector (HDAd). The pharmaceutical compositions of the present disclosure comprising the adenoviral-based biological delivery and expression system can comprise a total dose of $1.4\times10^{12}$ GC of the helper-dependent adenoviral vector (HDAd).

The pharmaceutical compositions of the present disclosure comprising the adenoviral-based biological delivery and expression system can comprise a total dose of $2.8\times10^{10}$ GC of the helper-dependent adenoviral vector (HDAd). The pharmaceutical compositions of the present disclosure comprising the adenoviral-based biological delivery and expression system can comprise a total dose of $2.8\times10^{11}$ GC of the helper-dependent adenoviral vector (HDAd). The pharmaceutical compositions of the present disclosure comprising the adenoviral-based biological delivery and expression system can comprise a total dose of $2.8\times10^{12}$ GC of the helper-dependent adenoviral vector (HDAd).

The pharmaceutical compositions of the present disclosure can be formulated for intra-tendinous, intra-muscular, intra-articular, or sub-acromial injection to the human joint. The pharmaceutical composition is formulated for intra-articular to the human joint.

The pharmaceutical composition comprising an adenoviral-based biological delivery and expression system of the present invention can comprise viral particles of a helper-dependent adenoviral vector quantified as either Genome copies (GC) of the helper-dependent adenoviral vector per milliliter (ml), or viral particles (VP) of the helper-dependent adenoviral vector per milliliter (ml), wherein the 1 VP/ml corresponds to 1.4 GC/ml.

While the pharmaceutical compositions of the present invention can comprise an adenoviral-based biological delivery and expression system comprising $1.4\times10^{8}$ to $1.4\times10^{12}$ Genome copies of the helper-dependent adenoviral vector (GC) per milliliter (ml), the pharmaceutical compositions can also comprise $10^{8}$ to $10^{12}$ viral particles (VP) of the helper-dependent adenoviral vector of the disclosure, per milliliter (ml) of synovial fluid in a joint.

In some aspects of the present invention the pharmaceutical compositions comprising the adenoviral-based biological delivery and expression system can comprise $10^{9}$ to $10^{12}$;

$10^9$ to $10^{11}$; or $10^9$ to $10^{10}$ VP of the helper-dependent adenoviral vector per ml of synovial fluid in a joint. Preferably the pharmaceutical compositions comprising the adenoviral-based biological delivery and expression system can comprise $10^9$ to $10^{11}$ VP of the helper-dependent adenoviral vector per ml of synovial fluid in a joint.

In some aspects of the present invention the pharmaceutical compositions comprising the adenoviral-based biological delivery and expression system can comprise $2.8\times10^9$ to $2.8\times10^{11}$ VP of the helper-dependent adenoviral vector per ml of synovial fluid in a joint. In other aspects of the present invention the pharmaceutical compositions comprising the adenoviral-based biological delivery and expression system can comprise $2.8\times10^9$ to $2.8\times10^{10}$ VP of the helper-dependent adenoviral vector per ml of synovial fluid in a joint. In certain aspects of the present invention the pharmaceutical compositions comprising the adenoviral-based biological delivery and expression system can comprise $2.8\times10^{10}$ to $2.8\times10^{11}$ VP of the helper-dependent adenoviral vector per ml of synovial fluid in a joint.

In some aspects of the pharmaceutical compositions comprising the adenoviral-based biological delivery and expression system can comprise $2\times10^9$ to $2\times10^{11}$ VP of the helper-dependent adenoviral vector per ml of synovial fluid in a joint. In other aspects of the present invention the adenoviral-based biological delivery and expression system comprises $2\times10^9$ to $2\times10^{10}$ VP of the helper-dependent adenoviral vector per ml of synovial fluid in a joint. In certain aspects of the present invention the pharmaceutical compositions comprising the adenoviral-based biological delivery and expression system can comprise $2\times10^{10}$ to $2\times10^{11}$ VP of the helper-dependent adenoviral vector per ml of synovial fluid in a joint.

In some aspects of the present invention the pharmaceutical compositions comprising the adenoviral-based biological delivery and expression system can comprise $2.8\times10^9$ VP of the helper-dependent adenoviral vector per ml of synovial fluid in a joint. In other aspects of the present invention the pharmaceutical compositions comprising the adenoviral-based biological delivery and expression system can comprise $2.8\times10^{10}$ VP of the helper-dependent adenoviral vector per ml of synovial fluid in a joint. In some aspects of the present invention the pharmaceutical compositions comprising the adenoviral-based biological delivery and expression system can comprise $2.8\times10^{11}$ VP of the helper-dependent adenoviral vector per ml of synovial fluid in a joint. In some aspects of the present invention the pharmaceutical compositions comprising the adenoviral-based biological delivery and expression system can comprise $2.8\times10^{11}$ VP of the helper-dependent adenoviral vector per ml of synovial fluid in a joint.

In some aspects of the present invention the pharmaceutical compositions comprising the adenoviral-based biological delivery and expression system can comprise $10^9$ to $10^{12}$; $10^9$ to $10^{11}$; or $10^9$ to $10^{10}$ VP of the helper-dependent adenoviral vector per ml of synovial fluid in a joint. Preferably the pharmaceutical compositions comprising the adenoviral-based biological delivery and expression system can comprise $10^9$ to $10^{11}$ VP of the helper-dependent adenoviral vector per ml of synovial fluid in a joint.

The method of infecting joint cells of one or more osteoarthritis-affected joints of a human suffering from osteoarthritis or an osteoarthritic condition with an adenoviral-based biological delivery and expression system, of the present invention can comprise infecting the one or more osteoarthritis-affected joints of the human in need thereof with $10^8$ to $10^{12}$ viral particles (VP) of the helper-dependent adenoviral vector of the disclosure, per milliliter (ml) of synovial fluid in a joint.

In some aspects of the present invention the pharmaceutical compositions comprising the adenoviral-based biological delivery and expression system can comprise $10^9$ to $10^{12}$; $10^9$ to $10^{11}$; or $10^9$ to $10^{10}$ VP of the helper-dependent adenoviral vector per ml of synovial fluid in a joint. Preferably the pharmaceutical compositions comprising the adenoviral-based biological delivery and expression system can comprise $10^9$ to $10^{11}$ VP of the helper-dependent adenoviral vector per ml of synovial fluid in a joint.

In some aspects of the present invention the pharmaceutical compositions comprising the adenoviral-based biological delivery and expression system can comprise $2.8\times10^9$ to $2.8\times10^{11}$ VP of the helper-dependent adenoviral vector per ml of synovial fluid in a joint. In other aspects of the present invention the pharmaceutical compositions comprising the adenoviral-based biological delivery and expression system can comprise $2.8\times10^9$ to $2.8\times10^{10}$ VP of the helper-dependent adenoviral vector per ml of synovial fluid in a joint. In certain aspects of the present invention the pharmaceutical compositions comprising the adenoviral-based biological delivery and expression system can comprise $2.8\times10^{10}$ to $2.8\times10^{11}$ VP of the helper-dependent adenoviral vector per ml of synovial fluid in a joint.

In some aspects of the present invention the pharmaceutical compositions comprising the adenoviral-based biological delivery and expression system can comprise $2.8\times10^9$ VP of the helper-dependent adenoviral vector per ml of synovial fluid in a joint. In other aspects of the present invention the pharmaceutical compositions comprising the adenoviral-based biological delivery and expression system can comprise $2.8\times10^{10}$ VP of the helper-dependent adenoviral vector per ml of synovial fluid in a joint. In some aspects of the present invention the pharmaceutical compositions comprising the adenoviral-based biological delivery and expression system can comprise $2.8\times10^{11}$ VP of the helper-dependent adenoviral vector per ml of synovial fluid in a joint. In some aspects of the present invention the pharmaceutical compositions comprising the adenoviral-based biological delivery and expression system can comprise $2.8\times10^{11}$ VP of the helper-dependent adenoviral vector per ml of synovial fluid in a joint. In some aspects of the present invention, the joint contains about 0.5 ml to about 20 ml of synovial fluid. In some aspects of the present invention, the joint can contain about 0.5 ml to 10 ml of synovial fluid. In some aspects of the present invention, the joint can contain about 0.5 ml to 5 ml of synovial fluid.

Methods of the Present Disclosure

The present invention provides a method of infecting joint cells of one or more osteoarthritis-affected joints of a human suffering from osteoarthritis or an osteoarthritic condition with an adenoviral-based biological delivery and expression system, wherein the method comprises the steps of: a) infecting the joint cells of the osteoarthritis-affected joint of the human in need thereof, with the pharmaceutical composition comprising an adenoviral-based biological delivery and expression system as disclosed herein; and b) expressing IL-1Ra in the target area within the osteoarthritis-affected joint.

The joint cells can be infected once with the adenoviral-based biological delivery and expression system. The joint cells can be infected two or more times with the adenoviral-based biological delivery and expression system.

When the joint cells are infected two or more times with an adenoviral-based biological delivery and expression system each infection comprises a different number of genome copies of the helper-dependent adenoviral vector. When the joint cells are infected at least twice with an adenoviral-based biological delivery and expression system, the first infection can comprise a number of GC per ml that is less than the number of GC per ml of the second or any subsequent infection.

When the joint cells are infected two or more times with an adenoviral-based biological delivery and expression system, wherein each infection comprises a different number of genome copies of the helper-dependent adenoviral vector, the first infection can comprise $1.4\times10^9$ GC per ml to $1.4\times10^{10}$ GC/ml, and the second or subsequent infection can comprise $1.4\times10^{11}$ to $1.4\times10^{12}$ GC per ml.

When the joint cells are infected two or more times with an adenoviral-based biological delivery and expression system, wherein each infection comprises a different number of genome copies of the helper-dependent adenoviral vector, the first infection can comprise $1.4\times10^{10}$ to $1.4\times10^{11}$ GC/ml, and the second or subsequent infection can comprise $1.4\times10^{11}$ to $1.4\times10^{12}$ GC per ml.

When the joint cells are infected two or more times with an adenoviral-based biological delivery and expression system, wherein each infection comprises a different number of genome copies of the helper-dependent adenoviral vector, the first infection can comprise $1.4\times10^9$ to $1.4\times10^{10}$ GC/ml, and the second or subsequent infection can comprise $1.4\times10^{10}$ to $1.4\times10^{11}$ GC per ml.

When the joint cells are infected two or more times with an adenoviral-based biological delivery and expression system, wherein each infection comprises a different number of genome copies of the helper-dependent adenoviral vector, the first infection can comprise $1.4\times10^9$ GC per ml to $5.6\times10^9$ GC/ml, and the second or subsequent infection can comprise $1.4\times10^{10}$ to $5.6\times10^{10}$ GC per ml.

When the joint cells are infected two or more times with an adenoviral-based biological delivery and expression system, wherein each infection comprises a different number of genome copies of the helper-dependent adenoviral vector, the first infection can comprise $1.4\times10^{10}$ to $5.6\times10^{10}$ GC/ml, and the second or subsequent infection can comprise $1.4\times10^{11}$ to $5.6\times10^{11}$ GC per ml.

When the joint cells are infected two or more times with an adenoviral-based biological delivery and expression system, wherein each infection comprises a different number of genome copies of the helper-dependent adenoviral vector, the first infection can comprise $1.4\times10^9$ to $5.6\times10^9$ GC/ml, and the second or subsequent infection can comprise $1.4\times10^{11}$ to $5.6\times10^{11}$ GC per ml.

When the joint cells are infected two or more times with an adenoviral-based biological delivery and expression system, wherein each infection comprises a different number of genome copies of the helper-dependent adenoviral vector, the first infection can comprise $2.8\times10^9$ GC per ml and the second or subsequent infection can comprise $2.8\times10^{10}$ GC per ml.

When the joint cells are infected two or more times with an adenoviral-based biological delivery and expression system, wherein each infection comprises a different number of genome copies of the helper-dependent adenoviral vector, the first infection can comprise $2.8\times10^{10}$ GC per ml and the second or subsequent infection can comprise $2.8\times10^{11}$ GC per ml.

When the joint cells are infected two or more times with an adenoviral-based biological delivery and expression system, wherein each infection comprises a different number of genome copies of the helper-dependent adenoviral vector, the first infection can comprise $2.8\times10^9$ GC per ml and the second or subsequent infection can comprise $2.8\times10^{11}$ GC per ml.

When the joint cells are infected at least twice with an adenoviral-based biological delivery and expression system, the first infection can comprise a number of GC per ml that is more than the number of GC per ml of the second or any subsequent infection.

When the joint cells are infected two or more times with an adenoviral-based biological delivery and expression system, wherein each infection comprises a different number of genome copies of the helper-dependent adenoviral vector, the first infection can comprise $1.4\times10^{11}$ to $1.4\times10^{12}$ GC per ml, and the second or subsequent infection can comprise $1.4\times10^9$ GC per ml to $1.4\times10^{10}$ GC/ml.

When the joint cells are infected two or more times with an adenoviral-based biological delivery and expression system, wherein each infection comprises a different number of genome copies of the helper-dependent adenoviral vector, the first infection can comprise $1.4\times10^{11}$ to $1.4\times10^{12}$ GC per ml, and the second or subsequent infection can comprise $1.4\times10^{10}$ to $1.4\times10^{11}$ GC/ml.

When the joint cells are infected two or more times with an adenoviral-based biological delivery and expression system, wherein each infection comprises a different number of genome copies of the helper-dependent adenoviral vector, the first infection can comprise $1.4\times10^{10}$ to $1.4\times10^{11}$ GC per ml, and the second or subsequent infection can comprise $1.4\times10^9$ to $1.4\times10^{10}$ GC/ml.

When the joint cells are infected two or more times with an adenoviral-based biological delivery and expression system, wherein each infection comprises a different number of genome copies of the helper-dependent adenoviral vector, the first infection can comprise $1.4\times10^{10}$ to $5.6\times10^{10}$ GC per ml, and the second or subsequent infection can comprise $1.4\times10^9$ GC per ml to $5.6\times10^9$ GC/ml.

When the joint cells are infected two or more times with an adenoviral-based biological delivery and expression system, wherein each infection comprises a different number of genome copies of the helper-dependent adenoviral vector, the first infection can comprise $1.4\times10^{11}$ to $5.6\times10^{11}$ GC per ml, and the second or subsequent infection can comprise $1.4\times10^{10}$ to $5.6\times10^{10}$ GC/ml.

When the joint cells are infected two or more times with an adenoviral-based biological delivery and expression system, wherein each infection comprises a different number of genome copies of the helper-dependent adenoviral vector, the first infection can comprise $1.4\times10^{11}$ to $5.6\times10^{11}$ GC per ml, and the second or subsequent infection can comprise $1.4\times10^9$ to $5.6\times10^9$ GC/ml.

When the joint cells are infected two or more times with an adenoviral-based biological delivery and expression system, wherein each infection comprises a different number of genome copies of the helper-dependent adenoviral vector, the first infection can comprise $2.8\times10^{10}$ GC per ml and the second or subsequent infection can comprise $2.8\times10^9$ GC per ml.

When the joint cells are infected two or more times with an adenoviral-based biological delivery and expression system, wherein each infection comprises a different number of genome copies of the helper-dependent adenoviral vector, the first infection can comprise $2.8\times10^{11}$ GC per ml and the second or subsequent infection can comprise $2.8\times10^{10}$ GC per ml.

When the joint cells are infected two or more times with an adenoviral-based biological delivery and expression system, wherein each infection comprises a different number of genome copies of the helper-dependent adenoviral vector, the first infection can comprise $2.8\times10^{11}$ GC per ml and the second or subsequent infection can comprise $2.8\times10^{9}$ GC per ml.

When the joint cells are infected two or more times with an adenoviral-based biological delivery and expression system each infection can comprise the same number of genome copies of the helper-dependent adenoviral vector.

When the joint cells are infected at least twice with an adenoviral-based biological delivery and expression system, each infection can comprise $1.4\times10^{9}$ to $5.6\times10^{9}$ GC per ml. When the joint cells are infected at least twice with an adenoviral-based biological delivery and expression system, each infection can comprise $1.4\times10^{10}$ to $5.6\times10^{10}$ GC per ml. When the joint cells are infected at least twice with an adenoviral-based biological delivery and expression system, each infection can comprise $1.4\times10^{11}$ to $5.6\times10^{11}$ GC per ml.

When the joint cells are infected at least twice with an adenoviral-based biological delivery and expression system, each infection can comprise $2.8\times10^{9}$ GC per ml. When the joint cells are infected at least twice with an adenoviral-based biological delivery and expression system, each infection can comprise $2.8\times10^{10}$ GC per ml. When the joint cells are infected at least twice with an adenoviral-based biological delivery and expression system, each infection can comprise $2.8\times10^{11}$ GC per ml.

When the joint cells are infected two or more times with an adenoviral-based biological delivery and expression system, each infection can be done in the same osteoarthritis-affected joint of the human.

When the joint cells are infected two or more times with an adenoviral-based biological delivery and expression system, every second and subsequent infection can be done in an osteoarthritis-affected joint of the human that is different than the osteoarthritis-affected joint in which the previous infection was done.

The infecting of the joint cells can comprise intra-tendinous, intra-muscular, intra-articular, or sub-acromial injection of a pharmaceutical composition of the present disclosure. The infecting of the joint cells can comprise intra-articular injection of pharmaceutical composition of the present disclosure. The "infecting of the joint cells" as described herein means administering the pharmaceutical composition of the present invention to the joint(s) affected by osteoarthritis or an osteoarthritic condition, wherein the administering comprises injecting the pharmaceutical composition into the joint(s) affected by osteoarthritis or an osteoarthritic condition intra-articularly, intra-tediously, intra-muscularly, or sub-acromial into the joint(s). In a preferred embodiment, the administering of the pharmaceutical composition of the present invention to the joint(s) affected by osteoarthritis or an osteoarthritic condition is done by injecting the pharmaceutical composition into the joint(s) affected by osteoarthritis or an osteoarthritic condition intra-articularly.

Treatment Monitoring

The methods of the present disclosure can further comprise the step of: c) monitoring the treatment or progress of osteoarthritis or an osteoarthritic condition in the osteoarthritis-affected joint following the expression of the IL-1Ra in the target area within the osteoarthritis-affected joint.

The monitoring of the treatment or progress of osteoarthritis or an osteoarthritic condition in the human joint can be carried out by determining pain, physical function, patient global assessment, and joint imaging of the human in need thereof. The monitoring of the treatment or progress of osteoarthritis or an osteoarthritic condition in the human joint can comprise evaluating progress of osteoarthritis using a Western Ontario McMasters Universities Osteoarthritis (WOMAC) Index. The monitoring of the treatment or progress of osteoarthritis or an osteoarthritic condition in the human joint can comprise evaluating progress of osteoarthritis using a Knee Injury and Osteoarthritis Outcome Score (KOOS). The monitoring of the treatment or progress of osteoarthritis or an osteoarthritic condition in the human joint can comprise evaluating progress of osteoarthritis using Average daily pain (ADP) scoring system. The monitoring of the treatment or progress of osteoarthritis or an osteoarthritic condition in the human joint can comprise evaluating progress of osteoarthritis using WOMAC, KOOS and ADP.

The monitoring of the treatment or progress of osteoarthritis or an osteoarthritic condition in the human joint can comprise physically examining the joint of the human in need thereof, for any one or all of joint pain, joint stiffness, crepitus, redness, tenderness, Baker's Cyst and joint swelling or a combination thereof. The monitoring of the treatment or progress of osteoarthritis or an osteoarthritic condition in the human joint can comprise physically examining the human in need thereof for depression, sleep deprivation, hyperalgesia, central sensitization, and catastrophization or a combination thereof.

The monitoring of the treatment or progress of osteoarthritis or an osteoarthritic condition in the human joint can comprise using radiograph imaging to determine osteophyte formation and joint space narrowing (JSN). The monitoring of the treatment or progress of osteoarthritis or an osteoarthritic condition in the human joint can comprise imaging the joint of the human in need thereof using any one or a combination of magnetic resonance imaging (MRI), ultrasound (US), and optical coherence tomography (OCT). The monitoring of the treatment or progress of osteoarthritis or an osteoarthritic condition in the human joint can comprise measurement of Interleukin-1 receptor antagonist (IL-1Ra) and Interleukin-1 beta (IL-1β) protein concentrations in the index knee. The monitoring of the treatment or progress of osteoarthritis or an osteoarthritic condition in the human joint can comprise evaluating the immunological response to the helper-dependent adenoviral vector (HDAd) of the present invention. The monitoring of the treatment or progress of osteoarthritis or an osteoarthritic condition in the human joint can comprise testing blood samples of the human treated with the pharmaceutical composition or method of the present invention, for the presence of anti-Capsid and anti-IL-1Ra antibodies. The monitoring of the treatment or progress of osteoarthritis or an osteoarthritic condition in the human joint can comprise testing IL-1Ra and IL-1β protein concentrations in IA synovial fluid samples of the human treated with the pharmaceutical composition or method of the present invention.

The method can further comprise the steps of: (d) continuing administering the amount of the adenoviral-based biological delivery and expression system to the osteoarthritis-affected joint of the human in need thereof, if the step of monitoring of the treatment or progress of osteoarthritis or an osteoarthritic condition in the osteoarthritis-affected joint shows that the osteoarthritis or an osteoarthritic condition in the human joint is not managed or treated; or (e) further adjusting the number of genome copies of the helper-dependent adenoviral vector in the amount of the adenoviral-based biological delivery and expression system and administering to the osteoarthritis-affected joint of the human in need thereof, if the step of monitoring of the treatment or progress of osteoarthritis or an osteoarthritic condition in the osteoarthritis-affected joint shows that the osteoarthritis or an osteoarthritic condition in the human joint has progressed.

Subjects, Osteoarthritis and Osteoarthritic Condition

In the methods of the present disclosure, the human suffering from osteoarthritis or an osteoarthritic condition can be a male or a female. The human suffering from osteoarthritis or an osteoarthritic condition can be a female.

The human suffering from osteoarthritis or an osteoarthritic condition can be 30-80 years of age. The human suffering from osteoarthritis or an osteoarthritic condition can be more than 80 years of age. The human suffering from osteoarthritis or an osteoarthritic condition can be—suffering from osteoarthritis of joint. The human suffering from osteoarthritis or an osteoarthritic condition can be suffering from osteoarthritis of shoulder, hip, ankle, knee, hand or spine. The human suffering from osteoarthritis or an osteoarthritic condition can have Osteoarthritis of knee (OAK). The human suffering from osteoarthritis or an osteoarthritic condition can have painful OA of the index knee with Kellgren-Lawrence (K-L) Grade 2, 3 or 4. The human can be suffering from osteoarthritis or an osteoarthritic condition caused by ageing, gender (female) related predisposition, obesity, metabolic diseases, joint injuries, repeated stress on the joint, genetic predisposition or bone deformities or a combination thereof. The human can be suffering from osteoarthritis or an osteoarthritic condition caused by joint injury leading to torn cartilage, dislocated joints or ligament injuries or a combination thereof. The human can be suffering from osteoarthritis or an osteoarthritic condition caused by anterior cruciate ligament (ACL) strains and tears. The human can be suffering from osteoarthritis or an osteoarthritic condition caused by meniscal strains and tears.

Osteoarthritis is the most commonly diagnosed type of joint arthritis disease, which can affect shoulder, hands, knees, toes, fingers, wrist and hips. Knee arthritis is known to affect joint functionality causing knee pain and even leading to disability as it progresses. There are different grades of knee osteoarthritis (OA), with 0 assigned to a normal, healthy knee right up to the advanced stage 4, that is severe OA, as characterized by Kellgren & Lawrence, 1997.

Grade 1 is characterized doubtful joint space narrowing and possible osteophytic lipping. OA patients will develop very minor wear & tear and bone spur growths at the end of the knee joints. However, at this stage it is unlikely you will feel pain or discomfort.

Grade 2 (minimal) is characterized by definite osteophytes and possible joint space narrowing Diagnostic images or X-rays of knee joints will show more bone spur growth, and though the space between the bones appear normal, people will begin experiencing symptoms of joint pain. Typically, the area around the knee joints will feel stiff and uncomfortable, particularly when sitting for an extended period, after rising in the morning, or after a workout. Though the cartilage and soft tissues remains at a healthy size, there is proteolytic breakdown of the cartilage matrix from an increased production of enzymes, such as metalloproteinases.

Grade 3 (moderate) is characterized by moderate multiple osteophytes, definite narrowing of joint space and some sclerosis and possible deformity of bone ends. There is obvious erosion to the cartilage surface between bones and fibrillation narrows the gap between the bones. There are proteoglycan and collagen fragments released into the synovial fluid as the disease progresses, wherein the bones develop spurs at the joints as it becomes rougher.

Grade 4 (severe) is characterized by large osteophytes, marked narrowing of joint space, severe sclerosis and definite deformity of bone ends. The joint space between the bones are considerably reduced, causing the cartilage to wear off, leaving the joint stiff. The breakdown of cartilage leads to a chronic inflammatory response, with decreased synovial fluid that causes friction, greater pain and discomfort when walking or moving the joint. There is increased production of synovial metalloproteinases, cytokines and TNF that can diffuse back into the cartilage to destroy soft tissue around the knee. The advanced stage of the disease shows development of more spurs causing excruciating pain, which makes even everyday chores, including walking and descending stairs a challenge.

With the progression of osteoarthritis of the knee, there is obvious joint inflammation which causes frequent pain when walking, running, squatting, extending or kneeling. Along with joint stiffness after sitting for long or when waking up in the morning, there may be popping or snapping sounds when walking.

The human suffering from osteoarthritis or an osteoarthritic condition can have a Body mass index (BMI)≤40 kilograms per meters squared (kg/m$^2$). The human suffering from osteoarthritis or an osteoarthritic condition can have symptoms associated with OA of the index knee for ≥12 months. The human suffering from osteoarthritis or an osteoarthritic condition can have Index knee pain for >15 days over the last month prior to treatment with the pharmaceutical composition or method of the present invention. The human suffering from osteoarthritis or an osteoarthritic condition can have any one or a combination of characteristics defined by American College of Rheumatology (ACR) Criteria (clinical and radiological) for OA as follows: a) Knee pain, b) at least one of (i) age>50 years; (ii) morning stiffness<30 minutes, and (iii) crepitus on knee motion, and c) osteophytes.

The human suffering from osteoarthritis or an osteoarthritic condition can have failed two or more types of conservative therapy for index knee osteoarthritis. The human suffering from osteoarthritis or an osteoarthritic condition may have failed a structured land-based exercise program. The human suffering from osteoarthritis or an osteoarthritic condition can have failed prior treatment with topical non-steroidal anti-inflammatory drugs (NSAIDs). The human suffering from osteoarthritis or an osteoarthritic condition can have failed prior treatment with topical non-steroidal anti-inflammatory drugs (NSAIDs). The human suffering from osteoarthritis or an osteoarthritic condition can have failed prior treatment with nonselective NSAIDs, or COX-2 inhibitors. The human suffering from osteoarthritis or an osteoarthritic condition can have failed one prior type of conservative therapy and at least one prior index knee IA treatment (corticosteroid or hyaluronic acid).

The human suffering from osteoarthritis or an osteoarthritic condition can have a Kellgren-Lawrence (K-L) Grade 2 in the index knee based on X-ray and physical examination. The human suffering from osteoarthritis or an osteoarthritic condition can have a Kellgren-Lawrence (K-L) Grade 3 in the index knee based on X-ray and physical examination. The human suffering from osteoarthritis or an osteoarthritic condition can have a Kellgren-Lawrence (K-L) Grade 4 in the index knee based on X-ray and physical examination.

The human suffering from osteoarthritis or an osteoarthritic condition can have an index knee and the intended area for injection of the pharmaceutical composition of the present invention can be free of any signs of local or joint infection. The human suffering from osteoarthritis or an osteoarthritic condition can have a Western Ontario and McMaster Universities Osteoarthritis Index (WOMAC®) pain score in index knee between ≥4.0 and ≤9.0 (0-10 numeric rating scale [NRS] scale), including the end points. The human suffering from osteoarthritis or an osteoarthritic condition can be a female that is not pregnant or a female that can use one or more of methods of contraception at the time of or for at least 12 months following treatment with the pharmaceutical composition or by the method of the present invention.

The human suffering from osteoarthritis or an osteoarthritic condition can have no current or prior diagnosis of reactive arthritis, rheumatoid arthritis, psoriatic arthritis, ankylosing spondylitis, or arthritis associated with inflammatory bowel disease. The human suffering from osteoarthritis or an osteoarthritic condition can have no present clinical signs and symptoms of active crystal disease including gout, calcium pyrophosphate deposition disease, of the index knee. The human suffering from osteoarthritis or an osteoarthritic condition can have no present clinical signs and symptoms of active crystal disease within three months prior to treatment with the pharmaceutical composition or by the method of the present invention. The human suffering from osteoarthritis or an osteoarthritic condition can have no inability to undergo Magnetic Resonance Imaging (MRI) due to presence of surgical hardware or other foreign body in the index knee. The human suffering from osteoarthritis or an osteoarthritic condition can have no unstable index knee joint.

The human suffering from osteoarthritis or an osteoarthritic condition can have not received any prior treatment with intra-articular (IA) drug/biologic use in index knee, within six months of treatment with the pharmaceutical composition or by the method of the present invention. The human suffering from osteoarthritis or an osteoarthritic condition can have not received treatment with any one or a combination of corticosteroid, hyaluronic acid, platelet rich plasma, stem cells, prolotherapy and amniotic fluid injection, within six months of treatment with the pharmaceutical composition or by the method of the present invention. The human suffering from osteoarthritis or an osteoarthritic condition can have not received cold or radiofrequency nerve ablation of the index knee within 12 months of treatment with the pharmaceutical composition or by the method of the present invention. The human suffering from osteoarthritis or an osteoarthritic condition can have not undergone arthroscopic or open surgery on the index knee within 12 months of treatment with the pharmaceutical composition or by the method of the present invention. The human suffering from osteoarthritis or an osteoarthritic condition can have not planned or anticipated surgery on the index knee within 12 months of treatment with the pharmaceutical composition or by the method of the present invention. The human suffering from osteoarthritis or an osteoarthritic condition can have not suffered from loss of skin integrity over the index knee where intra-articular injection will be given.

The human suffering from osteoarthritis or an osteoarthritic condition may not exhibit any laboratory evidence of infection with human immunodeficiency virus (HIV), positive test for hepatitis B surface antigen (HBsAg) or positive serology for hepatitis C virus (HCV) with positive test for hepatitis C virus ribonucleic acid (HCV RNA).

The human suffering from osteoarthritis or an osteoarthritic condition may not exhibit any ECG abnormality. The human suffering from osteoarthritis or an osteoarthritic condition can have not received or used immunomodulators, immunosuppressive, or chemotherapeutic agents within 5 years of treatment with the pharmaceutical composition or by the method of the present invention. The human suffering from osteoarthritis or an osteoarthritic condition can have not received any prior investigational or approved gene therapy treatment does not have an active or history of malignancy within the 5 years of treatment with the pharmaceutical composition or by the method of the present invention, with the exception of resected basal cell carcinoma, squamous cell carcinoma of the skin, or effectively managed cervical carcinoma in situ.

The human suffering from osteoarthritis or an osteoarthritic condition can have not received active pharmacologic treatment for depression, including selective serotonin reuptake inhibitors (SSRIs), serotonin and norepinephrine reuptake inhibitors (SNRIs) and non-selective serotonin reuptake inhibitors (NSRIs) or tricyclics if dose/regimen has not been stable for ≥6 months prior to treatment with the pharmaceutical composition or by the method of the present invention. The human suffering from osteoarthritis or an osteoarthritic condition can have not done active substance abuse (drugs or alcohol) or has history of substance abuse within the 12 months prior to treatment with the pharmaceutical composition or by the method of the present invention. The human suffering from osteoarthritis or an osteoarthritic condition can have not been administered any investigational drug, biologic or device within 3 months prior to treatment with the pharmaceutical composition or by the method of the present invention.

The human suffering from osteoarthritis or an osteoarthritic condition does not have any systemic or local bacterial or viral infection requiring intravenous (IV) antibiotics or antivirals within 4 weeks prior to treatment with the pharmaceutical composition or by the method of the present invention, or oral antibiotics or antivirals within 2 weeks prior to treatment with the pharmaceutical composition or by the method of the present invention.

The human suffering from osteoarthritis or an osteoarthritic condition can have bilateral knee OA, pain in the contralateral knee is not ≥4.0 (0-10 NRS scale) within 1 month prior to treatment with the pharmaceutical composition or by the method of the present invention. The human suffering from osteoarthritis or an osteoarthritic condition can have not undergone prior total or partial knee arthroplasty procedures in index knee. The human suffering from osteoarthritis or an osteoarthritic condition may not have a temperature above 99.5° F. at the time of treatment with the pharmaceutical composition or by the method of the present invention.

The human suffering from osteoarthritis or an osteoarthritic condition may not have a Prothrombin Time (PT)/International Normalized Ratio (INR)>1.5. The human suffering from osteoarthritis or an osteoarthritic condition may not have an Activated Partial Thromboplastin Time (aPTT) >5 seconds above the Upper Limit of Normal (ULN).

The human suffering from osteoarthritis or an osteoarthritic condition may not have Alanine aminotransferase (ALT), aspartate aminotransferase (AST)>1.5×ULN, alkaline phosphatase (ALP)>1.5×ULN, and total bilirubin outside of normal range. The human suffering from osteoarthritis or an osteoarthritic condition may not have known allergy or sensitivity to acetaminophen.

The human suffering from osteoarthritis or an osteoarthritic condition may not have any clinically significant acute or chronic medical conditions that would preclude the use of an IA injection or that could compromise safety of the human. The human suffering from osteoarthritis or an osteoarthritic condition may not have any bleeding disorder.

The human suffering from osteoarthritis or an osteoarthritic condition can be administered Aspirin for cardio protection at a maximum dose of 81 milligrams (mg) per day provided the dose has been stable over the 3 months prior to treatment with the pharmaceutical composition or by the method of the present invention. The human suffering from osteoarthritis or an osteoarthritic condition can be administered medical therapy for depression, including SSRIs, SNRIs and NSRIs or tricyclics provided dose/regimen has been stable for 6 months prior to treatment with the pharmaceutical composition or by the method of the present invention. The human suffering from osteoarthritis or an osteoarthritic condition can be administered any treatment or rescue medication for adverse effects related to treatment with the pharmaceutical composition or by the method of the present invention.

The human suffering from osteoarthritis or an osteoarthritic condition can have not been administered any one of Oral NSAIDs, Topical therapies applied to the index knee cannot be any one topical NSAIDs, capsaicin, lidocaine patches, Cannabinoids, Aspirin at a dose of >325 mg per day, centrally acting pain medications, opioids, muscle relaxants, any IA injection in the index knee, cold or radiofrequency nerve ablation of the index knee, any investigational drug, device or biologic, any immunomodulator, immunosuppressive, or chemotherapeutic agents or a combination thereof. The human suffering from osteoarthritis or an osteoarthritic condition can have not been administered pregabalin or gabapentin. The human suffering from osteoarthritis or an osteoarthritic condition human can have not been administered oxycodone, hydrocodone, codeine, morphine, tramadol. The human suffering from osteoarthritis or an osteoarthritic condition can have not been administered cyclobenzaprine, tetrazepam, diazepam. The human suffering from osteoarthritis or an osteoarthritic condition can have not been administered local anesthetics, corticosteroids, hyaluronic acid, platelet rich plasma, stem cells, prolotherapy, amniotic fluid injection Method of Manufacturing The present invention provides a method for manufacturing the pharmaceutical composition of the present invention, wherein the process comprises: a) culturing and serially expanding host cells; b) infecting the serially expanded host cells of (a) with the Helper-dependent Adenovirus (HDAd) of the present invention and a Helper Virus; c) culturing the infected cells of b); d) harvesting and lysing the infected cells of c) to produce a cell lysate; e) digesting host cell DNA in the cell lysate of d); f) clarifying the cell lysate of e); g) conducting ultracentrifugation of the clarified cell lysate of f); h) collecting the virus from the ultracentrifugated cell lysate of (g); i) conducting gradient ultracentrifugation the virus sample of (h); j) collecting virus from the gradient ultracentrifugated virus sample of (i); k) conducting isopycnic ultracentrifugation of the virus sample of (j); l) collecting the virus from the isopycnic ultracentrifugated virus sample of (k); m) conducting isopycnic ultracentrifugation of the virus sample of (l); n) collecting the virus from the isopycnic ultracentrifugated virus sample of (m); o) dialyzing the collected virus of (n); p) collecting and diluting the dialyzed virus of (o); q) formulating the diluted virus of (p); and r) filtering the formulated virus of (o).

The host cells used in the method for manufacturing the pharmaceutical composition of the present invention, can be 116 cell line, derived from HEK293 cells. The host cells can be expanded using CellStacks® culture chambers (Corning, Inc., Corning, NY) (CS). The host cells can be serially expanded in growth medium (DMEM supplemented with FBS, L-glutamine, and Hygromycin B). The 116 cells can be cultured at 37° C. and 5% CO2 and expanded to prepare one batch and one additional 10-layer CellStacks® culture chamber (Corning, Inc., Corning, NY) (CS10) prior to initiating infection.

The helper virus used in the method for manufacturing the pharmaceutical composition of the present invention, can be AdNG178 virus. The step of infecting the serially expanded host cells of (a) with the Helper-dependent Adenovirus (HDAd) of the present invention and a Helper Virus can be done at 37° C. and 5% $CO_2$. The step of infecting the serially expanded host cells of (a) with the Helper-dependent Adenovirus (HDAd) of the present invention and a Helper Virus can be done in a volume of 600 ml per CS10. The culturing the infected cells can be done for 24 hours at 37° C. and 5% $CO_2$. The culturing the infected cells can be done in DMEM supplemented with FBS and L-glutamine.

The harvesting of the infected cells can comprise (i) detaching and collecting infected cells, including the spent medium, yielding unprocessed bulk harvest containing the Helper-dependent Adenovirus (HDAd) of the present invention; (ii) clarifying the unprocessed bulk harvest by centrifugation; (iii) discarding the resulting supernatants and resuspending the cell pellets in lysis buffer; and (iv) freezing the harvested cells at −65° C. The lysis buffer used in the method for manufacturing the pharmaceutical composition of the present invention, can be 100 mM Tris, 10% glycerol at pH 8.0.

The unprocessed bulk harvest of the method for manufacturing the pharmaceutical composition of the present invention, is characterized by undetectable levels of *mycoplasma*, undetectable levels of Adventitious viruses, and microbial levels of <10 CFU/mL for TAMC and <10 CFU/mL for TYMC The step of lysing of the infected cells to produce a cell lysate can comprise at least two cycles of freeze-and-thaw lysing the resuspended cell pellets in the lysis buffer, each freeze and thaw lysing cycle comprising first placing the resuspended cell pellets in freezing bath and then in warm (37° C.) water bath.

The step of digesting DNA in the cell lysate can comprise treating the cell lysate with Benzonase to digest residual host cell DNA. The step of digesting DNA in the cell lysate can comprise adding Benzonase diluted in a buffer containing 10 mM Tris and 10 mM $MgCl_2$ prior to the cell lysate for digestion.

The step of clarifying the cell lysate can comprise centrifugation of the cell lysate.

The step of conducting ultracentrifugation the cell lysate can comprise conducting three rounds of cesium chloride (CsCl) ultracentrifugation to separate the Helper-dependent Adenovirus (HDAd) of the present invention, from impurities based on the specific gravity. The Helper-dependent Adenovirus (HDAd) collected from the rounds of conducting ultracentrifugation the cell lysate can be concentrated.

The concentrated Helper-dependent Adenovirus (HDAd) from the ultracentrifugation process of the method for manufacturing the pharmaceutical composition of the present invention, can be dialyzed to further remove impurities including CsCl and potential residual Hygromycin B. The dialysis can be done in formulation buffer comprising 5% sucrose w/v, 0.5% ethanol v/v, 75 mM sodium chloride, 10 mM L-histidine, 10 mM Tris, 1.0 mM magnesium chloride, 0.02% Polysorbate 80 v/v, and 100 μM EDTA. The step of dialysis can be done four times. The step of collecting and diluting the dialyzed virus can be done in the formulation buffer.

The step of formulating and diluting can comprise diluting the purified Helper-dependent Adenovirus (HDAd) to a desired target concentration in formulation buffer. The formulation buffer comprises 5% sucrose w/v, 0.5% ethanol v/v, 75 mM sodium chloride, 10 mM L-histidine, 10 mM Tris, 1.0 mM magnesium chloride, 0.02% Polysorbate 80 v/v, and 100 μM EDTA. The step of sterile filtering the formulated virus is done through a 0.22 μm filter.

A "therapeutically effective amount" or "effective amount" of the adenoviral-based biological delivery and expression system of the invention relates generally to the amount needed to achieve a therapeutic objective. As noted above, this may be a complete to partial recovery from osteoarthritis or osteoarthritic condition in the joints of a human subject in need thereof. As noted above, this may be a partial or complete prevention of development of osteoarthritis or osteoarthritic condition in the progression of osteoarthritis in the joints of a human subject in need thereof. The amount required to be administered will furthermore depend on the binding affinity of the fusion protein for its specific target, and will also depend on the rate at which an administered fusion protein is depleted from the free volume other subject to which it is administered. Common ranges for therapeutically effective dosing of the adenoviral-based biological delivery and expression system of the invention may be, by way of non-limiting example, from about $1.4\times10^{8}$ to $1.4\times10^{12}$ Genome copies (GC) per ml.

As used in this disclosure and the appended claims, the singular forms "a", "an", and "the" include plural referents unless the context clearly dictates otherwise. Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination). Ranges may be expressed herein as from about one particular value, and/or to about another particular value. When such a range is expressed, another aspect includes from the one particular value and/or to the other particular value. Similarly, when values are expressed as approximations, by use of the antecedent "about", it will be understood that the particular value forms another aspect. It will be further understood that the endpoints of each of the ranges are significant both in relation to the other endpoint, and independently of the other endpoint.

As used herein, the term "cell line" refers to a population of cells capable of continuous or prolonged growth and division in vitro. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. In some embodiments, the terms "HEK293 cells", "293 cells" or their grammatical equivalents are used interchangeably here and refer to the host/packing cell line used in the methods disclosed herein.

The present disclosure is further illustrated by the following examples that should not be construed as limiting.

EXAMPLES

Example 1: Comparison of Transduction Efficiency of Helper-Dependent Adenoviral Vectors and Adeno-Associated Virus Vectors in Mouse Joints Aim of Study: Described herein is a study done to evaluate and compare transduction efficiency of HDAd Vectors and AAV vectors in murine joints.

Methodology: The test items in this study were HDAd (Ad5 serotype) and AAV vectors pseudotyped with AAV2, AAV2.5 and AAV6 capsids all encoding for GFP under control of a cytomegalovirus (CMV) promoter to mark the transduced cells. Eight-week old male FVB/N mice were divided into 5 groups comprising 2 mice each. Vectors were administered IA into both knee joints at a dose volume of 5 μL. Group 1 received $5\times10^{9}$ VP/knee HDAd-GFP. Groups 2-4 received AAV2-GFP, AAV2.5-GFP and AAV6-GFP, respectively, at a dose of $5\times10^{9}$ vector genome (vg)/knee. Group 5 received vehicle phosphate buffered saline (PBS). One week later, mice were euthanized, knee joints were prepared for histology (decalcified and paraffin-embedded), sectioned and stained with a fluorescent-labeled anti-GFP antibody.

Figure 3A:
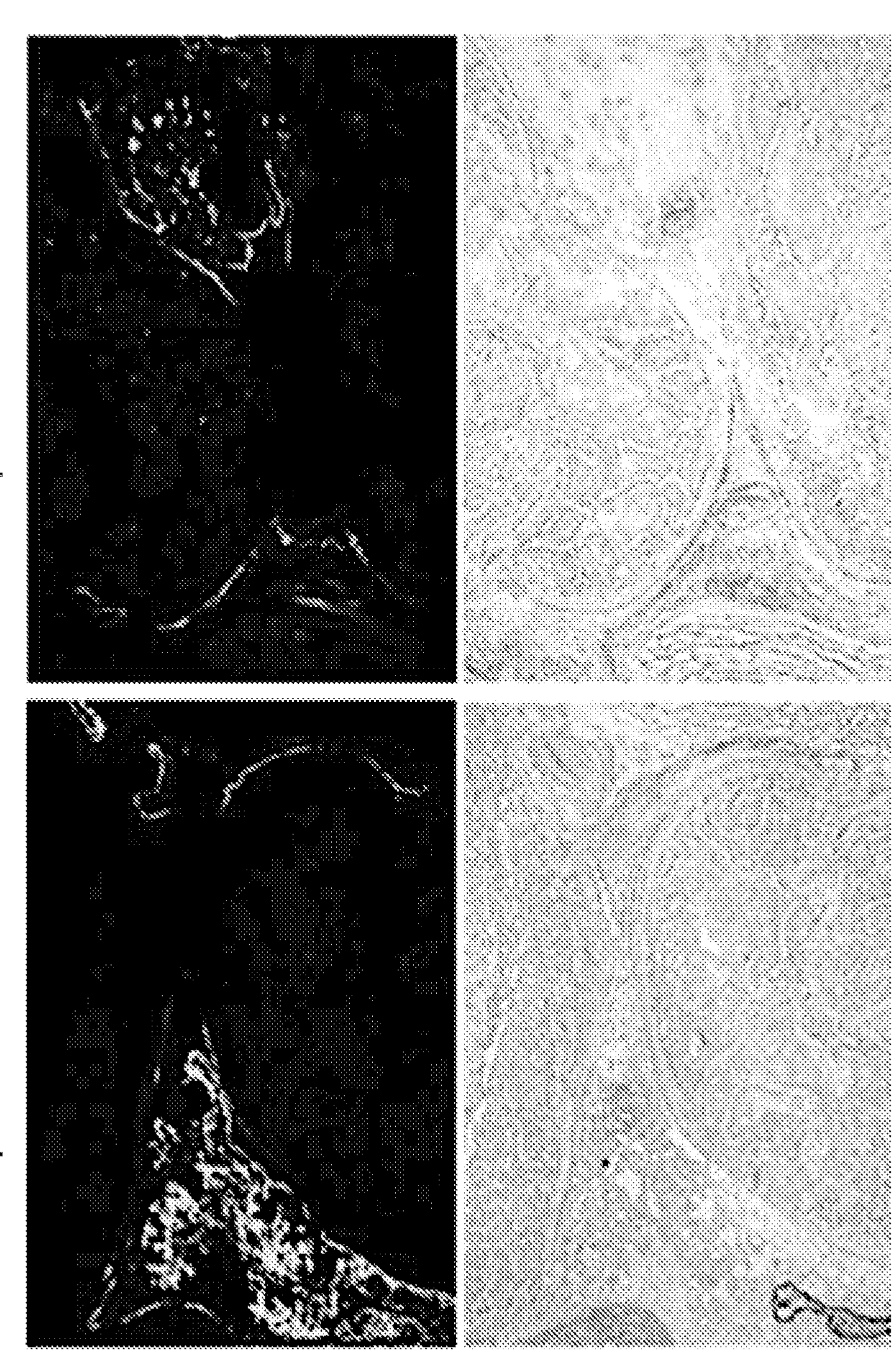
FIG. 3A and FIG. 3B depicts transduction efficiency of HDAd and AAV vectors in murine joints.
Figure 3B:
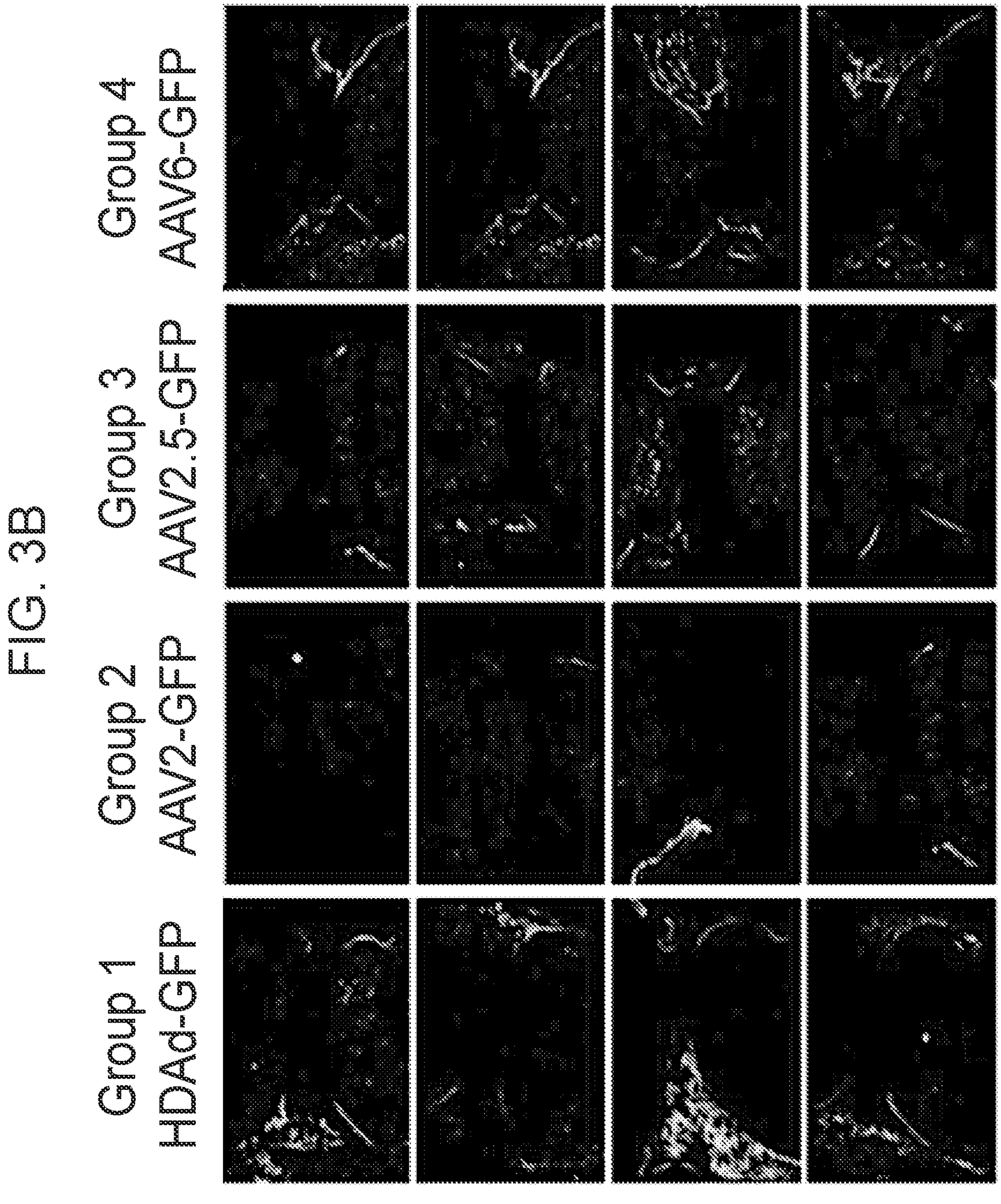

Results: Injection of HDAd-GFP resulted in robust GFP staining, which was somewhat variable among the individual injected joints in the group. The staining appeared to localize mostly to the synovial tissue (FIG. 3A). Compared to the HDAd-injected joints, GFP expression was weaker in all AAV injected knees (FIG. 3B). Among the AAV groups, AAV6 appeared to result in the strongest GFP expression. No staining was observed in vehicle-injected joints (Group 5), not shown.

Conclusion: HDAd (Ad5) robustly transduced joint cells following IA injection. In particular, cells of the synovial lining seem to be transduced. In comparison, transduction with AAV vectors of the serotypes 2, 2.5, and 6 appeared to be less efficient.

Example 2: HDAd Mediates Long-Term Marker Gene Expression in Joints

Aim of study: Described herein is a study done to determine long-term gene expression for up to one year in joints, in mice that were injected intra-articularly with a helper-dependent adenoviral vector of the invention (HDAd) and, for comparison, a first-generation adenovirus (Ad) vector expressing firefly luciferase (luc) under the control of a CMV promoter.

Methodology: Mice were injected intra-articularly with 108 virus particles (VP) of a luciferase expressing helper-dependent (HDAd-luc) or a respective first-generation (Ad-luc) adenoviral vector. Both knee joints of four mice per group were injected. Three days later mice were imaged using MS 200™ series imaging system (Caliper Life Sciences, Hopkinton MA). Luciferase expression of the mice was followed by repeated bioluminescence imaging and quantified using Living Image 2.5™ imaging software (Caliper Life Sciences, Hopkinton MA).

Figure 4A:
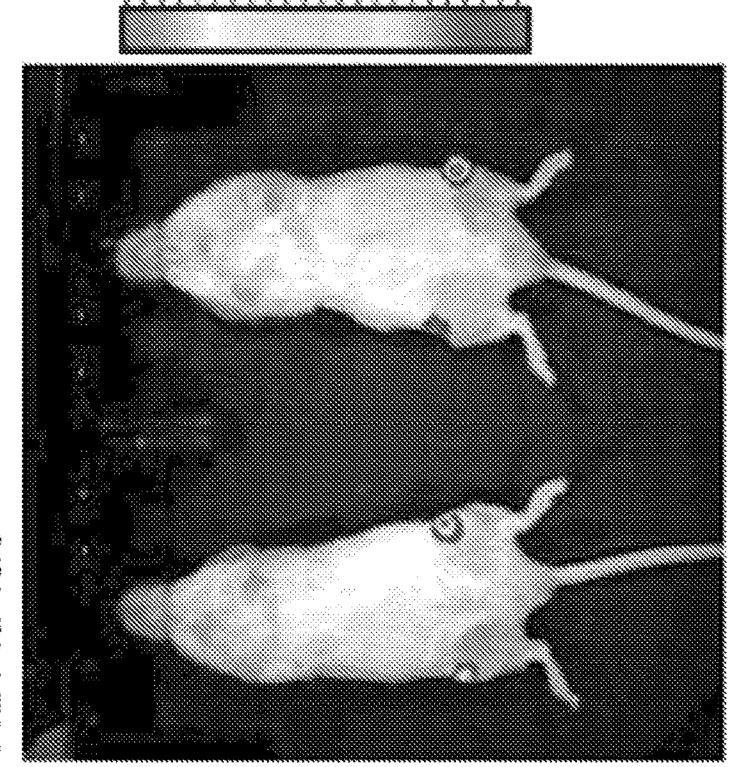
FIG. 4A and FIG. 4B depict comparison of the level and time period of marker gene expression between a Helper-dependent and first-generation adenoviral vector.
Figure 4B:
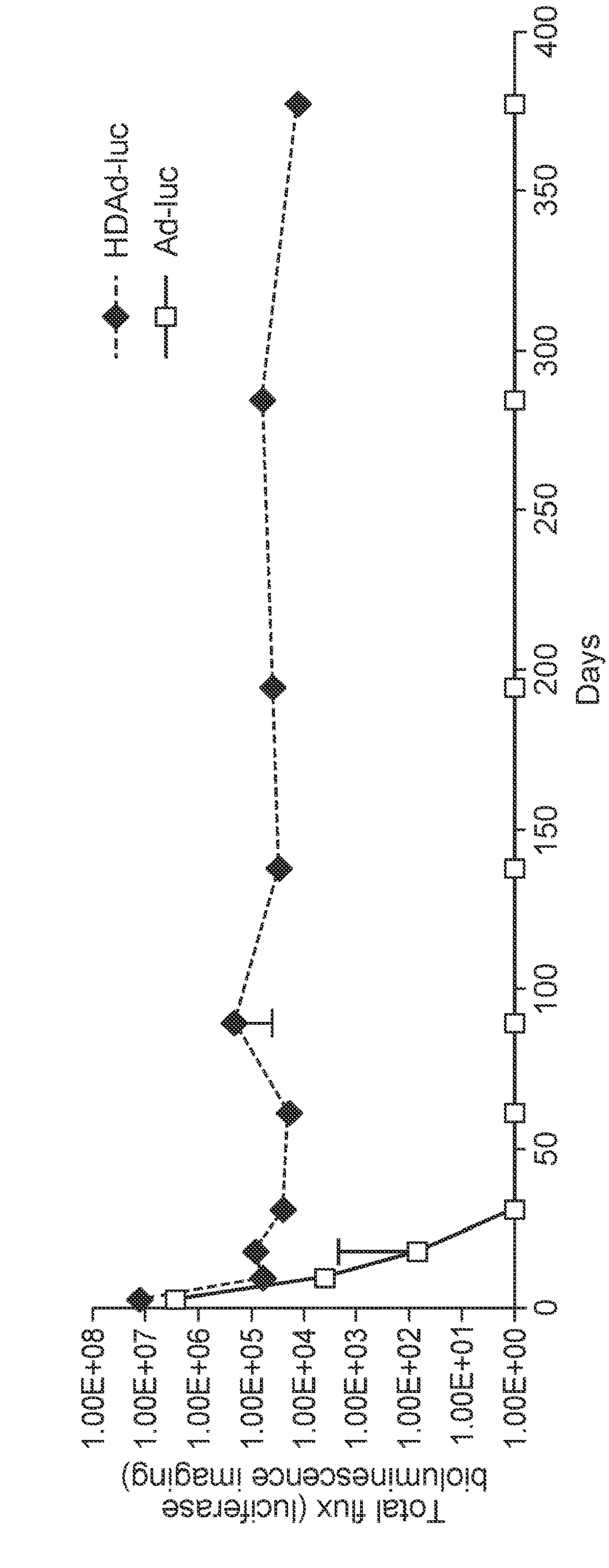

Results: Strong bioluminescence signals were detected in the joints injected with both HDAd-luc and Ad-luc adenoviral vector. Strong initial luc signals were detected three days after injection with both vectors (FIG. 4A). Expression decreased with both vectors thereafter and was undetectable after one month with the first-generation vector Ad-luc (FIG. 4B). However, HDAd-luc luciferase expression stabilized at day 10 and remained at this level for 380 days.

Conclusion: Helper-dependent and first-generation adenoviral vectors mediate the same level of marker gene expression. Helper-dependent adenoviral vector mediates long-term marker gene expression in joints.

Example 3: HDAd Transduces Synovial Cells Following Intraarticular Injection

Figure 5B:
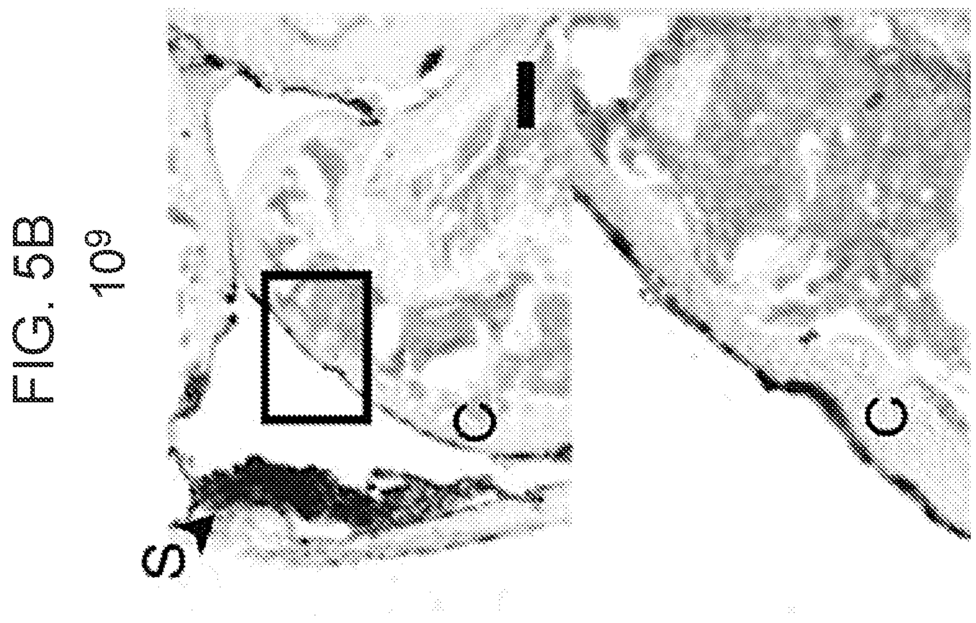
FIG. 5A and FIG. 5B depict Helper-dependent adenoviral vector infects synoviocytes and chondrocytes efficiently. Mice were injected intra-articularly with $10^{8}$ or $10^{9}$ VP of a LacZ expressing HDAd. One day later, mice were sacrificed and LacZ staining on sectioned joints was performed.
Figure 5A:
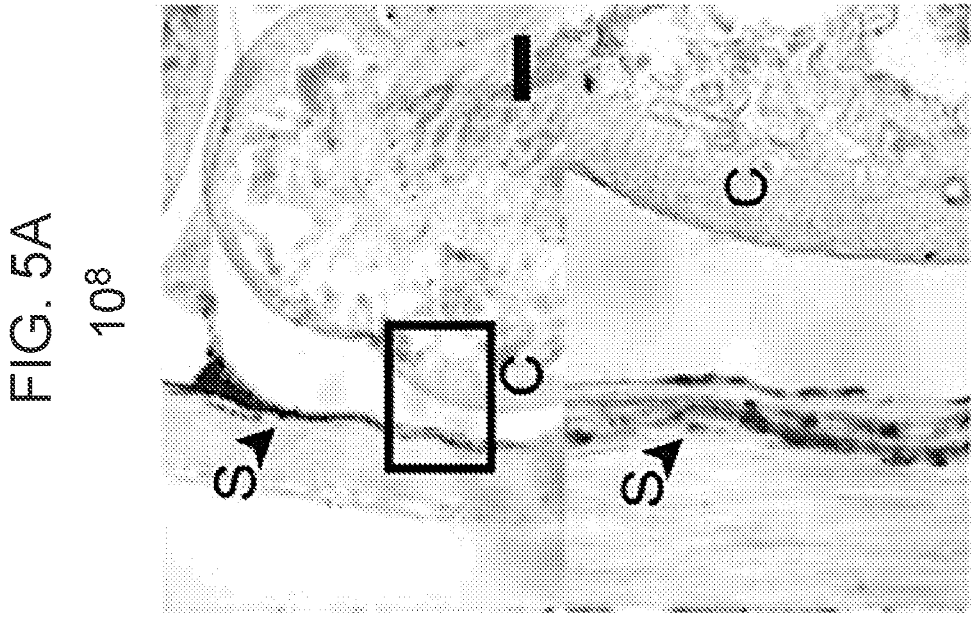

Described herein is a study done to evaluate HDAd transduction in mouse joints in detail, where mice were injected intra-articularly with a $10^8$ or $10^9$ VP of LacZ expressing HDAd. Strong expression of LacZ was seen in both the synovium and chondrocytes of the joints infected with $10^9$ VP of LacZ expressing HDAd (FIG. 5B), while no staining could be observed in chondrocytes in the $10^8$ VP infected joints (FIG. 5A). The livers of these animals were analyzed to assess whether virus escapes from the joints or is spilled during the injection. Most importantly, no detectable vector concentrations over background could be measured by quantitative PCR (data not shown). Therefore, the vector specifically locates in the joints and remains there, which is of great benefit in the treatment or prevention of an osteoarthritic condition since it suggests minimal side effects.

Example 4: HDAd-ll-1 Ra Infected Cells Secrete IL-1Ra. Injection

Aim of study: Described herein is a study done to generate and in vitro test the functionality of an HDAd expressing IL-1Ra under the control of the inflammation-sensitive NF-KB5-ELAM promoter.

Methodology: Human embryonic kidney cells (HEK293) were infected with 100 VP/cell of HDAd-IM Ra, HDAd-GFP or mock. Two days later IL-1Ra ELISA was performed with cell culture supernatant. Concentrations of about 700 pg/ml were measured for HDAd-IL-1 Ra infected cells, whereas no IL-1Ra was detectable in the supernatant of HDAd-GFP or mock infected cells. To induce an inflammatory reaction, lipopolysaccharides (LPS, 100 μg/ml) were added to half of the samples and IL-1Ra concentrations were again determined one day later (day 4). Levels in HDAd-IL-1Ra samples increased to about 1600 pg/ml whereas uninduced cells produced less IL-1Ra compared to the previous day. No IL-1Ra expression was detected in any of the control samples (HDAd-GFP and mock).

Figure 6:
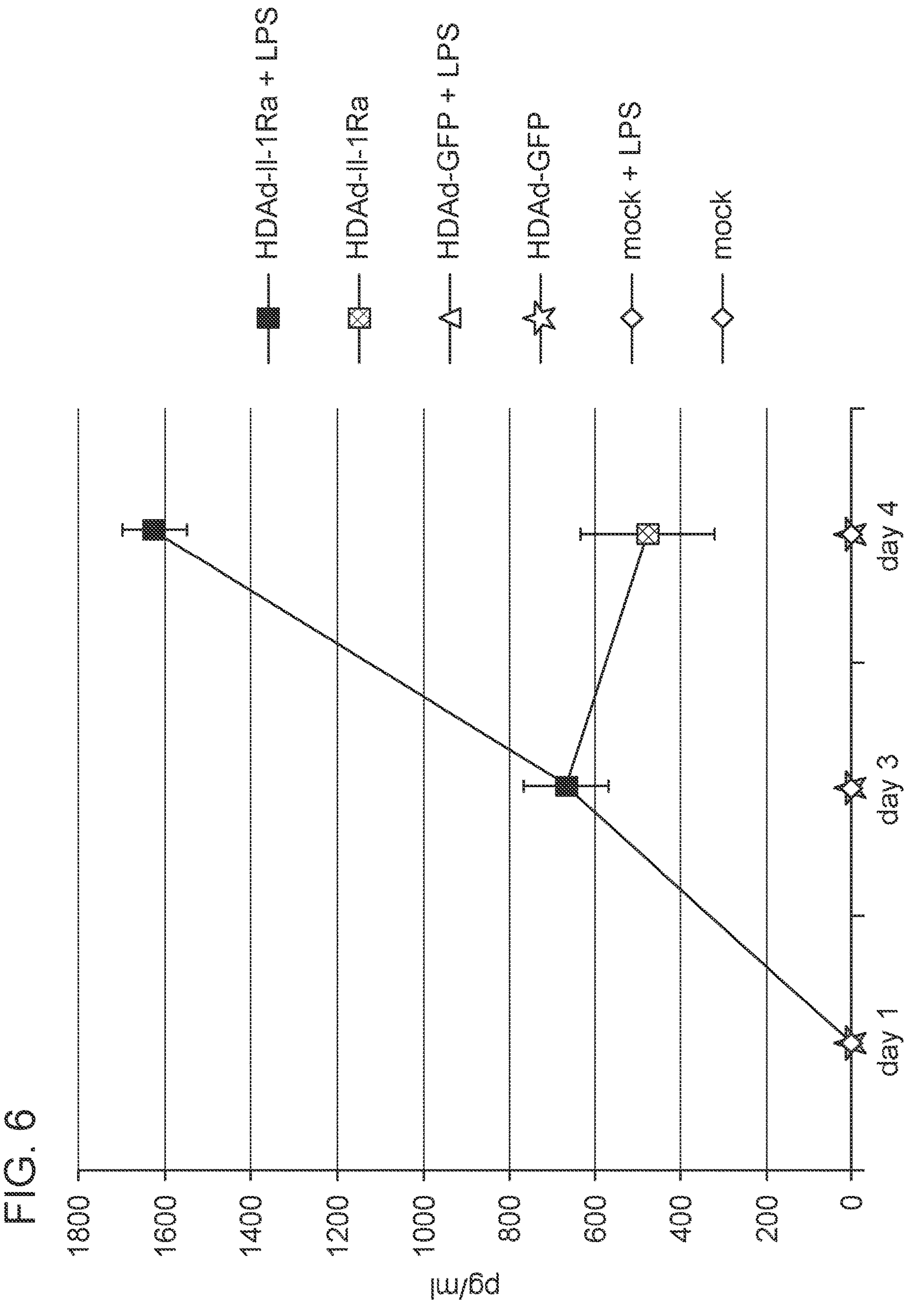
FIG. 6 depicts that cells infected with HDAd-IL-1Ra produce large amounts of IL-1 Ra. The y-axis depicts level of IL-1Ra measured by ELISA performed with cell culture supernatant of Human embryonic kidney cells (HEK293) that were infected with HDAd-IL-1 Ra, HDAd-GFP or mock, with or without LPS stimulation, as indicated. X-axis depicts the time periods for measurement of IL-1Ra. Each data point is indicative of 3 independent experiments and error bars indicate SD.

Results: High levels of IL-1Ra were measured in the supernatant of HDAd-ll-1 Ra infected cells on day 3 (FIG. 6). Induction of inflammation with lipopolysaccharide (LPS) led to a dramatic increase of IL-1Ra concentration compared with uninduced samples. No IL-1Ra was detected in non-infected samples (mock) or samples infected with a control vector (HDAd-GFP). High levels of IL-1Ra were measured in supernatants of synovial cells that were infected with a helper-dependent adenoviral vector (HDAd) of the invention. As shown in FIG. 6, the induction of inflammation with lipopolysaccharide (LPS) led to a dramatic increase of IL-1Ra concentration as compared with uninduced samples. No IL-1Ra was detected in non-infected samples (mock) or samples infected with a control vector (HDAd-GFP).

Conclusion: The results disclosed herein demonstrate that cells infected with HDAd-mll-1Ra can produce high levels of II-1Ra. It further shows that IL-1Ra is efficiently secreted from those cells, and that inflammatory conditions activate the NF-κB5-ELAM promoter leading to increased IL-1Ra levels.

Acute injury to the anterior cruciate ligament (ACL) is a common cause of post-traumatic OA in humans, and ACL transection (ACLT) in rats and mice are established animal models of traumatic injury-induced OA. FX201, a helper-dependent adenovirus (HDAd)-based intra-articular (IA) gene therapy candidate designed to induce the production of an Interleukin (IL)-1 receptor antagonist (IL-1Ra) in the presence of inflammation, is in development as a potential therapeutic agent for OA. Described herein are studies demonstrate the effectiveness of treatment of with FX201 or its equivalent HDAd-mIL-1Ra in prevention and treatment of OA.

Example 5: HDAd-ll-1 Ra Prevents the Development of OA in Mice

Aim of Study: Described herein is a study done to evaluate whether an HDAd vector expressing murine IL-1Ra (HDAd-mIL-1Ra) under the control of NF-κB-inducible promoter upregulated by inflammatory stimuli is able to prevent progression of OA in a murine model of the disease. HDAd-mIL-1Ra has the identical vector backbone to FX201 but encodes for a murine-specific IL-1Ra transgene (mIL-1Ra).

Methodology: To assess whether an HDAd expressing IL-1Ra is able to prevent the development of OA, knee joints of mice were injected intra-articularly with HDAd-IL-1Ra or a GFP expressing control vector (HDAd-GFP). Mice were injected intra-articularly into the knee joints with $10^8$ VP of HDAd-IL-1Ra, HDAd-GFP or mock. Two days after injection, cruciate ligament transection was performed to induce OA development. This osteoarthritis model was developed in Dr. Brendan Lee's research group and validated in several experiments (Ruan, Z., Dawson, B., Jiang M. M., Gannon, F., Heggeness, M., Lee, B. (2012). Quantitative volumetric imaging of murine osteoarthritic condition cartilage by phase contrast micro-computed tomography, submitted). The model involves transection of anterior and posterior cruciate ligaments of the knee joints, which leads to development of severe OA. Mice were sacrificed one month after OA induction and joints were prepared histologically and stained with Safranin O. The development of OA was scored by a blinded pathologist according to OARSI (Osteoarthritis Research Society International) standard (assignment of scores on a scale of 1-6, 1: no signs of OA at all, 6: maximum OA).

Figure 7:
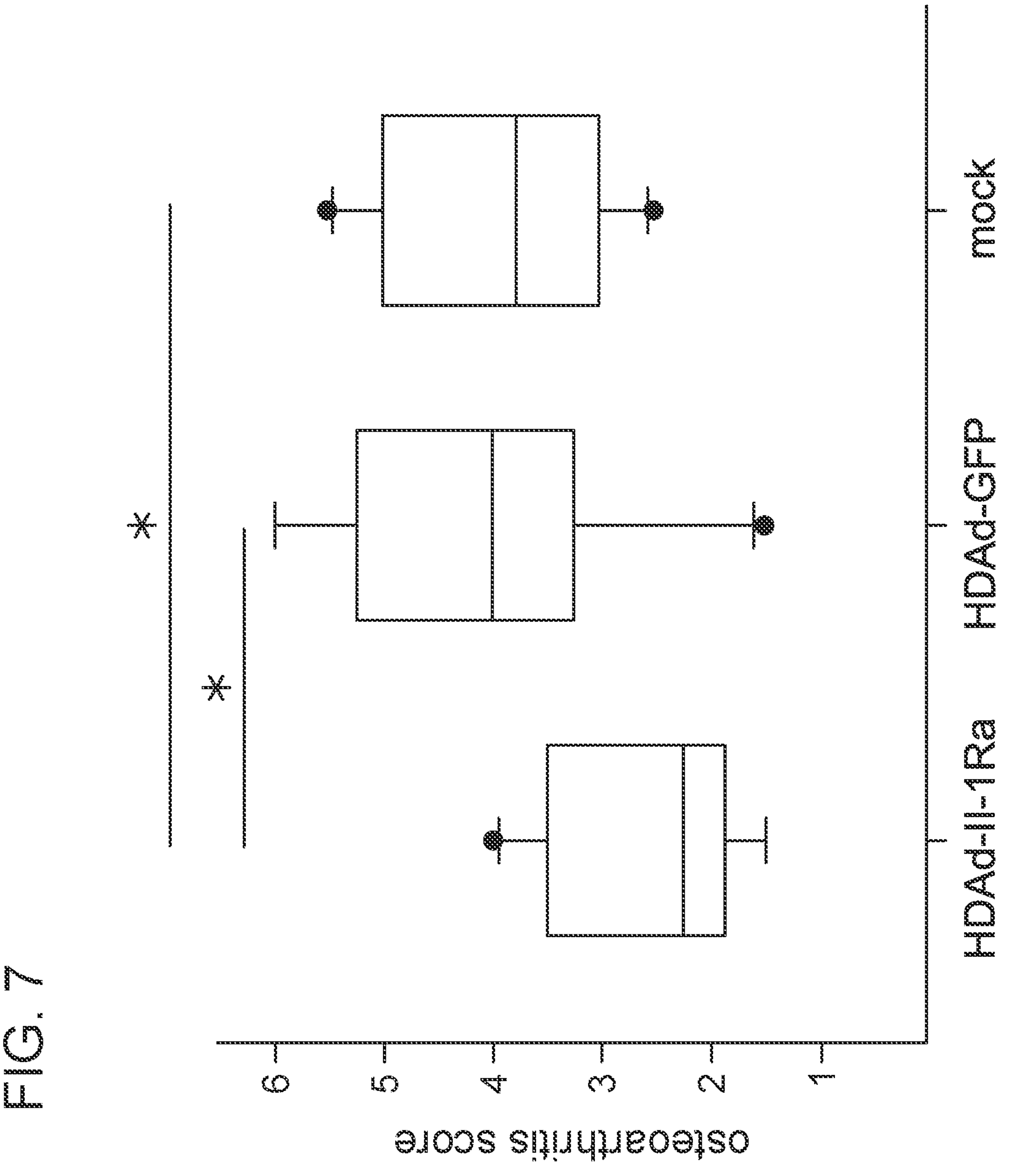
FIG. 7 depicts that HDAd-IL-1 Ra prevents the development of OA in mice. The Y-axis depicts the level of OA evaluated by a blinded pathologist according to OARSI (Osteoarthritis Research Society International) standards (assignment of scores on a scale of 1-6, 1: no signs of OA at all, 6: maximum OA). X-axis depicts the three treatment groups: HDAd-IL-1 Ra, HDAd-GFP or mock. * indicates significant difference: p<0.05 by one-way ANOVA; n=10 joints per group.

Results: HDAd-IL-1Ra treated joints had significantly lower OA scores than HDAd-GFP treated or untreated joints, suggesting that HDAd-IL-1Ra prevented the development of OA (FIG. 7). The control vector HDAd-GFP did not seem to have any effect on the development of OA since the average OA score was comparable to the score of the untreated group.

Conclusion: The results disclosed herein demonstrate that infecting the joints of mice with HDAd-IL-1Ra prevents development of OA.

Example 6: Prevention of Osteoarthritis with Locally Administered HDAd-mIL-1Ra in Mice Aim of Study: Described herein is a study to evaluate whether an HDAd vector expressing murine IL-1Ra (HDAd-mIL-1Ra) under the control of NF-κB-inducible promoter upregulated by inflammatory stimuli is able to prevent progression of OA in a murine model of the disease. HDAd-mIL-1Ra has the identical vector backbone to FX201 but encodes for a murine-specific IL-1Ra transgene (mIL-1Ra).

Methodology: The test item HDAd-mIL-1Ra (Group 1) or the control vector HDAd-GFP (Group 2) were injected into both knees of 8-week-old male FVB/N mice IA at a dose of $10^8$ VP/knee (5 mice per group) and dose volume of 3 μL, as indicated in Table 1. Control Group 3 received vehicle (PBS). Two days later, OA was induced by transection of the cruciate ligaments on all injected knees. Thirty days later, mice were euthanized and histologic evaluations of the treated joints were performed. For assessment of cartilage damage, sections from the lateral compartment were scored according to the OARSI histological grading system and scores for tibia and femur were added together (scoring system is detailed in Table 3). To assess for synovitis, sections were scored using a 3-point scale described in Table 4; osteophytes were scored as being present or absent from histological sections and expressed as a percentage of joints with osteophytes in relation to all analyzed joints.

TABLE 1

Experimental Groups and Treatment

| Group | Test Item | Dose Level (VP/knee) | Dose Volume (μL) | Group size |
|---|---|---|---|---|
| 1 | HDAd-mIL-1Ra | $10^8$ | 3 | 5 |
| 2 | HDAd-GFP | $10^8$ | 3 | 5 |
| 3 | Vehicle (PBS) | — | 3 | 5 |

PBS, phosphate buffered saline:
VP, viral particle.

Figures 8A, 8B, 8C:
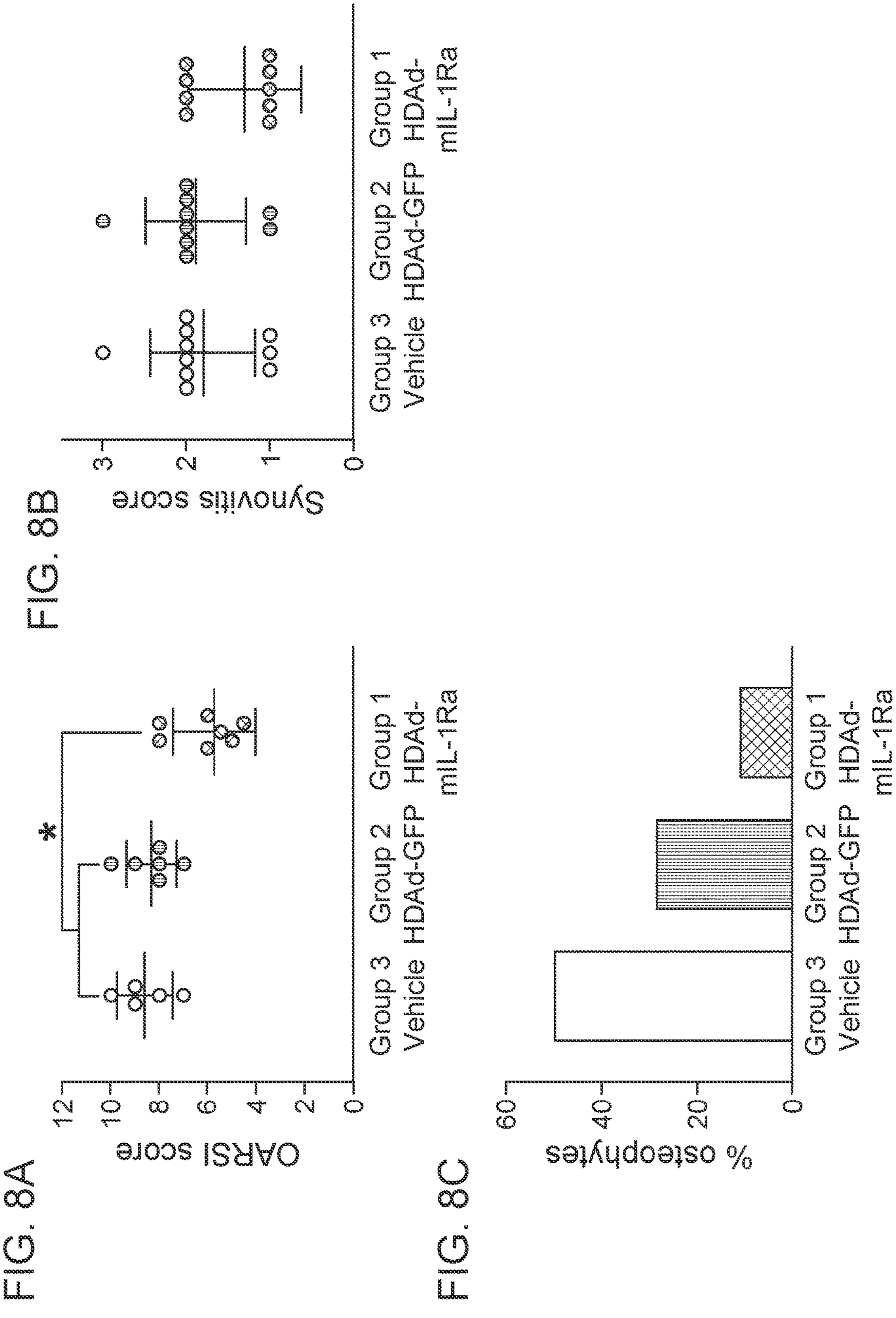
FIG. 8A-FIG. 8C depict histopathological Evaluation of OA in Mice.

Results: Mean OARSI scores of the Vehicle group (Group 3) and the control HDAd-GFP vector-treated Group 2 were both approximately 8.5 and not significantly different from each other (FIG. 8A). However, the mean OA score of the group administered HDAd-mIL-1Ra (Group 1) was approximately 6 and significantly lower compared with the scores of the Vehicle and HDAd-GFP groups, which indicates there were significantly less histological OA features in the HDAd-mIL-1Ra-treated joints. No difference in the synovitis scores of the vehicle and the HDAd-GFP groups was observed (FIG. 8B). The mean synovitis score of the HDAd-mIL-1Ra treated Group 1 was lower, albeit not statistically significant, compared to the mean scores of the Vehicle and HDAd-GFP groups. Fewer osteophytes were detected in the HDAd-GFP group compared to the vehicle-treated group, shown in FIG. 8C. In the HDAd-mIL-1Ra-treated Group 1, fewer osteophytes were seen compared to both Groups 2 and 3.

Conclusion: The results described herein demonstrate that vehicle-treated mice that underwent transection of cruciate ligaments developed severe OA within one month as indicated by high OARSI scores and the presence of synovitis and osteophytes. An HDAd vector expressing GFP did not significantly alter histological features of OA. This indicates that the HDAd vector itself does not have any effect on disease progression. An HDAd expressing murine IL-1Ra demonstrated improved OA pathology compared to vehicle and HDAd-GFP treated-mice as indicated by the significantly improved OARSI scores, trend towards lower synovitis scores (not statistically significant) and fewer osteophytes in the joints compared to the HDAd-GFP and vehicle-treated groups.

Example 7: HDAd-mIL-1Ra Treats OA in a Murine Model of the Disease

Aim of study: Described herein is a study to evaluate the efficacy of HDAd-mIl-1 Ra in the treatment of OA in the murine disease model described above.

Methodology: OA was induced in mouse knee joints by cruciate ligament transection and the disease was allowed to develop. Two weeks after transection, mice were injected intra-articularly with $10^8$ VP of HDAd-IL-1 Ra, HDAd-GFP or mock. Mice were sacrificed 6 weeks later and joints were histologically prepared, sectioned and stained with Safranin O. A blinded pathologist evaluated the level of OA according to OARSI (Osteoarthritis Research Society International) standard (assignment of scores on a scale of 1-6, 1: no signs of OA at all, 6: maximum OA). Joints were further evaluated by microcomputer tomography (μCT) analysis. This technique combines high resolution (down to 0.5 micron) x-ray CT scanning with phase contrast optics, which enables visualization of cartilage in small animal joints. Three-dimensional reconstruction of joints and computational tissue analysis tools can be used to quantify several cartilage parameters such as volume and surface area. Whole knee joints of mice treated the same way as described above were fixed in electron microscopy fixative and embedded in paraffin. Samples were scanned using X-radia microXCT scanner (Xradia, Pleasanton, CA, USA) and visualized at 4-micron resolution. Computational 3D reconstruction of joints was performed and cartilage volume and surface area were quantified semi-automatically using TRI BON software (RATOC System Engineering, Tokyo, Japan).

Figure 9A:
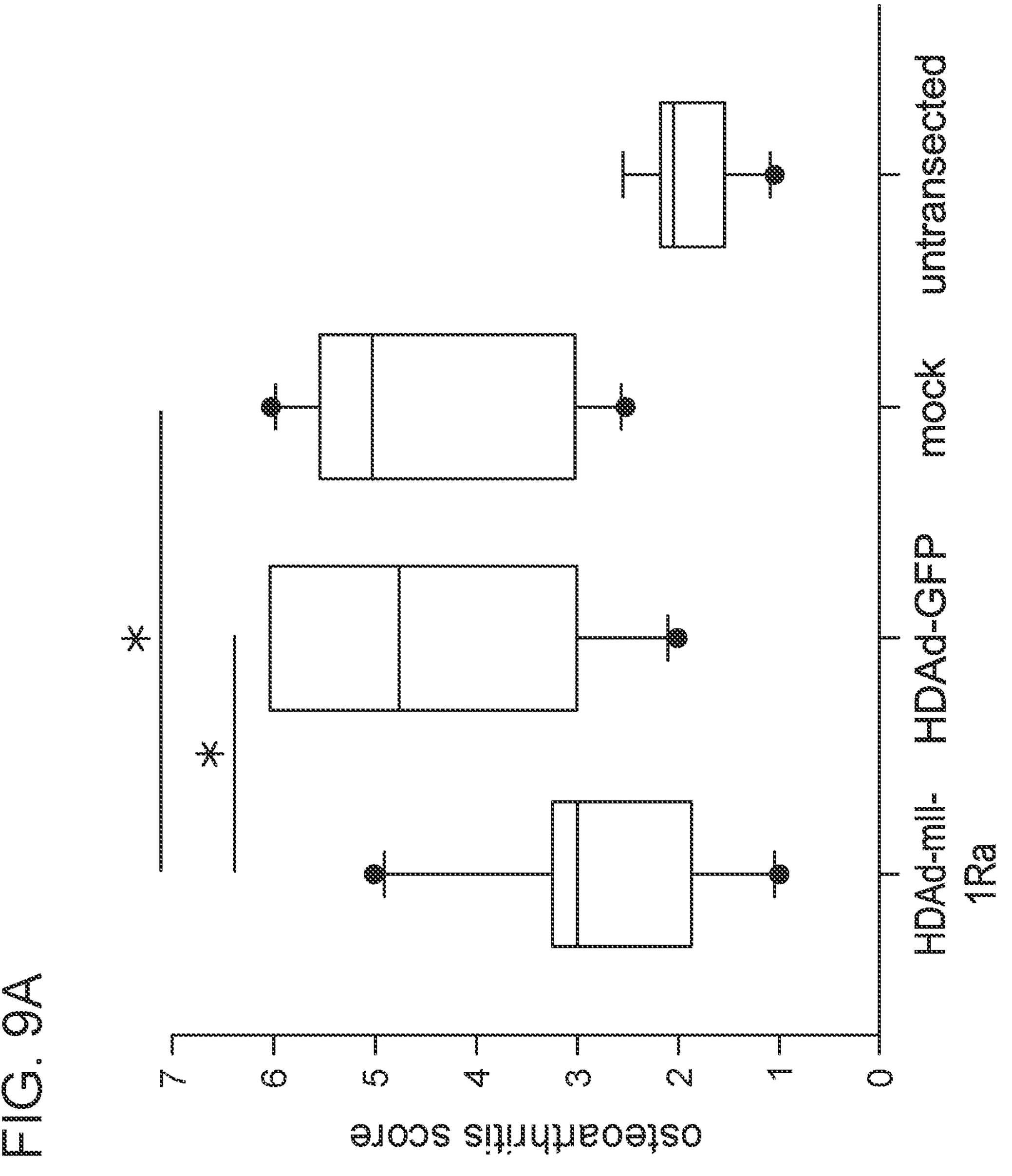
FIG. 9A-FIG. 9C depict that HDAd-IM Ra efficiently treats OA in mice.
Figures 9B, 9C:
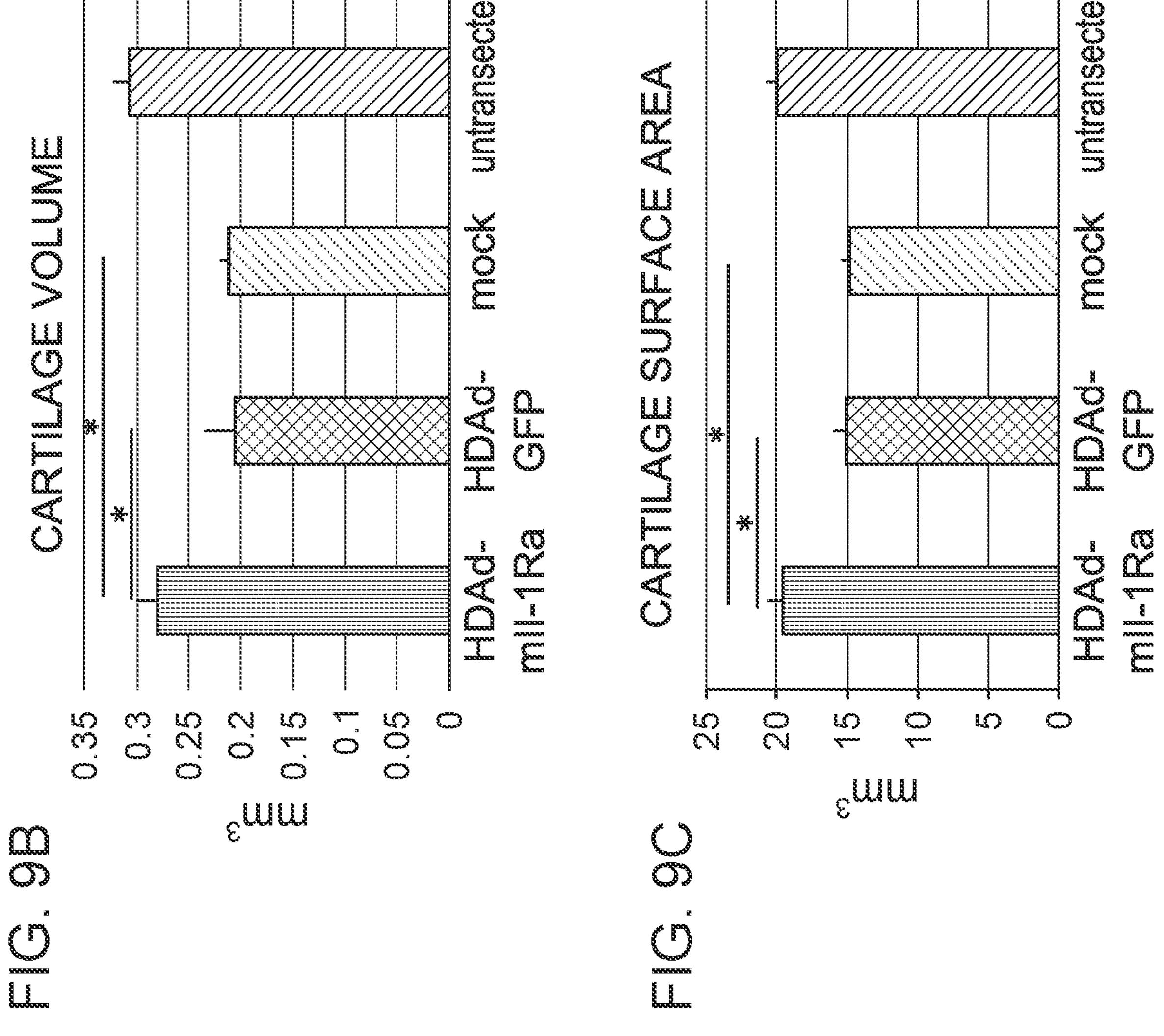

Results: The model was used to assess whether HDAd-IL-1Ra can efficiently treat OA. Therefore, OA was induced by cruciate ligament transection (except in the untransected group) and OA was allowed to develop for two weeks. HDAd-IL-1Ra, the control vector (HDAd-GFP) or vehicle was then injected and mice were sacrificed to analyze the joints another six weeks later. HDAd-GFP treated and uninjected mice developed OA to the same extent with an average score of approximately 4.5 (FIG. 9A). However, HDAd-IL-1Ra treated mice had significantly lower OA scores compared with HDAd-GFP and mock treated. No significant difference was found between HDAd-IL-1Ra and untransected (OA-free) mice suggesting efficient treatment of the disease or its prevention. HDAd-IL-1Ra treated joints demonstrated significantly higher cartilage volume compared with HDAd-GFP and mock treated joints (FIG. 9B). No significant difference was seen between the HDAd-IL-1Ra and transfected (OA-free) groups. Furthermore, cartilage surface area was significantly larger in HDAd-IL-1Ra treated mice compared with HDAd-GFP and mock groups (FIG. 9C), while no significant difference was seen between HDAd-IL-1Ra and transfected (OA-free) joints.

Conclusion: The results disclosed herein show that infection with HDAd-IL-1Ra effectively treats OA in mice. The results disclosed herein also show that infection with HDAd-IL-1Ra prevents loss of cartilage surface area and volume due to induction of OA, as compared to untreated control mice.

Example 8: Locally Administered HDAd-mIL-1Ra for Treatment of Osteoarthritis in Skeletally Mature Mice Aim of Study: Described herein is a study to evaluate whether HDAd-mIL-1Ra is able to delay progression of OA in skeletally mature mice. HDAd-mIL-1 Ra has an identical vector backbone to FX201 but encodes for a murine-specific IL-1 Ra transgene.

Methodology: OA was induced by transection of the cruciate ligaments in both knee joints in 60 twelve-week-old male FVB/N mice (Day 0). Seventy-two hours later (Day 3), the test item HDAd-mIL-1Ra (Group 1) or the control vector HDAd-GFP (Group 2) were injected IA into both knees at a dose of $10^9$ VP and dose volume of 5 μL (16 mice per group) (Table 2). Group 3 received IA injection of PBS (8 mice per group). Group 4 comprised 12 control mice subjected to sham surgery that did not receive any treatment. Hotplate nociception analysis to assess thermal hyperalgesia was performed in all mice on Days 57 to 59. The latency period to hind limb flicking and hind limb licking or jumping were recorded as minor and major response time, respectively. Mice were sacrificed on Day 60. The left and right knees of each animal were processed for histological and phase contrast micro-CT analysis, respectively.

For assessments of cartilage damage, sections from the lateral compartment were scored in a blinded fashion according to the OARSI histological grading system and scores for tibia and femur were added together (scoring system is detailed in Table 3). To assess for synovitis, sections were scored using a 3-point scale described in Table 4; osteophytes were scored as being present or absent from histological sections and expressed as a percentage of joints with osteophytes in relation to all analyzed joints. Micro-CT imaging was used to analyze cartilage volume and bone area covered by cartilage by a blinded evaluator.

TABLE 2

Experimental Groups and Treatment

| Group | Test Item | Dose Level (VP/knee) | Dose Volume (μL) | ACL-T | Group Size |
|---|---|---|---|---|---|
| 1 | HDAd-mIL-1Ra | $10^9$ | 5 | Yes | 16 |
| 2 | HDAd-GFP | $10^9$ | 5 | Yes | 16 |
| 3 | Vehicle (PBS) | — | 5 | Yes | 16 |
| 4 | — | — | — | No | 12 |

ACL-T, anterior cruciate ligament transection;
PBS, phosphate buffered saline;
VP, viral particle.

TABLE 3

OARSI Scoring System Used in Mouse Efficacy Studies

| Score | Histological Features |
|---|---|
| 0 | Normal |
| 0.5 | Loss of Safranin-O without structural changes |
| 1 | Small fibrillations without loss of cartilage |
| 2 | Vertical clefts down to the layer immediately below the superficial layer and some loss of surface lamina |
| 3 | Vertical clefts/erosion to the calcified cartilage extending to <25% of the articular surface |
| 4 | Vertical clefts/erosion to the calcified cartilage extending to 25-50% of the articular surface |
| 5 | Vertical clefts/erosion to the calcified cartilage extending to 50-75% of the articular surface |
| 6 | Vertical clefts/erosion to the calcified cartilage extending >75% of the articular surface |

TABLE 4

Synovitis Scoring System Used in Mouse Efficacy Studies

| Score | Histological Features |
|---|---|
| 0 | Synovium is two cell layers thick; only mild edema |
| 1 | Synovium exhibits increased thickness; mild inflammatory cell infiltration |
| 2 | Synovium is multiple cell layers thick; moderate inflammatory cell infiltration; some papillary excrescence |
| 3 | Marked papillary excrescence; severe inflammatory cell infiltration |

Results: A trend towards lower mean histologic scores for cartilage damage in HDAd-mIL-1Ra-treated animals was observed (5.75; Group 1), compared to groups injected with HDAd-GFP (8.21; Group 2) or vehicle (7.13; Group 3); however, the differences were not statistically significant. All treatment groups had significantly higher scores compared with the sham-operated group (1.25; Group 4). In the hotplate nociception analysis, HDAd-mIL-1Ra treatment led to a significantly longer mean minor response time (4.14 seconds) compared with HDAd-GFP (2.93 seconds) and vehicle treatment (2.64 seconds). The minor response time of HDAd-mIL-1Ra-treated mice was not significantly different from that of healthy mice in the sham group, indicating protection from thermal hyperalgesia. A trend towards longer major response times in the hot plate nociception analysis of HDAd-mIL-1Ra-treated mice was observed (12.65 seconds) compared to the HDAd-GFP group (8.64 seconds) and vehicle group (8.97 seconds), but the differences were not statistically significant.

The synovitis scores of joints treated with HDAd-mIL-1Ra, HDAd-GFP or vehicle were equivalent. Similarly, no effect of the HDAd-mIL-1Ra vector on the number of osteophytes was evident. The synovitis scores and number of osteophytes were significantly lower in the sham control group compared to the groups with induced OA.

Figures 10A, 10B:
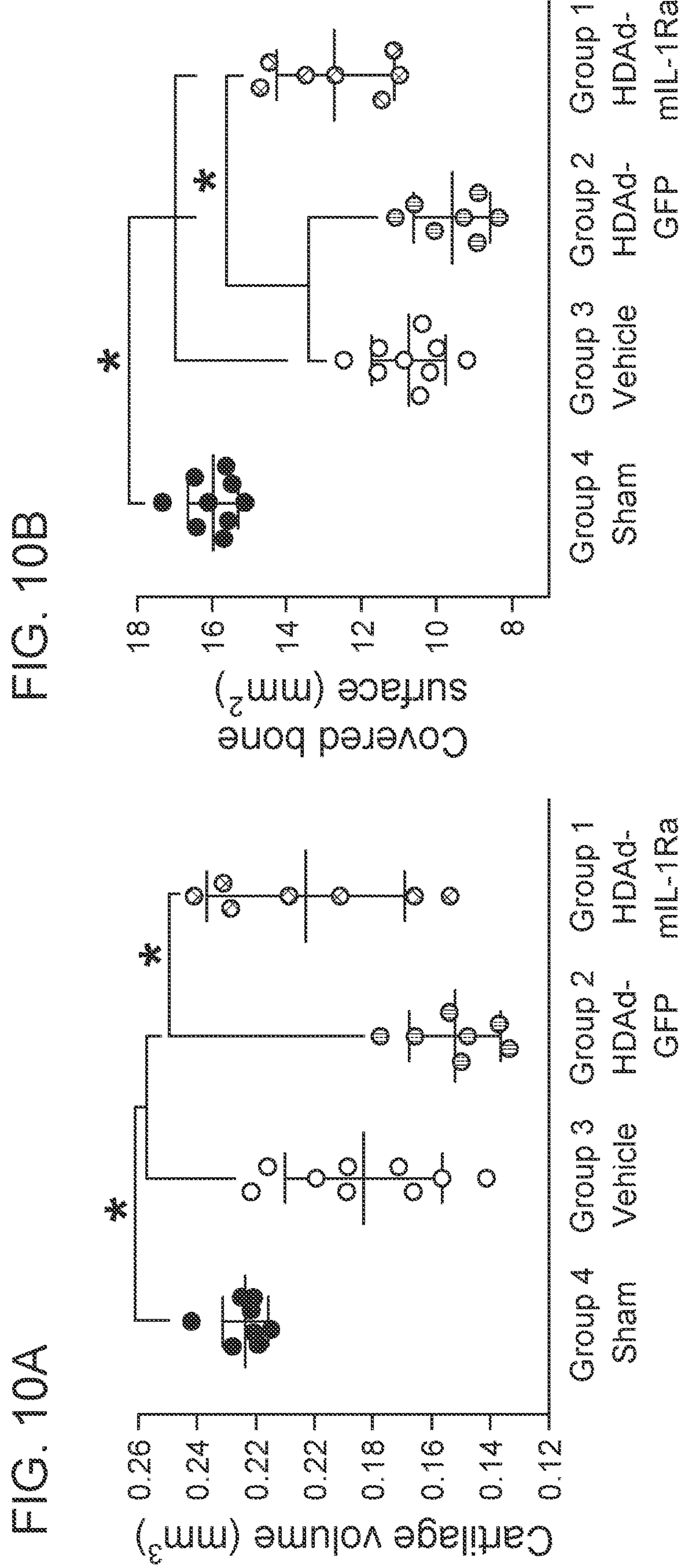
FIG. 10A-FIG. 10B depict evaluation of therapeutic efficacy with micro-computed tomography.

Micro-CT imaging showed significantly lower cartilage volume and bone area covered by cartilage in the joints of the vehicle and HDAd-GFP groups compared to healthy joints in Group 4 (FIG. 10). Cartilage volume and surface area in the HDAd-mIL-1 Ra group were significantly higher compared with the vehicle and HDAd-GFP groups and were not significantly different from the healthy joints of Group 4.

In the hotplate nociception analysis, HDAd-mIL-1Ra treatment led to a significantly longer mean minor response time (4.14 seconds) compared with HDAd-GFP (2.93 seconds) and vehicle treatment (2.64 seconds). The minor response time of HDAd-mIL-1Ra-treated mice was not significantly different from that of healthy mice in the sham group, indicating protection from thermal hyperalgesia. A trend towards longer major response times in the hot plate nociception analysis of HDAd-mIL-1Ra-treated mice was observed (12.65 seconds) compared to the HDAd-GFP group (8.64 seconds) and vehicle group (8.97 seconds), but the differences were not statistically significant.

Conclusions: The results disclosed herein show that twelve-week-old, skeletally mature mice that underwent transection of cruciate ligament and were injected IA with vehicle developed severe OA during the course of 60 days, as indicated by significantly higher OARSI and synovitis scores, higher number of osteophytes, as well as significantly lower cartilage volume and bone area covered by cartilage, and significantly shorter times to minor and major responses in the hotplate nociceptive assay compared to healthy sham control mice. A control HDAd vector expressing GFP did not have an effect on any of those parameters.

A tendency towards lower OARSI scores was observed for the mice treated with HDAd-mIL-1Ra, compared to HDAd-GFP- or vehicle-treated animals, while no effect of the treatment on synovitis scores or number of osteophytes was evident in this OA model. Micro-CT analysis of the HDAd-mIL-1Ra-treated joints revealed significantly higher cartilage volume and bone area covered by cartilage compared to joints treated with the control vector HDAd-GFP or vehicle. Mice treated with HDAd-mIL-1Ra showed a tendency towards decreased thermal nociceptive responses compared to controls, but the differences were not statistically significant. These data suggest that in this severe model of OA in skeletally mature mice, IA injection of HDAd-mIL-1Ra slows down cartilage degeneration and improves pain parameters. The fact that the efficacy endpoints evaluated by micro-CT were statistically significant while the histological evaluation did not show statistically significant differences might be attributed to the increased sensitivity of the former analytical method.

Example 9: Effect of HDAd-ratIL-1Ra in the Anterior Cruciate Ligament Transection (ACLT) Model of Osteoarthritis in Rat Aim of study: Described herein is a study to evaluate the effects of HDAd-ratIL-1Ra, the rat surrogate of FX201, when administered as a single IA injection in rats 1 week following ACLT surgery. The objective of the present study was to evaluate the effects of HDAd-ratIL-1Ra (the rat surrogate of FX201, the adenoviral-based biological delivery and expression system of the U.S. Pat. No. 10,301,647, incorporated herein by reference), a helper-dependent adenovirus encoding for a rat interleukin-1 receptor antagonist protein, when given by a single intra-articular injection in the rat one week following ACLT surgery.

Methodology: Experimental procedures applicable to pathology investigations are summarized in Table 5.

TABLE 5

Experimental Design

| Groups | Treatment | TI Dose Level (VP/dose) | Route | Dose volume (μL) | Dose Concentration (VP/mL) | Dosing schedule | N |
|---|---|---|---|---|---|---|---|
| 1 | Sham/ untreated | — | — | — | — | — | 10 |
| 2 | ACLT/ Vehicle | 0 | I.A. | 15 | 0 | Only once on Day 1 | 12 |
| 3 | ACLT/ HDAd IL-1Ra | $3 \times 10^7$ | I.A. | 15 | $2 \times 10^9$ | Only once on Day 1 | 12 |
| 4 | ACLT/ HDAd IL-1Ra | $2.43 \times 10^8$ | I.A. | 15 | $1.62 \times 10^{10}$ | Only once on Day 1 | 12 |

In Table 5 as shown above, I.A is Intra-articular injection; TI is Test item. The surgery date was considered as Day −7.

Upon termination at Week 12 post surgery, right knee joints were harvested from all rats, pinned on a paraffin block to maintain an approximate angle of 1100 and fixed in 10% neutral buffered formalin (NBF). These knees were used for micro-CT imaging and histopathological evaluation.

For histopathological evaluation, whole right knee joints were decalcified, embedded in paraffin wax and sectioned coronally. Three sections were stained with Safranin O fast green (SOFG) and one section with H&E which were evaluated using a semi-quantitative grading system (OARSI), as detailed in Appendix 1, to individually score the cartilage/bone and synovial membrane, respectively. Individual score was recorded from representative sections in an Excel spreadsheet and the sum of all individual scores generated the global composite score.

A total of 46 Sprague Dawley rats were assigned to 1 of 4 study groups: high-dose HDAd-ratIL-1Ra (ACLT/HDAd-ratIL-1Ra; $2.4 \times 10^8$ viral particles [VP]/dose; n=12), low-dose HDAd-ratIL-1Ra (ACLT/HDAd-ratIL-1Ra; $3 \times 10^7$ VP/dose; n=12), vehicle (ACLT/vehicle; n=12), or sham/untreated (n=10). Rats underwent ACLT surgery (except sham animals) under isoflurane anesthesia on Day −7. Seven days post-surgery (Day 1) rats received a single IA injection of HDAd-ratIL-1Ra or vehicle in the right knee joint under anesthesia. At Week 12, animals were sacrificed and whole right knee joints were harvested and analyzed for histopathology. For histopathological evaluation, whole right knee joints were stained with Safranin O fast green (SOFG) and hematoxylin and eosin and assessed using a semi-quantitative grading system (OARSI score) to score cartilage/bone and synovial membrane, respectively. Individual scores were recorded, and composite scores for each parameter were generated by the sum of all individual scores.

Results: Anterior cruciate ligament transection (ACLT) successfully induced OA microscopic changes in the knee joint of all rats 12 weeks following surgery. The single intra articular injection of HDAd-ratIL-1Ra at $3 \times 10^7$ and $2.43 \times 10^8$ VP/dose at Week 1 post ACLT to Sprague Dawley rats resulted in a dose-dependent decrease in incidence/severity of the OA-related lesions to the cartilage/bone as well as the synovial membrane with their respective median and mean scores being lower in ACLT-operated treated groups when compared with the ACLT-operated vehicle group.

In sham-operated rats, microscopic changes at Week 12 were limited to low incidence of superficial articular cartilage changes graded minimal in severity as assessed by surface irregularities with focal fibrillation/clefts/fissure, chondrocyte loss, and/or SOFG staining. All ACLT-operated rats developed OA microscopic changes that were minimal-to-severe in 1 or more of the examined articular compartments at Week 12. These changes were minimal to severe and consisted of surface irregularities to complete fibrillation/clefts/fissure/loss of articular cartilage, SOFG staining loss, clone formation and/or loss of chondrocytes.

Figure 11:
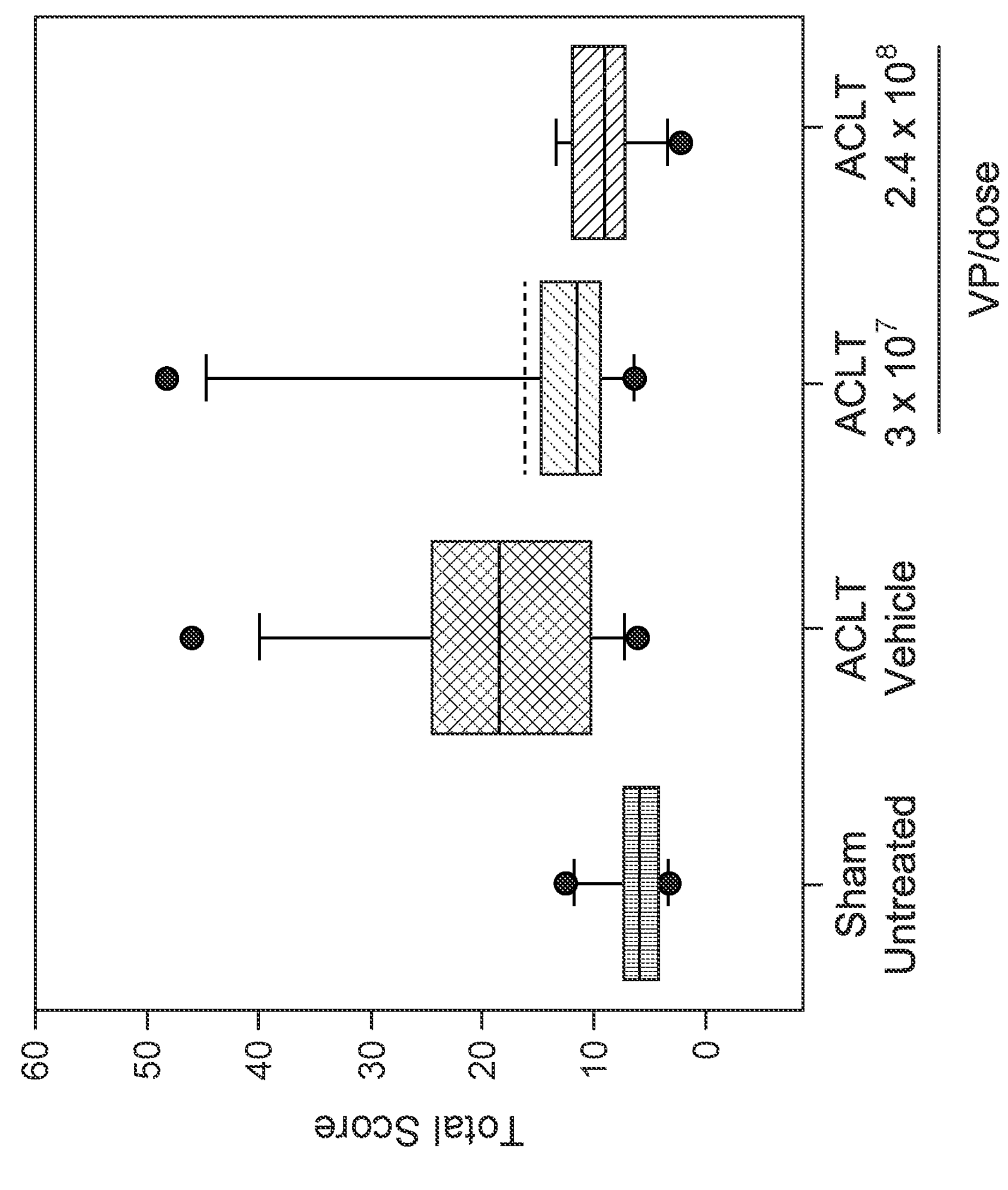
FIG. 11 depicts the Composite (Total) Scores by Group for Cartilage/Bone Evaluation in Sham- and ACLT-Operated Rats for Cartilage/bone OARSI Scores. The y-axis indicates the total OARSI composite score and the x-axis indicates the different treatments and dosages. Dashed line indicates mean; solid line indicates median; dots indicates outliers; box extremities indicate quartile 1 (bottom) and quartile 3 (top); end of whiskers indicate min and max. ACLT, anterior cruciate ligament transection; Min, minimum; Max, maximum; VP, viral particle.
Figure 12A:
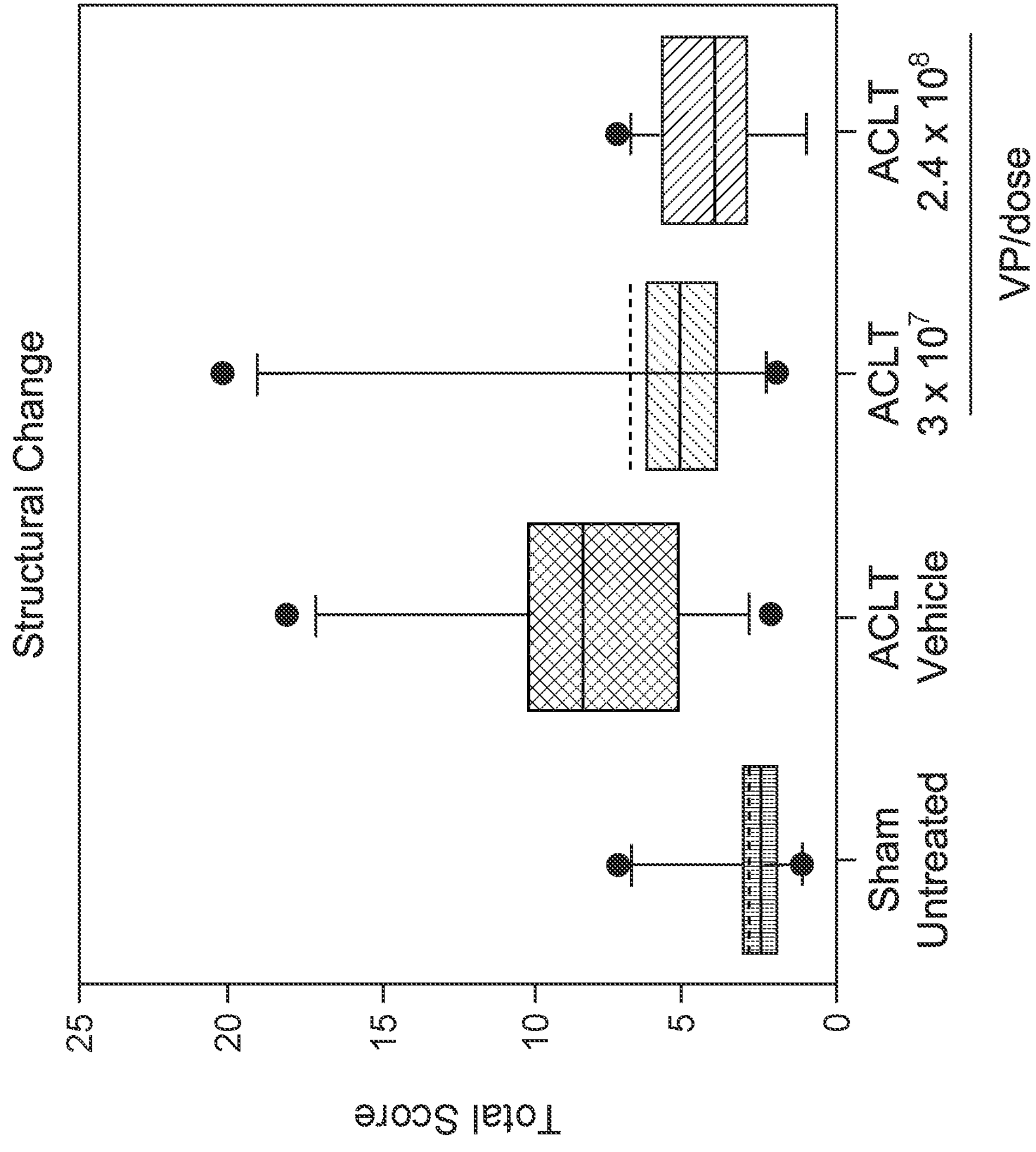
FIG. 12A-FIG. 12D depict the Total Scores by Group for (A) Structural Change (B) SOFG Staining Loss (C) Clone Formation and (D) Chondrocyte Loss in Sham- and ACLT-Operated Rats. The y-axis indicates the total OARSI sub-score and the x-axis indicates the different treatments and dosages. Dashed line indicates mean; solid line indicates median: dots indicates outliers; box extremities indicate quartile 1 (bottom) and quartile 3 (top); end of whiskers indicate min and max. ACLT, anterior cruciate ligament transection; Min, minimum; Max, maximum; VP, viral particle.
Figure 12B:
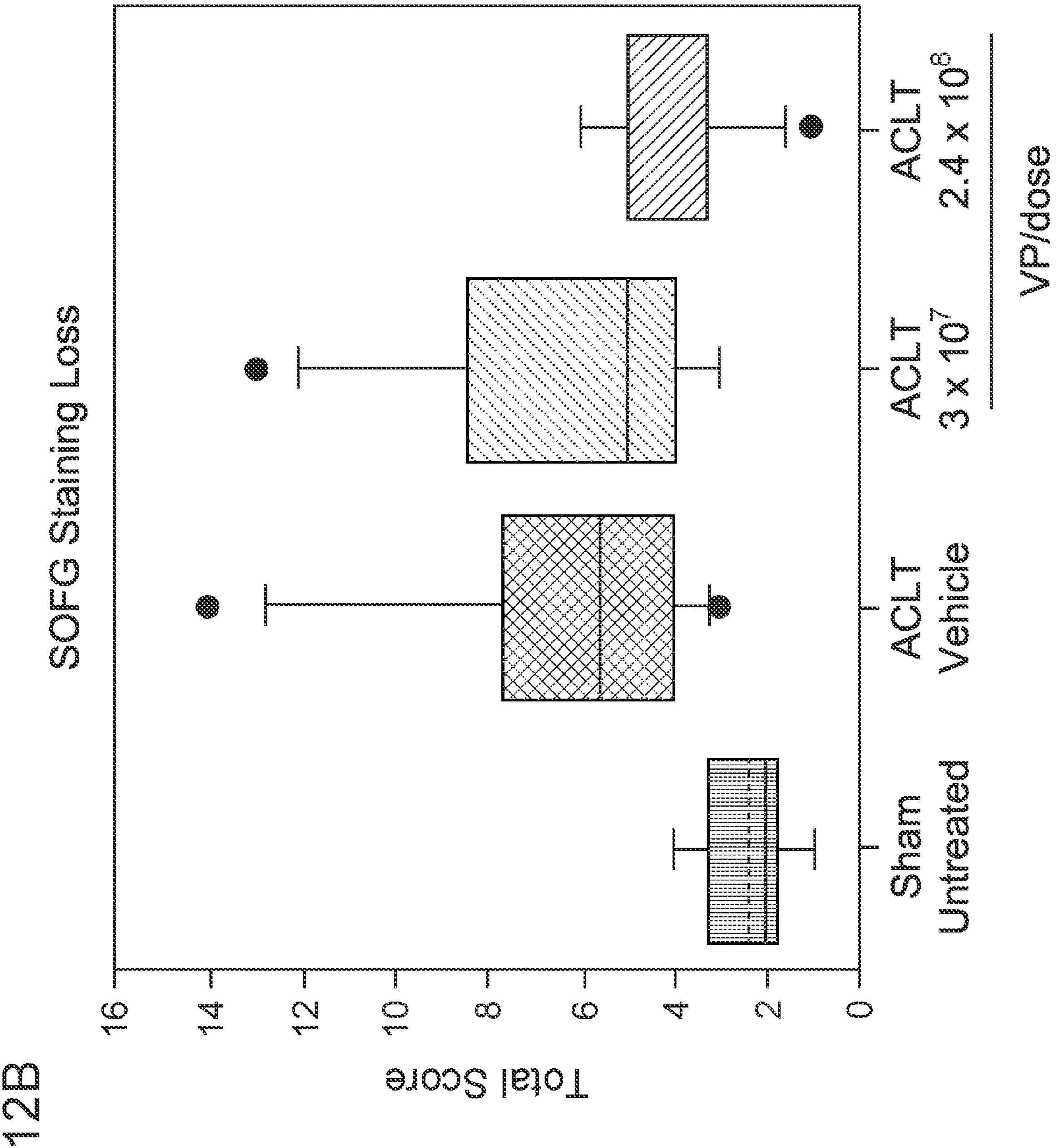
Figure 12C:
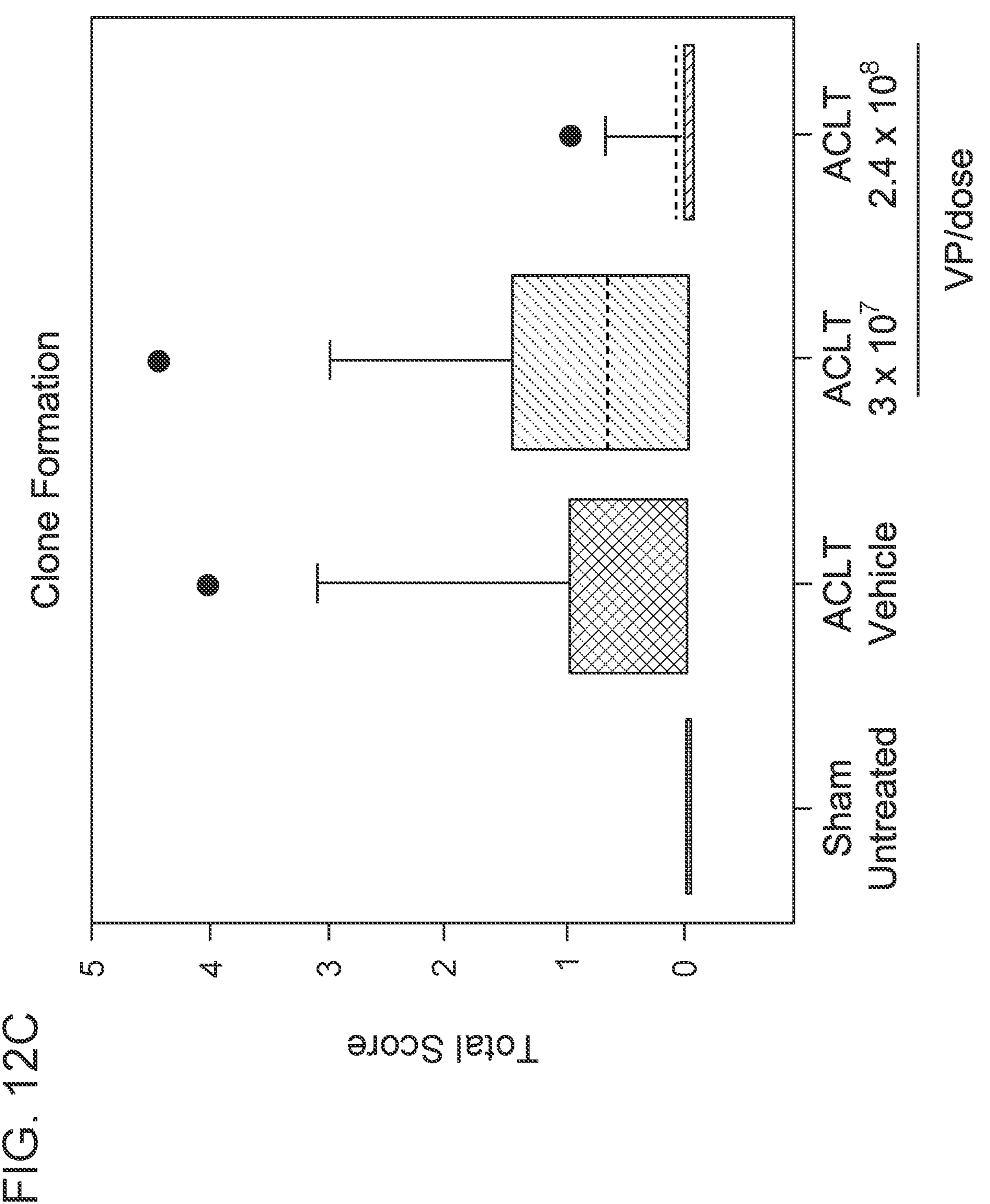
Figure 12D:
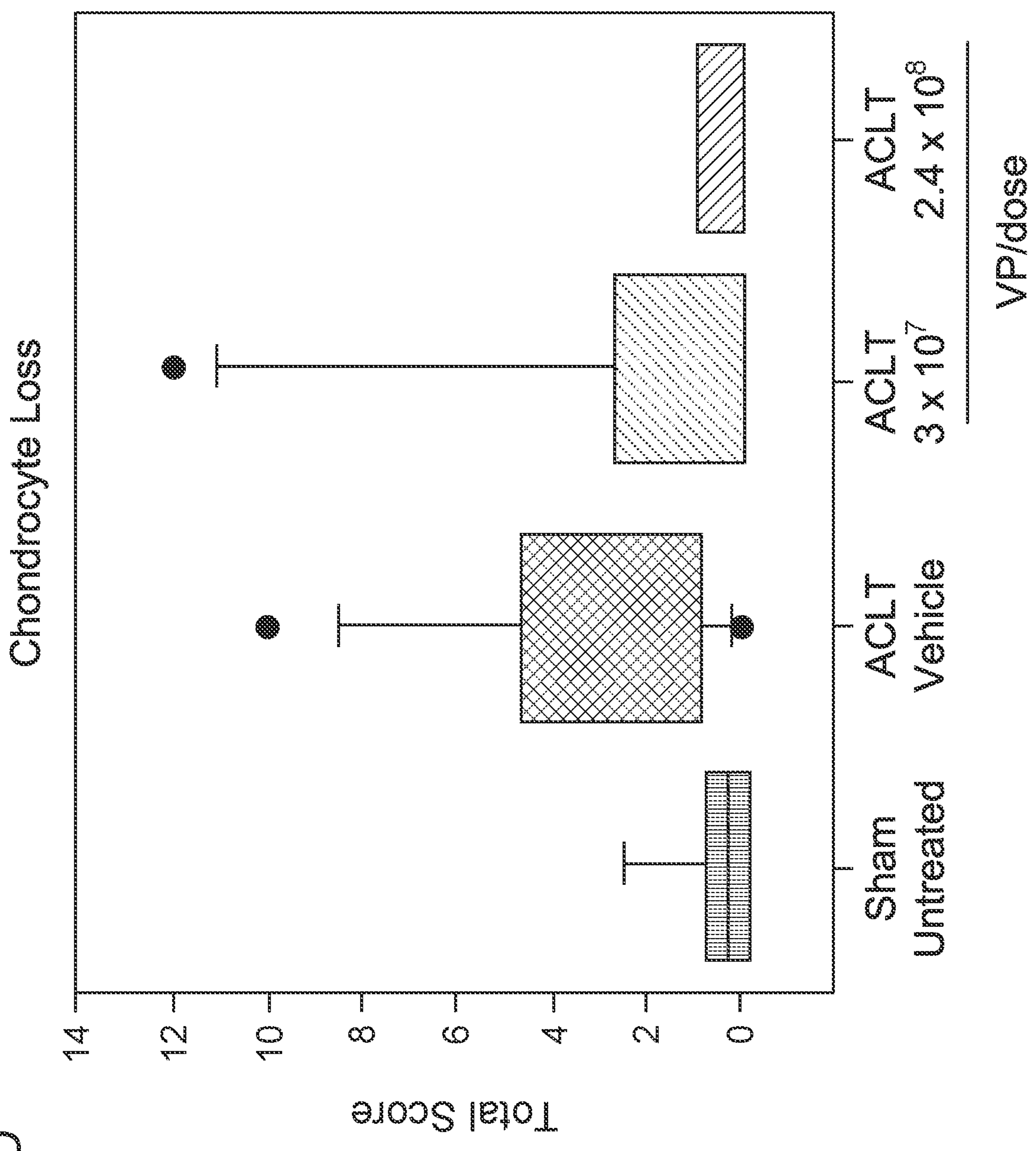
Figure 13:
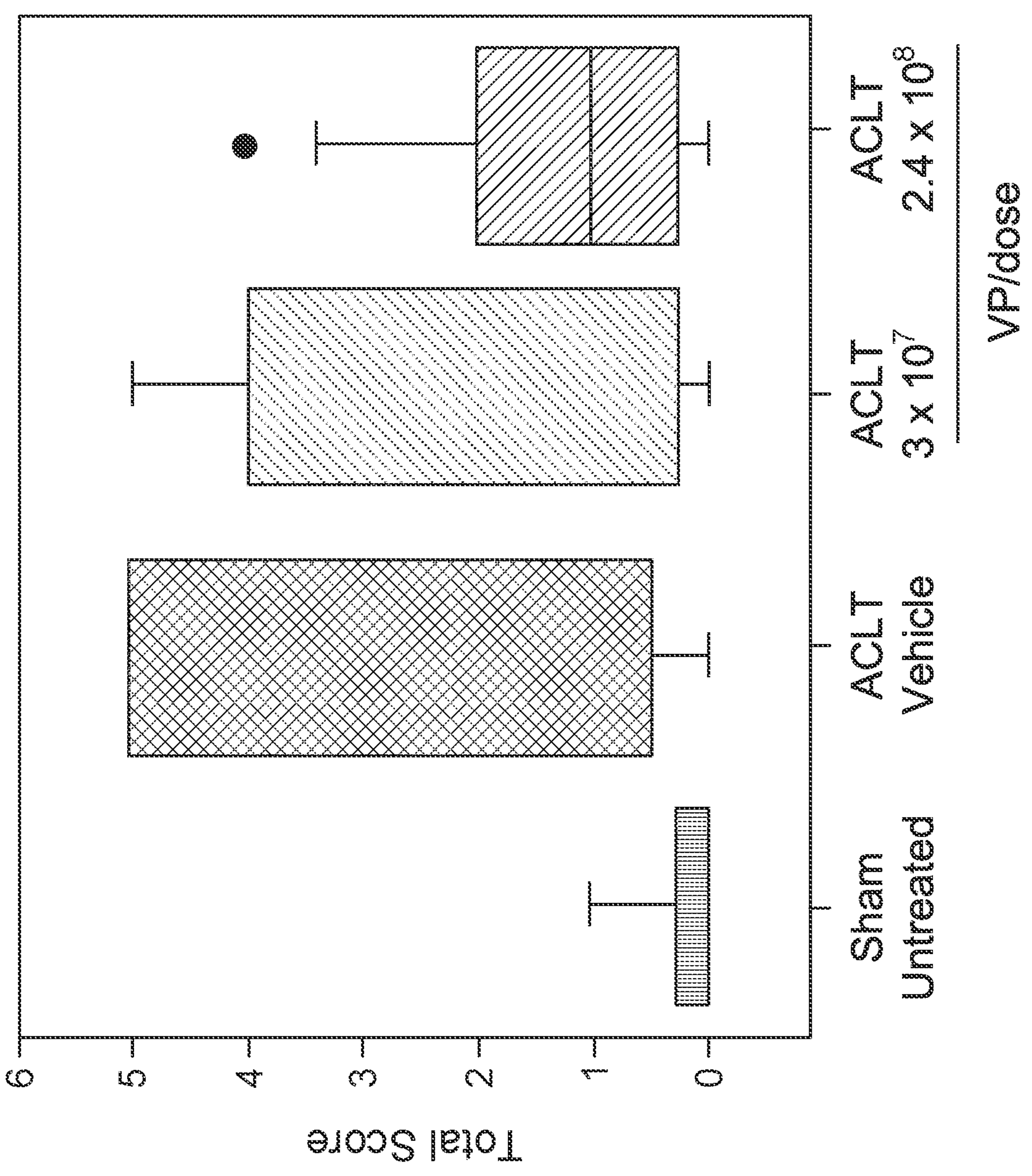
FIG. 13 depicts the Composite (Total) Scores by Group for Synovial Membrane Evaluation in Sham- and ACLT-Operated Rats by H&E Staining. The y-axis indicates the total score and the x-axis indicates the different treatments and dosages. Dashed line indicates mean; solid line indicates median; dots indicates outliers; box extremities indicate quartile 1 (bottom) and quartile 3 (top); end of whiskers indicate min and max. ACLT, anterior cruciate ligament transection; Min, minimum; Max, maximum; VP, viral particle.

In sham-operated rats, microscopic changes at Week 12 were limited to low incidence of superficial articular cartilage changes graded minimal in severity as assessed by surface irregularities with focal fibrillation/clefts/fissure, chondrocyte loss, and/or SOFG staining. All ACLT-operated rats developed OA microscopic changes that were minimal-to-severe in 1 or more of the examined articular compartments at Week 12. Among ACLT-operated rats, HDAd-ratIL-1Ra resulted in a dose-dependent decrease in composite scores for cartilage/bone compared with vehicle (FIG. 11). Among ACLT-operated rats, HDAd-ratIL-1Ra resulted in a dose-dependent decrease in composite scores for cartilage/bone compared with vehicle (FIG. 11); these decreases are likely due to reduced severity of structural changes and chondrocyte loss with HDAd-rat IL-1Ra treatment compared with vehicle (FIG. 12). Slight decreases in severity of SOFG staining loss and incidence of clone formation were also observed with HDAd-ratIL-1Ra treatment compared with vehicle (FIG. 12). There was a dose-related decrease in the median and mean composite scores of OA microscopic changes to the synovial membrane in rats administered HDAd-ratIL-1Ra when compared with ACLT-operated rats of the vehicle group. All synovial microscopic findings were minimal in severity and included proliferation/hypertrophy of synoviocytes, lymphoplasmacytic infiltrates rarely forming aggregates/follicles, villous hyperplasia with proliferation of fibroblasts/blood vessels and cartilage/bone detritus (FIG. 13). There was a dose-related decrease in the median and mean composite scores mostly due to lower severity of the structural changes and chondrocyte loss in rats administered HDAd-ratIL-1Ra at Week 1 when compared with ACLT-operated rats of the vehicle group, as illustrated in FIGS. 11 and 12, respectively. There was a slight decrease in severity of SOFG staining loss and incidence of clone formation in treated rats when compared with animals from the ACLT/Vehicle group.

Conclusion: The results described herein demonstrate that a single administration of HDAd-ratIL-1Ra, the rat surrogate of FX201, resulted in a dose-dependent decrease in the incidence and severity of OA-related lesions to cartilage/bone and the synovial membrane 12 weeks post-surgery; these results support further development of FX201 as a potential therapeutic agent for OA.

Example 10. Establishing the Efficacy, Safety, and Biodistribution of FX201, a Helper-Dependent Adenoviral Gene Therapy for the Treatment of Osteoarthritis, in an Anterior Cruciate Ligament Transection Rat Model Aim of study: Described herein is a study to evaluate the efficacy, safety, and biodistribution of HDAd-ratIL-1Ra, the rat surrogate of FX201, and the biodistribution of FX201, when administered as a single intra-articular (IA) injection in the anterior cruciate ligament transection (ACLT) rat model of OA.

Methodology: Sprague-Dawley rats underwent ACLT surgery in the right knee (except sham animals). To assess safety and vector biodistribution, rats received a single IA injection of HDAd-ratIL-1Ra, FX201, or vehicle in the right knee joint 28 days postsurgery. Safety was assessed throughout the study in a cohort that included male rats (N=144) equally assigned to 6 study groups: HDAd-ratIL-1Ra ($3.2\times10^{8}$, $3.1\times10^{9}$, or $4.3\times10^{10}$ GC/dose), ACLT/vehicle, ACLT/untreated, or sham/untreated. Vector biodistribution was assessed in a cohort of ACLT-operated rats receiving HDAd-ratIL-1Ra ($4.3\times10^{10}$ GC/dose) or FX201 ($4.1\times10^{10}$ GC/dose) at Days 8, 29, and 92 (n=12 [1:1 sex ratio] per group at each time point).

Results: In the efficacy study described herein, HDAd-ratIL-1Ra demonstrated decreases in OARSI composite scores compared with vehicle. In the safety study, HDAd-ratIL-1Ra had no adverse effects on mortality, body weight and food consumption, or clinical or anatomical pathology at any dose studied. Anti-Ad5 titers increased with HDAd-ratIL-1Ra dose and decreased from Day 29 to 92. Similarly, dose-dependent anti-Ad5 T cell responses decreased from Day 29 to 92 as assessed by interferon-γ ELISpot with splenocytes from HDAd-ratIL-1Ra-treated rats. In the biodistribution study, HDAd-ratIL-1Ra and FX201 were detected up to Day 92, with the highest concentrations at the injection site. Both were sporadically detected at low levels in the liver, spleen, lung, and bone marrow at Days 8 and 29; however, neither was detected in plasma or organs such as the brain, heart, and kidney at any time point examined, confirming absence of systemic circulation.

Conclusions: The results described herein demonstrate that following a single local IA injection in rats, HDAd-ratIL-1Ra ameliorated OA-related lesions to cartilage 12 weeks postsurgery at all doses tested in the efficacy study. HDAd-ratIL-1Ra was well tolerated, and the no-observed-adverse effect level (NOAEL) was considered to be $4.3\times10^{10}$ GC, the highest dose tested, indicating a 1000-fold difference between the minimal efficacious dose ($3.6\text{-}10^{7}$ GC/dose) and NOAEL in the rat ACLT model of OA. Furthermore, HDAd-ratIL-1Ra and FX201 did not enter systemic circulation. These results described herein support further development of FX201; a Phase I study in patients with knee OA is currently underway (NCT04119687).

Example 11: In Vitro Expression of IL-1Ra from GQ-201 (HDAd-eqIL-1Ra)

Aim of Study: Described herein is a study to assess the levels of IL-1Ra secreted by HEK293 (human embryonic kidney) cells infected with HDAd-eqIL-1Ra (referred to as GQ-201 in study report) and to demonstrate that the NF-κB-inducible promoter encoded by the vector is functional, i.e., that an inflammatory stimulus increases the expression of IL-1 Ra. HDAd-eqIL-1Ra is an HDAd vector expressing equine IL-1Ra under the control of a NF-κB promoter. It is equivalent to FX201 except that HDAd-eqIL-1Ra carries the equine version of IL-1Ra as opposed to the human version, which is present in FX201. HDAd-GFP vector, used as a control, encodes for green fluorescent protein (GFP) instead of IL-1Ra, but shares an identical backbone with HDAd-eqIL-1Ra and FX201.

Methodology: HEK293 cells were plated in triplicate on a 12-well plate (250,000 cells per well) and incubated overnight in 1 mL minimal essential medium (MEM) containing 10% fetal bovine serum (10% MEM). The next day (Day 0), medium was replaced with 200 μL of the respective infection medium containing virus as listed in Table 6. Cells were incubated for 1 hour and thereafter the infection medium or vehicle was aspirated and replaced with $10^{0}$/MEM. On Day 1, supernatant samples were taken from the wells and frozen at −20° C. On Day 2, the medium of all wells was changed for fresh 10% MEM. On Day 3, supernatant samples were taken from the wells and frozen at −20° C. Medium from all wells was replaced either with 10% MEM containing 100 μg/mL LPS or plain 10% MEM, as indicated in Table 6. On Day 4, supernatants were collected and frozen at −20° C. Samples were analyzed by an enzyme-linked immunosorbent assay (ELISA) specific for equine IL-1Ra.

TABLE 6

| Experimental Groups and Treatment | | | |
|---|---|---|---|
| Group | Test Item | Multiplicity of Infection (VP/cell) | LPS (100 μg/mL) |
| 1A | HDAd-eqIL-1Ra | 100 | − |
| 1B | HDAd-eqIL-1Ra | 100 | + |
| 2A | HDAd-eqIL-1Ra | 1,000 | − |
| 2B | HDAd-eqIL-1Ra | 1,000 | + |
| 3A | HDAd-GFP | 100 | − |
| 3B | HDAd-GFP | 100 | + |
| 4A | HDAd-GFP | 1,000 | − |
| 4B | HDAd-GFP | 1,000 | + |
| 5A | Vehicle[a] | — | − |
| 5B | Vehicle[a] | — | + |

VP, viral particle.
[a]Tris-HCl buffer + 5% glycerol

Figure 14:
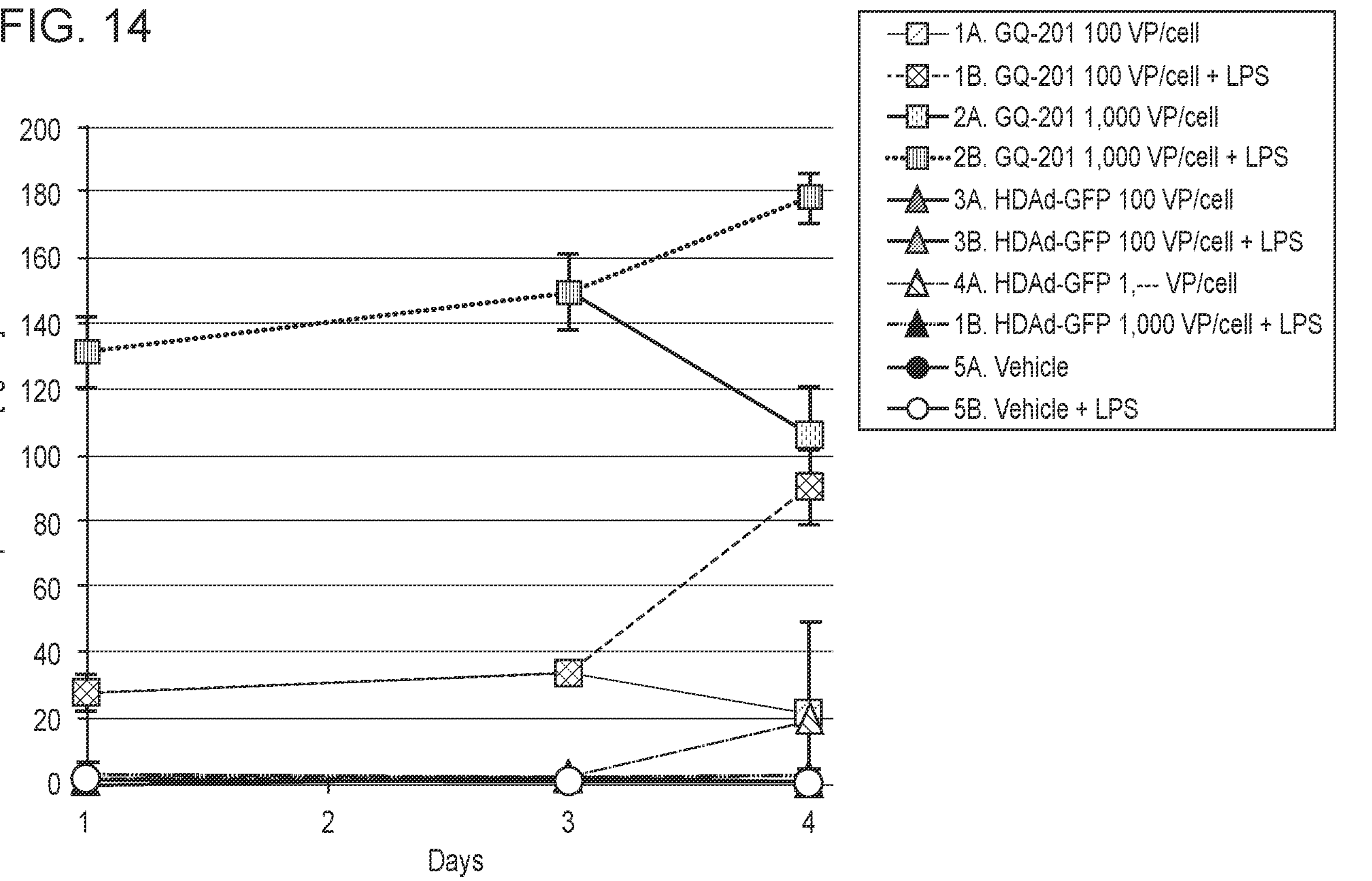
FIG. 14 depicts in vitro expression of equine IL-1Ra following infection with HDAd-eqIL-1Ra. Equine IL-1Ra concentrations in the media supernatants of cell cultures infected with different concentration of HDAd-eqIL-1Ra (GQ-201) or HDAd-GFP. "B" groups were incubated with 100 μg/mL LPS from Day 3 to Day 4. Mean f SEM values are shown.

Results: Equine IL-1Ra concentrations between 20-40 ng/mL were measured on Days 1 and 3 in Groups 1A and 1B, in which the cells were infected with 100 VP/cell HDAd-eqIL-1Ra. Upon addition of LPS on Day 3, IL-1Ra levels increased to ~90 ng/mL on Day 4 (Group 1B), whereas in absence of LPS, a concentration of ~20 ng/mL IL-1Ra was measured (Group 1A). In Groups 2A and 2B, where cells were infected with 1,000 VP/cell HDAd-eqIL-1Ra, equine IL-1Ra concentrations between 130-150 ng/mL were measured on Days 1 and 3. Increased IL-1Ra secretion following stimulation with LPS was also evident in cells infected with HDAd-eqIL-1Ra at 1,000 VP/cell, though the extent of induction was lower, compared to the cells infected with 100 VP/cell HDAd-eqIL-1Ra. (FIG. 14)

No significant IL-1Ra levels over baseline were detected in groups infected with HDAd-GFP or treated with vehicle, irrespective of LPS treatment. On Day 4, one replicate in Group 4A (HDAd-GFP) had an IL-1Ra concentration of 53.5 ng/mL: this is considered the result of a technical error.

Conclusion: The results described herein demonstrate that cells infected with HDAd-eqIL-1Ra secreted IL-1Ra into the medium. IL-1Ra production by cells infected with 1,000 VP/cell HDAd-eqIL-1Ra was higher compared to the IL-1Ra levels in the supernatant of cells infected with 100 VP/cell HDAd-eqIL-1Ra. Induction of inflammation by LPS on Day 3 led to increased levels of IL-1Ra on Day 4 in the cell supernatants of HDAd-eqIL-1Ra-infected cells at 100 VP/cell as well as 1,000 VP/cell. This suggests that the inflammation-sensitive promoter system that controls the expression of IL-1Ra is functional.

Example 12. Dose Escalation Trial of Helper-Dependent Adenovirus Delivered Equine IL-1Ra in Equine Joints Aim of Study: Described herein is a study to develop a dose of HDAd-IL-1Ra to the joint that provides high expression with acceptable synovial inflammatory response. HDAd-eqIL-1Ra has an identical vector backbone to FX201 or murine vector HDAd-mIL-1Ra but encodes for an equine-specific variant of IL-1Ra transgene.

Methodology: One normal adult horse, 6 years of age, was used for this study. The horse was examined clinically and radiographically to rule out pre-existing arthritis in the CarpJs and MCPJs in the forelimbs. On Day 0, the horse was injected IA in separate joints with escalating doses of HDAd-eqIL-1Ra formulated in PBS, at a dose volume of 3 mL, as indicated in Table 7. On Day 90, the MCPJ (previously injected with $2\times10^{11}$ VP HDAd-eqIL-1Ra), the left CarpJ (previously injected with $6\times10^{12}$ VP HDAd-eqIL-1Ra) and the right hind limb metatarsal-phalangeal joint (MTPJ) were injected with 0.125 ng LPS in a 1 mL volume of PBS per joint. Synovial fluid of all HDAd-eqIL-1Ra-injected joints was sampled on Day 0, 1, 2, 4, 7, 14, 21, 56, 90, and 92 after HDAd-eqIL-1Ra injection. Additionally, fluid from the right hind MTPJ was sampled on Days 56, 90, and 92, and fluid from the left hind MTPJ was sampled on Days 90 and 92. WBC counts, protein content and levels of IL-1Ra were determined in the sampled synovial fluid.

TABLE 7

| Experimental Design and Treatment | | |
|---|---|---|
| Joint | Dose Level (VP/joint) | LPS on Day 92 |
| Forelimb - right MCPJ | $2\times10^{11}$ | Yes |
| Forelimb - left MCPJ | $6\times10^{11}$ | No |
| Forelimb - right CarpJ | $2\times10^{12}$ | No |
| Forelimb - left CarpJ | $6\times10^{12}$ | Yes |
| Hindlimb - right MTPJ | Untreated | Yes |
| Hindlimb - left MTPJ | Untreated | Untreated |

EPS, lipopolysaccharides;
VP, viral particle.
CarpJ, carpal joint;
MCPJ, metacarpal-phalangeal joint;
MTPJ, metatarsal-phalangeal joint.

Results: Clinical signs: The results disclosed herein show that injection of HDAd-eqIL-1Ra into the left and right MCPJs resulted in moderate synovial effusion and heat on surface palpation. Both carpi were swollen and hot to the touch 24 hours after HDAd-eqIL-1Ra injection. Effusion was severe in the left carpus, and moderately severe in the right carpus. Pain resulting in a reluctance to bear weight affecting the left forelimb and to a lesser extent in the right forelimb were evident for 24 hours after injection. The horse preferred to remain recumbent for the first 24 hours following vector administration. NSAIDs were administered at a higher dose for pain control for the first 36 hours, and then at a standard dose until Day 5. A single dose of morphine was given intramuscularly 12 hours after HDAd-eqIL-1Ra injection to the four joints. Lameness was considerably reduced on Day 2, and the horse was comfortable at a walk on Day 4.

Synovial WBC counts: The results disclosed herein show significant increases in synovial fluid WBC counts were observed one day after vector injection at both dose levels. The increase in WBC counts was more severe at the higher vector dose. The mean total WBC count for all four injected joints was $35.2\times10^3$ cells/mL; total WBC counts in this range are classified as moderate to severe inflammatory synovitis, frequently indicating sepsis. The differential WBC count on Day 1 indicated neutrophilic infiltration, changing to predominantly large mononuclear cells by Day 2. In response to NSAID treatment, the WBC counts declined to normal by Day 4. A rebound in WBC counts was evident on Day 7, following cessation of NSAID treatment on Day 5. Total WBC counts then gradually declined to normal levels by Day 56 and remained normal until Day 90 (mean: $1.0\times10^3$ cells/mL).

Protein content in synovial fluid: The results disclosed show that total protein content on Day 1 post-injection was moderately elevated in the MCPJs, and markedly elevated in the CarpJs. The synovial protein content of the MCPJs decreased to normal values by Day 4, but the CarpJ total protein content remained elevated until Day 56. This result indicates that the higher dose level of HDAd-eqIL-1Ra induced significant synovitis.

Figure 15:
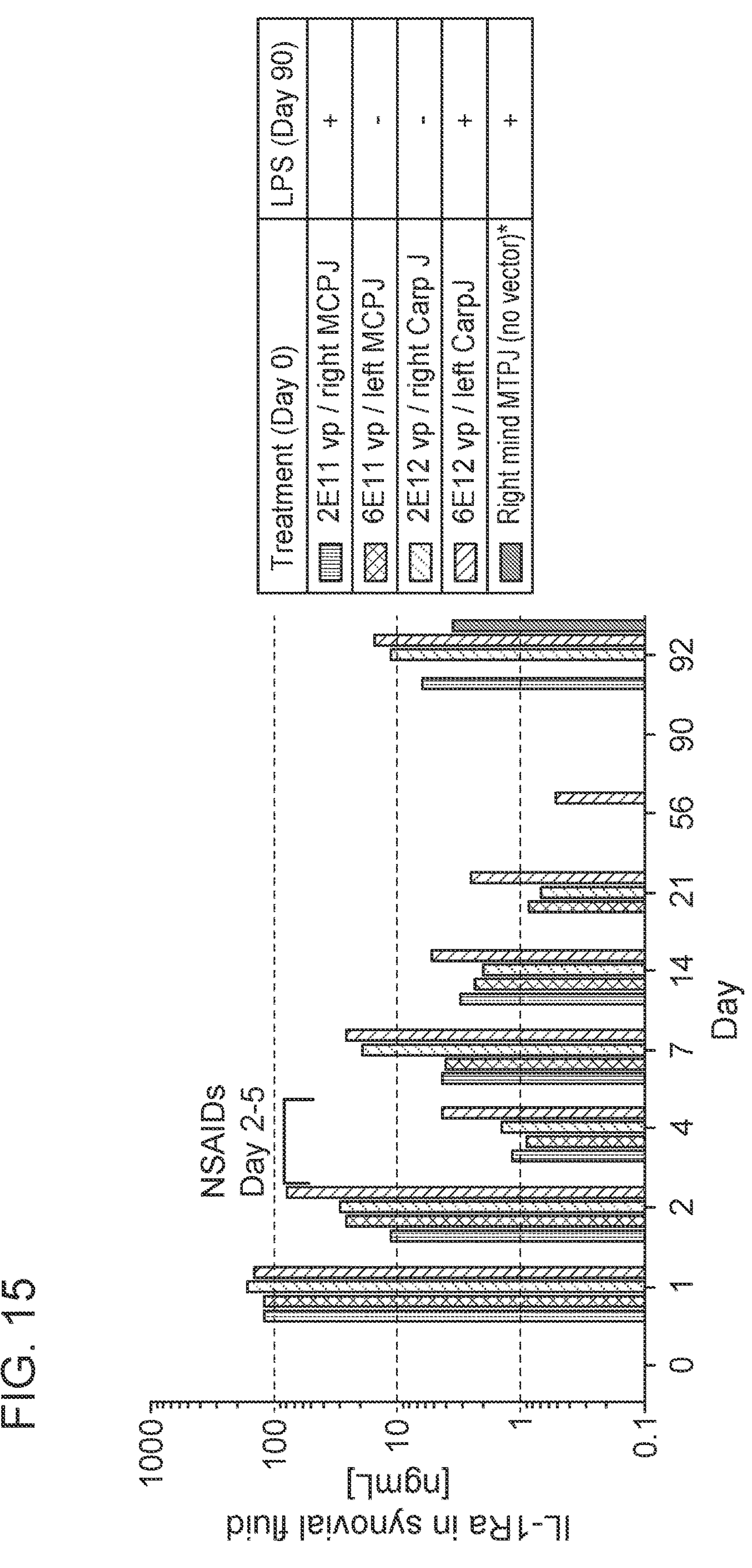
FIG. 15 depicts Synovial Levels of IL-1Ra. Equine synovial IL-1Ra levels were measured in synovial fluid for dose escalation trial of helper-dependent adenovirus delivered equine-IL-1Ra in equine joints. IL-1Ra in naïve joints was only measured on Day 90 (pre-injection) and Day 92. CarpJ, carpal joint; MCPJ, metacarpal-phalangeal joint; MTPJ, metatarsal-phalangeal joint; LPS, lipopolysaccharides; NSAIDs, non-steroidal anti-inflammatory drugs.

Synovial Levels of IL-1Ra: The results disclosed show that peak synovial concentrations of IL-1Ra were observed on Day 1 post-injection at all dose levels (FIG. 15). The highest dose of HDAd-IL-1Ra resulted in the more persistent elevation of IL-1Ra. Reduced levels of IL-1Ra were observed on Day 4, considered to be a response to the reduced inflammation elicited by the treatment with NSAIDs. Synovial concentrations of IL-1Ra increased again on Day 7, following cessation of NSAID treatment and rebound of inflammation. By Day 56, IL-1Ra was not detected in the injected joints, except for the CarpJ treated at the highest dose of $6\times10^{12}$ VP/joint. IL-1Ra was not detectable in the synovial fluid on Day 90 post-treatment. Following administration of LPS into the MCPJ (previously injected with $2\times10^{11}$ VP HDAd-eqIL-1Ra), increased levels of IL-1Ra were detected on Day 92 in the left CarpJ (previously injected with $6\text{-}10^{12}$ VP HDAd-eqIL-1Ra) and the untreated right hind limb MTPJ. Increased IL-1Ra was also present in right CarpJ that did not receive LPS. The highest reactivation of IL-1 Ra expression was evident in joints that had previously been injected with HDAd-eqIL-1Ra.

Conclusions: The results disclosed demonstrate that all dose levels of HDAd-eqIL-1Ra resulted in significant IL-1Ra production on Day 1. The highest dose ($6\times10^{12}$ VP) resulted in persistent IL-1Ra production over a period of at least 56 Days. Despite the increased IL-1Ra synthesis, there was a more profound synovitis induced at higher HDAd-eqIL-1Ra doses, with transient but high total WBC counts, and a persistent elevation in synovial protein content. The synovitis was associated with considerable short-term pain in CarpJs. It is possible that a transient inflammatory response observed in this study was exacerbated by a high total vector dose per animal due to the treatment of four joints, compared to single joint in the efficacy study. A rebound IL-1Ra formation on Day 92 was evident following an LPS insult to the joints. The levels in HDAd-eqIL-1Ra-injected joints were generally greater (6.24-15.09 ng/mL range), compared to the naïve joints injected with LPS (3.51 ng/mL). The right CarpJ not injected with LPS also showed increased IL-1Ra expression. This possibly reflects a local paracrine or lymphatic stimulation to the CarpJ from the more distal MCPJ, which was inflamed by LPS injection. This instant result suggests the vector can be reactivated by adjacent joint damage. In conclusion, the instant results indicate a potential for long-term (at least 3 months) inflammation-sensitive expression of IL-1Ra transgene.

Example 13: A Preliminary Trial of Helper-Dependent Adenovirus Delivered Equine IL-1Ra for the Treatment of Traumatic Osteoarthritis in an Equine Model Aim of Study: Described herein is a study to evaluate the potential of HDAd-eqIL-1Ra to treat early OA in a horse model of the disease. HDAd-eqIL-1Ra has an identical vector backbone to FX201 and murine vector HDAd-mIL-1Ra but encodes for an equine-specific IL-1Ra transgene.

Methodology: On Study Day (−5), the middle carpal joint in one randomly chosen forelimb of 12 skeletally mature (3 to 6 years old) Thoroughbred racehorses had a radial carpal bone osteochondral fragment surgically formed, paired with treadmill exercise, in order to induce early OA. A 10 mm curved gouge was used to separate the fragment from the dorsal aspect of the radial carpal bone and a motorized burr used to expand the fracture bed to 15 mm. Debris was deliberately retained in the joint to induce mild degenerative changes. All horses underwent radiographic and clinical evaluation to confirm lack of pre-existing carpal disease prior to inclusion in this study. The middle carpal joint in the opposite limb was sham operated by arthroscopic examination but no fracture formation. Five days after the surgery (Day 0), the horses were divided into experimental groups and treated with IA injections into the OA-induced carpal joint as indicated in Table 8.

TABLE 8

Experimental Groups and Treatment

| Group | Test Item | Dose Level (VP/carpal Joint) | Group Size |
|---|---|---|---|
| 1 | HDAd-eqIL-1Ra | $2\times10^{11}$ (low dose) | 4 |
| 2 | HDAd-eqIL-1Ra | $2\times10^{12}$ (high dose) | 4 |
| 3 | Vehicle (PBS) | — | 4 |

PBS, phosphate buffered saline;
VP, viral particle.

Horses were then exercised with a rigorous program 5 days a week. The lameness of the horses was assessed by examining the gait and assigning scores according to the American Association of Equine Practitioners (AAEP) scheme on a 0-5 scale (0: no lameness-5: severe lameness). To assess range of motion, the legs of the horses were flexed until resistance was felt and the reduction in range was scored on a 0-4 scale (0, no reduction; 1, <25% reduction; 2, 25-50% reduction; 3, 50-75% reduction; 4, >75% reduction). For evaluation of lameness after flexion, the joints were flexed for 20 seconds followed by lameness assessment according to AAEP on a 0-5 scale (0: no lameness-5: severe lameness). Finally, effusion was rated on a scale of 0-4 (0: no effusion-4: marked effusion). These clinical examinations were performed weekly throughout the experiment. Additionally, synovial fluid (cytology and IL-1Ra expression) and peripheral blood (complete blood counts) were sampled at Day (−5) and Days 0, 4, 7, 14, 21, 28, 56, and 72. At the end of the study (Day 72), horses were euthanized and carpal joints were evaluated macroscopically. Synovial membranes and cartilage were processed for histology and scored by a pathologist in a blinded manner.

Figure 16:
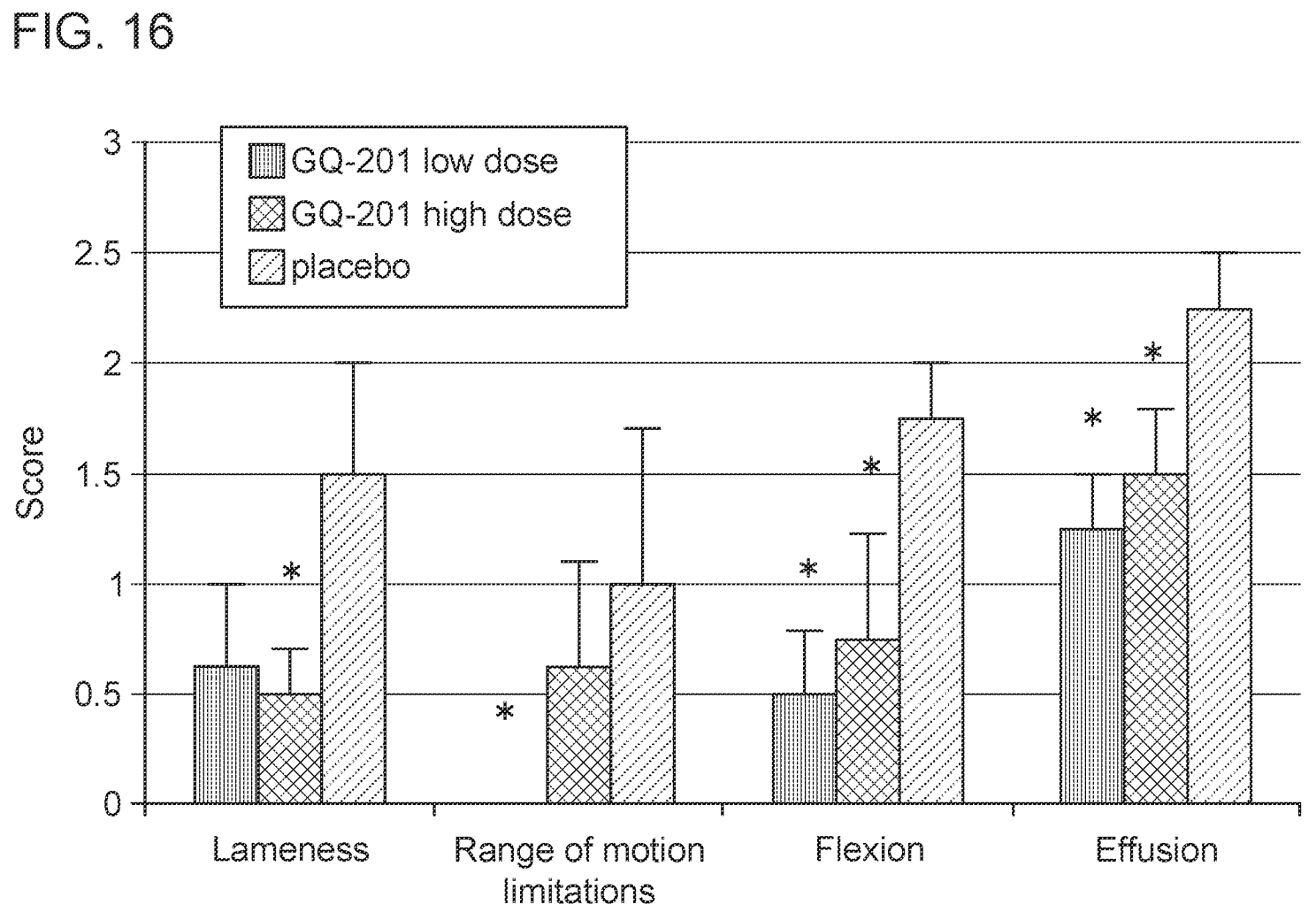
Figure 17:
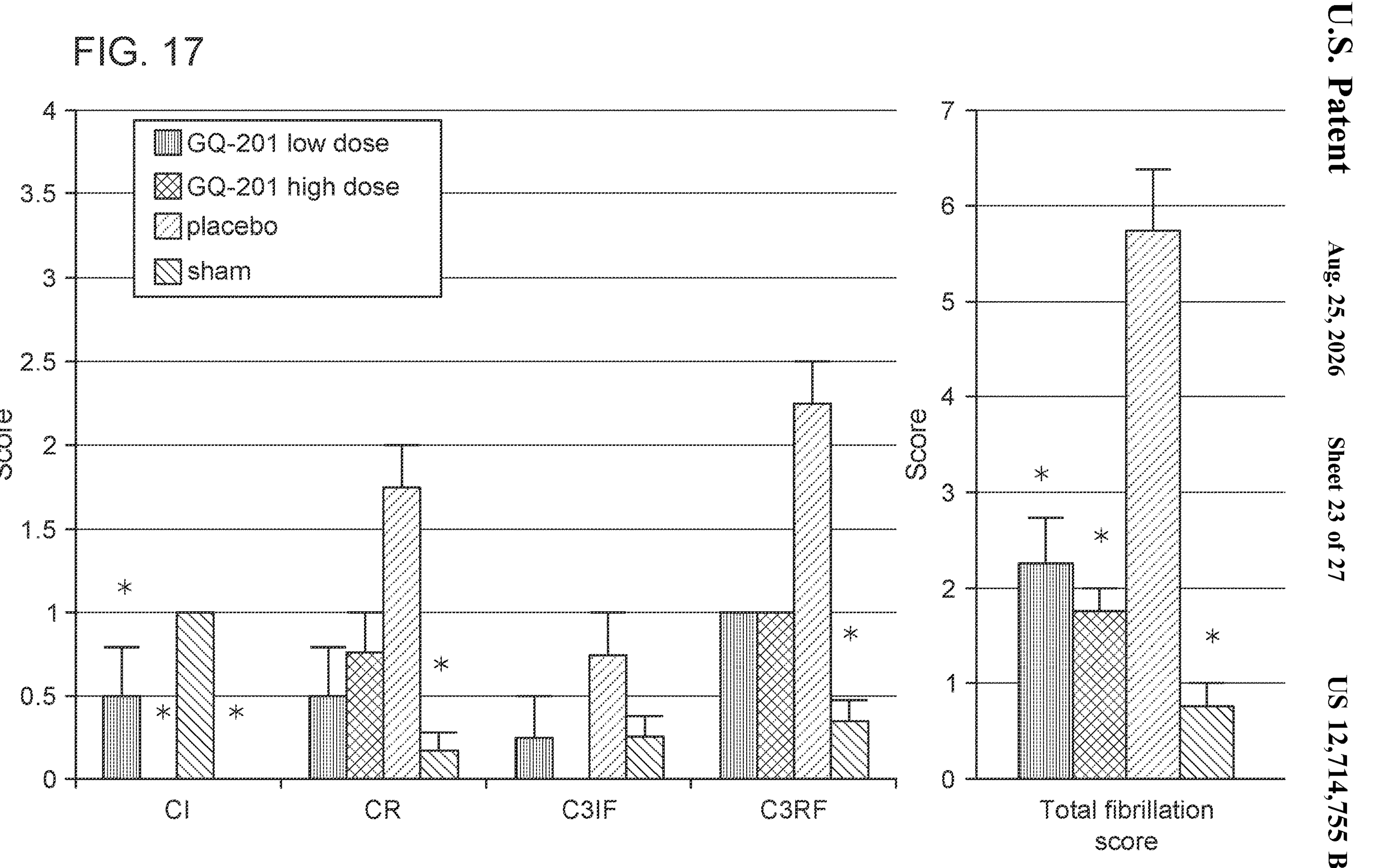
FIG. 17 depicts cartilage Fibrillation in Treated Joints in Horse Osteochondral Chip Model. Left panel depicts mean±SEM cartilage fibrillation scores in the intermediate carpal bone (CI), radial carpal bone (CR), third facet of the intermediate carpal bone (C3IF), and third facet of the radial carpal bone (C3RF) regions of the joints injected with HDAd-eqIL-1 Ra (GQ-201), PBS (placebo) or sham-operated joints. Right panel depicts mean±SEM total cartilage fibrillation score; sum of individual scores. *P<0.05; Kruskal-Wallis test with pairwise comparisons to the vehicle group.

Results: Clinical Scoring: The results described herein showed that no horses developed lameness in the week following injection, indicating good tolerability of the treatment. There was also no evidence of local inflammation at the injection site after the vector administration. OA joints had significantly worse effusion and range of motion scores on all days compared to sham-operated joints in weekly clinical examinations. Cumulative data for effusion, pain on flexion, range of motion, and lameness revealed marked improvements in all tested parameters in the HDAd-eqIL-1Ra-treated groups compared with vehicle-injected horses (FIG. 16). Injection of high dose HDAd-eqIL-1Ra resulted in significant improvements in clinical parameters, but other than lameness, the impact of higher vector dose was less profound than the lower vector dose. Hematology and Clinical Chemistry: The results described herein show that no changes related to the administration of HDAd-eqIL-1Ra vector were observed. Synovial Cytology: The results described herein show that administration of HDAd-eqIL-1Ra at low ($2\times10^{11}$ VP) and high ($2\times10^{12}$ VP) doses induced a transient increase in WBC counts in synovial fluid peaking at Day 4 post-injection compared to both pre-treatment sample and vehicle-injected controls, which resolved by Day 28. Synovial IL-1Ra: IL-1Ra concentration in the synovial fluid of the HDAd-eqIL-1Ra treated horses peaked at Day 4 with 14 ng/mL in the low-dose group and 21 ng/mL in the high-dose group. The synovial IL-1Ra levels gradually declined during the course of the experiment, until they were approximately 1 ng/mL and 0.1 ng/mL in the low- and high-dose groups, respectively, on Day 72. Macroscopic Examination of Injected Joints: The results described herein show that synovial membrane was discolored due to hemorrhage in most vehicle injected OA joints, and had normal tan color in HDAd-eqIL-1Ra injected joints. Untreated OA joints had significantly increased capsule thickness and abnormal coloration. HDAd-eqIL-1Ra injection reduced both parameters to similar levels compared to sham-operated normal carpi. Macroscopic evaluation of the joint surface showed less fibrillation (lower scores) in the intermediate carpal bone, radial carpal bone, third facet of the intermediate carpal bone, and third facet of the radial carpal bone regions of the joints injected with HDAd-eqIL-1Ra, compared with vehicle-injected control joints, and the total fibrillation score for all regions was significantly lower (better) in the HDAd-eqIL-1Ra groups compared with vehicle-injected controls (FIG. 17). Histological Examination: The results described herein show that osteochondral sections from the radial carpal and third carpal bones were stained with hematoxylin and eosin and examined for cartilage fibrillation, chondrocyte density, chondrocyte cloning, osteophyte formation, tidemark duplication or absence, subchondral bone erosion, and organized architecture under polarized light assessment. Additional sections were examined using toluidine blue histochemical staining to establish regional matrix proteoglycan content, and by collagen type II immunohistochemistry to determine collagen density and preservation. Mean severity scores were calculated, in a blinded manner, for each of the individual histological parameters listed above, together with a total histological score combining all parameters (FIG. 18). Total histological scores were significantly lower in groups treated with HDAd-eqIL-1Ra, compared to vehicle-injected controls. HDAd-eqIL-1 Ra-treated joints had generally lower scores for individual parameters, compared with vehicle-injected joints; however, only chondrocyte cloning was significantly reduced compared to vehicle control. Synovial sections from vehicle-injected OA joints had increased thickening and fibrosis compared to OA joints injected with HDAd-eqIL-1Ra.

Conclusion: The results described herein demonstrate that surgical formation of the osteochondral fragment in the radial joint induced OA accompanied by moderate synovitis with early cartilage changes, which manifested as significant differences in several clinical parameters, synovial cytology parameters and histology when compared with sham-operated joints. Cumulative improvement in degree of lameness, range of motion, pain on flexion, and degree of effusion were evident in HDAd-eqIL-1Ra-treated joints over the course of the study. Combined with gross and histologic improvements of cartilage and synovial membrane in treated joints, compared to untreated OA, the instant results indicate that the use of HDAd vector for direct IA delivery of the IL-1Ra transgene appears to be safe and effective. Two HDAd-eqIL-1Ra doses were tested, $2\times10^{11}$ and $2\times10^{12}$ VP/joint, and both had significant benefit without one dose being consistently more efficacious than the other. In conclusion, the instant results demonstrate a substantial benefit of IA injection of HDAd expressing equine IL-1Ra on clinical and morphological manifestations of OA in a large animal model of the disease.

Example 14: Pharmacokinetics of FX201 or the Relevant Species-Specific Construct (HDAd-eqIL-1Ra or HDAd-ratIL-1Ra)

Described herein is a study to evaluate the pharmacokinetics of FX201 or the relevant species-specific construct (HDAd-eqIL-1Ra or HDAd-ratIL-1Ra). The results of the study described herein show that FX201 or the relevant species-specific construct (HDAd-eqIL-1Ra or HDAd-ratIL-1Ra) administered as a single IA injection into the knee joint at doses up to 800-fold greater than the planned clinical starting dose demonstrated limited biodistribution outside of the injected knee. In horses, no significant vector biodistribution was observed at the termination of the study 72 days after administration. In addition, no vector shedding occurred throughout the study, further demonstrating the localization of the injected vector. In rats, vector biodistribution was primarily limited to the local site of injection, including the skin, synovial fluid lavage, quadriceps femoris muscle and draining iliac and popliteal lymph nodes for the duration of the study. Sporadic, low levels of vector were observed in liver, spleen, lung, and bone marrow. Importantly, no vector distribution to gonads was detected.

The instant results show that a single administration of either FX201 or HDAd-ratIL-1Ra was well-tolerated in rats following ACL-T surgery. All vector-treated rats developed an expected immune response to the capsid, consisting of increased WBC counts, T cell responses in splenocytes, enlarged local draining lymph nodes (iliac and/or popliteal) correlating with increased lymph node cellularity, and slight increases in joint inflammation and degenerative joint disease. The increases in WBC counts, lymph node enlargement, and lymph node cellularity were all resolved or resolving by Day 92, indicating the reversibility of this response. Slight increases in degenerative joint disease were observed in animals treated with both HDAd-ratIL-1Ra and FX201 at Day 92, despite no difference from controls at the Day 29 time point, and this increase was thought to be primarily driven by the slight increase in joint inflammation.

Inflammatory responses against the vector observed in the study described herein, which may have contributed to the slight increase in severity of degenerative joint disease in the treated knees, are not anticipated at the lower dose levels planned for administration to humans. At lower doses ($3\text{-}10^7$ or $2.43\times10^8$ VP/knee) given in the rat model of OA (ACL-T one week prior to dosing) in the efficacy study, exacerbation of the joint disease was not observed; instead, administration of HDAd-ratIL-1Ra vector showed clear therapeutic benefits on progression of OA. In the GLP toxicology study, worsening of the degenerative joint disease was observed on Day 29 post treatment at the high dose of $2.43\times10^{10}$VP/knee, along with increased infiltration of mononuclear cells into peri-articular tissues and hyperplasia/hypertrophy of synovium. However, on Day 92, mononuclear infiltrates and synovial hyperplasia/hypertrophy were fully resolved with no clear increase in degenerative joint disease. The increased inflammation of treated joints observed in animals given FX201 at the last sacrifice time point (Day 92) may be explained by an immune response against the human IL-1Ra protein and is thus not considered of relevance for human safety. Consistent with this, increased inflammation was not observed on Day 92 in rats treated with HDAd-ratIL-1Ra.

In conclusion, the instant results strongly support that a single, local administration of FX201 or the species-specific construct is well-tolerated up to doses approximately 1,000-fold greater than the planned clinical starting dose (see Table 9). In addition, limited biodistribution outside of the injected joint has been observed in two species. The injection of FX201 and HDAd-ratIL-1Ra resulted in an expected, non-adverse immune response to the capsid which was resolved or resolving by the end of the study period.

TABLE 9

Target and Actual Safety Margins

| | VP per knee | VP/mL synovial fluid | GC per knee* | GC per ml synovial fluid | Safety Margin via VP/dose to Rat Dose** | Safety Margin via GC/dose to Rat Dose** |
|---|---|---|---|---|---|---|
| HDAd-ratIL-1Ra dose | $2.43 \times 10^{10}$ | $1.62 \times 10^{12}$ | $4.2 \times 10^{10}$ | $2.83 \times 10^{12}$ | — | — |
| Human Starting Dose Target | $1 \times 10^{10}$ | $2 \times 10^{9}$ | $1.4 \times 10^{10}$ | $2.8 \times 10^{9}$ | 810-fold | 1,000-fold |

*Assumes 15 μL rat synovial fluid (Emami 2018) and 5 mL in human (Heilmann 1996, Hansen 2011);

**Calculated by extrapolating dose levels based on synovial fluid volumes in rat and human.

VP, viral particle;

GC, genome copies

Example 15: Toxicology Study of HDAd-ratIL-1Ra, the Rat Surrogate of FX201

Described herein is a study to evaluate the toxicity and efficacy of HDAd-ratIL-1Ra, the rat surrogate of FX201, in a single dose GLP-compliant study in rat ACL-T model of OA. Degenerative joint disease (DJD), evaluated using the OARSI scoring system, was present in all index knee joints that underwent ACL-T surgery and sporadically in some sham-surgery animals. As expected, the severity of DJD progressed from the Day 29 to the Day 92 time points, as indicated by increases in median composite OARSI scores for all ACL-T groups at Day 92 compared to Day 29, confirming induction of OA.

All three dose levels were well tolerated, with no systemic toxicity noted at any time point. This is consistent with the findings of limited biodistribution outside of the injected knee after a single IA administration observed in the GLP biodistribution study.

The study described herein show that an expected immune response to the Ad5 capsid was present in most animals, though the prevalence and magnitude were both dose- and time-dependent. A dose-dependent increase in seroprevalence and titer level of anti-Ad5 circulating antibodies was observed. The titer level was highest at Day 29 compared to Day 92, indicating a gradual reduction in the level of circulating antibodies. In addition, a T cell immune response to the Ad5 vector capsid was observed in splenocytes at the doses of $2.43\times10^{9}$ and $2.43\text{-}10^{10}$ VP/dose. At the highest dose tested, $2.43\times10^{10}$ VP/dose, the T cell response was maintained from Day 29 to Day 92, whereas the response waned in the mid dose group, $2.43\times10^{9}$ VP/dose, at the Day 92 time point. No significant T cell response to the Ad5 vector was observed at the lowest dose of $2.43\times10^{8}$VP/dose at any time point evaluated.

The study described herein showed no systemic effects of the elicited immune response evident in the GLP toxicology study. At the Day 29 time point in the biodistribution study, non-adverse minimal increases in lymph node cellularity, white blood cell (WBC) and differential counts were noted at the dose level equivalent to the highest dose administered in the GLP toxicology study. Absence of these findings in the toxicology study further underscores their non-adverse nature.

The study described herein showed that at the highest dose tested, $2.43\times10^{10}$ VP/dose, there was an increased incidence and severity of mononuclear cell infiltration and hypertrophy/hyperplasia of the synovium in the treated femorotibial joint compared to untreated ACL-T rats and rats administered Reference Item or lower doses of HDAd-ratIL-1Ra at the Day 29 time point. Mononuclear cell infiltration was generally characterized by few mononuclear cells in the periarticular tissues and was often associated with hypertrophy/hyperplasia of the synovium. This increase in mononuclear cell infiltration is thought to underlie the slight increase in OARSI scores observed on Day 29 in this group when compared to animals who underwent ACL-T surgery and were either untreated or received Reference Item. At the Day 29 time point in the GLP biodistribution study, animals administered the same $2.43\times10^{10}$ VP/dose of HDAd-ratIL-1Ra demonstrated a slightly more severe local immune response to the vector, compared to untreated control. In the GLP biodistribution study, joint inflammation, which was composed of mononuclear or mixed cell infiltrates often associated with hyperplasia-hypertrophy of the synovial membrane of the joint and adjacent tendon sheaths, was present in most animals. Importantly, and consistent with the GLP biodistribution study, the increased incidence and severity of mononuclear cell infiltration and hypertrophy/hyperplasia of the synovium in animals administered $2.43\times10^{10}$ VP/dose was no longer present at Day 92, indicating reversibility of this finding. In both studies, these transient effects observed in the synovium were considered non-adverse.

No additional histopathological findings related to treatment with HDAd-ratIL-1Ra were noted in the GLP toxicology study, described herein. Histopathological evaluation in the GLP biodistribution study also confirmed the absence of systemic effects following treatment with HDAd-ratIL-1Ra or FX201 (with the exception of a non-adverse increase in cellularity of draining lymph nodes).

In conclusion, the study described herein strongly support that a single, local administration of HDAd-ratIL-1Ra, the rat species-specific construct of FX201, was well tolerated and resulted in no systemic toxicity findings. Based on these results, the NOAEL is considered to be $2.43\times10^{10}$ VP/dose of HDAd ratIL 1Ra, the highest dose tested. To calculate a safety margin between the NOAEL and the planned doses in the first-in-human study, a dose scaling approach based on synovial fluid volumes has been adopted. According to Emami 2018, a range of 10-20 μL is an appropriate synovial fluid volume based on body weights in rats. Based on the weight of rats included in this study, 15 μL was chosen for purposes of scaling between rat and human doses. As shown in Table 10, the human starting dose has a more than 800-fold safety margin to the NOAEL and the maximum clinical dose has an estimated 8.1-fold safety margin to the NOAEL from the GLP toxicology study based on VP per ml. Importantly, clinical dosing will be based on a GC per mL basis as the concentration of the lower proposed dose levels are below the limit of quantitation (BLOQ) for detection by the viral particle assay (OD260). Considering this quantitative measure, we have a 1,000-fold safety margin on the starting dose and a 10-fold margin on the maximum clinical dose (see Table 11).

TABLE 10

| Clinical Safety Margin Target | | | |
|---|---|---|---|
| | VP per knee | VP per mL synovial fluid* | Safety Margin to Rat High Dose** |
| GLP Toxicology (NOAEL) | $2.43 \times 10^{10}$ | $1.62 \times 10^{12}$ | — |
| Human Starting Dose Target | $1 \times 10^{10}$ | $2 \times 10^{9}$ | 810-fold |
| Human Maximum Dose Target | $1 \times 10^{12}$ | $2 \times 10^{11}$ | 8.1-fold |

*Assumes 15 μL rat synovial fluid (Emami 2018) and 5 mL in human (Heilmann 1996, Hansen 2011);
**Calculated by extrapolating dose levels based on synovial fluid volumes in rat and human.
VP, Viral Particle

TABLE 11

| Actual Safety Margins | | | |
|---|---|---|---|
| | GC per knee | GC per mL synovial fluid* | Safety Margin to Rat High Dose** |
| GLP Toxicology (NOAEL) | $4.2 \times 10^{10}$ | $2.8 \times 10^{12}$ | — |
| Human Starting Dose | $1.4 \times 10^{10}$ | $2.8 \times 10^{9}$ | 1,000-fold |
| Human Maximum Dose | $1.4 \times 10^{12}$ | $2.8 \times 10^{11}$ | 10-fold |

*Assumes 15 μL rat synovial fluid (Emami 2018) and 5 mL in human (Heilmann 1996, Hansen 2011);
**Calculated by extrapolating dose levels based on synovial fluid volumes in rat and human.
GC, Genome Copy In addition to toxicological endpoints, assessment of therapeutic efficacy was also included in the GLP toxicology study. DJD, evaluated using the OARSI scoring system, was present in all index knee joints that underwent ACL-T surgery and sporadically in some sham-surgery animals. As expected, the severity of DJD progressed from the Day 29 to the Day 92 time points, as indicated by increases in median composite OARSI scores for all ACL-T groups at Day 92 compared to Day 29, confirming induction of OA. A modest reduction in median OARSI scores was observed at Day 29 for animals treated with $2.43\times10^{9}$VP/dose HDAd-ratIL-1Ra compared to the untreated ACL-T group, but not the ACL-T/Reference Item group. Additionally, at Day 92, animals treated with $2.43\times10^{8}$VP/dose had lower median OARSI scores compared to untreated and Reference Item ACL-T groups. Despite the minor decreases in OARSI scores described above, a therapeutic benefit of HDAd-ratIL-1Ra on histopathological manifestations of OA was not clearly evident in this study, compared to the efficacy observed in the pharmacology study in the rat ACL-T model. This can be explained by the increased disease severity at the time of the treatment in the present study where HDAd-ratIL-1Ra was administered 4 weeks post-ACL-T, compared to 1 week post-ACL-T in the pharmacology study. It should be noted that the primary endpoint of the study was safety and, therefore, in order to obtain a safety profile, a severe disease model was selected for the GLP toxicology study.

The instant results show the ability of the HDAd vector to express IL-1Ra in an inflammation-sensitive manner was evaluated in an in vitro study using HEK293 cells transduced with equine-specific variant of FX201 (FIG. 6). Lipopolysaccharides (LPS) was used to stimulate NF-κB signaling and resulted in increased expression of equine IL-1Ra over unstimulated control, confirming functionality of the NF-κB-inducible promoter.

The instant results confirm the functionality of the HDAd vector system in vivo, in a dose escalation study performed in a single healthy horse. Four dose levels of equine variant of FX201 HDAd-eqIL-1Ra ($2\times10^{11}$ to $6\times10^{12}$ VP/dose) were administered to separate joints of the horse (left and right carpal joints (CarpJ) and left and right metacarpal phalangeal joints (MCPJ)). The instant results show that robust IL-1Ra expression in synovial fluid was observed 1 day following administration from all dose levels. Injection of vector in this study was associated with transient impairment of mobility attributed to joint inflammation, increased white blood cell (WBC) counts and total protein levels in synovial fluid. Since local intolerance was not observed in any other study, it is presumed that the transient inflammatory response observed in the instant results was exacerbated by a high total vector dose per animal ($8.8\times10^{12}$ VP total combined exposure in a single animal) due to the treatment of four joints, compared to single joint in the efficacy study (highest dose tested was $2\times10^{12}$).

The levels of IL-1Ra decreased in response to systemic nonsteroidal anti-inflammatory drug (NSAID) administration on Days 2-5, with rebound expression observed following cessation of NSAIDs. IL-1Ra was detectable in synovial fluid 56 days following injection. An increase in IL-1Ra expression was induced via injection of LPS into the previously vector-treated joints 90 days following treatment. As such, the instant results indicate a potential for long-term (at least 3 months, the total length of the study) inflammation-sensitive expression of the IL-1Ra transgene.

The results disclosed herein indicate efficacy in a horse osteochondral chip model at doses of HDAd-eqIL-1Ra of $2\times10^{11}$ or $2\times10^{12}$ VP/dose both in pain and functional parameters as well as preservation of joint structure. Both dose levels of HDAd-eqIL-1Ra resulted in reductions in lameness, lameness after joint flexion, joint effusion and improved range of motion 72 days post-administration. Additionally, both dose levels of HDAd-eqIL-1Ra resulted in structural improvements in the damaged joint when compared to vehicle-treated animals at the conclusion of the study. These included reductions in overall macroscopic and microscopic joint findings in the cartilage as well as improvements in the color and thickness of the synovial lining.

The instant results further confirm in a rat anterior cruciate ligament transection (ACL-T) model of OA at doses of $3\times10^{7}$ and $2.43\times10^{8}$ VP/dose of HDAd-ratIL-1Ra. Animals received a single IA injection of HDAd-ratIL-1Ra one week following ACL-T surgery and the joints were evaluated for histopathology of the cartilage/bone and synovial membrane 11 weeks later. The instant results disclose that animals that underwent ACL-T surgery developed OA-related microscopic changes in the knee joint. The instant results disclose that HDAd-ratIL-1Ra dose-dependently reduced the incidence and severity of these changes in both the cartilage/bone and the synovial membrane, demonstrating the therapeutic benefit of this treatment on OA structural progression.

Efficacy of HDAd-ratIL-1Ra was observed in a more severe model of OA, where a single IA injection of either $2.43\times10^8$ or $2.43\times10^9$ VP/dose given 4 weeks after ACL-T surgery reduced median composite OARSI scores for cartilage/bone 1-month post-administration (at the Day 29 time point). The lower dose of $2.43\times10^8$ VP/dose also resulted in a reduction in OARSI scores compared to ACL-T untreated or vehicle-treated (Reference Item) animals 3-months post-administration (at the Day 92 time point).

In summary, the instant results from the nonclinical pharmacology studies described herein, demonstrated the functionality of the HDAd-IL-1Ra vector to produce therapeutic levels of IL-1Ra in the presence of inflammation. Additionally, single administration of HDAd-IL-1Ra resulted in reductions in OA-like symptoms of pain and loss of function in horses, and structural damage to the joint in mice, rats, and horses.

For the clinic, FX201 can be quantifying the vector using Droplet Digital™ polymerase chain reaction (ddPCR). Table 12 below establishes how the lowest efficacious non-clinical dose relates to our target clinical doses.

TABLE 12

Comparison of VP/Dose and GC/Dose

| | VP/dose[a] | VP/mL synovial fluid | GC/dose[a] | GC per ml synovial fluid |
|---|---|---|---|---|
| Lowest Efficacious Dose (Study No. FX201 PHARM-2018-023 (5900916)) | $3\times10^7$ | $2\times10^9$ | $4.25\times10^7$ | $2.83\times10^9$ |
| NOAEL (Study No. FX201 TOX-2018-015 (6700518)) | $2.43\times10^{10}$ | $1.62\times10^{12}$ | $4.2\times10^{10}$ | $2.83\times10^{12}$ |
| Human Starting Dose | $1\times10^{10}$ | $2\times10^9$ | $1.4\times10^{10}$ | $2.8\times10^9$ |
| Human Mid Dose | $1\times10^{11}$ | $2\times10^{10}$ | $1.4\times10^{11}$ | $2.8\times10^{10}$ |
| Human Maximum Dose | $1\times10^{12}$ | $2\times10^{11}$ | $1.4\times10^{12}$ | $2.8\times10^{11}$ |

[a]Assumes a 5 mL injection volume in human (Heilmann 1996, Hansen 2011) and a 15 μL injection volume in rat (Emami 2018)
VP, Viral particle;
GC, Genome copy The instant results show that following IA injection, FX201 infects cells in the joint to produce IL-1 Ra locally in response to inflammation. The results described herein show that the HDAd vector provides a desirable profile for maintaining durable therapeutic levels of IL-1 Ra locally in the injected joint. This is evidenced by the robust expression pattern of marker genes (GFP and LacZ) observed after single injections into mouse joints, demonstrating a favorable pattern of expression in cells of the synovial membrane and the superficial layer of chondrocytes. Transgene expression after delivery via HDAd is durable—with continued expression of transgene for 378 days after a single IA injection in normal mouse joints, a timeframe that was limited by the lifespan of the animals, not a gradual decline in transgene expression. In addition, quantifiable levels of IL-1Ra were present in synovial fluid from horses 72 days post-vector administration, further supporting the durable nature of the transgene expression.

The efficacy observed after HDAd-lL-1Ra administration across the totality of the nonclinical efficacy studies (in mice, rats, and horses) demonstrate that efficacious levels of IL-1Ra are achievable in joints for the duration of the study periods, up to 3 months post-administration. A range of dose levels were tested across the 5 efficacy studies. To allow for comparison of efficacious dose levels among the mouse, rat and horse OA models, a scaling approach based on synovial fluid volumes was adopted (Table 13). The lowest efficacious dose was defined as $2\times10^9$ VP/mL synovial fluid, based on the study in rat ACL-T.

TABLE 13

Therapeutically Efficacious Doses Identified in Animal Models of OA

| Study No. | Study Type | Efficacious Dose VP per joint | VP per mL synovial fluid[a] | Human Equivalent Dose (VP per joint) |
|---|---|---|---|---|
| Mouse | | | | |
| PC-G-011 | Skeletally immature ACL-T model/preventative efficacy study | $1\times10^8$ | $2\times10^{10}$ | $1\times10^{11}$ |
| PC-G-012 | Skeletally immature ACL-T model/efficacy in pre-established OA | $1\times10^8$ | $2\times10^{10}$ | $1\times10^{11}$ |
| PC-G-013 | Skeletally mature ACL-T/preventative efficacy study | $1\times10^9$ | $2\times10^{11}$ | $1\times10^{12}$ |
| Rat | | | | |
| FX201 PHARM-2018-023 (5900916) | ACL-T model of severe OA/preventative efficacy study | $3\times10^7$ | $2\times10^9$ | $1\times10^{10}$ |
| | | $2.43\times10^8$ | $1.62\times10^{10}$ | $8\times10^{10}$ |

TABLE 13-continued

Therapeutically Efficacious Doses Identified in Animal Models of OA

| Study No. | Study Type | Efficacious Dose: VP per joint | VP per mL synovial fluid[a] | Human Equivalent Dose (VP per joint) |
|---|---|---|---|---|
| Horse | | | | |
| PC-E-012 | Osteochondral chip model/ mild non-progressive OA | $2 \times 10^{11}$ | $2 \times 10^{10}$ | $1 \times 10^{11}$ |
| | | $2 \times 10^{12}$ | $2 \times 10^{11}$ | $1 \times 10^{12}$ |

[a]Dose extrapolation based on synovial fluid volumes; assuming 5 μL synovial fluid volume in mouse, 15 μL in rat (Emami 2018), 10 mL in horse and 5 mL in human (Heilmann 1996, Hansen 2011)

The instant results show that HDAd-IL-1Ra treatment resulted in reductions in pain and functional impairment, as well as structural progression. Improvements in structural progression included reductions in cartilage fibrillation and cleft formation, chondrocyte death and cloning, subchondral bone remodeling, and osteophyte growth. Importantly, these efficacious effects on joint structure were observed when HDAd-IL-1Ra was administered at varying time points in relation to the joint injury (spanning pre-injury to up to 4 weeks post-injury).

In summary, the results of the nonclinical pharmacology studies performed with FX201 (HDAd-IL-1Ra) disclosed herein, demonstrated the ability to deliver durable local transgene expression that is sufficient to provide robust efficacy in reducing pain, functional impairment and structural progression of OA-like joint changes in both small and large animal models of OA. The results of the studies described herein strongly support and provide the basis for use of the effective amount of the HDAd encoding IL-1RA of the present invention, for treatment and prevention of osteoarthritis in humans suffering from osteoarthritis or osteoarthritic condition.

Example 16: Clinical Study Design for Evaluating Safety and Efficacy of IL-1Ra Gene Therapy (FX201, Humantakinogene Hadenovec), for IA Administration that is being Developed for the Treatment of Patients with Osteoarthritis of Knee (OAK)

Patient and Study Procedure

Described herein is an open-label, single ascending dose study to assess the safety and tolerability of FX201 in patients with Osteoarthritis of the Knee (OAK). The primary objective of the study described herein is to assess the safety and tolerability of a single IA injection of FX201 in patients with OAK as measured by Adverse Events (AEs) spontaneously reported by the patient or discovered by the Investigator and findings from the following assessments: physical examinations, index knee assessments, vital signs, electrocardiograms (ECGs) and clinical laboratory evaluations. In addition, the index knee will be evaluated by Xray and assessed by a central imaging vendor for chondrolysis, subchondral bone changes, osteonecrosis and insufficiency fracture.

All patients will receive a single IA injection of FX201 at the low ($2.8\times10^9$ GC/ml), mid ($2.8\times10^{10}$ GC/ml) or high dose ($2.8\times10^{11}$ GC/ml). Patients will be assigned to doses by cohort, starting with the lowest dose and then escalating. Up to three ascending doses of FX201 will be tested in cohorts of 5-8 patients. Each patient will only receive one injection of FX201 and will be followed for 104 weeks. The study will be conducted in male and female patients, 30-80 years of age with painful OA of the index knee with Kellgren-Lawrence (K-L) Grade 2, 3 or 4 (K-L Grade 4 for mid- and high-Dose cohorts only). Following informed consent, patients meeting eligibility criteria will be selected for enrollment. Up to three ascending doses of FX201 will be tested in cohorts of 5-8 patients. A total of maximum 24 patients will be recruited for the study. Each patient will only receive one injection of FX201 and will be followed for 104 weeks.

Adverse Events will be graded for severity per Common Terminology Criteria for Adverse Events (CTCAE) v5.0. If an AE severity is not specifically graded, the Investigator should apply the general guidelines for determination of Grade 1 through Grade 5 as listed in CTCAE v5.0, using medical judgment. The specifics of the dose escalation protocol are as follows: a) Low Dose Cohort (Dose A—$2.8\times10^9$ GC/ml): b) Mid Dose (Dose B—$2.8\times10^{10}$ GC/ml): and c) High Dose Cohort (Dose C—$2.8\times10^{11}$ GC/ml).

Each cohort will comprise 5-8 patients. The first patient will be treated and monitored for 7 days to evaluate safety. If no Grade 3 or higher AEs deemed related or possibly related to the study drug or study injection procedure are observed for 7 days post treatment, a second patient will be treated and monitored. If no Grade 3 or higher AEs deemed related or possibly related to the study drug or study injection procedure are observed for 7 days post treatment, an additional 3 patients will be enrolled and followed for a minimum of 4 weeks. If no Grade 3 or higher AEs deemed related or possibly related to the study drug or study injection procedure occur in the first 5 patients, the data will be collated and reviewed for further recommendation. If a Grade 3 or higher AE deemed related or possibly related to the study drug or study injection procedure occurs in any of the first 5 patients, 3 additional patients will be enrolled in the cohort. If a second Grade 3 or higher AE deemed related or possibly related to the study drug or study injection procedure occurs, enrollment of patients will be halted until the data is reviewed and a recommendation is made to either continue the protocol as planned, modify the protocol, or stop enrollment. If a Serious Adverse Event (SAE) occurs at any time, regardless of relatedness, enrollment of patients will be halted and the data will be reviewed to provide a recommendation to either continue the protocol as planned, modify the protocol, or stop enrollment. The safety data of all patients will be reviewed through a minimum of 4 weeks after the last patient in the cohort is dosed to determine a) if escalation to the next dose level will proceed to the next dose study will happen for the low and mid dose Cohorts; or b) level(s) for future studies in case of the high dose cohort.

Selection of Study Population

Number of Patients. A maximum of 24 patients (range 15 to 24) will be enrolled and treated with a single IA injection of FX201.

Inclusion Criteria

To be included in the trial, patients must fulfill the following criteria: 1. Written consent to participate in the study; 2. Willingness and ability to comply with the study procedures and visit schedule and ability to follow verbal and written instructions; 3. Male or female 30 to 80 years of age, inclusive, on the day of enrollment (Day1); 4. Body mass index (BMI)≤40 kilograms per meters squared (kg/m2) at Screening; 5. Symptoms associated with OA of the index knee for ≥12 months prior to Screening (patient reported is acceptable); 6. Index knee pain for >15 days over the last month prior to screening (patient reported is acceptable); 7. American College of Rheumatology (ACR) Criteria (clinical and radiological) for OA (Altman et al, 1986) as follows: a) knee pain, b) at least 1 of the following: age>50 years, morning stiffness<30 minutes, crepitus on knee motion and c) osteophytes; 8. failed two or more types of conservative therapy for index knee osteoarthritis (e.g., structured land-based exercise programs (strengthening and/or cardio and/or balance training/neuromuscular exercise and/or mind-body exercise including Tai Chi or Yoga)); topical non-steroidal anti-inflammatory drugs (NSAIDs); non-selective NSAIDs, or COX-2 inhibitors; or failed one prior type of conservative therapy and at least one prior index knee IA treatment (corticosteroid or hyaluronic acid) (Bannuru R R et al, 2019); 9. Kellgren-Lawrence (K-L) Grade 2, 3 or 4 (K-L Grade 4 for Cohorts B and C only) in the index knee based on X-ray performed during Screening and confirmed by trained radiographers at a central facility prior to enrollment (Grade 2: definite osteophytes and possible narrowing of joint space, Grade 3: moderate multiple osteophytes, definite narrowing of joint space and some sclerosis and possible deformity of bone ends, and Grade 4: large osteophytes, marked narrowing, severe sclerosis and definite deformity of bone ends); 10. Index knee examination indicating the index knee and the intended injection site area are free of any signs of local or joint infection at Baseline; 11. Western Ontario and McMaster Universities Osteoarthritis Index (WOMAC®) pain score in index knee≥4.0 and ≤9.0 (0-10 numeric rating scale [NRS] scale) at Screening Visit and Baseline; 12. An enrollment slot is available within the 21-day screening period as confirmed by Sponsor; 13. An enrollment slot is available for patients with K-L Grade 4 in the index knee based on central read of Screening X-ray as confirmed by the Sponsor (maximum of two K-L Grade 4 per cohort in Cohorts B and C only); 14. Sexually active females of childbearing potential (defined as not surgically sterile or postmenopausal [defined as 12 consecutive months with no menses without an alternative medical cause as documented in medical history]) must have negative serum pregnancy test at Baseline (prior to enrollment) and must agree to use one of the following highly effective methods of contraception: abstinence; oral, injected or implanted hormonal methods of contraception; intrauterine device or intrauterine system; condom or occlusive cap (diaphragm or cervical/vault caps) with spermicidal foam/gel/film/cream/suppository; or monogamous intercourse with a partner who is surgically sterile (must be 6 months postvasectomy) for at least 12 months after the administration of the study drug. Sexually active males must agree to use a condom during any sexual contact with females for at least 12 months after the administration of the study drug.

During the study, all existing (started prior to study entry), new or changes in concomitant medications during the course of the course of the study and the associated reasons for use or change will be documented and reported.

Exclusion Criteria

Disease-related criteria: 1. Any current or prior diagnosis of reactive arthritis, rheumatoid arthritis, psoriatic arthritis, ankylosing spondylitis, or arthritis associated with inflammatory bowel disease, 2. Any current or prior history of infection in the index knee joint, 3. Clinical signs and symptoms of active crystal disease (gout, calcium pyrophosphate deposition disease) of the index knee within 3 months of Screening, 4. Inability to undergo Magnetic Resonance Imaging (MRI) due to presence of surgical hardware or other foreign body in the index knee, 5. Unstable index knee joint (e.g., torn anterior cruciate ligament, etc.) within 12 months of Screening.

Previous or concomitant treatment-related criteria: 1. Any IA drug/biologic use in index knee within 6 months of Screening (e.g., corticosteroid, hyaluronic acid, platelet rich plasma, stem cells, prolotherapy and amniotic fluid injection, etc.), Cold or radiofrequency nerve ablation of the index knee within 12 months of Screening, 3. Arthroscopic or open surgery on the index knee within 12 months of Screening.

Patient-related criteria: 1. Females who are pregnant or nursing or plan to become pregnant within 12 months after dosing; men who plan to conceive within 12 months after dosing, 2. Loss of skin integrity over the index knee where the injection would take place, 3. Anticipated major surgery within 12 months after dosing, 4. Laboratory evidence of infection with human immunodeficiency virus (HIV), positive test for hepatitis B surface antigen (HBsAg) or positive serology for hepatitis C virus (HCV) with positive test for hepatitis C virus ribonucleic acid (HCV RNA), 5. ECG abnormality at Screening or Baseline visit judged clinically significant by the Investigator or designee, 6. Use of immunomodulators, immunosuppressive, or chemotherapeutic agents within 5 years of Screening, 7. Received any prior investigational or approved gene therapy treatment, 8. Active or history of malignancy within the last 5 years, with the exception of resected basal cell carcinoma, squamous cell carcinoma of the skin, or effectively managed cervical carcinoma in situ, 9. Active pharmacologic treatment for depression, including selective serotonin reuptake inhibitors (SSRIs), serotonin and norepinephrine reuptake inhibitors (SNRIs) and non-selective serotonin reuptake inhibitors (NSRIs) or tricyclics if dose/regimen has not been stable for ≥6 months prior to Screening, 10. Active substance abuse (drugs or alcohol) or history of substance abuse within the past 12 months, 11. Use of any other investigational drug, biologic or device within 3 months of Screening, 12. Any systemic or local bacterial or viral infection requiring IV antibiotics or antivirals within 4 weeks of Screening or oral antibiotics or antivirals within 2 weeks of Screening, 13. If bilateral knee OA exists, pain in the contralateral knee≥4.0 (0-10 NRS scale) within 1 month prior to Screening Visit, 14. Prior total or partial knee arthroplasty procedures in index knee, 15. Temperature above 99.5° F. at Baseline, 16. Prothrombin Time (PT)/International Normalized Ratio (INR)>1.5; Activated Partial Thromboplastin Time (aPTT) >5 seconds above the Upper Limit of Normal (ULN), 17. Alanine aminotransferase (ALT) or aspartate aminotransferase (AST)>1.5×ULN; alkaline phosphatase (ALP)>1.5×ULN; total bilirubin outside of normal range, 18. Known allergy or sensitivity to acetaminophen, and 19. Any other clinically significant acute or chronic medical conditions (e.g., bleeding disorder) that, in the judgment of the Investigator, would preclude the use of an IA injection or that could compromise patient safety, limit the patient's ability to complete the study, and/or compromise the objectives of the study.

Investigational Medicinal Product Administration Procedure

FX201: humantakinogene hadenovec; low, mid and high dose will be administered as a single 5 mL IA injection. Concentrations of the three drug products: Dose Level A: 2.8E9 GC/mL (genome copy number per milliliter); Dose Level B: 2.8E10 GC/mL; and Dose Level C: 2.8E11 GC/mL.

As part of eligibility, the index knee should have been examined at Baseline to ensure the knee and the intended injection site area are free of any signs of local or joint infection. Intra-articular injections of study drug will be performed by the assigned Injector. The Injector may choose the position of the knee (e.g., extended or flexed), the approach for the injection (e.g., medial or lateral) and the numbing agent (e.g., EMLA cream, subcutaneous lidocaine 1%, etc.) to be used based on standard of care. Sterile technique should be used. Prior to injection, the index knee should be thoroughly cleansed using a bactericidal solution. The index knee will be aspirated in all cases prior to administration of study medication and synovial fluid will be collected for IL-1Ra and IL-1β protein concentrations.

Synovial fluid may be collected using mechanical compression. If IA effusion is detected using ultrasound guidance, the Injector should withdraw to near dryness prior to injection. Following attempted synovial fluid aspiration, 5 mL of FX201 will be injected into the synovial space using ultrasound guidance. After the aspiration and injection, pressure should be applied to the injection site with sterile gauze. The injection site should be swabbed with alcohol and covered with an absorbent pad and dressing. All injection/aspiration supplies should be disposed in accordance with local institutional procedures for disposal of biohazard materials.

The same needle used for synovial fluid aspiration may also be used for IA injection of study drug, thereby allowing for a single injection with syringe replacement. The Injector will use a 21 gauge or larger needle for injection and aspiration of synovial fluid. Injector will record injection procedure and any issues relating to administration of FX201 and report the occurrence to the Site Monitor.

Prior and Concomitant Medications

Allowable Medications/Non-Pharmacologic Therapies

The following medications and non-pharmacologic therapies may be taken or used throughout the study: a) any treatment for an AE; b) study-allocated rescue medication; c) rest, elevation or locally applied ice to the index knee; d) any treatment for a pre-existing condition outside of the study indication, that is not listed as restricted; e) aspirin for cardio protection at a maximum dose of 81 mg per day provided the dose has been stable over the 3 months prior to study entry; f) medical therapy for depression, including SSRIs, SNRIs and NSRIs or tricyclics provided dose/regimen has been stable for 6 months prior to screening; g) patients should be advised to maintain a stable lifestyle with regard to physical activity, physical therapy, acupuncture, TENS or bracing throughout the 52-week treatment period after dosing.

Prohibited Medications/Non-Pharmacologic Therapies

The following medications and non-pharmacologic therapies should not be taken after the patient signs informed consent or used for the 52-week treatment period after dosing: a) Oral NSAIDs; b) Topical therapies applied to the index knee (e.g., topical NSAIDs, capsaicin, lidocaine patches, other local treatments); c) Cannabinoids; d) Aspirin (>325 mg per day); e) Centrally acting pain medications (e.g., pregabalin, gabapentin); f) Opioids (oxycodone, hydrocodone, codeine, morphine, tramadol, etc.); g) Muscle relaxants (e.g., cyclobenzaprine, tetrazepam, diazepam); h) any IA injection in the index knee (e.g., local anesthetics, corticosteroids, hyaluronic acid, platelet rich plasma, stem cells, prolotherapy, amniotic fluid injection); i) cold or radiofrequency nerve ablation of the index knee; j) any investigational drug, device or biologic; k) any immunomodulator, immunosuppressive, or chemotherapeutic agents.

Oral NSAIDs, topical therapies and topical cannabinoids applied to the index knee are prohibited from informed consent until 60 days following treatment. After 60 days following treatment, they are restricted to use at the discretion of the Investigator. The washout (at least 5 half-lives) must be completed at least 10 days prior to the Baseline Visit.

Restricted Medications

After the first 60 days following treatment, use of the following medications are restricted to the discretion of the Investigator based upon clinical need for additional analgesia if the designated rescue medication is inadequate. However, patients should not take these medications in the 72 hours prior to a study visit during the 52-week treatment period after dosing: Oral NSAIDs, Topical therapies applied to the index knee (e.g., topical NSAIDs, capsaicin, lidocaine patches, other local treatments) and Topical Cannabinoids.

Rescue Medication

To standardize pain-relief rescue medication across all patients, starting at screening (after informed consent), patients will discontinue all prohibited medications. The designated rescue medication is acetaminophen 500 mg. Patients will be instructed to take 1-2 tablets every 6 hours, as needed and will be instructed not to exceed 6 tablets (3000 mg) in 24 hours. Starting at screening and through the 52-week treatment period, patients will be provided with rescue medication. As instructed, patients will return the rescue medication for rescue medication accountability and be issued a new supply. Patients will be provided sufficient quantity of rescue medication until Day 1 visit, from Day 1 to week 1 of visit, and through week 52 of subsequent visit. Patients will record rescue medication usage from screening through 60 days post dose for Cohort A and from screening through 84 days (12 weeks) post dose for Cohorts B and C. No rescue medication is to be provided during long-term follow-up period (Week 52-Week 104 visit).

Study Variables

Safety Variables: Safety and tolerability will be evaluated on the basis of AEs spontaneously reported by the patient or discovered by the Investigator and findings from the following assessments: physical examinations, index knee assessments, vital signs, ECGs and clinical laboratory evaluations. The index knee will be evaluated by X-ray and assessed by a central imaging vendor for chondrolysis, subchondral bone changes, osteonecrosis and insufficiency fracture.

Efficacy Variables: Efficacy will be evaluated based on the results of the WOMAC 3.1 pain subscale (0-10 NRS scale) and WOMAC 3.1 stiffness subscale (0-10 NRS scale) independently and KOOS pain, other symptoms, function in activities of daily living (ADL) (0-100 NRS scale), and sport and recreation function and knee-related Quality of Life (QoL) (5-point Likert scales). The index knee will be evaluated by MRI and assessed by a central imaging vendor for quantitative change in bone shape.

Biodistribution Variables: Plasma exposure will be analyzed from blood plasma samples. Shedding will be analyzed from urine samples and from skin swabs at the injection site samples.

Bioanalytical Variables: Presence of anti-Capsid antibodies and anti-IL-1Ra antibodies will be analyzed from blood samples. High-sensitivity C-reactive protein (hs-CRP) levels will be analyzed from blood samples. IL-1Ra and IL-1β protein concentrations will be analyzed from synovial fluid samples. Synovial fluid and blood samples will be preserved for a maximum of 5 years past the end of the study for potential future analyses of biomarkers that may contribute to the pathogenesis of OA and/or be associated with responsiveness to FX201 treatment. No genomic analyses (gene sequencing studies) will be performed using these samples. Patients will be able to withdraw consent throughout the duration of storage. Once analysis has begun, consent will no longer be able to be withdrawn.

Statistical Methods:

Four analysis populations are planned for the study. The Safety Population will include all patients who receive study drug. The Safety Population will be used to assess safety and tolerability. The Biodistribution Population will include patients who receive study drug and have at least one post-treatment biodistribution sample. The Biodistribution Population will be used to assess the biodistribution of FX201 vector copies. The Bioanalytical Population will include patients who receive study drug and have at least one post-treatment bioanalytical sample. The Bioanalytical Population will be used to assess the bioanalytical effects of FX201. The Full Analysis Set (FAS) Population will include all patients who receive a complete dose of study drug and have Baseline and at least one post-dose evaluation. The FAS Population will be used to assess exploratory efficacy endpoints.

Safety analyses will be performed on the Safety Population. Adverse Events will be coded using the Medical Dictionary for Regulatory Activities (MedDRA) dictionary and graded for severity per CTCAE v5.0. Incidences (number and percent) of treatment emergent adverse events (TEAEs), those events that started after dosing or worsened in severity after dosing, will be presented by dose group. Incidences of TEAEs will also be presented by maximum severity and relationship to study medication. Similar presentations will be provided for SAEs, AEs leading to death, AEs leading to withdrawal from the study, and for AEs related to the index knee. Clinical laboratory, ECG, vital sign information and screening X-ray data will be summarized as summary statistics for value and change from Baseline at each individual time point. Summary statistics will include n, mean, median, standard deviation (SD), minimum, and maximum. Categorical variables will be summarized using frequencies and percentages.

CTCAE displays Grades 1 through 5 with unique clinical descriptions of severity for each AE based on this general guideline: Grade 1: asymptomatic or mild symptoms; clinical or diagnostic observations only; intervention not indicated; Grade 2: minimal, local or noninvasive intervention indicated, or limiting age appropriate instrumental ADL; Grade 3: Severe or medically significant but not immediately life-threatening; hospitalization or prolongation of hospitalization indicated; disabling; limiting self-care ADL; Grade 4: Life-threatening consequences or urgent intervention indicated; and Grade 5: Death related to AE.

The percentage of patients positive for FX201 at each time point will be presented by dose group. The number of vector copies of FX201 observed will be summarized at each biodistribution sampling time point by dose group and by sample type. The ratio of IL-1Ra to IL-1β will be reported. The level of plasma hs-CRP at Baseline will be reported. Anti-drug antibodies to Adenoviral serotype 5 (Ad5) capsid and IL-1Ra will be reported. Additionally, neutralizing antibody titer will be reported for each Ad5 seroconverted patient.

Exploratory efficacy data collected in this study will be presented using summary tables, figures, and subject data listings. Summary tables will present data by dose group and, if applicable, by time of collection. Continuous variables will be summarized using descriptive statistics, specifically the mean, median, standard deviation, minimum and maximum.

Categorical variables will be summarized by frequencies and percentages. Confidence intervals may also be provided. Figures will be used to support the presentation of certain data. Sensitivity analyses may be performed to examine the effect of missing data, as well as the effect of any baseline imbalance. All Cis, statistical tests, and resulting p-values will be provided for informative purposes only and will be reported as 2-sided. Significance will be assessed at $\alpha=0.05$ level and the significance level will not be adjusted for multiplicity.

Initial Observation-Preliminary Data from Low Dose Cohort of Clinical Study

Treatment responses observed to date in the initial clinical trial of FX201 (FX201-2019-001; NCT04119687) following administration of the lowest dose of FX201 [are] strongly support the potential of FX201 treatment to provide benefit to patients with osteoarthritis knee pain. Individual patient responses measured via Western Ontario and McMaster Universities Osteoarthritis Index (WOMAC) A (pain) were assessed using thresholds defined by the Initiative in Methods, Measurements and Pain Assessment in Clinical Trials (IMMPACT) group for clinically important improvements in pain treatment outcomes. In this cohort of patients with baseline moderate-severe osteoarthritis knee pain, 3 out of 5 dosed patients (60%) of reported reductions in WOMAC-A pain scores measures at 8 weeks after treatment which met IMMPACT criteria for substantial (>50% improvement from day 1).

Considering the low dose of FX201 ($2.8\times10^{9}$ GC per molar $1.4\times10^{10}$ GC total dose) administered to the patients tested in the initial phase, the improvement seen in the patients with moderate to severe osteoarthritis as described above is truly surprising and unexpected.

Example 17: FX201 Drug Product Specifications

Described herein are the methods for evaluating quality with the acceptance criteria for the FX201 drug product comprising the adenoviral-based biological delivery and expression system of the instant disclosure.

Appearance: Visual Observation

Acceptance Criteria: Clear to slightly opalescent, colorless solution with no visible particulates.

Visual assessment is the standard technique for appearance. FX201 drug product contains colorless excipients and may appear slightly opalescent due to the concentration of viral particles in the drug product.

Identity of Target Gene Sequence: DNA Sequencing

Acceptance Criteria: IL-1Ra sequence conforms with reference sequence.

The purpose of this method is to accurately identify FX201. The DNA sequence obtained through Sanger sequencing is compared to the human IL-1Ra reference sequence. The sequenced IL-1Ra must be consistent with the reference sequence to ensure that the drug product contains the gene of interest.

Identity of Viral Vector: Droplet Digital Polymerase Chain Reaction (ddPCR)

Acceptance Criteria: Helper-Dependent Adenovirus (HDAd) detected

The FX201 HDAd viral genome copy (GC) number is measured by ddPCR using FX201-specific primers that target a unique region of the genome. Because the method is specific for the FX201 HDAd genome, the ability to detect the HDAd genome confirms the identity of the viral vector.

Chemical/Physical Properties pH:

Acceptance Criterion: 7.0±1.0

Potentiometry is the chosen technique based on accuracy and industry standards. pH is tested using USP<791>, Ph. Eur. 2.2.3 to ensure the stability of FX201 drug product and that it is physiologically compatible with intra-articular administration.

Particle Size/Aggregation: Dynamic Light Scattering (DLS)

Cumulant: Hd and Pd (%)

Regularization Major Peak(s): Hd, % Intensity, and Pd (%)

The purpose of this method is to measure the size distribution of viral particles present in FX201 drug product using a dynamic light scattering instrument. The level of aggregated viral particles is monitored since aggregation has the potential for reduced potency and increased immunogenicity. The reported result includes particle size, standard deviation, and peak polydispersity of the mean cumulant and all regularized major peak(s).

Osmolality: USP<785>

Acceptance Criteria: ≤600 mOsm/kg

Osmolality is determined using the USP<785> compendial method. The selected freezing point depression method is the industry standard method. The osmolality of an injectable solution may impact the tolerability or physiological compatibility of a product. A specification limit of ≤600 mOsm/kg is established to ensure the tolerability of the FX201 injection (Roethlisberger 2017). The osmolality of FX201 is primarily driven by the formulation buffer (approx. 450 mOsm/kg), with the specification of ≤600 mOsm/kg establishing an upper limit for final drug product. The range for each dose level represents an allowed two-fold error around the target concentration of 2.8E+X at each dose level. As the target dose levels for the three doses represent a ten-fold difference, the ranges are suitable for this stage of development.

Infectivity Assay: Median Tissue Culture Infectious Dose ($TCID_{50}$)

The purpose of this method, as described herein is to determine the infectious titer of FX201 drug product in HEK293 cells. FX201 is an HDAd which is a replication incompetent recombinant viral vector containing the human IL-1Ra sequence. The HDAd requires adenovirus 5 (Ad5) virus as a helper to replicate. The $TCID_{50}$ assay is conducted in HEK293 cells in which the cells are co-infected with serial dilutions of FX201 drug product sample and saturating concentrations of Ad5. Following incubation, amplified virus is detected by qPCR that targets a unique sequence of the recombinant HDAd vector. Based on the results of qPCR the wells inoculated with the serial dilutions of HDAd samples are scored for presence or absence of virus and the $TCID_{50}$ (infectious units ($TCID_{50}$)/mL) is calculated by Spearman-Karber's method.

Viral Particle to Infectious Unit Ratio: Calculation

Acceptance Criteria: ≤300 GC/$TCID_{50}$

This is the calculation of the ratio of viral particles as expressed in GC per ml to infectious units as expressed in $TCID_{50}$/mL. At the current stage of development, the maximum viral particle infectious unit ratio is set to ≤300 GC/$TCID_{50}$ to define a maximum acceptable limit while allowing for further batch experience and method refinement. This acceptance criterion is based upon the batch history data collected to date considering the precision of the collective assays used to determine the ratio. Batch data will continue to be collected and method improvements made during development of the program.

$TCID_{50}$ is a measurement of the number of infectious units per mL of neat FX201 drug product. An infectious unit is one infection event, a measurement that determines the infectious ability of the viral particles. In the event that viral particles in FX201 batches had the same infectious ability, the changes in the concentration of viral particles in the sample would impact the $TCID_{50}$ readout. At the same time, if FX201 batches had different infectious ability but similar viral particle loads, there would be different $TCID_{50}$ values obtained for the batches. Therefore, the infectious ability of the viral particles is ultimately determined by the ratio of viral particles to infectious units.

IL-1Ra Expression Assay: Enzyme-Linked Immunosorbent Assay (ELISA)

Acceptance Criteria: IL-1Ra detected

HEK293 cells which do not express IL-1Ra are infected with FX201. After incubation the cell supernatant is collected, concentrated, and analyzed for the presence of IL-1Ra. A commercially available sandwich ELISA kit is used for detecting human IL-1Ra expression.

Cellular expression of IL-1Ra after FX201 transfection requires the presence of an inflammatory promoter, resulting in variable and temporal production of IL-1Ra. Due to this potential for variable expression and the early stage of development, the current acceptance criterion is that expression of IL-1Ra is detected. The method has been suitably qualified to demonstrate the ability to detect IL-1Ra expression in HEK293 cells that have been infected with FX201.

Sterility as per ICH Q4B Annex 8 (R1)

Acceptance Criteria: Sterile/No growth

Sterility is tested using a direct inoculation method on the FX201 drug product final vial, using the sterility test and requisite number of samples are defined in USP<71>/Ph.Eur.2.6.1/JP 4.06. The three compendia are harmonized under ICH Q4B Annex 8 (R1), and product specific qualification has demonstrated that the compendial method is compatible with the FX201 drug product. As a sterile product FX201 drug product must not exhibit bacterial/fungal growth.

Endotoxin

Acceptance Criteria: ≤35 EU/mL

The bacterial endotoxin assay is performed in accordance with USP<85> to quantify the level of gram-negative bacterial endotoxin in FX201 drug product.

FX201 is dosed at 5 mL. The endotoxin limit of 35 EU/mL corresponds to 175 EU/dose. This represents 2.5 EU/kg for an average 70 kg adult, within the parenteral drug product guidance of ≤5 EU/kg.

The method of manufacturing an adenoviral-based biological delivery and expression system as disclosed herein is based on the method of large-scale production of high-quality helper-dependent adenoviral vectors using adherent cells in cell factories as described in Suzuki et al., HUMAN GENE THERAPY 21:120-126 (January 2010).

Example 18: Overview of Manufacturing Process

The manufacturing process described herein is based on adherent cell growth as described by Suzuki, 2010 using CellStacks® culture chambers (Corning, Inc., Corning, NY) (CS). The 116 cell line, derived from HEK293 cells, is co-infected with FX201 and helper virus banks. After co-incubation, cells are harvested and lysed. The amplified FX201 is purified through three rounds of cesium chloride (CsCl) gradient ultracentrifugation where a band containing enriched FX201 is extracted out for further processing upon each cycle of ultracentrifugation. The resulting purified FX201 in CsCl is dialyzed with formulation buffer removing CsCl, which is then diluted to the target concentration, filtered and filled. The resulting FX201 drug substance is stored frozen at ≤−65° C. and tested for release.

Upstream Process

Cell Culture Process

Described herein is a cell culture process that begins with thawing a vial of 116 master cell bank (MCB). The thawed cells are expanded and co-infected with FX201 and helper virus banks. Post-infection, cells are fed and harvested completing the cell culture process before taken further for purification.

Vial Thaw: A vial of 116 MCB is thawed in a water bath at 37° C. cell viability upon thawing should be ≥270%. The preservative in the vial (dimethyl sulfoxide) is removed and the cells are placed in a culture flask with medium and incubated at 37° C. in a 5% C02 incubator, until cells reach the confluency sufficient to passage to the next cell expansion step. The medium used for vial thaw and the first passage is composed of Dulbecco's Modified Eagle Medium (DMEM) supplemented with fetal bovine serum (FBS), and L-glutamine.

Cell Expansion: Upon vial thaw, once the culture reaches confluency sufficient to passage to the next cell expansion step, the cell culture is serially expanded at 37° C. in a 5% CO2 incubator, in growth medium (DMEM supplemented with FBS, L-glutamine, and Hygromycin B). The cells are expanded until enough cells are grown to make one batch. One additional 10-layer CellStacks® culture chamber (Corning, Inc., Corning, NY) (CS10) is prepared for each set of CS10 to measure the total viable cells prior to initiating infection. Cell viability at the end of each passage should be ≥80%. TrypLE™ (recombinant trypsin, Life Technologies Corporation, Carlsbad, CA) is used to detach cells from the surface during the cell expansion step. Additionally, the culture is visually evaluated for cell morphology, cytopathic effect (CPE), and potential contamination.

Infection: Once the cell expansion reaches the scale of one batch plus one additional CS10, cells are infected by replacing the spent medium with freshly prepared medium (DMEM supplemented with FBS and L-glutamine) containing FX201 and helper virus seeds. Prior to the infection, one of the CS10's is randomly selected to measure viable cell density and viability. The infected CS10's are transferred to the humidified $CO_2$ incubator, at 37° C. and 5% $CO_2$. The target volume for the infection is approximately 600 g (or mL) per CS10. The total amount of FX201 and helper virus is as required to amplify FX201.

Feed: The infected 116 cells in CS10's are fed with fresh medium (DMEM supplemented with FBS and L-glutamine) and further incubated before being harvested. The culture is visually inspected for cell morphology, CPE, and potential contamination. Incubation is done at 37° C. in 5% $CO_2$, for approximately 24 hours. The target volume for the feeding is approximately 600 g (or mL) per CS10

Harvest: At this stage, cells are expected to show signs of CPE and detach from the culture surface. To initiate harvest, cells are gently detached from the CS10 by gently tapping to promote dislodging from the surface. The detached cells, including the spent medium, are collected yielding unprocessed bulk harvest containing FX201. Samples are taken from the unprocessed bulk harvest for *mycoplasma*, bioburden, and in vitro adventitious virus testing. The in-process testing of the unprocessed bulk harvest should show undetectable levels of *Mycoplasma* (USP<63>, Ph. Eur. 2.6.7, 1993 PTC) and adventitious virus (In Vitro Assay for Adventitious Viruses Using 3 Cell Lines). Microbial Enumeration Test using a Spread Plate Method, USP<61>. Ph. Eur. 2.6.12 should detect<10 CFU/mL for TAMC and <10 CFU/mL for TYMC.

The unprocessed bulk harvest is clarified by centrifugation where the resulting supernatants, including FBS and residual Hygromycin B in the medium, are discarded and the cell pellets are resuspended in the lysis buffer (100 mM Tris, 10% glycerol, pH 8.0). The resuspended cell pellets are held frozen at ≤−65° C. prior to further purification.

Downstream Process

Purification Manufacturing Process

Described herein is a purification manufacturing process that is comprised of cell lysis, Benzonase digestion, clarification, ultracentrifugation, dialysis and formulation, and final filtration, to remove process and product related impurities. For each unit operation, appropriate controls are in place to help ensure consistency of the manufacturing process.

Lysis: FX201 is not lysogenic and requires lysing of the infected 116 cells to release viral particles for further processing. The resuspended cell pellets in the lysis buffer (100 mM Tris, 10% glycerol, pH 8.0) are freeze-and-thaw lysed by placing the containers in freezing (dry ice in isopropanol) and warm water (37° C.) baths. Upon completion of two freeze-and-thaw cycles and at the third freeze cycle, the resulting process intermediate may be held at <−65° C. and harvested cells from additional sets of CS10's may be pooled upon the third thaw cycle to form one lot of drug substance.

Benzonase Digestion: The cell lysates containing FX201 are treated with Benzonase to digest residual host cell DNA. The Benzonase is first diluted in a buffer containing 10 mM Tris and 10 mM $MgCl_2$ prior to being added to the cell lysate for digestion. The process is carried out in a temperature-controlled water bath at 23° C. and the timespan of Benzonase digestion is recorded.

Clarification: The Benzonase digested cell lysate is clarified by centrifugation. After the centrifugation, the supernatant is collected for further processing and a sample is taken to measure total viral particles to monitor the overall process yield.

Ultracentrifugation: The clarified cell lysates are purified by three rounds of cesium chloride (CsCl) ultracentrifugation to separate FX201 from impurities based on the specific gravity. FX201 and helper virus have different genome sizes (29.3 kb versus 36.0 kb) resulting in different specific gravities, which are separated upon ultracentrifugation. Upon each cycle of ultracentrifugation, every tube is monitored for clear separation of the bands containing enriched FX201 from impurity bands.

For the first cycle of ultracentrifugation, the Benzonase digested and clarified cell lysate is diluted in a dilution buffer (10 mM Tris and 10 mM $MgCl_2$) and overlaid in centrifuge tubes containing two layers of CsCl at different specific densities. Two bands appear in the first cycle of ultracentrifugation where enriched FX201 can be collected by extracting the lower band containing FX201 while discarding the upper band that contains impurities. The collected bands containing FX201 are pooled, diluted, and purified by two additional cycles of isopycnic ultracentrifugation process containing single layer of CsCl.

Dialysis: The purified FX201 from the ultracentrifugation process is loaded into dialysis cassettes to further remove impurities including CsCl and potential residual Hygromycin B. After loading, the dialysis cassettes are immersed in a container of formulation buffer (5% sucrose w/v, 0.5% ethanol v/v, 75 mM sodium chloride, 10 mM L-histidine, 10 mM Tris, 1.0 mM magnesium chloride, 0.02% Polysorbate 80 v/V, 100 μM EDTA) replacing the entire container content for each exchange. After exchanging dialysis buffer four times, the purified FX201 is removed from the dialysis cassettes, pooled, and diluted in the formulation buffer. An in-process testing sample is taken and the concentration of the total viral particles is measured by UV spectrometry (OD260). The purified FX201 is held frozen at ≤−65° C. before being further processed.

Formulation and Final Filtration of Drug Substance: To finalize the drug substance manufacturing process, frozen bottles of purified FX201 are thawed in a water bath. Upon the thaw, the purified FX201 is diluted to a target concentration, for example $2.3\times10^{11}$ viral particles per mL (VP/mL) in the formulation buffer (5% sucrose w/v, 0.5% ethanol v/v, 75 mM sodium chloride, 10 mM L-histidine, 10 mM Tris, 1.0 mM magnesium chloride, 0.02% Polysorbate 80 v/v, 100 μM EDTA). The formulated FX201 is filtered through a 0.22 μm filter. The resulting filtrate is filled into polyethylene terephthalate copolymer, glycol modified (PETG) bottles with high-density polyethylene (HDPE) caps and stored frozen at ≤−65° C., completing the manufacture of FX201 drug substance.

Example 19: Development of a Highly Productive and Reproducible Manufacturing Process for FX201, a Novel Helper-Dependent Adenovirus-Based Gene Therapy for the Treatment of Osteoarthritis Background of Study: Gene therapy is a promising treatment option for osteoarthritis (OA) with the potential to provide long-term efficacy and disease modification. FX201 (humantakinogene hadenovec) is a gene therapy in development for the treatment of OA delivered locally via intra-articular (IA) injection. FX201 is a novel helper-dependent adenovirus (HDAd), an engineered human serotype 5 adenovirus with all viral genes removed. An expression cassette encoding for human interleukin-1 receptor antagonist (IL-1Ra) under the control of inflammation-sensitive NF-κB promoter is inserted into the HDAd genome. Upon IA injection of FX201, cells in the joints are transduced and conditionally express the highly potent inflammatory inhibitor IL-1Ra, thereby reducing the inflammation associated with OA of the knee.

Using a fit-for-purpose manufacturing process suitable for early development, four batches of drug product were successfully produced enabling Good Laboratory Practice toxicology, pharmacology, and Good Manufacturing Practice (GMP) clinical studies. Four batches of FX201 including a single lot designed to express the rat ortholog of IL-1RA, and three lots encoding the human ortholog of IL-1RA were produced at a sufficient scale to enable a Phase 1 clinical study. Presented herein is the manufacturing and product quality data across the four batches, demonstrating reproducibility of the early-stage manufacturing process.

Methodology: A manufacturing process described in Suzuki et al. (Hum Gene Ther. 2010; 21(1), 120-126) was transferred to a contract manufacturing organization and adapted for GMP. A vial of a cGMP cell bank containing a packaging cell line is thawed and serially expanded using an adhesion cell culture platform. Once the expanded cells reach the scale appropriate for production, FX201 and HV seed stocks are introduced to the culture. In co-infected packaging cells, FX201 is trans-propagated, borrowing elements encoded in the HV genome and the packaging cell. HV packaging signal is excised by a recombinase, leaving the vast majority of HV genome un-encapsidated. Only the amplified genome with intact packaging signal is encapsidated. After incubation of the co-infection step, cells are harvested via centrifugation for downstream processing.

After the harvest supernatant is decanted, the cells are subjected to freeze-and-thaw cycles in a cell lysis buffer. The cell lysate is then digested with Benzonase to allow for removal of fragmented DNA through subsequent centrifugation processes. Process and product-related impurities, including rDNA, HCP, empty capsids, and residual HV are removed from the Benzonase-digested cell lysate through multiple cycles of ultracentrifugation. Purified FX201 is then buffer exchanged by dialyzing into the final formulation buffer. For final clinical materials, the purified FX201 is diluted to the proper dose strength and aseptically filled into vials. Details of the manufacturing process are also described in Example 18.

Three batches of non-clinical and one batch of clinical grade materials were produced at two different scales. Two of the four batches were used for toxicology and efficacy studies in rats, which included one batch of HDAd vector encoding the rat variant of IL-1Ra. Each batch was analyzed for productivity, purification yield, and product quality which included physicochemical properties, infectious and genome titers, product and process related impurities, expression of the transgene, and safety.

Results: The two non-clinical batches each encoding the human or rat variant of IL-1Ra were produced at twice the scale as the following engineering (ENG) and the GMP batches. The increased scale of the two non-clinical batches was due to the material needs required to support animal studies, analytical development, lead-in stability program, and establishment of reference standard.

Figures 19A, 19B:
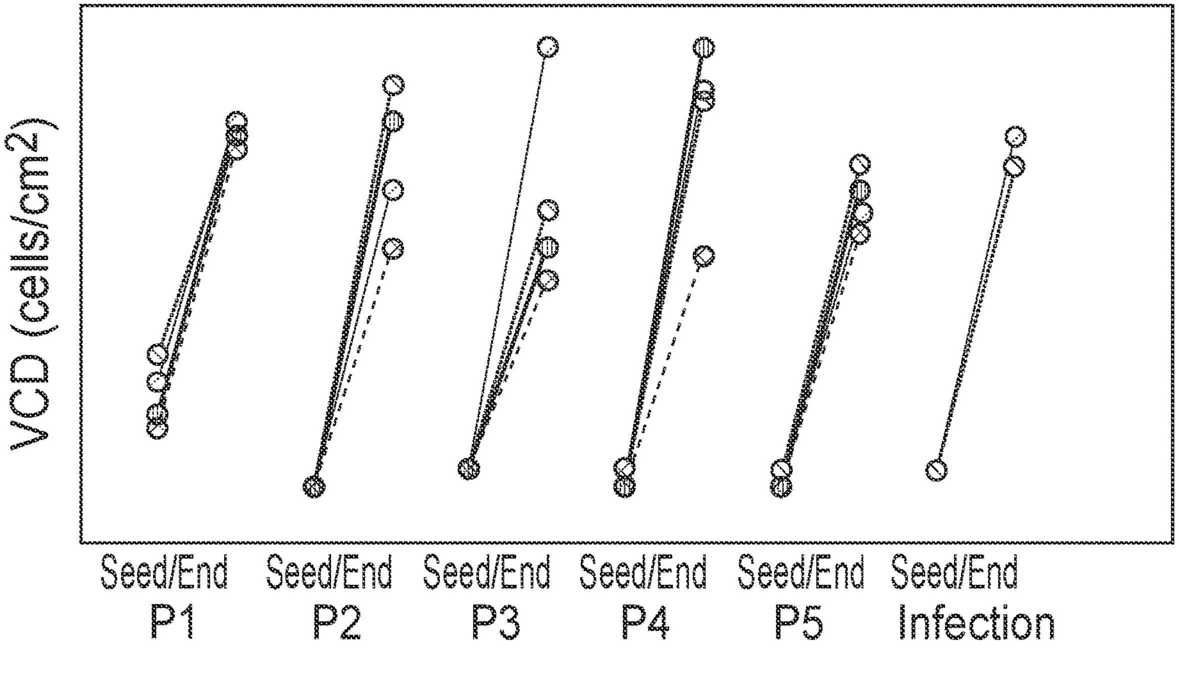
FIG. 19A-FIG. 19B depicts graphs showing the viable cell density and end of stage viability of cells in adhesion culture.

Cell growth in Adhesion Culture: The packaging cells grew to the target density required for final expansion and subsequent co-infection. Target cell seeding density and culture time at the final expansion stage were controlled, allowing for consistent production across the four lots manufactured. Acceptable viable cell densities were achieved at the end of each passage (FIG. 19A). Cell viabilities were recovered from the initial thaw and maintained high viability throughout the expansion process (FIG. 19B), demonstrating adequate cell growth for robust manufacturing operations. Pre-infection total number of viable cells were within 20% of the respective averages of the four batches accounting for the differences in the production scale.

Figure 20:
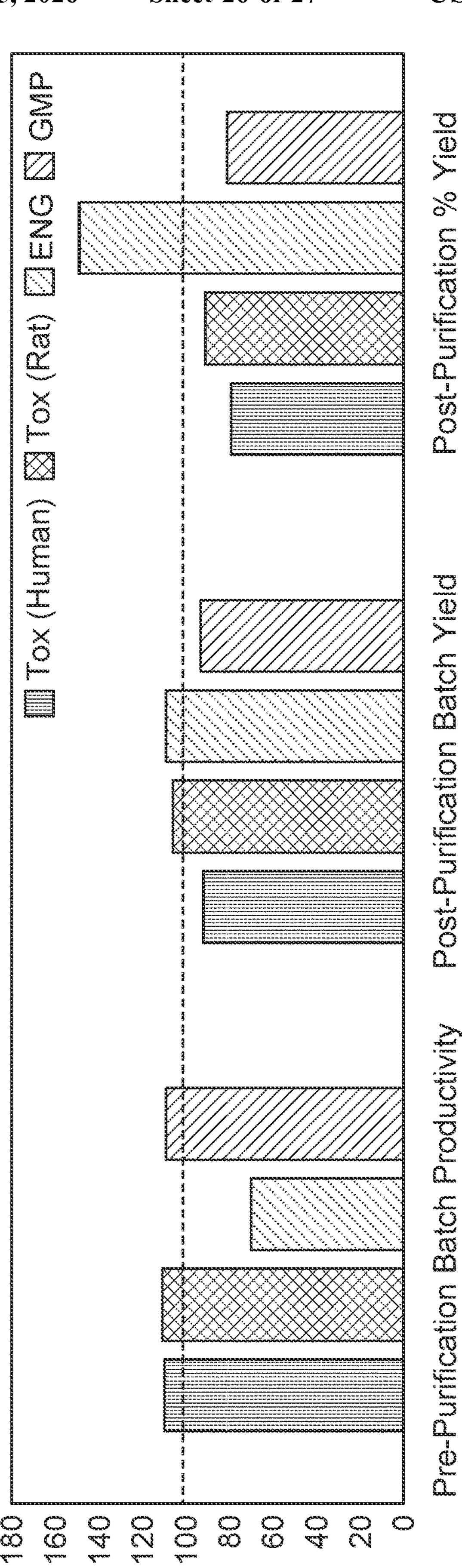
FIG. 20 depicts the product yield in downstream processing steps. Viral particle (VP) production (pre-purification batch productivity) and yield values (post-purification batch yield and post-purification % yield) normalized for batch size is depicted on the y-axis for the Tox (Human), Tox (Rat), ENG and GMP lots as indicated. The data for each lot is displayed as percent difference to the average of the four lots.

Product Yield in Downstream Processing Steps:

Across all three batches of FX201 and one batch of rat ortholog, pre-purification batch productivities were calculated using measurements of total viral particles at harvest and were within 30% of the average, indicating a similar starting amount of VP for each purified lot. Post-purification batch yields were within 10% of the average (FIG. 20). This accounted for the differences in the production scale. The higher overall yield observed in the ENG run was likely caused by underestimation of pre-purification batch productivity. Viral particles measured in unpurified intermediates have higher assay variability due to impurities, which are removed later in the process.

Figure 21:
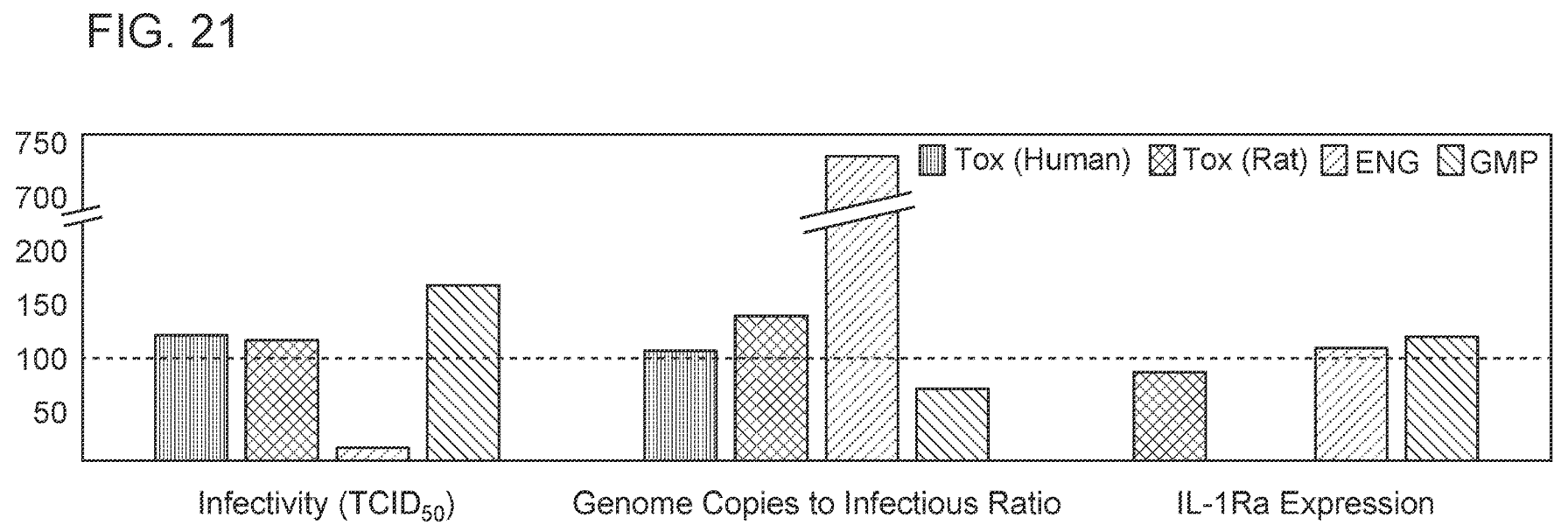

Infectivity and Gene Expression: Expression of human IL-1Ra was measured using a cell-based assay for three lots of FX201 and were within 20% of the average based on the ELISA endpoint measurement (FIG. 21). Infectivity of the ENG lot was lower than the other three lots, however the expression level of ENG human IL-1Ra was within 20% of the FX201 average, indicating that assay variability at this stage of development likely caused the observed difference. Infectivity ($TCID_{50}$) and Genome Copies to Infectious Ratio (also referred to herein as viral particles to infectivity ratio, VP/TCID50 ratio, or viral particles to infectious unit ratio, these terms are utilized interchangeably) averages exclude ENG lot data. Assay variability of the $TCID_{50}$ method is high, and the difference observed in the ENG lot is within the assay variability. Separate cell-based assay infers consistent infection of vectors and expression of transgene. Expression of IL-1Ra in Tox (Rat) was detected (data not shown).

Analysis of Impurities in Drug Substance: All process related impurities (including host cell proteins (HCP)) apart from rDNA were mostly below the level of detection or quantification and met the clinical acceptance criteria. The amount of residual DNA (rDNA) in the two non-clinical batches used in the toxicology study was approximately 150-fold higher compared to that of the ENG and GMP batches. The two Tox lots with elevated rDNA (136 and 33-fold greater than acceptance criteria) were used in non-clinical studies establishing efficacy, safety, and biodistribution of FX201 (Table 14). The established purification process sufficiently reduced residual HV, demonstrating the suitability of the purification process. Purified FX201 was characterized as mostly monomeric in final formulation.

TABLE 14

| | Analysis of Impurities in Drug Substance | | | |
|---|---|---|---|---|
| | Tox (Human) | Tox (Rat) | ENG | GMP |
| HCP, rBenzonase, rCesium | Pass (<LoD) | Pass (<LoD) | Pass (<LoD) | Pass (<LoD) |
| rDNA (ng/mL) | 136-fold* | 33-fold* | Pass | Pass |
| rBSA (ng/mL) | Pass (<LoQ) | Pass | Pass (<LoQ) | Pass (<LoQ) |
| Residual Helper Virus | Pass | Pass | Pass | Pass |
| % Monomer (based on peak intensity) | 98% | 99% | 94% | 95% |

(*rDNA listed as Pass, or fold above pass threshold;
rBenzonase: residual Benzonase;
rCesium: residual Cesium;
rBSA residual Bovine Serum Albumin;
LoD: limit of detection: and
LoQ: limit of Quantification).

Conclusions: Productivity, purification yields, and product quality were generally consistent across three batches of FX201 and one batch of rat ortholog. These data suggest that an early-stage FX201 process has shown to be reproducible across multiple lots, showing consistent productivity, purification yield, and product quality attributes. A single GMP drug substance batch yielded sufficient material to execute a Phase 1 study for evaluation of safety and tolerability in patients, covering three doses over a 100-fold range of total genome copy number. Given that a single lot of drug substance is adequate to supply drug product requirements for the full dose range of the Phase I study, this demonstrates a viable manufacturing process to carry the FX201 gene therapy program through clinical development.

What is claimed:

1. A method of treating an osteoarthritis-affected joint of a human suffering from osteoarthritis or an osteoarthritic condition with a helper-dependent adenoviral vector, the method comprising administering by intra-articular injection to the osteoarthritis-affected joint of the human suffering from osteoarthritis or an osteoarthritic condition a pharmaceutical composition comprising, $0.7\times10^{10}$ to $2.8\times10^{12}$ genome copies (GC) of the helper-dependent adenoviral vector, wherein the helper-dependent adenoviral vector comprises a nucleic acid comprising:

i) a sequence encoding a human interleukin-1 receptor antagonist (IL-1Ra) protein comprising the amino acid sequence of SEQ ID NO: 6, ii) left and right inverted terminal repeats, iii) an adenoviral packaging signal, iv) stuffer nucleic acid sequence that is non-viral and non-coding, and v) a NF-KB inducible promoter, wherein the expression of the nucleic acid sequence encoding the human IL-1Ra protein is regulated by the NF-KB inducible promoter, which NF-KB inducible promoter is located upstream of the reading frame of the nucleic acid sequence encoding the human IL-1Ra protein, and wherein the nucleic acid sequence of the nucleic acid comprising the sequence encoding the human IL-1Ra protein, the left and the right inverted terminal repeats, the adenoviral packaging signal, the stuffer nucleic acid sequence that is non-viral and non-coding, and the NF-KB inducible promoter, is at least 95% identical to the nucleic acid sequence of SEQ ID NO: 7.

2. The method of claim 1, wherein the nucleic acid sequence of the nucleic acid comprising the sequence encoding the human IL-1Ra protein, the left and the right inverted terminal repeats, the adenoviral packaging signal, the stuffer nucleic acid sequence that is non-viral and non-coding, and the NF-KB inducible promoter, is at least 99% identical to the nucleic acid sequence of SEQ ID NO: 7.

3. The method of claim 1, wherein the nucleic acid sequence of the nucleic acid comprising the sequence encoding the human IL-1Ra protein, the left and the right inverted terminal repeats, the adenoviral packaging signal, the stuffer nucleic acid sequence that is non-viral and non-coding, and the NF-KB inducible promoter, comprises the nucleic acid sequence of SEQ ID NO: 7.

4. The method of claim 1, wherein the nucleic acid sequence of the nucleic acid comprising the sequence encoding the human IL-1Ra protein, the left and the right inverted terminal repeats, the adenoviral packaging signal, the stuffer nucleic acid sequence that is non-viral and non-coding, and the NF-KB inducible promoter, consists of the nucleic acid sequence of SEQ ID NO: 7.

5. The method of claim 1, wherein the nucleic acid sequence encoding the human IL-1Ra protein comprises a nucleic acid sequence at least 97% identical to the nucleic acid sequence of SEQ ID NO 4.

6. The method of claim 1, wherein the nucleic acid sequence encoding the human IL-1Ra protein comprises the nucleic acid sequence of SEQ ID NO 4.

7. The method of claim 1, wherein the nucleic acid sequence encoding the human IL-1Ra protein consists of the nucleic acid sequence of SEQ ID NO 4.

8. The method of claim 1, wherein the nucleic acid sequence encoding the human IL-1Ra protein encodes a human IL-1Ra protein consisting of the amino acid sequence of SEQ ID NO: 6.

9. The method of claim 2, wherein the nucleic acid sequence encoding the human IL-1Ra protein encodes a human IL-1Ra protein consisting of the amino acid sequence of SEQ ID NO: 6.

10. The method of any one of claims 1, 2-4, 8 and 9, wherein the pharmaceutical composition comprises $1.4\times10^{10}\pm10\%$ GC, and wherein the volume of the pharmaceutical composition is 1 ml to 5 ml.

11. The method of any one of claims 1, 2-4, 8 and 9, wherein the pharmaceutical composition comprises $1.4\times10^{11}\pm10\%$ GC, and wherein the volume of the pharmaceutical composition is 1 ml to 5 ml.

12. The method of any one of claims 1, 2-4, 8 and 9, wherein the pharmaceutical composition comprises $1.4\times10^{12}\pm10\%$ GC, and wherein the volume of the pharmaceutical composition is 1 ml to 5 ml.

13. The method of claim 10, wherein the volume of the pharmaceutical composition is 5 ml, wherein the pharmaceutical composition is administered by a single intra-articular injection of the pharmaceutical composition, and wherein the osteoarthritis-affected joint is a knee joint.

14. The method of claim 11, wherein the volume of the pharmaceutical composition is 5 ml, wherein the pharmaceutical composition is administered by a single intra-articular injection of the pharmaceutical composition, and wherein the osteoarthritis-affected joint is a knee joint.

15. The method of claim 12, wherein the volume of the pharmaceutical composition is 5 ml, wherein the pharmaceutical composition is administered by a single intra-articular injection of the pharmaceutical composition, and wherein the osteoarthritis-affected joint is a knee joint.

* * * * *